(12) United States Patent
Kishikawa et al.

(10) Patent No.: US 7,906,522 B2
(45) Date of Patent: Mar. 15, 2011

(54) 2-AMINOQUINAZOLINE DERIVATIVES

(75) Inventors: Kuniyuki Kishikawa, Tokyo (JP);
Hidetomo Imase, Cambridge, MA (US);
Hajime Kashima, Shizuoka (JP);
Kiyotoshi Mori, La Jolla, CA (US);
Toshihide Ikemura, Tokyo (JP);
Yoshisuke Nakasato, Shizuoka (JP);
Misato Tomuro, Tokyo (JP)

(73) Assignee: Kyowa Hakko Kirin Co., Ltd, Tokyo (JP)

( * ) Notice: Subject to any disclaimer, the term of this patent is extended or adjusted under 35 U.S.C. 154(b) by 286 days.

(21) Appl. No.: 11/912,679

(22) PCT Filed: Apr. 28, 2006

(86) PCT No.: PCT/JP2006/309000
§ 371 (c)(1),
(2), (4) Date: Oct. 26, 2007

(87) PCT Pub. No.: WO2006/118256
PCT Pub. Date: Nov. 9, 2006

(65) Prior Publication Data
US 2009/0137583 A1    May 28, 2009

(30) Foreign Application Priority Data
Apr. 28, 2005    (JP) ................. 2005-130704

(51) Int. Cl.
A01N 43/54     (2006.01)
A61K 31/517    (2006.01)
C07D 239/72    (2006.01)

(52) U.S. Cl. ..................... 514/266.4; 544/292

(58) Field of Classification Search ............ 514/266.4; 544/292
See application file for complete search history.

(56) References Cited

U.S. PATENT DOCUMENTS

| | | | |
|---|---|---|---|
| 6,156,758 A | 12/2000 | Kung et al. | |
| 6,982,260 B1 * | 1/2006 | Barvian et al. | 514/218 |
| 2004/0209904 A1 | 10/2004 | Dunn et al. | |
| 2007/0054916 A1 * | 3/2007 | Patel et al. | 514/251 |

FOREIGN PATENT DOCUMENTS

| | | |
|---|---|---|
| JP | 39-25050 B1 | 11/1964 |
| JP | 6-324437 A | 11/1994 |
| JP | 1998-251235 * | 9/1998 |
| WO | 93/07124 A1 | 4/1993 |
| WO | 93/22460 A1 | 11/1993 |
| WO | 98/50370 A1 | 11/1998 |
| WO | 01/38315 A1 | 5/2001 |
| WO | 03/026667 A1 | 4/2003 |
| WO | 2004/092144 A2 | 10/2004 |
| WO | 2004/098494 A2 | 11/2004 |
| WO | 2005/087742 A1 | 9/2005 |
| WO | 2005/087749 A1 | 9/2005 |
| WO | 2006/015859 A1 | 2/2006 |
| WO | 2006/039718 A2 | 4/2006 |

OTHER PUBLICATIONS

Davis, American Journal of Pathology, 2003, American Society for Investigative Pathology, vol. 162, No. 5, pp. 1399-1402.*
Schett et. al., Arthritis & Rheumatism, 2000, American College of Rheumatology, vol. 43, No. 11, pp. 2501-2512.*

* cited by examiner

*Primary Examiner* — Sreeni Padmanabhan
*Assistant Examiner* — Sarah Pihonak
(74) *Attorney, Agent, or Firm* — Sughrue Mion, PLLC

(57) ABSTRACT

The present invention provides 2-aminoquinazoline derivatives represented by formula (I):

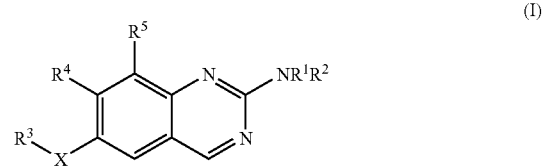

wherein $R^1$ and $R^2$ may be the same or different and each represents a hydrogen atom, substituted or unsubstituted lower alkyl, and the like;
X represents a bond or $CR^{7a}R^{7b}$ wherein $R^{7a}$ and $R^{7b}$ may be the same or different and each represents a hydrogen atom, and the like;
when X is a bond, $R^3$ represents substituted or unsubstituted aryl or a substituted or unsubstituted aromatic heterocyclic group;
when X is $CR^{7a}R^{7b}$ wherein $R^{7a}$ and $R^{7b}$ have the same meanings as defined above, respectively, $R^3$ represents substituted or unsubstituted lower alkoxy, substituted or unsubstituted aryl, and the like;
$R^4$ represents a hydrogen atom, hydroxy, substituted or unsubstituted lower alkoxy, and the like; and
$R^5$ represents a hydrogen atom, substituted or unsubstituted aryl, and the like, or a pharmaceutically acceptable salt thereof.

7 Claims, No Drawings

2-AMINOQUINAZOLINE DERIVATIVES

TECHNICAL FIELD

The present invention relates to 2-aminoquinazoline derivatives having p38 mitogen-activated protein (p38MAP) kinase inhibitory activity, and the like.

BACKGROUND ART p38 Mitogen-activated protein (p38 MAP) (p38α/Mpk2/RK/SAPK2a/CSBP) kinase (hereinafter referred to as "p38MAP kinase") is cloned as an enzyme that is tyrosine-phosphorylated in monocytes stimulated by lipopolysaccharide (LPS) [Nature, vol. 372, p. 739 (1994)], and is a kinase that is activated by various extracellular stimuli (physical stimuli: osmotic shock, heat shock, UV irradiation, etc.; chemical stimuli: endotoxin, hydrogen peroxide, inflammatory cytokines, growth factors, etc.) [Molecular and Cellular Biology, vol. 19 (4), p. 2435 (1999)]. Furthermore, since p38MAP kinase is involved in the production of inflammatory cytokines such as tumor necrosis factor-α (TNF-α), interleukin-1 (IL-1), IL-6, and IL-8, and chemokines, association between activation of this enzyme and diseases is strongly suggested [Nature, vol. 372, p. 739 (1994)]. Therefore, it is expected that suppression of activation of p38MAP kinase would produce a improving effect for various diseases, such as inflammatory diseases.

Accordingly, a p38MAP kinase inhibitor is expected to be useful in the prevention and/or treatment of diseases that are believed to be caused or deteriorated by abnormal production of inflammatory cytokines and chemokines, or by overresponse thereto, for example, various inflammatory diseases, rheumatoid arthritis, osteoarthritis, arthritis, osteoporosis, autoimmune diseases, infectious diseases, sepsis, cachexia, cerebral infarction, Alzheimer's disease, asthma, chronic inflammatory pulmonary diseases, chronic obstructive pulmonary diseases (COPD), reperfusion injury, thrombosis, glomerulonephritis, diabetes, graft-versus-host reaction, inflammatory bowel diseases, Crohn's disease, ulcerative colitis, multiple sclerosis, tumor growth and metastasis, multiple myeloma, plasma cell leukemia, Castleman's disease, atrial myxoma, psoriasis, dermatitis, gout, adult respiratory distress syndrome (ARDS), arteriosclerosis, restenosis after percutaneous transluminal coronary angioplasty (PTCA), pancreatitis, and pains.

Also disclosed are 2-aminoquinazoline derivative which are hypotensive drugs (Patent Document 1), phosphodiesterase (PDE) inhibitors (Patent Document 2), PDE-IV inhibitors (Patent Document 3), serine/threonine protein kinase modulators (Patent Document 4), antibacterial agents (Patent Documents 5 and 8), neuropeptide ligands (Patent Document 6), developer compositions (Patent Document 7), pesticides (Patent Document 9), kinase inhibitors (Patent Document 10), cyclin-dependent kinase inhibitors (Patent Document 11), etc.

Quinazoline derivatives having p38MAP kinase inhibitory activity are also known (Patent Documents 12 and 13).

Patent Document 1: Japanese Published Examined Patent Application No. 25050/1964
Patent Document 2: WO93/07124
Patent Document 3: WO93/22460
Patent Document 4: WO98/50370
Patent Document 5: U.S. Pat. No. 6,156,758
Patent Document 6: WO03/26667
Patent Document 7: Japanese Published Unexamined Patent Application No. 324437/1994
Patent Document 8: WO2004/098494
Patent Document 9: WO2005/087742
Patent Document 10: WO2006/015859
Patent Document 11: WO01/38315
Patent Document 12: United States Patent Application No. 2004/0209904
Patent Document 13: WO2004/092144

DISCLOSURE OF INVENTION

Problems to be Solved by the Invention

An object of the present invention is to provide a 2-aminoquinazoline derivative having p38MAP kinase inhibitory activity or a pharmaceutically acceptable salt thereof and the like.

Means for Solving the Problems

The present invention relates to the following (1) to (72):
(1) A 2-aminoquinazoline derivative represented by formula (I):

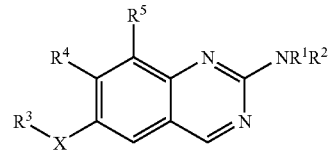

{wherein $R^1$ and $R^2$ may be the same or different and each represents a hydrogen atom, substituted or unsubstituted lower alkyl, substituted or unsubstituted lower alkenyl, substituted or unsubstituted lower alkynyl, substituted or unsubstituted cycloalkyl, substituted or unsubstituted cycloalkenyl, substituted or unsubstituted lower alkanoyl, substituted or unsubstituted cycloalkylcarbonyl, substituted or unsubstituted aryl, a substituted or unsubstituted heterocyclic group, or $CONR^{6a}R^{6b}$ (wherein $R^{6a}$ and $R^{6b}$ may be the same or different and each represents a hydrogen atom or substituted or unsubstituted lower alkyl);
X represents a bond or $CR^{7a}R^{7b}$ (wherein $R^{7a}$ and $R^{7b}$ may be the same or different and each represents a hydrogen atom, halogen, hydroxy, substituted or unsubstituted lower alkyl, or substituted or unsubstituted lower alkoxy, or $R^{7a}$ and $R^{7b}$ are combined to form an oxygen atom);
when X is a bond, $R^3$ represents substituted or unsubstituted aryl or a substituted or unsubstituted aromatic heterocyclic group;
when X is $CR^{7a}R^{7b}$ (wherein $R^{7a}$ and $R^{7b}$ have the same meanings as defined above, respectively), $R^3$ represents substituted or unsubstituted lower alkoxy, substituted or unsubstituted aryl, a substituted or unsubstituted aromatic heterocyclic group, or $NR^{8a}R^{8b}$ (wherein $R^{8a}$ and $R^{8b}$ may be the same or different and each represents a hydrogen atom, substituted or unsubstituted lower alkyl, substituted or unsubstituted lower alkenyl, substituted or unsubstituted lower alkynyl, substituted or unsubstituted cycloalkyl, substituted or unsubstituted lower alkoxy, substituted or unsubstituted aryl, or a substituted or unsubstituted heterocyclic group; or $R^{8a}$ and $R^{8b}$ are combined together with the adjacent nitrogen atom thereto to form a substituted or unsubstituted heterocyclic group);
$R^4$ represents a hydrogen atom, halogen, hydroxy, substituted or unsubstituted lower alkyl, substituted or unsubstituted lower alkenyl, substituted or unsubstituted lower alkynyl, substituted or unsubstituted lower alkoxy, substituted or unsubstituted lower alkanoyloxy, substituted or unsubstituted aryl, substituted or unsubstituted aroyloxy, or a substituted or unsubstituted heterocyclic group; or R⁴ and R⁵ are combined together with the respective adjacent carbon atoms to form

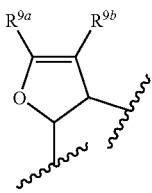

[wherein $R^{9a}$ and $R^{9b}$ may be the same or different and each represents a hydrogen atom, halogen, hydroxy, substituted or unsubstituted lower alkyl, substituted or unsubstituted lower alkenyl, substituted or unsubstituted lower alkoxy, substituted or unsubstituted lower alkoxycarbonyl, substituted or unsubstituted aryl, a substituted or unsubstituted heterocyclic group, or $CONR^{10a}R^{10b}$ (wherein $R^{10a}$ and $R^{10b}$ may be the same or different and each represents a hydrogen atom, substituted or unsubstituted lower alkyl, substituted or unsubstituted lower alkenyl, substituted or unsubstituted lower alkynyl, substituted or unsubstituted cycloalkyl, substituted or unsubstituted lower alkoxy, substituted or unsubstituted aryl, or a substituted or unsubstituted heterocyclic group; or $R^{10a}$ and $R^{10b}$ are combined together with the adjacent nitrogen atom thereto to form a substituted or unsubstituted heterocyclic group)], or

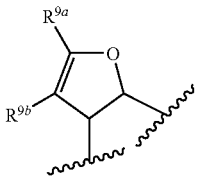

(wherein $R^{9a}$ and $R^{9b}$ have the same meanings as defined above, respectively);
and R⁵ represents a hydrogen atom, halogen, hydroxy, substituted or unsubstituted lower alkyl, substituted or unsubstituted lower alkenyl, substituted or unsubstituted lower alkoxy, substituted or unsubstituted aryl, a substituted or unsubstituted heterocyclic group, $CONR^{11a}R^{11b}$ (wherein $R^{11a}$ and $R^{11b}$ have the same meanings as those of $R^{10a}$ and $R^{10b}$ defined above, respectively), or $COR^{12}$ (wherein $R^{12}$ represents a hydrogen atom, hydroxy, substituted or unsubstituted lower alkyl, substituted or unsubstituted lower alkenyl, substituted or unsubstituted lower alkynyl, substituted or unsubstituted cycloalkyl, substituted or unsubstituted lower alkoxy, substituted or unsubstituted aryl, or a substituted or unsubstituted heterocyclic group); or R⁵ and R⁴ are combined together with the respective adjacent carbon atoms to form

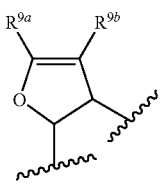

(wherein $R^{9a}$ and $R^{9b}$ have the same meanings as defined above, respectively) or

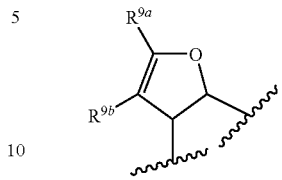

(wherein $R^{9a}$ and $R^{9b}$ have the same meanings as defined above, respectively)} or a pharmaceutically acceptable salt thereof.

(2) The 2-aminoquinazoline derivative or the pharmaceutically acceptable salt thereof according to the above (1), wherein R¹ and R² are each a hydrogen atom.

(3) The 2-aminoquinazoline derivative or the pharmaceutically acceptable salt thereof according to the above (1), wherein R¹ is a hydrogen atom and R² is substituted or unsubstituted lower alkyl, substituted or unsubstituted cycloalkyl, substituted or unsubstituted aryl, or a substituted or unsubstituted heterocyclic group.

(4) The 2-aminoquinazoline derivative or the pharmaceutically acceptable salt thereof according to any one of the above (1) to (3), wherein X is a bond.

(5) The 2-aminoquinazoline derivative or the pharmaceutically acceptable salt thereof according to any one of the above (1) to (3), wherein X is C=O.

(6) The 2-aminoquinazoline derivative or the pharmaceutically acceptable salt thereof according to any one of the above (1) to (5), wherein R³ is substituted or unsubstituted aryl.

(7) The 2-aminoquinazoline derivative or the pharmaceutically acceptable salt thereof according to any one of the above (1) to (6), wherein R⁴ is hydroxy or substituted or unsubstituted lower alkoxy.

(8) The 2-aminoquinazoline derivative or the pharmaceutically acceptable salt thereof according to any one of the above (1) to (6), wherein R⁴ is substituted or unsubstituted aryl.

(9) The 2-aminoquinazoline derivative or the pharmaceutically acceptable salt thereof according to any one of the above (1) to (6), wherein R⁴ is a substituted or unsubstituted aromatic heterocyclic group.

(10) The 2-aminoquinazoline derivative or the pharmaceutically acceptable salt thereof according to any one of the above (1) to (6), wherein R⁴ is substituted or unsubstituted aroyloxy.

(11) The 2-aminoquinazoline derivative or the pharmaceutically acceptable salt thereof according to any one of the above (1) to (10), wherein R⁵ is a hydrogen atom, halogen, or substituted or unsubstituted lower alkyl.

(12) The 2-aminoquinazoline derivative or the pharmaceutically acceptable salt thereof according to any one of the above (1) to (10), wherein R⁵ is substituted or unsubstituted aryl.

(13) The 2-aminoquinazoline derivative or the pharmaceutically acceptable salt thereof according to any one of the above (1) to (10), wherein R⁵ is a substituted or unsubstituted aromatic heterocyclic group.

(14) A 2-aminoquinazoline derivative represented by formula (IA):

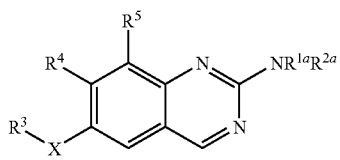

{wherein X, $R^3$, $R^4$, and $R^5$ have the same meanings as defined above, respectively;
$R^{1a}$ represents a hydrogen atom, substituted or unsubstituted lower alkyl, substituted or unsubstituted lower alkenyl, substituted or unsubstituted lower alkynyl, substituted or unsubstituted cycloalkyl, substituted or unsubstituted cycloalkenyl, substituted or unsubstituted lower alkanoyl, substituted or unsubstituted cycloalkylcarbonyl, substituted or unsubstituted aryl, a substituted or unsubstituted heterocyclic group, or $CONR^{6a}R^{6b}$ (wherein $R^{6a}$ and $R^{6b}$ have the same meanings as defined above, respectively);
and $R^{2a}$ represents substituted or unsubstituted aryl, substituted or unsubstituted aralkyl, a substituted or unsubstituted aromatic heterocyclic group, or $CR^{13}R^{14}R^{15}$ [wherein $R^{13}$ represents a hydrogen atom or substituted or unsubstituted lower alkyl; and $R^{14}$ and $R^{15}$ may be the same or different and each represents a hydrogen atom, substituted or unsubstituted lower alkyl, $OR^{16}$ (wherein $R^{16}$ represents a hydrogen atom, substituted or unsubstituted lower alkyl, substituted or unsubstituted lower alkenyl, substituted or unsubstituted lower alkynyl, substituted or unsubstituted cycloalkyl, substituted or unsubstituted aryl, or a substituted or unsubstituted heterocyclic group), $S(O)_pR^{16a}$ (wherein $R^{16a}$ has the same meaning as that of $R^{16}$ defined above, and p represents an integer of 0 to 2), $COR^{16b}$ (wherein $R^{16b}$ has the same meaning as that of $R^{16}$ defined above), $CO_2R^{16c}$ (wherein $R^{16c}$ has the same meaning as that of $R^{16}$ defined above), $CONR^{17a}R^{17b}$ (wherein $R^{17a}$ and $R^{17b}$ have the same meanings as those of $R^{10a}$ and $R^{10b}$ defined above, respectively), or $S(O)_2NR^{17c}R^{17d}$ (wherein $R^{17c}$ and $R^{17d}$ have the same meanings as those of $R^{10a}$ and $R^{10b}$ defined above, respectively); or $R^{14}$ and $R^{15}$ are combined together with the adjacent carbon atom thereto to form substituted or unsubstituted cycloalkyl or a substituted or unsubstituted aliphatic heterocyclic group, provided that, when $R^{13}$ is a hydrogen atom, $R^{14}$ and $R^{15}$ do not simultaneously represent a hydrogen atom]} or a pharmaceutically acceptable salt thereof.

(15) The 2-aminoquinazoline derivative or the pharmaceutically acceptable salt thereof according to the above (14), wherein $R^{1a}$ is a hydrogen atom.

(16) The 2-aminoquinazoline derivative or the pharmaceutically acceptable salt thereof according to the above (14) or (15), wherein $R^{2a}$ represents substituted or unsubstituted aryl, a substituted or unsubstituted aromatic heterocyclic group, or $CR^{13a}R^{14a}R^{15a}$ (wherein $R^{13a}$ represents a hydrogen atom or substituted or unsubstituted lower alkyl; and $R^{14a}$ and $R^{15a}$ may be the same or different and each represents a hydrogen atom or substituted or unsubstituted lower alkyl, or $R^{14a}$ and $R^{15a}$ are combined together with the adjacent carbon atom thereto to form substituted or unsubstituted cycloalkyl or a substituted or unsubstituted aliphatic heterocyclic group, provided that, when $R^{13a}$ is a hydrogen atom, $R^{14a}$ and $R^{15a}$ do not simultaneously represent a hydrogen atom).

(17) The 2-aminoquinazoline derivative or the pharmaceutically acceptable salt thereof according to any one of the above (14) to (16), wherein X is a bond.

(18) The 2-aminoquinazoline derivative or the pharmaceutically acceptable salt thereof according to any one of the above (14) to (16), wherein X is $CR^{7a}R^{7b}$ (wherein $R^{7a}$ and $R^{7b}$ have the same meanings as defined above, respectively), and $R^3$ is substituted or unsubstituted aryl or a substituted or unsubstituted aromatic heterocyclic group.

(19) The 2-aminoquinazoline derivative or the pharmaceutically acceptable salt thereof according to the above (18), wherein $R^{7a}$ and $R^{7b}$ are combined to form an oxygen atom.

(20) The 2-aminoquinazoline derivative or the pharmaceutically acceptable salt thereof according to any one of the above (14) to (19), wherein $R^4$ is hydroxy or substituted or unsubstituted lower alkoxy.

(21) The 2-aminoquinazoline derivative or the pharmaceutically acceptable salt thereof according to any one of the above (14) to (19), wherein $R^4$ is substituted or unsubstituted aryl.

(22) The 2-aminoquinazoline derivative or the pharmaceutically acceptable salt thereof according to any one of the above (14) to (19), wherein $R^4$ is a substituted or unsubstituted aromatic heterocyclic group.

(23) The 2-aminoquinazoline derivative or the pharmaceutically acceptable salt thereof according to any one of the above (14) to (19), wherein $R^4$ is substituted or unsubstituted aroyloxy.

(24) The 2-aminoquinazoline derivative or the pharmaceutically acceptable salt thereof according to any one of the above (14) to (23), wherein $R^5$ is a hydrogen atom.

(25) The 2-aminoquinazoline derivative or the pharmaceutically acceptable salt thereof according to any one of the above (14) to (23), wherein $R^5$ is substituted or unsubstituted aryl.

(26) The 2-aminoquinazoline derivative or the pharmaceutically acceptable salt thereof according to any one of the above (14) to (23), wherein $R^5$ is a substituted or unsubstituted aromatic heterocyclic group.

(27) The 2-aminoquinazoline derivative or the pharmaceutically acceptable salt thereof according to any one of the above (14) to (19), wherein $R^4$ and $R^5$ are combined together with the respective adjacent carbon atoms to form

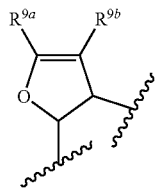

(wherein $R^{9a}$ and $R^{9b}$ have the same meanings as defined above, respectively) or

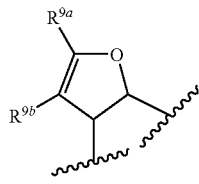

(wherein $R^{9a}$ and $R^{9b}$ have the same meanings as defined above, respectively).

(28) A 2-aminoquinazoline derivative represented by formula (IB):

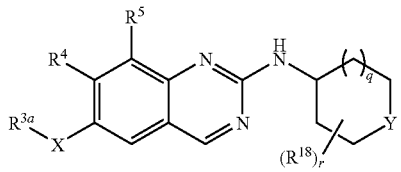

<wherein $R^4$, $R^5$ and X have the same meanings as defined above, respectively;
q represents 0 or 1;
r represents an integer of 0 to 4;
Y represents an oxygen atom, C=O, $NR^{19}$ (wherein $R^{19}$ represents a hydrogen atom, sulfino, carboxy, substituted or unsubstituted lower alkyl, substituted or unsubstituted lower alkanoyl, substituted or unsubstituted lower alkoxycarbonyl, or substituted or unsubstituted lower alkylsulfonyl), or $CHR^{20}$ {wherein $R^{20}$ represents a hydrogen atom, hydroxy, amino, carboxy, sulfino, substituted or unsubstituted lower alkyl, substituted or unsubstituted lower alkoxy, mono- or di-(substituted or unsubstituted lower alkyl)amino, substituted or unsubstituted lower alkanoyl, substituted or unsubstituted lower alkoxycarbonyl, substituted or unsubstituted lower alkylsulfonyl, $NR^{21}COR^{22}$ [wherein $R^{21}$ represents a hydrogen atom or substituted or unsubstituted lower alkyl; $R^{22}$ represents amino, substituted or unsubstituted lower alkyl, substituted or unsubstituted lower alkoxy, or mono- or di-(substituted or unsubstituted lower alkyl)amino], or $NR^{21a}S(O)_2R^{22a}$ (wherein $R^{21a}$ and $R^{22a}$ have the same meanings as those of $R^{21}$ and $R^{22}$ defined above, respectively)};
$R^{3a}$ represents substituted or unsubstituted aryl or a substituted or unsubstituted aromatic heterocyclic group;
and $R^{18}$ represents amino, hydroxy, sulfino, carboxy, substituted or unsubstituted lower alkyl, substituted or unsubstituted lower alkoxy, mono- or di-(substituted or unsubstituted lower alkyl)amino, substituted or unsubstituted lower alkanoyl, substituted or unsubstituted lower alkoxycarbonyl, substituted or unsubstituted lower alkylsulfonyl, $NR^{23a}COR^{24a}$ (wherein $R^{23a}$ and $R^{24a}$ have the same meanings as those of $R^{21}$ and $R^{22}$ defined above, respectively), or $NR^{23b}S(O)_2R^{24b}$ (wherein $R^{23b}$ and $R^{24b}$ have the same meanings as those of $R^{21}$ and $R^{22}$ defined above, respectively), provided that, when r is an integer of 2 to 4, $R^{18}$s may be the same or different> or a pharmaceutically acceptable salt thereof.

(29) The 2-aminoquinazoline derivative or the pharmaceutically acceptable salt thereof according to the above (28), wherein $R^4$ is hydroxy or substituted or unsubstituted lower alkoxy.

(30) The 2-aminoquinazoline derivative or the pharmaceutically acceptable salt thereof according to the above (28), wherein $R^4$ is substituted or unsubstituted aryl.

(31) The 2-aminoquinazoline derivative or the pharmaceutically acceptable salt thereof according to the above (28), wherein $R^4$ is a substituted or unsubstituted aromatic heterocyclic group.

(32) The 2-aminoquinazoline derivative or the pharmaceutically acceptable salt thereof according to the above (28), wherein $R^4$ is substituted or unsubstituted aroyloxy.

(33) The 2-aminoquinazoline derivative or the pharmaceutically acceptable salt thereof according to any one of the above (28) to (32), wherein X is a bond.

(34) The 2-aminoquinazoline derivative or the pharmaceutically acceptable salt thereof according to any one of the above (28) to (33), wherein $R^5$ is a hydrogen atom.

(35) The 2-aminoquinazoline derivative or the pharmaceutically acceptable salt thereof according to any one of the above (28) to (33), wherein $R^5$ is substituted or unsubstituted aryl.

(36) The 2-aminoquinazoline derivative or the pharmaceutically acceptable salt thereof according to any one of the above (28) to (33), wherein $R^5$ is a substituted or unsubstituted aromatic heterocyclic group.

(37) A 2-aminoquinazoline derivative represented by formula (IC):

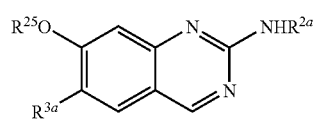

(wherein $R^{2a}$ and $R^{3a}$ have the same meanings as defined above, respectively;
and $R^{25}$ represents a hydrogen atom or substituted or unsubstituted lower alkyl) or a pharmaceutically acceptable salt thereof.

(38) The 2-aminoquinazoline derivative or the pharmaceutically acceptable salt thereof according to the above (37), wherein $R^{2a}$ is $CR^{13a}R^{14a}R^{15a}$ (wherein $R^{13a}$, $R^{14a}$, and $R^{15a}$ have the same meanings as defined above, respectively).

(39) The 2-aminoquinazoline derivative or the pharmaceutically acceptable salt thereof according to the above (37) or (38), wherein $R^{3a}$ is substituted or unsubstituted aryl.

(40) The 2-aminoquinazoline derivative or the pharmaceutically acceptable salt thereof according to the above (37) or (38), wherein $R^{3a}$ is substituted or unsubstituted phenyl.

(41) The 2-aminoquinazoline derivative or the pharmaceutically acceptable salt thereof according to the above (37) or (38), wherein $R^{3a}$ is

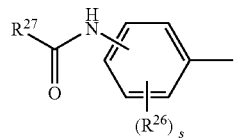

[wherein s represents an integer of 0 to 4;
$R^{26}$ represents a hydrogen atom, halogen, or lower alkyl; and
$R^{27}$ represents lower alkyl, cycloalkyl, lower alkoxy, aryl, aryl substituted by one to substitutable number of substituents selected from substituents A, an aromatic heterocyclic group, or an aromatic heterocyclic group substituted by one to substitutable number of substituents selected from substituents A,
Provided that, when s is an integer of 2 to 4, $R^{26}$s may be the same or different,
the substituents A including halogen, lower alkyl, cycloalkyl, $-NR^{28a}R^{28b}$ (wherein $R^{28a}$ and $R^{28b}$ may be the same or different and each represents a hydrogen atom, lower alkyl, or cycloalkyl; or $R^{28a}$ and $R^{28b}$ are combined together with the adjacent nitrogen atom thereto to form an aliphatic heterocyclic group or an aliphatic heterocyclic group substituted by one to substitutable number of lower alkyl)].

(42) The 2-aminoquinazoline derivative or the pharmaceutically acceptable salt thereof according to the above (41), wherein $R^{27}$ is phenyl substituted by —$NR^{28a}R^{28b}$ (wherein $R^{28a}$ and $R^{28b}$ have the same meanings as defined above, respectively) or pyridyl substituted by —$NR^{28a}R^{28b}$ (wherein $R^{28a}$ and $R^{28b}$ have the same meanings as defined above, respectively).

(43) The 2-aminoquinazoline derivative or the pharmaceutically acceptable salt thereof according to the above (41), wherein $R^{27}$ is phenyl substituted by phenyl substituted by one to substitutable number of halogen and/or one to substitutable number of lower alkyl, or pyridyl substituted by phenyl substituted by one to substitutable number of halogen and/or one to substitutable number of lower alkyl.

(44) The 2-aminoquinazoline derivative or the pharmaceutically acceptable salt thereof according to the above (37) or (38), wherein $R^{3a}$ is

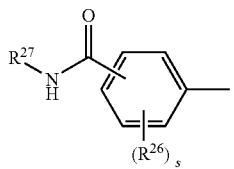

(wherein s, $R^{26}$, and $R^{27}$ have the same meanings as defined above, respectively).

(45) The 2-aminoquinazoline derivative or the pharmaceutically acceptable salt thereof according to the above (44), wherein s is 1, $R^{26}$ is lower alkyl, and $R^{27}$ is cycloalkyl.

(46) A 2-aminoquinazoline derivative represented by formula (ID):

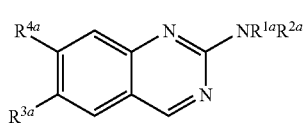

(wherein $R^{1a}$, $R^{2a}$, and $R^{3a}$ have the same meanings as defined above, respectively;
and $R^{4a}$ represents substituted or unsubstituted aryl, substituted or unsubstituted aroyloxy, or a substituted or unsubstituted aromatic heterocyclic group) or a pharmaceutically acceptable salt thereof.

(47) The 2-aminoquinazoline derivative or the pharmaceutically acceptable salt thereof according to the above (46), wherein $R^{1a}$ is a hydrogen atom, and $R^{2a}$ is $CR^{13a}R^{14a}R^{15a}$ (wherein $R^{13a}$, $R^{14a}$, and $R^{15a}$ have the same meanings as defined above, respectively).

(48) The 2-aminoquinazoline derivative or the pharmaceutically acceptable salt thereof according to the above (46), wherein $R^{1a}$ is a hydrogen atom, and $R^{2a}$ is an aromatic heterocyclic group.

(49) The 2-aminoquinazoline derivative or the pharmaceutically acceptable salt thereof according to any one of the above (46) to (48), wherein $R^{3a}$ is substituted or unsubstituted aryl.

(50) The 2-aminoquinazoline derivative or the pharmaceutically acceptable salt thereof according to any one of the above (46) to (48), wherein $R^{3a}$ is substituted or unsubstituted phenyl.

(51) The 2-aminoquinazoline derivative or the pharmaceutically acceptable salt thereof according to any one of the above (46) to (50), wherein $R^{4a}$ is substituted or unsubstituted aryl.

(52) The 2-aminoquinazoline derivative or the pharmaceutically acceptable salt thereof according to any one of the above (46) to (50), wherein $R^{4a}$ is substituted or unsubstituted phenyl.

(53) The 2-aminoquinazoline derivative or the pharmaceutically acceptable salt thereof according to any one of the above (46) to (50), wherein $R^{4a}$ is a substituted or unsubstituted aromatic heterocyclic group.

(54) The 2-aminoquinazoline derivative or the pharmaceutically acceptable salt thereof according to any one of the above (46) to (50), wherein $R^{4a}$ is substituted or unsubstituted pyridyl.

(55) A 2-aminoquinazoline derivative represented by formula (IE):

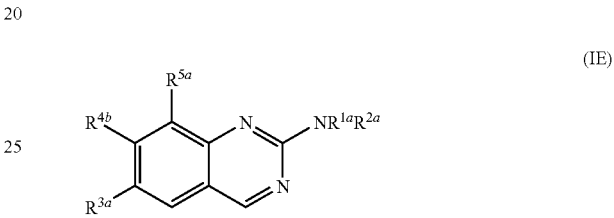

(wherein $R^{1a}$, $R^{2a}$, and $R^{3a}$ have the same meanings as defined above, respectively;
$R^{4b}$ represents a hydrogen atom, hydroxy, or substituted or unsubstituted alkoxy;
and $R^{5a}$ represents substituted or unsubstituted aryl or a substituted or unsubstituted aromatic heterocyclic group) or a pharmaceutically acceptable salt thereof.

(56) The 2-aminoquinazoline derivative or the pharmaceutically acceptable salt thereof according to the above (55), wherein $R^{1a}$ is a hydrogen atom and $R^{2a}$ is $CR^{13a}R^{14a}R^{15a}$ (wherein $R^{13a}$, $R^{14a}$, and $R^{15a}$ have the same meanings as defined above, respectively).

(57) The 2-aminoquinazoline derivative or the pharmaceutically acceptable salt thereof according to the above (55) or (56), wherein $R^{3a}$ is substituted or unsubstituted aryl.

(58) The 2-aminoquinazoline derivative or the pharmaceutically acceptable salt thereof according to the above (55) or (56), wherein $R^{3a}$ is substituted or unsubstituted phenyl.

(59) The 2-aminoquinazoline derivative or the pharmaceutically acceptable salt thereof according to any one of the above (55) to (58), wherein $R^{4b}$ is a hydrogen atom.

(60) The 2-aminoquinazoline derivative or the pharmaceutically acceptable salt thereof according to any one of the above (55) to (58), wherein $R^{4b}$ is hydroxy.

(61) The 2-aminoquinazoline derivative or the pharmaceutically acceptable salt thereof according to any one of the above (55) to (58), wherein $R^{4b}$ is substituted or unsubstituted lower alkoxy.

(62) The 2-aminoquinazoline derivative or the pharmaceutically acceptable salt thereof according to any one of the above (55) to (61), wherein $R^{5a}$ is substituted or unsubstituted aryl.

(63) The 2-aminoquinazoline derivative or the pharmaceutically acceptable salt thereof according to any one of the above (55) to (61), wherein $R^{5a}$ is substituted or unsubstituted phenyl.

(64) The 2-aminoquinazoline derivative or the pharmaceutically acceptable salt thereof according to any one of the above (55) to (61), wherein $R^{5a}$ is a substituted or unsubstituted aromatic heterocyclic group.

(65) The 2-aminoquinazoline derivative or the pharmaceutically acceptable salt thereof according to any one of the above (55) to (61), wherein $R^{5a}$ is substituted or unsubstituted pyridyl.

(66) A pharmaceutical composition which comprises, as an active ingredient, the 2-aminoquinazoline derivative or the pharmaceutically acceptable salt thereof described in any one of the above (1) to (65).

(67) A kinase inhibitor which comprises, as an active ingredient, the 2-aminoquinazoline derivative or the pharmaceutically acceptable salt thereof described in any one of the above (1) to (65).

(68) A serine/threonine kinase inhibitor which comprises, as an active ingredient, the 2-aminoquinazoline derivative or the pharmaceutically acceptable salt thereof described in any one of the above (1) to (65).

(69) A p38 mitogen-activated protein (p38MAP) kinase inhibitor which comprises, as an active ingredient, the 2-aminoquinazoline derivative or the pharmaceutically acceptable salt thereof described in any one of the above (1) to (65).

(70) A preventive and/or therapeutic agent for a disease associated with the function of a p38 mitogen-activated protein (p38MAP) kinase, which comprises, as an active ingredient, the 2-aminoquinazoline derivative or the pharmaceutically acceptable salt thereof described in any one of the above (1) to (65).

(71) A method for treating a disease associated with the function of a p38 mitogen-activated protein (p38MAP) kinase, which comprises administering an effective amount of the 2-aminoquinazoline derivative or the pharmaceutically acceptable salt thereof described in any one of the above (1) to (65).

(72) Use of the 2-aminoquinazoline derivative or the pharmaceutically acceptable salt thereof described in any one of the above (1) to (65), for the manufacture of a therapeutic agent for a disease associated with the function of a p38 mitogen-activated protein (p38MAP) kinase.

Effects of the Invention

The present invention provides 2-aminoquinazoline derivatives having p38MAP kinase inhibitory activity, and the like.

BEST MODE FOR CARRYING OUT THE INVENTION

Hereinafter, the compounds represented by formulae (I), (IA), (IB), (IC), (ID), and (IE) will be referred to as Compounds (I), (IA), (IB), (IC), (ID), and (IE), respectively. The same applies to compounds represented by other formula numbers.

In the definitions of the groups in Compounds (I), (IA), (IB), (IC), (ID), and (IE), examples of the lower alkyl, and the lower alkyl moiety of lower alkoxy, lower alkoxycarbonyl, mono- or di-(lower alkyl)amino, and lower alkylsulfonyl include linear or branched alkyl having 1 to 10 carbon atoms, and more specifically, methyl, ethyl, propyl, isopropyl, butyl, isobutyl, sec-butyl, tert-butyl, pentyl, isopentyl, neopentyl, hexyl, heptyl, octyl, nonyl, decyl, and the like. The two lower alkyl moieties of the di-(lower alkyl)amino may be the same or different.

Examples of the lower alkenyl include linear or branched alkenyl having 2 to 10 carbon atoms, and more specifically, vinyl, allyl, 1-propenyl, methacryl, crotyl, 1-butenyl, 3-butenyl, 2-pentenyl, 4-pentenyl, 2-hexenyl, 5-hexenyl, 2-heptenyl, 2-octenyl, 2-nonenyl, 2-decenyl, and the like.

Examples of the lower alkynyl include linear or branched alkynyl having 2 to 10 carbon atoms, and more specifically, ethynyl, 2-propynyl, 2-butynyl, 2-pentynyl, 2-hexynyl, 2-heptynyl, 2-octynyl, 2-nonynyl, 2-decynyl, and the like.

Examples of the cycloalkyl include cycloalkyl having 3 to 8 carbon atoms, and more specifically, cyclopropyl, cyclobutyl, cyclopentyl, cyclohexyl, cycloheptyl, cyclooctyl, and the like.

Examples of the cycloalkenyl include cycloalkenyl having 3 to 8 carbon atoms, and more specifically, cyclopropenyl, cyclobutenyl, cyclopentenyl, cyclohexenyl, cycloheptenyl, cyclooctenyl, and the like.

Examples of the lower alkanoyl, and the lower alkanoyl moiety of lower alkanoyloxy include linear or branched alkanoyl having 1 to 8 carbon atoms, and more specifically, formyl, acetyl, propionyl, butyryl, isobutyryl, valeryl, isovaleryl, pivaloyl, hexanoyl, heptanoyl, octanoyl, and the like.

The cycloalkyl moiety of cycloalkylcarbonyl has the same meaning as the cycloalkyl defined above.

Examples of the aryl, and the aryl moiety of aroyloxy include aryl having 6 to 14 carbon atoms, and more specifically, phenyl, naphthyl, anthryl, and the like.

Examples of the aralkyl include aralkyl having 7 to 15 carbon atoms, and more specifically, benzyl, phenethyl, benzhydryl, naphthylmethyl, and the like.

Examples of the aromatic heterocyclic group include a 5- or 6-membered monocyclic aromatic heterocyclic group containing at least one atom selected from a nitrogen atom, an oxygen atom, and a sulfur atom, a fused bicyclic or tricyclic aromatic heterocyclic group in which 3- to 8-membered rings are fused, containing at least one atom selected from a nitrogen atom, an oxygen atom, and a sulfur atom, and the like. More specifically, examples thereof include pyridyl (a group formed by oxidation of the nitrogen atom of the pyridyl is also being covered by the present invention), pyrazinyl, pyrimidinyl, pyridazinyl, quinolyl, isoquinolyl, phthalazinyl, quinazolinyl, quinoxalinyl, naphthylidinyl, cinnolinyl, pyrrolyl, pyrazolyl, imidazolyl, triazolyl, tetrazolyl, thienyl, furyl, thiazolyl, oxazolyl, indolyl, indazolyl, benzimidazolyl, benzotriazolyl, benzothiazolyl, benzoxazolyl, purinyl, and the like.

Examples of the heterocyclic group include the aromatic heterocyclic group defined above, an aliphatic heterocyclic group, and the like.

Examples of the aliphatic heterocyclic group include a 5- or 6-membered monocyclic aliphatic heterocyclic group containing at least one atom selected from a nitrogen atom, an oxygen atom, and a sulfur atom, a fused bicyclic or tricyclic aliphatic heterocyclic group in which 3- to 8-membered rings are fused, containing at least one atom selected from a nitrogen atom, an oxygen atom, and a sulfur atom, and the like. More specifically, examples thereof include pyrrolidinyl, piperidyl, piperazinyl, morpholinyl, thiomorpholinyl, homopiperidyl, homopiperazinyl, tetrahydropyridinyl, tetrahydroquinolyl, tetrahydroisoquinolyl, tetrahydrofuranyl, tetrahydropyranyl, dihydrobenzofuranyl, and the like.

Examples of the heterocyclic group formed together with the adjacent nitrogen atom includes a 5- or 6-membered monocyclic heterocyclic group containing at least one nitrogen atom (wherein the monocyclic heterocyclic group may contain other nitrogen atom(s), oxygen atom(s) or sulfur atom(s)), a fused bicyclic or tricyclic heterocyclic group in which 3- to 8-membered rings are fused, containing at least one nitrogen atom (wherein the fused heterocyclic group may contain other nitrogen atom(s), oxygen atom(s) or sulfur atom(s)), and the like. More specifically, examples thereof include pyrrolidinyl, piperidino, piperazinyl, morpholino, thiomorpholino, homopiperidino, homopiperazinyl, tetrahydropyridyl, tetrahydroquinolyl, tetrahydroisoquinolyl, and the like.

The cycloalkyl formed together with the adjacent carbon atom has the same meaning as that of the cycloalkyl defined above.

The aliphatic heterocyclic group formed together with the adjacent carbon atom has the same meaning as that of the aliphatic heterocyclic group defined above.

The halogen means each atoms of fluorine, chlorine, bromine, or iodine.

The substituents (substituents a) in the substituted lower alkyl, the substituted lower alkoxy, the substituted lower alkenyl, the substituted lower alkynyl, the substituted cycloalkyl, the substituted cycloalkenyl, the substituted mono- or di(lower alkyl)amino, the substituted lower alkanoyl, the substituted cycloalkylcarbonyl, the substituted lower alkoxycarbonyl, the substituted lower alkylsulfonyl, and the substituted cycloalkyl formed together with the adjacent carbon atom include 1 to 3 substituents, which may be the same or different. More specifically, examples thereof include halogen, hydroxyimino, lower alkoxyimino, cyano, cycloalkyl, lower alkanoyloxy, substituted or unsubstituted aryl (wherein examples of the substituent in the substituted aryl include 1 to 3 substituents, which may be the same or different, and more specifically, halogen, amino, hydroxy, cyano, carboxy, lower alkyl, lower alkoxy, lower alkanoyl, mono- or di(lower alkyl)amino, a heterocyclic group, and the like), a substituted or unsubstituted heterocyclic group (wherein examples of the substituent in the substituted heterocyclic group include 1 to 3 substituents, which may be the same or different, and more specifically, halogen, amino, hydroxy, cyano, carboxy, lower alkyl, lower alkoxy, lower alkanoyl, lower alkylsulfonyl, and the like), $CONR^{29a}R^{29b}$ {wherein $R^{29a}$ and $R^{29b}$ may be the same and different and each represents a hydrogen atom, substituted or unsubstituted lower alkyl (wherein examples of the substituent in the substituted lower alkyl include 1 to 3 substituents, which may be the same or different, and more specifically, halogen, hydroxy, lower alkoxy, aryl, and the like), substituted or unsubstituted lower alkenyl (wherein examples of the substituent in the substituted lower alkenyl include 1 to 3 substituents, which may be the same or different, and more specifically, halogen, hydroxy, lower alkoxy, and the like), substituted or unsubstituted lower alkynyl (wherein examples of the substituent in the substituted lower alkynyl include 1 to 3 substituents, which may be the same or different, and more specifically, halogen, hydroxy, lower alkoxy, and the like), substituted or unsubstituted cycloalkyl (wherein examples of the substituent in the substituted cycloalkyl include 1 to 3 substituents, which may be the same or different, and more specifically, halogen, hydroxy, lower alkyl, lower alkoxy, and the like), substituted or unsubstituted cycloalkenyl (wherein examples of the substituent in the substituted cycloalkenyl include 1 to 3 substituents, which may be the same or different, and more specifically halogen, hydroxy, lower alkyl, lower alkoxy, and the like), substituted or unsubstituted lower alkoxy (wherein examples of the substituent in the substituted lower alkoxy include 1 to 3 substituents, which may be the same or different, and more specifically, halogen, hydroxy, lower alkoxy, and the like), substituted or unsubstituted aryl [wherein examples of the substituent in the substituted aryl include 1 to 3 substituents, which may be the same or different, and more specifically halogen, hydroxy, substituted or unsubstituted lower alkyl (wherein examples of the substituent in the substituted lower alkyl include 1 to 3 substituents, which may be the same or different, and more specifically, halogen, hydroxy, lower alkoxy, and the like), substituted or unsubstituted lower alkoxy (wherein examples of the substituent in the substituted lower alkoxy include 1 to 3 substituents, which may be the same or different, and more specifically, halogen, hydroxy, lower alkoxy, and the like), lower alkylsulfonylamino, and the like], a substituted or unsubstituted heterocyclic group [wherein examples of the substituent in the substituted heterocyclic group include 1 to 3 substituents, which may be the same or different, and more specifically halogen, hydroxy, lower alkyl, lower alkoxy, substituted or unsubstituted aryl (wherein examples of the substituent in the substituted aryl include 1 to 3 substituents, which may be the same or different, and more specifically, halogen, hydroxy, lower alkyl, lower alkoxy, and the like), and the like], $COR^{30}$ [wherein $R^{30}$ represents a hydrogen atom, substituted or unsubstituted lower alkyl (wherein examples of the substituent in the substituted lower alkyl include 1 to 3 substituents, which may be the same or different, and more specifically, halogen, hydroxy, lower alkoxy, and the like), substituted or unsubstituted cycloalkyl (wherein examples of the substituent in the substituted cycloalkyl include 1 to 3 substituents, which may be the same or different, and more specifically, halogen, hydroxy, lower alkyl, lower alkoxy, and the like), substituted or unsubstituted lower alkoxy (wherein examples of the substituent in the substituted lower alkoxy include 1 to 3 substituents, which may be the same or different, and more specifically, halogen, hydroxy, lower alkoxy, and the like), substituted or unsubstituted aryl (wherein examples of the substituent in the substituted aryl include 1 to 3 substituents, which may be the same or different, and more specifically, halogen, amino, hydroxy, substituted or unsubstituted lower alkyl (wherein examples of the substituent in the substituted lower alkyl include 1 to 3 substituents, which may be the same or different, and more specifically, halogen, hydroxy, lower alkoxy, and the like), substituted or unsubstituted lower alkoxy (wherein examples of the substituent in the substituted lower alkoxy include 1 to 3 substituents, which may be the same or different, and more specifically, halogen, hydroxy, lower alkoxy, and the like), mono- or di-(lower alkyl)amino, a heterocyclic group, and the like), or a substituted or unsubstituted aromatic heterocyclic group (wherein examples of the substituent in the substituted aromatic heterocyclic group include 1 to 3 substituents, which may be the same or different, and more specifically, halogen, hydroxy, lower alkyl, lower alkoxy, mono- or di-(lower alkyl)amino, a heterocyclic group, and the like)], or $S(O)_2R^{30a}$ (wherein $R^{30a}$ has the same meaning as that of $R^{30}$ defined above); or $R^{29a}$ and $R^{29b}$ are combined together with the adjacent nitrogen atom thereto to form a substituted or unsubstituted heterocyclic group (wherein examples of the substituent in the substituted heterocyclic group formed together with the adjacent nitrogen atom include 1 to 3 substituents, which may be the same or different, and more specifically, halogen, hydroxy, lower alkyl, lower alkoxy, and the like)}, $NR^{29c}R^{29d}$ (wherein $R^{29c}$ and $R^{29d}$ have the same meanings as those of $R^{29a}$ and $R^{29b}$ defined above, respectively), $OR^{30b}$ (wherein $R^{30b}$ has the same meaning as that of $R^{30}$ defined above), $COR^{30c}$ (wherein $R^{30c}$ has the same meaning as that of $R^{30}$ defined above), $CO_2R^{30d}$ (wherein $R^{30d}$ has the meaning as that of $R^{30}$ defined above), $S(O)_{p1}R^{30e}$ (wherein p1 represents an integer of 0 to 2, and $R^{30e}$ has the same meaning as that of $R^{30}$ defined above), $SO_2NR^{29e}R^{29f}$ (wherein $R^{29e}$ and $R^{29f}$ have the same meanings as those of $R^{29a}$ and $R^{29b}$ defined above, respectively), and the like. Examples of the substituent in the substituted cycloalkyl and the substituted cycloalkenyl may include, in addition to the substituents described above, substituted or unsubstituted lower alkyl (wherein examples of the substituent in the substituted lower alkyl include 1 to 3 substituents, which may be the same or different, and more specifically, halogen, hydroxy, lower alkoxy, and the like).

Here, the halogen, the lower alkyl, the lower alkyl moiety of the lower alkoxy, the lower alkylsulfonyl and the mono- or di-(lower alkyl)amino, the lower alkenyl, the lower alkynyl, the cycloalkyl, the cycloalkenyl, lower alkanoyl and the lower alkanoyl moiety of the lower alkanoyloxy, the aryl, the aromatic heterocyclic group, the heterocyclic group, and the heterocyclic group formed together with the adjacent nitrogen atom have the same meanings as defined above, respectively. The lower alkyl moiety of each of the lower alkoxyimino and the lower alkylsulfonylamino has the same meaning as that of the lower alkyl defined above.

Examples of the substituents in the substituted aryl, the substituted phenyl, the substituted aralkyl, the substituted aroyloxy, the substituted aromatic heterocyclic group, the substituted heterocyclic group, the substituted heterocyclic group formed together with the adjacent nitrogen atom, and the substituted aliphatic heterocyclic group formed together with the adjacent carbon atoms include 1 to 3 substituents, which may be the same or different, and more specifically, halogen, nitro, hydroxy, cyano, carboxy, lower alkanoyloxy, substituted or unsubstituted lower alkyl (wherein the substituent in the substituted lower alkyl has the same meaning as that of the substituent a defined above), substituted or unsubstituted lower alkoxy (wherein the substituent in the substituted lower alkoxy has the same meaning as that of the substituent a defined above), substituted or unsubstituted lower alkanoyl (wherein the substituent in the substituted lower alkanoyl has the same meaning as that of the substituent a defined above), substituted or unsubstituted lower alkoxycarbonyl (wherein the substituent in the substituted lower alkoxycarbonyl has the same meaning as that of the substituent a defined above), substituted or unsubstituted lower alkylsulfonyl (wherein the substituent in the substituted lower alkylsulfonyl has the same meaning as that of the substituent a defined above), $CONR^{31a}R^{31b}$ (wherein $R^{31a}$ and $R^{31b}$ have the same meanings as those of $R^{29a}$ and $R^{29b}$ defined above, respectively), $NR^{31c}R^{31d}$ (wherein $R^{31c}$ and $R^{31d}$ have the same meanings as those of $R^{29a}$ and $R^{29b}$ defined above, respectively), $NR^{32}CONR^{31e}R^{31f}$ [wherein $R^{31e}$ and $R^{31f}$ have the same meanings as those of $R^{29a}$ and $R^{29b}$ defined above, respectively; and $R^{32}$ represents a hydrogen atom or substituted or unsubstituted lower alkyl (wherein the substituent in the substituted lower alkyl has the same meaning as that of the substituent a defined above)], and the like.

Here, the halogen, the lower alkyl, the lower alkyl moiety of the lower alkoxy, the lower alkoxycarbonyl and the lower alkylsulfonyl, and the lower alkanoyl and the lower alkanoyl moiety of the lower alkanoyloxy have the same meanings as defined above, respectively.

The pharmaceutically acceptable salts of Compounds (I), (IA), (IB), (IC), (ID), and (IE) include pharmaceutically acceptable acid addition salts, metal salts, ammonium salts, organic amine addition salts, amino acid addition salts, and the like. Examples of the pharmaceutically acceptable acid addition salts include inorganic acid salts, such as hydrochloride, sulfate, nitrate, and phosphate; and organic acid salts, such as acetate, maleate, fumarate, and citrate. Examples of the pharmaceutically acceptable metal salts include alkali metal salts, such as sodium salts and potassium salts; and alkaline earth metal salts, such as magnesium salts and calcium salts; aluminum salts; zinc salts; and the like. Examples of the pharmaceutically acceptable ammonium salts include salts of ammonium, tetramethylammonium, and the like. Examples of the pharmaceutically acceptable organic amine addition salts include addition salts of morpholine, piperidine, and the like. Examples of the pharmaceutically acceptable amino acid addition salts include addition salts of glycine, phenylalanine, lysine, aspartic acid, glutamic acid, and the like.

Examples of the diseases associated with the function of the p38MAP kinase include diseases that are believed to be caused or deteriorated by abnormal production of inflammatory cytokines and chemokines, or by overresponse thereto. More specifically, examples thereof include various inflammatory diseases, rheumatoid arthritis, osteoarthritis, arthritis, osteoporosis, autoimmune diseases, infectious diseases, sepsis, cachexia, cerebral infarction, Alzheimer's disease, asthma, chronic inflammatory pulmonary diseases, chronic obstructive pulmonary diseases (COPD), reperfusion injury, thrombosis, glomerulonephritis, diabetes, graft-versus-host reaction, inflammatory bowel diseases, Crohn's disease, ulcerative colitis, multiple sclerosis, cancers (e.g., leukemias such as chronic myelogenous leukemia, acute myelogenous leukemia, and plasma cell leukemia, myelomas such as multiple myeloma, lymphoma, breast cancer, cancer of uterine body, cancer of uterine cervix, prostate cancer, bladder cancer, kidney cancer, stomach cancer, esophagus cancer, liver cancer, biliary tract cancer, colon cancer, rectum cancer, pancreas cancer, lung cancer, laryngeal neck cancer, osteosarcoma, melanoma, and brain tumor cancer), Castleman's disease, atrial myxoma, psoriasis, dermatitis, gout, adult respiratory distress syndrome (ARDS), arteriosclerosis, restenosis after percutaneous transluminal coronary angioplasty (PTCA), pancreatitis, pains, and the like.

The 2-aminoquinazoline derivative or the pharmaceutically acceptable salt thereof according to the present invention can also be used as an inhibitor for the following kinases. KINASE INSERT DOMAIN RECEPTOR (KDR); ABELSON MURINE LEUKEMIA VIRAL ONCOGENE HOMOLOG 1 (ABL1); ACTIVATED P21CDC42HS KINASE (ACK); TYRO3 PROTEIN TYROSINE KINASE (TYRO3); CYTOPLASMIC TYROSINE KINASE (CSK); EPHRIN RECEPTOR EphA2 (EPHA2); EPHRIN RECEPTOR EphB4 (EPHB4); PROTEIN-TYROSINE KINASE, CYTOPLASMIC (FAK); FIBROBLAST GROWTH FACTOR RECEPTOR 1 (FGFR1); INSULIN-LIKE GROWTH FACTOR I RECEPTOR (IGF1R); JANUS KINASE 3 (JAK3); MET PROTOONCOGENE (MET); FMS-RELATED TYROSINE KINASE 3 (FLT3); PLATELET-DERIVED GROWTH FACTOR RECEPTOR ALPHA (PDGFRα); V-SRC AVIAN SARCOMA (SCHMIDT-RUPPIN A-2) VIRAL ONCOGENE (SRC); PROTEIN-TYROSINE KINASE SYK (SYK); TEC PROTEIN TYROSINE KINASE (TEC); TEK TYROSINE KINASE, ENDOTHELIAL (TIE2); NEUROTROPHIC TYROSINE KINASE, RECEPTOR, TYPE 1 (TRKA); PYRUVATE DEHYDROGENASE KINASE, ISOENZYME 1 (PDK1); RIBOSOMAL PROTEIN S6 KINASE, 90-KD, 3 (RSK2); CALCIUM/CALMODULIN-DEPENDENT PROTEIN KINASE IV (CaMK4); CALCIUM/CALMODULIN-DEPENDENT PROTEIN KINASE II-ALPHA (CaMK2α); CHECKPOINT, *S. POMBE*, HOMOLOG OF, 1 (CHK1); DEATH-ASSOCIATED PROTEIN KINASE 1 (DAPK1); MITOGEN-ACTIVATED PROTEIN KINASE-ACTIVATED PROTEIN KINASE 2 (MAPKAPK2); ONCOGENE PIM 1 (PIM1); CHECKPOINT KINASE 2, *S. POMBE*, HOMOLOG OF (CHK2); CYCLIN-DEPENDENT KINASE 2 (CDK2); GLYCOGEN SYNTHASE KINASE 3-BETA (GSK3β); MITOGEN-ACTIVATED PROTEIN KINASE 1 (Erk2);

MITOGEN-ACTIVATED PROTEIN KINASE 8 (JNK1); MITOGEN-ACTIVATED PROTEIN KINASE 14 (p38α); PROTEIN KINASE, SERINE/ARGININE-SPECIFIC, 1 (SRPK1); AURORA KINASE A (AurA); INHIBITOR OF KAPPA LIGHT CHAIN GENE ENHANCER IN B CELLS, KINASE OF, BETA (IKKβ); NEVER IN MITOSIS GENE A-RELATED KINASE 2 (NEK2); TTK PROTEIN KINASE (TTK); V-RAF-1 MURINE LEUKEMIA VIRAL ONCO-GENE HOMOLOG 1 (RAF1); MITOGEN-ACTIVATED PROTEIN KINASE KINASE KINASE 5 (MAP3K5); INTERLEUKIN 1 RECEPTOR-ASSOCIATED KINASE 4 (IRAK4); PHOSPHORYLASE KINASE, MUSCLE, GAMMA-1 (PHKG1); CASEIN KINASE I, DELTA (CK1δ); PROTEIN KINASE D2 (PKD2)

The serine/threonine kinase is an enzyme that phosphorylates the hydroxy group of the serine residue or threonine residue of the protein.

Production methods of Compound (I) will now be described.

In any of the production methods shown below, when a defined group changes under the conditions of the production method or is not suitable for carrying out the method, the desired compound can be produced by employing a process commonly used in synthetic organic chemistry, such as protection of functional groups and deprotection thereof [for example, refer to Protective Groups in Organic Synthesis, third edition, T. W. Greene, John Wiley & Sons Inc. (1999) and the like]. Furthermore, if necessary, the sequence of reaction steps, such as introduction of substituents, may be changed.

Compound (I) can be produced, for example, by the steps described below.

Production Method 1

Compound (Ic), i.e., Compound (I) in which X is a bond, and $R^3$ is substituted or unsubstituted aryl or a substituted or unsubstituted aromatic heterocyclic group, can be produced, for example, according to the following steps:

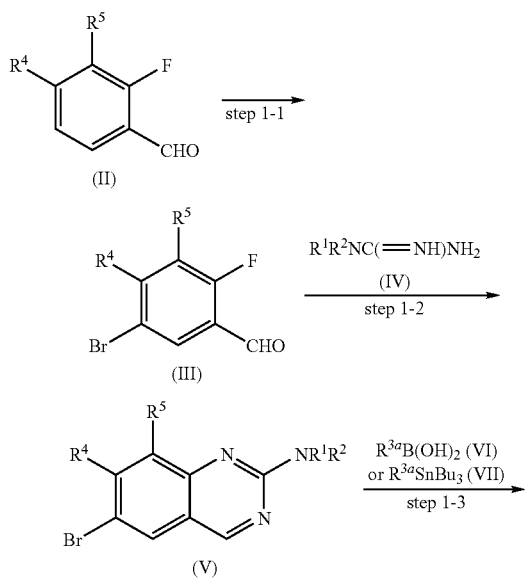

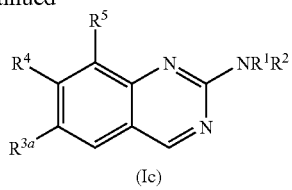

(wherein $R^1$, $R^2$, $R^{3a}$, $R^4$, and $R^5$ have the same meanings as defined above, respectively)

Step 1-1

Compound (III) can be obtained by reacting Compound (II) with 1 to 20 equivalents of bromine in a solvent.

As the solvent, for example, acetic acid, carbon tetrachloride, chloroform, dichloromethane, 1,2-dichloroethane, dioxane, tetrahydrofuran (THF), ethyl acetate, or the like can be used. Preferably, acetic acid can be used.

The reaction is carried out at a temperature between 0° C. and the boiling point of the solvent used, preferably at 60° C., and completes in about 5 minutes to 48 hours.

Instead of bromine, for example, N-bromosuccinimide, pyrrolidone tribromide, cuprous bromide, pyridinium tribromide, or the like may be used. In such a case, as the solvent, for example, acetonitrile, methanol, ethanol, dichloromethane, 1,2-dichloroethane, chloroform, dimethoxyethane, N,N-dimethylformamide (DMF), dioxane, THF, diethyl ether, diisopropyl ether, N,N-dimethylimidazolidinon, N-methylpyrrolidone (NMP), sulfolane, or the like can be used. Preferably, DMF can be used.

Compound (II) can be obtained as a commercially available product, or from a fluorobenzene derivative by a known method {in which the fluorobenzene derivative is subjected to lithiation [for example, refer to Chemical Reviews, vol. 90, p. 879 (1990) or the like] and then formulation [for example, refer to Jikken Kagaku Koza, vol. 21, p. 30 (1991) or the like]} or a similar method thereof.

Step 1-2

Compound (V) can be obtained by reacting Compound (III) with 1 to 20 equivalents of Compound (IV) in the presence of 1 to 20 equivalents of a base, in a solvent by a known method [for example, refer to Journal of Heterocyclic Chemistry, vol. 34, p. 385 (1997)] or a similar method thereof.

As the solvent, for example, N,N-dimethylacetamide (DMA), DMF, N-methylpyrrolidone, dimethylsulfoxide (DMSO), or the like can be used. Preferably, DMA can be used.

As the base, for example, potassium carbonate, cesium carbonate, sodium methoxide, potassium tert-butoxide, or the like can be used. Preferably, potassium carbonate or cesium carbonate can be used.

The reaction is carried out at a temperature between room temperature and 180° C., preferably at 160° C., and completes in about 5 minutes to 48 hours.

Compound (IV) can be obtained as a commercially available product, or by a known method [for example, refer to Journal of Organic Chemistry, vol. 57, p. 2497 (1992)] or a similar method thereof.

Step 1-3

Compound (Ic) can be obtained by reacting Compound (V) with 1 to 20 equivalents of Compound (VI) or (VII) in the presence of 0.1 to 10 equivalents of a base and 0.001 to 1 equivalent of a palladium catalyst, in a solvent.

As the solvent, for example, acetonitrile, methanol, ethanol, dichloromethane, 1,2-dichloroethane, chloroform, DMA, DMF, dioxane, THF, diethyl ether, diisopropyl ether, benzene, toluene, xylene, N,N-dimethylimidazolidinone, N-methylpyrrolidone, sulfolane, a mixed solution in which at least one solvent selected from these solvents and water are mixed at an appropriate ratio of 100:1 to 1:100, or the like can be used. Preferably, a mixed solution of water and dioxane at a ratio of 1:2 can be used.

As the base, for example, pyridine, triethylamine, N-methyl morpholine, N-methylpiperidine, piperidine, piperazine, potassium acetate, potassium carbonate, cesium carbonate, sodium carbonate, sodium hydrogencarbonate, sodium hydroxide, lithium hydroxide, potassium hydroxide, potassium phosphate, sodium tert-butoxide, 1,8-diazabicyclo [5.4.0]-7-undecene (DBU), diisopropylethylamine, or the like can be used. Preferably, sodium carbonate can be used. When Compound (VII) is used, the base may not be used.

In the palladium catalyst, as the palladium source, for example, palladium acetate, palladium trifluoroacetate, tris (dibenzylideneacetone)dipalladium, a chloroform adduct thereof, or the like can be used. As the ligand, for example, triphenyl phosphine, 1,1'-bis(diphenylphosphino)ferrocene, o-tolylphosphine, 1,2-bis(diphenylphosphino)ethane, 1,3-(bisdiphenylphosphino)propane, 1,4-bis(diphenylphosphino)butane, di-tert-butyldiphenylphosphine, 2-(di-tert-butylphosphino)biphenyl, 2-(dicyclohexylphosphino)biphenyl, or the like can be used. The ligand is used preferably in an amount of 1 to 10 equivalents relative to palladium. It is also possible to use a commercially available reagent in which a ligand that is suitable for carrying out the reaction is coordinated to palladium in advance, such as tetrakis(triphenylphosphine)palladium, or 1,1-bis(diphenylphosphino) ferrocenedichloropalladium/dichloromethane (1:1) adduct.

The reaction is carried out at a temperature between room temperature and the boiling point of the solvent, preferably at 100° C., and completes in about 5 minutes to 48 hours.

Compounds (VI) and (VII) can be obtained as a commercially available product, or by a known method [for example, refer to Jikken Kagaku Koza, vol. 24, Nippon Kagakukai (1992) or the like] or a similar method thereof.

Production Method 2

Compound (Ie), i.e., Compound (I) in which $R^5$ is a chlorine, bromine, or iodine atom and Compound (If), i.e., Compound (I) in which $R^5$ is substituted or unsubstituted lower alkenyl, substituted or unsubstituted aryl, or a substituted or unsubstituted heterocyclic group can be produced, for example, according to the following steps:

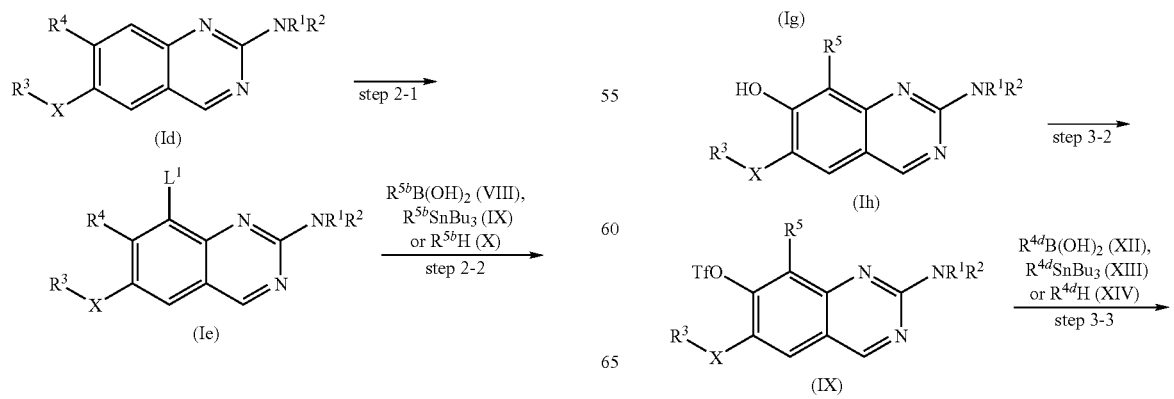

(wherein $R^1$, $R^2$, $R^3$, X, and $R^4$ have the same meanings as defined above, respectively; $R^{5b}$ represents substituted or unsubstituted lower alkenyl, substituted or unsubstituted aryl, or a substituted or unsubstituted heterocyclic group; and $L^1$ represents a chlorine atom, a bromine atom, or an iodine atom)

Step 2-1

Compound (Ie) can be synthesized, using Compound (Id) obtained in production method 1 or 8, in the case when $L^1$ is a bromine atom, according to step 1-1 of production method 1; in the case when $L^1$ is an iodine atom, by reacting Compound (Id) with a base such as sodium hydroxide or potassium hydroxide, and sodium iodide, in the presence of sodium chlorite, in a solvent such as methanol or ethanol; or in the case when $L^1$ is a chlorine atom, by reacting Compound (Id) with chlorine or N-chlorosuccinimide in a solvent, such as chloroform or carbon tetrachloride.

Step 2-2

Compound (If) can be synthesized according to step 1-3 of production method 1.

Compounds (VIII), (IX), and (X) can be obtained as a commercially available product. Compounds (VIII) and (IX) can also be obtained by a known method [for example, refer to Jikken Kagaku Koza, vol. 24, Nippon Kagakukai (1992) or the like] or a similar method thereof.

Production Method 3

Compound (Ih), i.e., Compound (I) in which $R^4$ is hydroxy and Compound (Ii) in which $R^4$ is substituted or unsubstituted lower alkenyl, substituted or unsubstituted aryl, or a substituted or unsubstituted aromatic heterocyclic group can be produced, for example, according to the following steps:

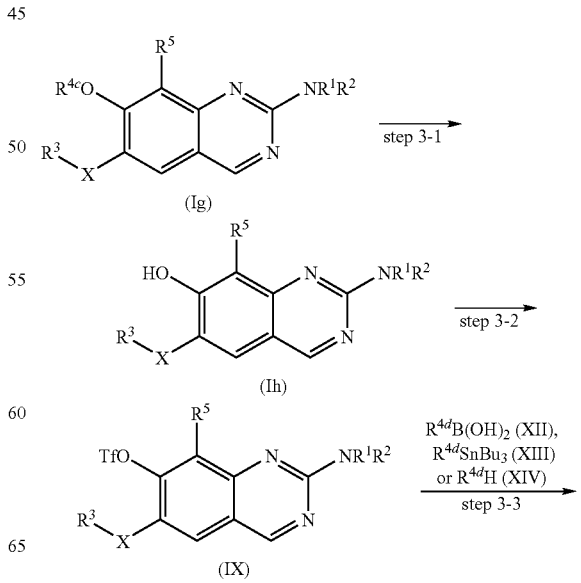

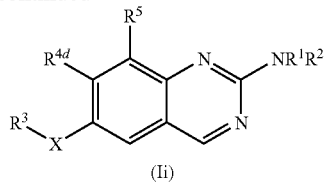

(wherein $R^1$, $R^2$, $R^3$, $R^5$, and X have the same meanings as defined above, respectively; Tf represents trifluoromethanesulfonyl; $R^{4c}$ is substituted or unsubstituted lower alkyl; and $R^{4d}$ represents substituted or unsubstituted lower alkenyl, substituted or unsubstituted aryl, or a substituted or unsubstituted aromatic heterocyclic group)

Step 3-1

Compound (Ih) can be produced by treating Compound (Ig) obtained by production method 1, 2, and 4 to 8 with 1 to 100 equivalents of a thiol compound, an acid, trimethylsilyl iodide, or sodium sulfide in a solvent at a temperature between −30° C. and the boiling point of the solvent for 5 minutes to 72 hours.

As the thiol compound, for example, thiophenol, methanethiol, ethanethiol, or the like can be used. An alkali metal salt thereof such as sodium thiophenoxide, sodium thiomethoxide, or sodium thioethoxide, can also be used.

As the acid, for example, hydrogen bromide/acetic acid, pyridinium chloride, boron trifluoride, boron tribromide, boron trichloride, aluminum bromide, aluminum chloride, or the like can be used.

As the solvent, for example, dichloromethane, chloroform, 1,2-dichloroethane, DMF, N-methylpyrrolidone (NMP), diethyl ether, THF, a mixed solvent thereof, or the like can be used.

When $R^{4c}$ of Compound (Ig) is substituted or unsubstituted benzyl, Compound (Ih) can also be produced by treating Compound (Ig) under a hydrogen atmosphere or in the presence of a hydrogen source, in the presence of an appropriate catalyst, in a solvent, at a temperature between −20° C. and the boiling point of the solvent, at normal pressures or under increased pressure, for 5 minutes to 72 hours.

As the catalyst, for example, palladium on carbon, palladium, palladium hydroxide, palladium acetate, palladium black, or the like can be used. The catalyst is used preferably in an amount of 0.01 to 50% by weight relative to Compound (Ig).

As the hydrogen source, for example, formic acid, ammonium formate, sodium formate, cyclohexadiene, hydrazine, or the like can be used. The hydrogen source is used preferably in an amount of 2 equivalents to a large excess.

As the solvent, for example, methanol, ethanol, toluene, ethyl acetate, acetonitrile, diethyl ether, THF, 1,2-dimethoxyethane (DME), dioxane, DMF, DMA, AMP, water, a mixed solvent thereof, or the like can be used.

Step 3-2

Compound (XI) can be synthesized by reacting Compound (Ih) with 1 to 30 equivalents of trifluoromethanesulfonic acid anhydride or trifluoromethanesulfonyl chloride in the presence of 1 to 30 equivalents of a base if necessary, in a solvent or without solvent, at a temperature between −30° C. and 100° C. for 5 minutes to 48 hours. Preferably, the reaction is carried out under an atmosphere of an inert gas, such as nitrogen or argon.

As the base, for example, pyridine, 2,6-lutidine, 2,4,6-collidine, N,N-dimethylaminopyridine (DMAP), triethylamine, tributylamine, diisopropylethylamine, DBU, diazabicyclononene (DBN), or the like can be used. As the solvent, for example, pyridine, DMF, NMP, THF, dichloromethane, 1,2-dichloroethane, 1,4-dioxane, or the like can be used. These can be used alone or as a mixture.

Step 3-3

Compound (Ii) can be produced by subjecting Compound (XI) to coupling reaction with Compound (XII), (XIII), or (XIV).

That is, Compound (Ii) can be produced by reacting Compound (XI) with 1 to 20 equivalents of Compound (XII), (XIII), or (XIV) in the presence of a catalytic amount to 30% by mole of a palladium catalyst, in the presence of a catalytic amount to 20 equivalents of an additive if necessary, in a solvent, at a temperature between −30° C. and the boiling point of the solvent used, for 5 minutes to 100 hours.

As the palladium catalyst, for example, tetrakis(triphenylphosphine)palladium, tris(dibenzylideneacetone)dipalladium, dichlorobis(triphenyl phosphine)palladium, bis(acetonitrile)dichloropalladium, or the like can be used.

As the additive, for example, copper iodide, zinc chloride, lithium chloride, cesium fluoride, lithium carbonate, sodium carbonate, triethylamine, 2,6-di-tert-butyl-4-methylphenol, 4-tert-butylcatechol, or the like can be used. These can be used alone or as a mixture.

As the solvent, for example, THF, DMF, NMP, DME, 1,4-dioxane, benzene, toluene, a mixed solvent thereof, or the like can be used.

Compounds (XII), (XIII), and (XIV) can be obtained as commercially available products. Compounds (XII) and (XIII) can be obtained by a known method [for example, a method described in Jikken Kagaku Koza, vol. 24, p. 189, Maruzen (1992), etc.] or a similar method thereof.

Production Method 4

Compound (Ij), i.e., Compound (I) in which $R^5$ is substituted or unsubstituted lower alkoxycarbonyl and Compound (Ik), i.e., Compound (I) in which $R^5$ is $CONR^{11a}R^{11b}$ (wherein $R^{11a}$ and $R^{11b}$ have the same meanings as defined above, respectively) can be produced, for example, according to the following steps:

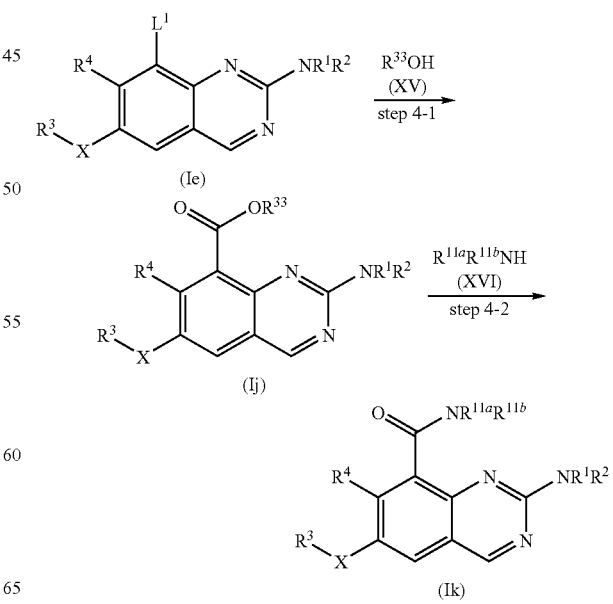

(wherein $R^1$, $R^2$, $R^3$, $R^4$, X, and $L^1$ have the same meanings as defined above, respectively; and $R^{33}$ represents substituted or unsubstituted lower alkyl)

Step 4-1

Compound (Ij) can be synthesized by reacting Compound (Ie) with 1 to 1,000 equivalents of Compound (XV), in the presence of 0.0001 to 2 equivalents of, preferably, 0.01 to 0.1 equivalents of a palladium complex, under an atmosphere of carbon monoxide at 0.1 to 100 atmospheric pressure, preferably, 1 to 10 atmospheric pressure, in the presence of 1 to 100 equivalents of a base if necessary, in 1 equivalent to a solvent amount of $R^{33}OH$ (XV), in a solvent or without solvent, at a temperature between 0° C. and 250° C., preferably, between 20° C. and 150° C., for 5 minutes to 48 hours.

As the palladium complex, for example, tetrakis(triphenylphosphine)palladium, dichlorobis(triphenylphosphine)palladium, [bis(1,2-diphenylphosphino)ethane]dichloropalladium, [1,1'-bis(diphenylphosphino)ferrocene]dichloropalladium, or the like can be used. In addition, a combination of a palladium precursor and a phosphine that forms a palladium complex in the reaction system, can also be used.

As the palladium precursor, for example, palladium acetate, palladium chloride, tris(dibenzylideneacetone)dipalladium, palladium on carbon, or the like can be used.

As the phosphine, for example, triphenylphosphine, 1,1'-bis(diphenylphosphino)ferrocene, bis(1,2-diphenylphosphino)ethane, bis(1,3-diphenylphosphino)propane, bis(1,4-diphenylphosphino)butane, 2,2'-bis(diphenylphosphino)-1,1'-binaphthyl, bis(1,4-dicyclohexylphosphino)butane, or the like can be used. Preferably, a combination of palladium acetate and bis(1,3-diphenylphosphino)propane or a combination of palladium on carbon and bis(1,3-diphenylphosphino)propane can be used.

As the base, for example, inorganic bases such as potassium carbonate, sodium carbonate, cesium carbonate, potassium phosphate, potassium hydroxide, and potassium acetate; and organic bases such as pyridine and triethylamine, can be used. Preferably, a carbonate such as potassium carbonate or cesium carbonate, can be used.

Compound (XV) is preferably methanol, ethanol, 1-propanol, or 2-butanol.

As the solvent, for example, aliphatic hydrocarbon solvents such as pentane, hexane, and cyclohexane; aromatic hydrocarbon solvents such as benzene, toluene, and xylene; alcoholic solvents such as methanol, ethanol, propanol, and butanol; tetralin, diphenyl ether, ethyl acetate, methylene chloride, chloroform, dichloroethane, carbon tetrachloride, pyridine, acetonitrile, DMF, DMA, 1-methyl-2-pyrrolidone, 1,3-dimethyl-2-imidazolidinone, DMSO, sulfolane, dimethyl sulfone, THF, dioxane, dimethoxyethane; and a mixed solvent thereof, can be used.

Step 4-2

Compound (Ik) can be synthesized by reacting Compound (Ij) with 1 to 100 equivalents of Compound (XVI) in the presence of 1 to 100 equivalents of, preferably, 1 to 10 equivalents of a base, in a solvent or without solvent, at a temperature between −78° C. and the boiling point of the solvent, preferably, between −78 and 30° C., for 5 minutes to 48 hours. Preferably, the reaction is carried out under an atmosphere of an inert gas such as nitrogen or argon.

As the base, for example, butyllithium, sec-butyllithium, tert-butyllithium, lithium diisopropylamide, or the like can be used. Preferably, butyllithium can be used.

As the solvent, for example, THF, diethyl ether, dioxane, diisopropyl ether, dimethoxyethane, or the like can be used. Preferably, THF can be used.

Compound (XVI) can be obtained as a commercially available product, or by a known method [for example, a method described in Jikken Kagaku Koza, vol. 20, p. 279, Maruzen (1992), etc.] or a similar method thereof.

Production Method 5

Compound (I) can be produced, for example, according to the following steps:

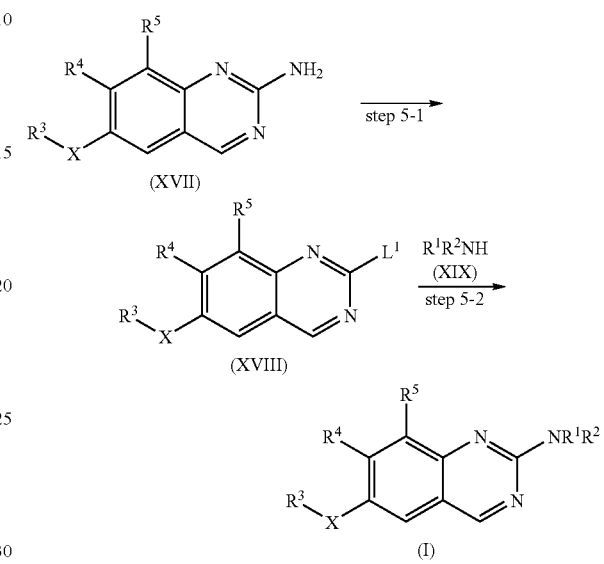

(wherein $L^1$, $R^1$, $R^2$, $R^3$, $R^4$, $R^5$, and X have the same meanings as defined above, respectively)

Step 5-1

Compound (XVIII) can be synthesized by subjecting Compound (XVII) to Sandmeyer's reaction.

Compound (XVIII) can be synthesized by reacting Compound (XVII) with 1 to 100 equivalents of a nitrite compound, and 1 to 1,000 equivalents of an acid if necessary, in the presence of 1 to 1,000 equivalents of a halogen source, in a solvent or without solvent, at a temperature between −30° C. and the boiling point of the solvent used, for 5 minutes to 100 hours.

As the nitrite compound, for example, nitrous acid, nitrite such as sodium nitrite, nitrosyl halides, such as nitrosyl chloride; and alkyl nitrites, such as tert-butyl nitrite and isoamyl nitrite can be used.

As the acid, for example, hydroiodic acid, hydrobromic acid, hydrochloric acid, or the like can be used.

As the halogen source, copper(I) chloride, copper(I) bromide, copper(I) iodide, copper(II) chloride, copper(II) bromide, copper(II) iodide, potassium iodide, diiodomethane, or the like can be used.

As the solvent, for example, alcohols such as methanol and ethanol; ethers such as THF and dioxane; acetone, DMSO, DMF, and water; and a mixed solvent thereof can be used.

Step 5-2

Compound (I) can be synthesized by reacting Compound (XVIII) with 1 to 1,000 equivalents of an amine (XIX) in the presence of 1 to 100 equivalents of a base if necessary, in a solvent or without solvent, at a temperature between 0° C. and the boiling point of the solvent used, preferably, between 0° C. and 100° C., for 5 minutes to 48 hours.

If necessary, the reaction may be carried out in the presence of 0.0001 to 2 equivalents of, preferably, 0.01 to 0.1 equivalents of a palladium complex.

As the palladium complex, for example, tetrakis(triphenylphosphine)palladium, dichlorobis(triphenylphosphine)palladium, [bis(1,2-diphenylphosphino)ethane]dichloropalladium, [1,1'-bis(diphenylphosphino)ferrocene]dichloropalladium, or the like can be used. In addition, a combination of a palladium precursor and a phosphine that forms a palladium complex in the reaction system can also be used.

As the palladium precursor, for example, palladium acetate, palladium chloride, tris(dibenzylideneacetone)dipalladium, palladium on carbon, or the like can be used.

As the phosphine, for example, triphenylphosphine, 1,1'-bis(diphenylphosphino)ferrocene, bis(1,2-diphenylphosphino)ethane, bis(1,3-diphenylphosphino)propane, bis(1,4-diphenylphosphino)butane, 2,2'-bis(diphenylphosphino)-1,1'-binaphthyl, bis(1,4-dicyclohexylphosphino)butane, or the like can be used.

As the base, for example, inorganic bases such as potassium carbonate, sodium carbonate, cesium carbonate, potassium phosphate, potassium hydroxide, and potassium acetate; and organic bases such as pyridine and triethylamine can be used.

As the solvent, for example, aliphatic hydrocarbon solvents such as pentane, hexane, and cyclohexane; aromatic hydrocarbon solvents such as benzene, toluene, and xylene; alcoholic solvents such as methanol, ethanol, propanol, and butanol; tetralin, diphenyl ether, ethyl acetate, methylene chloride, chloroform, dichloroethane, carbon tetrachloride, pyridine, acetonitrile, DMF, DMA, 1-methyl-2-pyrrolidone, 1,3-dimethyl-2-imidazolidinone, DMSO, sulfolane, dimethyl sulfone, THF, dioxane, dimethoxyethane; and a mixed solvent thereof can be used.

Compound (XIX) can be obtained as a commercially available product, or by a known method [for example, a method described in Jikken Kagaku Koza, vol. 20, p. 279, Maruzen (1992), etc.] or a method described in reference examples.

Production Method 6

Compound (In), i.e., Compound (I) in which $R^4$ is substituted or unsubstituted lower alkoxy, can be produced according to the following steps:

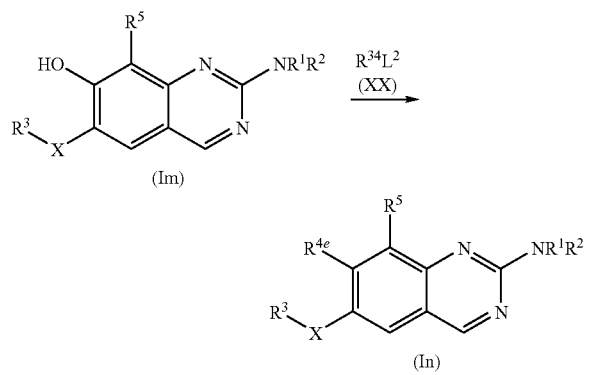

(wherein $R^1$, $R^2$, $R^3$, $R^5$, and X have the same meanings as defined above, respectively; $R^{4e}$ represents substituted or unsubstituted lower alkoxy; $R^{34}$ represents substituted or unsubstituted lower alkyl; and $L^2$ represents halogen, methylsulfonyloxy, p-toluenesulfonyloxy, or trifluoromethanesulfonyloxy)

Step 6-1

Compound (In) can be synthesized by reacting Compound (Im) with 1 to 100 equivalents of Compound (XX), in the presence of 1 to 100 equivalents of a base, in a solvent or without solvent, at a temperature between 0° C. and the boiling point of the solvent used, preferably, between room temperature and 60° C., for 5 minutes to 48 hours.

As the base, for example, triethylamine, pyridine, 2,6-lutidine, potassium carbonate, calcium carbonate, sodium carbonate, cesium carbonate, and the like.

As the solvent, for example, DMF, DMSO, chloroform, dichloromethane, diethyl ether, THF, acetonitrile, toluene, ethyl acetate, a mixed solvent thereof, or the like can be used.

Compound (XX) can be obtained as a commercially available product, or by a known method [for example, a method described in Jikken Kagaku Koza, vol. 19, p. 416, Maruzen (1992), etc.] or a similar method thereof.

Production Method 7

Compound (Io), i.e., Compound (I) in which X is C(=O) and $R^3$ is substituted or unsubstituted lower alkoxy, and Compound (Ip), i.e., Compound (I) in which X is C(=O) and $R^3$ is $NR^{8a}R^{8b}$ (wherein $R^{8a}$ and $R^{8b}$ have the same meanings as defined above, respectively) can be produced, for example, according to the following steps:

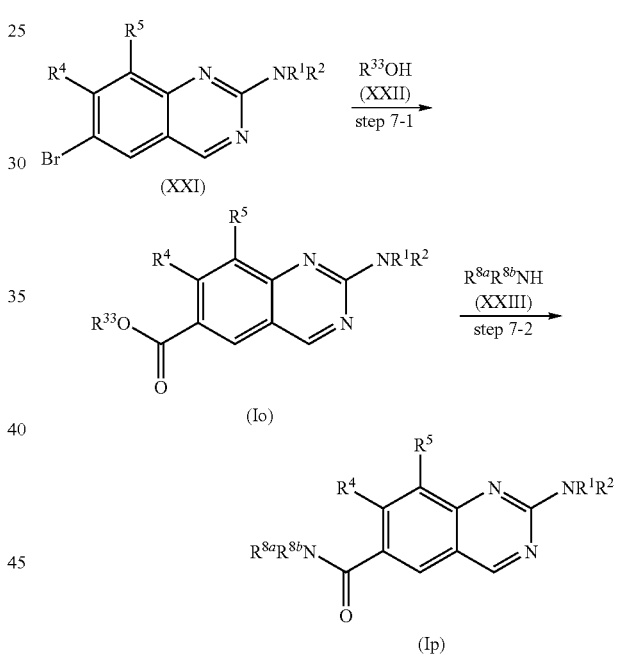

(wherein $R^1$, $R^2$, $R^4$, $R^5$, $R^{8a}$, $R^{8b}$, and $R^{33}$ have the same meanings as defined above, respectively)

Step 7-1

Compound (Io) can be synthesized from Compound (XXI) by a method according to step 4-1 of production method 4.

Compound (XXII) can be obtained as a commercially available product.

Step 7-2

Compound (Ip) can be synthesized from Compound (Io) by a method according to step 4-2 of production method 4.

Compound (XXIII) can be obtained as a commercially available product, or by a known method [for example, a method described in Jikken Kagaku Koza, vol. 20, p. 279, Maruzen (1992), etc.] or a similar method thereof.

Production Method 8

Compound (Iq), i.e., Compound (I) in which X is C(=O) or $C(OH)R^{7c}$ (wherein $R^{7c}$ represents a hydrogen atom or substituted or unsubstituted lower alkyl), can be produced, for example, according to the following steps:

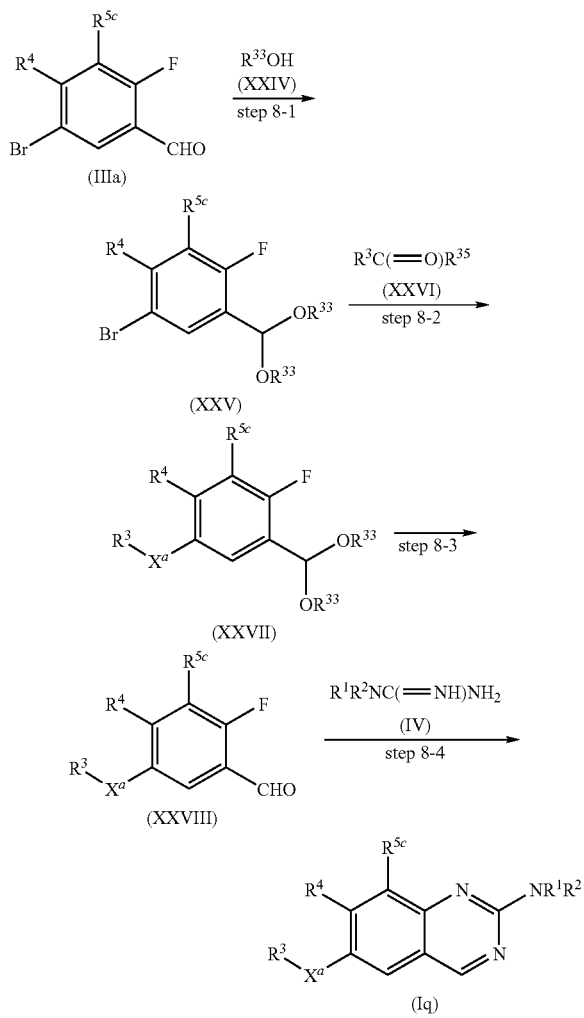

[wherein $R^1$, $R^2$, $R^3$, $R^4$, and $R^{33}$ have the same meanings as defined above, respectively; $X^a$ represents C(=O) or C(OH)$R^{7c}$ (wherein $R^{7c}$ represents a hydrogen atom or substituted or unsubstituted lower alkyl); $R^{5c}$ represents a hydrogen atom, halogen, hydroxy, substituted or unsubstituted lower alkyl, substituted or unsubstituted lower alkenyl, substituted or unsubstituted lower alkoxy, substituted or unsubstituted aryl, or substituted or unsubstituted heterocyclic group; and $R^{35}$ represents a hydrogen atom, substituted or unsubstituted lower alkyl, or $NR^{36a}R^{36b}$ (wherein $R^{36a}$ and $R^{36b}$ may be the same or different and each represents a hydrogen atom, substituted or unsubstituted lower alkyl, or substituted or unsubstituted lower alkoxy)]

Step 8-1

Compound (XXV) can be produced using Compound (IIIa), for example, according to a formyl protection process described in Protective Groups in Organic Synthesis, third edition, T. W. Greene, John Wiley & Sons Inc. (1999) and the like.

Compound (XXV) can be synthesized by reacting Compound (IIIa) with 1 to 200 equivalents of Compound (XXIV) in the presence of a catalytic amount to 5 equivalents of an acid and 1 to 10 equivalents of a dehydrating agent, in a solvent or without solvent, at a temperature between −30° C. and the boiling point of the solvent, for 5 minutes to 48 hours.

As the acid, for example, p-toluenesulfonic acid or the like can be used. As the dehydrating agent, for example, trimethyl orthoformate or the like can be used.

As the solvent, for example, THF, 1,4-dioxane, a mixed solvent thereof, or the like can be used.

Compound (XXIV) can be obtained as a commercially available product. Instead of Compound (XXIV), a diol, such as ethylene glycol or 1,3-propylene glycol, may be used.

Step 8-2

Compound (XXVII) can be produced by treating Compound (XXV) with 1 to 20 equivalents of a base in a solvent, at a temperature between −100° C. and the boiling point of the solvent, for 5 minutes to 48 hours, and then reacting with 1 to 20 equivalents of Compound (XXVI) at a temperature between −100° C. and the boiling point of the solvent, for 5 minutes to 48 hours. If necessary, after treatment with the base, 1 to 20 equivalents of cerium chloride, triisopropoxytitanium chloride, or the like may be added to the reaction mixture at the same temperature, and then reaction may be carried out with Compound (XXVI). Preferably, the reaction is carried out under an atmosphere of an inert gas such as nitrogen or argon.

Compound (XXVI) can be obtained as a commercially available product, or by amidation of the corresponding carboxylic acid and amine [for example, refer to Jikken Kagaku Koza, vol. 22, p. 258 (1992), etc.] or the like.

As the base, for example, n-butyllithium, sec-butyllithium, tert-butyllithium, lithium hexamethyldisilazide, or the like can be used.

As the solvent, for example, diethyl ether, THF, DME, 1,4-dioxane, n-hexane, toluene, a mixed solvent thereof, or the like can be used.

Step 8-3

Compound (XXVIII) can be synthesized by treating Compound (XXVII) with a catalytic amount to 200 equivalents of an acid in the presence of water, in a solvent or without solvent, at a temperature between 0° C. and 150° C., for 5 minutes to 48 hours.

As the acid, for example, hydrochloric acid, sulfuric acid, 10-camphorsulfonic acid, trifluoroacetic acid, p-toluenesulfonic acid, methanesulfonic acid, trifluoromethanesulfonic acid, titanium tetrachloride, boron trifluoride, aluminum chloride, or the like can be used.

As the solvent, for example, THF, 1,4-dioxane, DME, a mixed solvent thereof, and the like.

Step 8-4

Compound (Iq) can be synthesized from Compound (XXVIII) in a similar manner to step 1-2 of production method 1.

Compound (Is), i.e., Compound (I) in which $R^4$ and $R^5$ are combined together to form

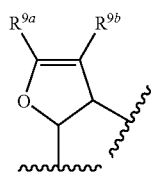

(wherein $R^{9a}$ and $R^{9b}$ have the same meanings as defined above, respectively), can be produced, for example, by production methods 9 and 10 below.

Production Method 9

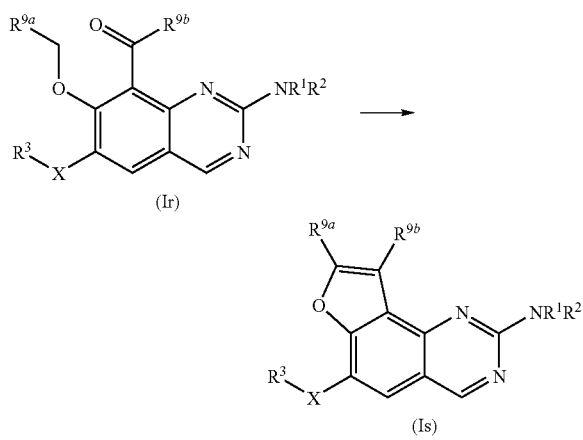

(wherein $R^1$, $R^2$, $R^3$, $R^{9a}$, $R^{9b}$ and X have the same meanings as defined above, respectively)

Compound (Is) can be synthesized by reacting Compound (Ir) obtained by, for example, production method 4, in the presence of 1 to 100 equivalents of a base, in a solvent, at a temperature between 0° C. and the boiling point of the solvent, preferably, between room temperature and 80° C., for 5 minutes to 48 hours.

As the base, for example, sodium hydroxide, potassium hydroxide, potassium carbonate, calcium carbonate, sodium carbonate, cesium carbonate, or the like can be used.

As the solvent, for example, DMF, DMSO, diethyl ether, THF, methanol, ethanol, water, a mixed solvent thereof, or the like can be used.

Production Method 10

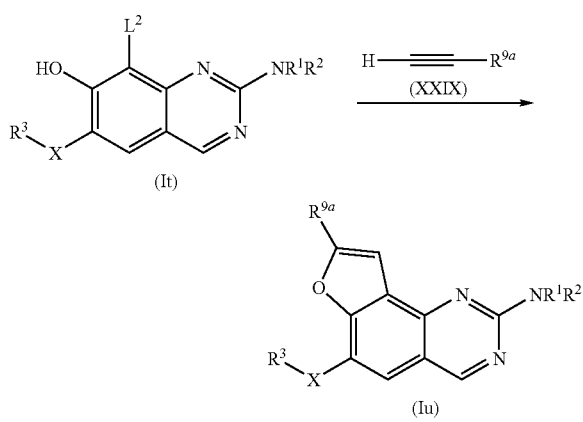

(wherein $R^1$, $R^2$, $R^3$, $R^{9a}$, X, and $L^2$ have the same meanings as defined above, respectively)

Compound (Iu) can be obtained by reacting Compound (It) with 1 to 10 equivalents of Compound (XXIX) in the presence of 0.001 to 5 equivalents of a palladium complex, in the presence of 1 to 10 equivalents of a base and 0.1 to 5 equivalents of an inorganic salt if necessary, in a solvent, at a temperature between 0° C. and the boiling point of the solvent, for 5 minutes to 48 hours.

As the palladium complex, for example, tetrakis(triphenylphosphine)palladium, dichlorobis(triphenylphosphine)palladium, dichlorobis(acetonitrile)palladium, [1,1'-bis(diphenylphosphino)ferrocene]dichloropalladium, palladium acetate, or the like can be used.

As the base, for example, pyridine, triethylamine, diisopropylamine, N-methyl morpholine, potassium tert-butoxide, sodium tert-butoxide, sodium carbonate, sodium hydrogencarbonate, potassium carbonate, cesium carbonate, tetramethylguanidine, or the like can be used.

As the inorganic salt, for example, lithium chloride, lithium bromide, copper iodide, copper bromide, or the like can be used.

As the solvent, for example, THF, dioxane, diethyl ether, ethylene glycol, triethylene glycol, 1,2-dimethoxyethane, diethylene glycol dimethyl ether, methanol, ethanol, 1-butanol, 2-propanol, dichloromethane, chloroform, acetonitrile, benzene, toluene, dimethylacetamide, DMF, DMSO, or the like can be used.

Compound (XXIX) can be obtained as a commercially available product, or by a known method [for example, refer to Jikken Kagaku Koza, vol. 19, p. 298, Maruzen (1992)] or a similar method thereof.

Production Method 11

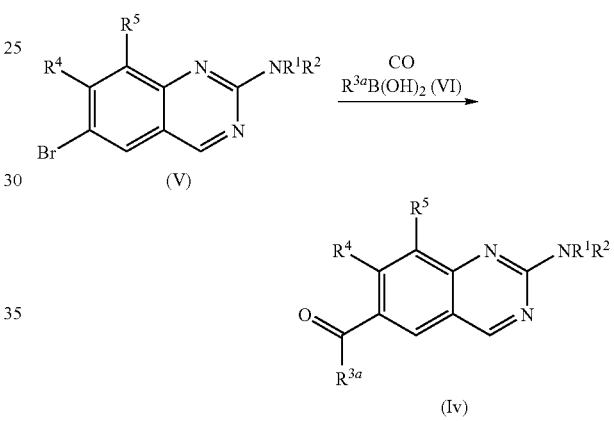

(wherein $R^1$, $R^2$, $R^{3a}$, $R^4$, and $R^5$ have the same meanings as defined above, respectively)

Compound (Iv) can be synthesized by reacting Compound (V) with 1 to 1,000 equivalents of Compound (VI), in the presence of 0.0001 to 2 equivalents of, preferably, 0.01 to 0.1 equivalents of a palladium complex, and preferably, in the presence of 0.01 to 10 equivalents of an additive, under an atmosphere of carbon monoxide at 0.1 to 100 atmospheric pressure, preferably, 1 to 10 atmospheric pressure, in the presence of 1 to 100 equivalents of a base if necessary, in a solvent or without solvent, at a temperature between 0 and 250° C., preferably, between 20 and 150° C., for 5 minutes to 48 hours.

As the palladium complex, for example, tetrakis(triphenylphosphine)palladium, dichlorobis(triphenylphosphine)palladium, [bis(1,2-diphenylphosphino)ethane]dichloropalladium, [1,1'-bis(diphenylphosphino)ferrocene]dichloropalladium, or the like can be used. In addition, a combination of a palladium precursor and a phosphine that forms a palladium complex in the reaction system can also be used.

As the palladium precursor, for example, palladium acetate, palladium chloride, tris(dibenzylideneacetone)dipalladium, palladium on carbon, or the like can be used.

As the phosphine, for example, triphenylphosphine, 1,1'-bis(diphenylphosphino)ferrocene, bis(1,2-diphenylphosphino)ethane, bis(1,3-diphenylphosphino)propane, bis(1,4- diphenylphosphino)butane, 2,2'-bis(diphenylphosphino)-1,1'-binaphthyl, bis(1,4-dicyclohexylphosphino)butane, or the like can be used.

As the base, for example, inorganic bases such as potassium carbonate, sodium carbonate, cesium carbonate, potassium phosphate, potassium hydroxide, and potassium acetate; and organic bases such as pyridine and triethylamine can be used. Preferably, a carbonate such as potassium carbonate or cesium carbonate, can be used.

As the additive, for example, potassium iodide, sodium iodide, potassium bromide, sodium bromide, or the like can be used.

As the solvent, for example, aliphatic hydrocarbon solvents such as pentane, hexane, and cyclohexane; aromatic hydrocarbon solvents such as benzene, toluene, xylene, and anisole; tetralin, diphenyl ether, ethyl acetate, methylene chloride, chloroform, dichloroethane, carbon tetrachloride, pyridine, acetonitrile, DMF, DMA, NMP, 1,3-dimethyl-2-imidazolidinone, DMSO, sulfolane, dimethyl sulfone, THF, dioxane, DME; and a mixed solvent thereof, can be used.
Production Method 12

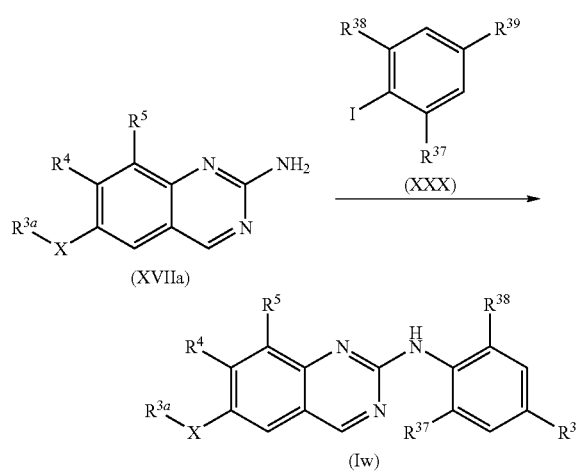

(wherein $R^{3a}$, $R^4$, and $R^5$ have the same meanings as defined above, respectively; $R^{37}$ and $R^{38}$ may be the same or different and each represents a hydrogen atom, halogen, or substituted or unsubstituted lower alkyl; and $R^{39}$ represents a hydrogen atom, lower alkoxy, or substituted or unsubstituted lower alkyl)

Compound (Iw) can be synthesized by reacting Compound (XXX) with, preferably, 0.8 to 10 equivalents of Compound (XVIIa) in the presence of, preferably, 0.1 to 10 equivalents of a base and, preferably, 0.001 to 1 equivalent of a palladium catalyst, in the presence of 0.001 to 1 equivalent of a phosphine if necessary, in a solvent, at a temperature between −20° C. and the boiling point of the solvent, for 5 minutes to 72 hours.

As the base, for example, potassium carbonate, cesium carbonate, potassium phosphate, potassium tert-butoxide, sodium tert-butoxide, or the like can be used.

As the palladium catalyst, for example, palladium acetate, palladium trifluoroacetate, tris(dibenzylideneacetone)dipalladium and a chloroform adduct thereof, tetrakis(triphenyl phosphine)palladium, 1,1'-bis(diphenylphosphino)ferrocenedichloropalladium/dichloromethane (1:1) adduct, or the like can be used.

As the phosphine, for example, 2,2'-bis(diphenylphosphino)-1,1'-binaphthyl, o-tolylphosphine, tributylphosphine, di-tert-butyldiphenylphosphine, 2-(di-tert-butylphosphino)biphenyl, 2-(dicyclohexylphosphino)biphenyl, 9,9-dimethyl-4,5-bis(diphenylphosphino)xanthene, or the like can be used.

As the solvent, for example, toluene, xylene, ethyl acetate, acetonitrile, diethyl ether, THF, DME, dioxane, a mixed solvent thereof, or the like can be used.
Production Method 13

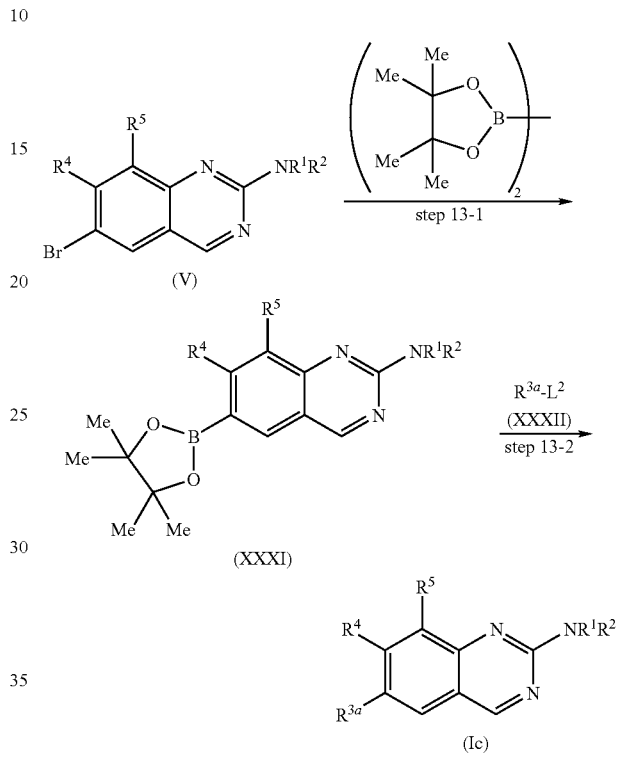

(wherein $R^1$, $R^2$, $R^{3a}$, $R^4$, $R^5$, and $L^2$ have the same meanings as defined above, respectively)
Step 13-1

Compound (XXXI) can be synthesized by subjecting Compound (V) and bis(pinacolato)diboron (commercially available product) to coupling reaction.

Compound (XXXI) can be synthesized by reacting Compound (V) with 1 to 20 equivalents of bis(pinacolato)diboron in the presence of a catalytic amount to 30% by mole of a palladium catalyst, in the presence of a catalytic amount to 20 equivalents of an additive if necessary, in a solvent, at a temperature between −30° C. and the boiling point of the solvent, for 5 minutes to 100 hours.

As the palladium catalyst, for example, tetrakis(triphenyl phosphine)palladium, tris(dibenzylideneacetone)dipalladium, dichlorobis(triphenyl phosphine)palladium, bis(acetonitrile)dichloropalladium, 1,1'-bis(diphenylphosphino)ferrocenedichloropalladium/dichloromethane (1:1) adduct, or the like can be used.

As the additive, for example, copper iodide, zinc chloride, lithium chloride, cesium fluoride, lithium carbonate, sodium carbonate, triethylamine, 2,6-di-tert-butyl-4-methylphenol, 4-tert-butylcatechol, potassium acetate, sodium acetate, or the like can be used. These can be used alone or as a mixture.

As the solvent, for example, THF, DMF, NMP, DME, 1,4-dioxane, benzene, toluene, a mixed solvent thereof, or the like can be used.

Step 13-2

Compound (Ic) can be synthesized by subjecting Compound (XXXI) and Compound (XXXII) to coupling reaction.

Compound (Ic) can be synthesized by reacting Compound (XXXI) with 1 to 20 equivalents of Compound (XXXII) in the presence of a catalytic amount to 30% by mole of a palladium catalyst, in the presence of a catalytic amount to 20 equivalents of an additive if necessary, in a solvent, at a temperature between −30° C. and the boiling point of the solvent, for 5 minutes to 100 hours.

As the palladium catalyst, for example, tetrakis(triphenylphosphine)palladium, tris(dibenzylideneacetone)dipalladium, dichlorobis(triphenylphosphine)palladium, bis(acetonitrile)dichloropalladium, 1,1'-bis(diphenylphosphino)ferrocenedichloropalladium/dichloromethane (1:1) adduct, or the like can be used.

As the additive that can be used include copper iodide, zinc chloride, lithium chloride, cesium fluoride, lithium carbonate, sodium carbonate, triethylamine, 2,6-di-tert-butyl-4-methylphenol, 4-tert-butylcatechol, or the like can be used. These can be used alone or as a mixture.

As the solvent, for example, THF, DMF, NMP, DME, 1,4-dioxane, benzene, toluene, a mixed solvent thereof, or the like can be used.

Compound (XXXII) can be obtained as a commercially available product, or by a known method [for example, a method described in Jikken Kagaku Koza, vol. 13, p. 374, Maruzen (2004), etc.] or a similar method thereof.

By appropriately combining the methods described above, it is possible to obtain Compound (I) which has a desired functional group at a desired position.

The intermediates and the desired compounds in the production methods described above can be isolated and purified by performing methods of separation and purification that are usually used in synthetic organic chemistry, for example, filtration, extraction, washing, drying, concentration, recrystallization, various types of chromatography, and the like. Furthermore, the intermediates can be subjected to subsequent reaction without being particularly purified.

In Compounds (I), (IA), (IB), (IC), (ID), and (IE), isomers such as geometric isomers, optical isomers, and tautomers, may be present. The present invention covers all possible isomers including these isomers and mixtures thereof.

In the case when a salt of Compounds (I), (IA), (IB), (IC), (ID), and (IE) is desired, the salt can be directly subjected to purification if obtained in a form of salt. In the case when Compounds (I), (IA), (IB), (IC), (ID), and (IE) is produced in the free form, a salt can be isolated and purified by dissolving or suspending each of Compounds (I), (IA), (IB), (IC), (ID), and (IE) in a suitable solvent, followed by addition of an acid or a base.

Compounds (I), (IA), (IB), (IC), (ID), and (IE) and pharmaceutically acceptable salts thereof may exist in the form of adducts with water or various kinds of solvents. These adducts are also covered by the present invention.

Tables 1 to 41 show specific examples of Compound (I) obtained by the present invention. In Tables 1 to 41, Me, Et, Pr, i-Pr, t-Bu, Ph, Ac, and Boc represent methyl, ethyl, propyl, isopropyl, tert-butyl, phenyl, acetyl, and tert-butoxycarbonyl, respectively.

TABLE 1

| Example Number | Compound Number | $NR^1R^2$ | $R^3$ | $R^4$ | $R^5$ |
|---|---|---|---|---|---|
| 1 | 1 | $NH_2$ | 2-F, 4-F phenyl | OMe | H |
| 2 | 2 | $NH_2$ | 2-Cl phenyl | OMe | H |
| 3 | 3 | NHi-Pr | 2-F, 4-F phenyl | OMe | H |
| 4 | 4 | NHi-Pr | 2-Cl phenyl | OMe | H |

TABLE 1-continued
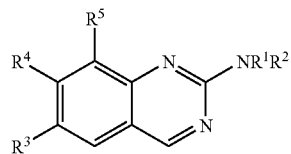
| Example Number | Compound Number | NR¹R² | R³ | R⁴ | R⁵ |
|---|---|---|---|---|---|
| 5 | 5 | HN(trans)-cyclohexyl-NH₂ | 2-Cl-phenyl | OMe | H |
| 6 | 6 | HN-cyclopentyl | 2-Cl-phenyl | OMe | H |
| 7 | 7 | HN-CH(Me)-C(Me)₂-OH | 2-Cl-phenyl | OMe | H |
| 8 | 8 | HN-CH(Me)-phenyl | 2-Cl-phenyl | OMe | H |
| 9 | 9 | HN-CH(Me)-phenyl | 2-Cl-phenyl | OMe | H |
| 10 | 10 | HN(trans)-cyclohexyl-OH | 2-Cl-phenyl | OMe | H |
| 11 | 11 | HN-(tetrahydropyran-4-yl) | 2-Cl-phenyl | OMe | H |

TABLE 2
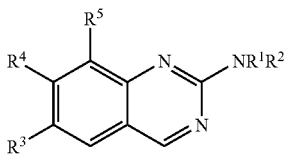
| Example Number | Compound Number | NR¹R² | R³ | R⁴ | R⁵ |
|---|---|---|---|---|---|
| 12 | 12 |  | 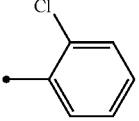 | OMe | H |
| 13 | 13 |  | 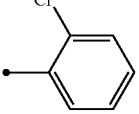 | OMe | H |
| 14 | 14 |  | 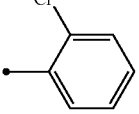 | OMe | H |
| 15 | 15 |  | 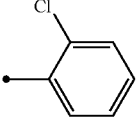 | OMe | H |
| 16 | 16 | 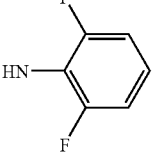 | 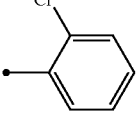 | OMe | H |
| 17 | 17 | 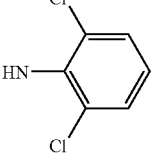 | 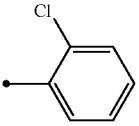 | OMe | H |
| 18 | 18 | 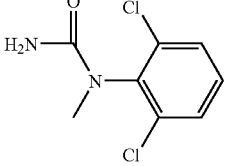 | 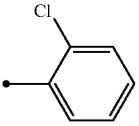 | OMe | H |
| 19 | 19 | NHi-Pr | 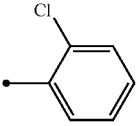 | OH | H |
| 20 | 20 | NHi-Pr | 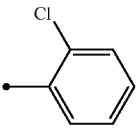 | OCOPh | H |

TABLE 2-continued
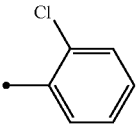
| Example Number | Compound Number | NR¹R² | R³ | R⁴ | R⁵ |
|---|---|---|---|---|---|
| 21 | 21 | NHi-Pr |  2-Cl-phenyl | OCH₂CN | H |
TABLE 3
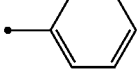
| Example Number | Compound Number | NR¹R² | R³ | R⁴ | R⁵ |
|---|---|---|---|---|---|
| 22 | 22 | NHi-Pr | 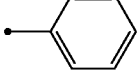 2-Cl-phenyl | OCH₂CH₂OAc | H |
| 23 | 23 | NHi-Pr | 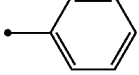 2-Cl-phenyl | OCH₂CH₂OH | H |
| 24 | 24 | NHi-Pr | 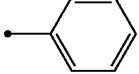 2-Cl-phenyl | OCH₂CH₂CH₂OH | H |
| 25 | 25 | NHi-Pr | 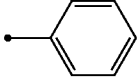 2-Cl-phenyl | OCH₂CH₂CH₂CH₂OH | H |
| 26 | 26 | NHi-Pr | 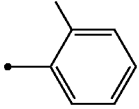 2-Cl-phenyl | OCH₂OMe | H |
| 27 | 27 | NHi-Pr |  2-Cl-phenyl | OCH₂-phenyl | H |

TABLE 3-continued

*[Quinazoline core structure with R³, R⁴, R⁵ substituents and NR¹R² group]*

| Example Number | Compound Number | NR¹R² | R³ | R⁴ | R⁵ |
|---|---|---|---|---|---|
| 28 | 28 | NHi-Pr | 2-Cl-phenyl | OCH₂-(4-CO₂H-phenyl) | H |
| 29 | 29 | NHi-Pr | 2-Cl-phenyl | OCH₂-(3-CO₂H-phenyl) | H |
| 30 | 30 | NHi-Pr | 2-Cl-phenyl | OCH$_2$CH$_2$CO$_2$H | H |
| 31 | 31 | NHi-Pr | 2-Cl-phenyl | OCH$_2$CH$_2$CH$_2$CO$_2$H | H |

TABLE 4

*[Quinazoline core structure with R³, R⁴, R⁵ substituents and NR¹R² group]*

| Example Number | Compound Number | NR¹R² | R³ | R⁴ | R⁵ |
|---|---|---|---|---|---|
| 32 | 32 | NHi-Pr | 2-Cl-phenyl | OCH$_2$CO$_2$Et | H |
| 33 | 33 | NHi-Pr | 2-Cl-phenyl | OCH$_2$CO$_2$H | H |
| 34 | 34 | NHi-Pr | 2-Cl-phenyl | OCH$_2$C(Me)$_2$OH | H |

TABLE 4-continued
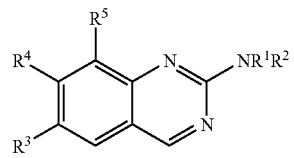
| Example Number | Compound Number | NR¹R² | R³ | R⁴ | R⁵ |
|---|---|---|---|---|---|
| 35 | 35 | NHi-Pr | 2-Cl-C₆H₄ | OCH₂CONH₂ | H |
| 36 | 36 | NHi-Pr | 2-Cl-C₆H₄ | OCH₂CONHMe | H |
| 37 | 37 | NHi-Pr | 2-Cl-C₆H₄ | OCH₂CONMe₂ | H |
| 38 | 38 | NHi-Pr | 2-Cl-C₆H₄ | OCH₂CO-piperidinyl | H |
| 39 | 39 | NHi-Pr | 2-Cl-C₆H₄ | OCH₂CO-morpholinyl | H |
| 40 | 40 | NHi-Pr | 2-Cl-C₆H₄ | OCH₂CO-(4-Me-piperazinyl) | H |
| 41 | 41 | NHi-Pr | 2-Cl-C₆H₄ | 4-CO₂H-C₆H₄ | H |
| 42 | 42 | NHi-Pr | 2-Cl-C₆H₄ | 3-CO₂H-C₆H₄ | H |
| 43 | 43 | NHi-Pr | 2-Cl-C₆H₄ | 3-Cl-C₆H₄ | H |

TABLE 5
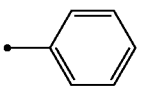
| Example Number | Compound Number | NR¹R² | R³ | R⁴ | R⁵ |
|---|---|---|---|---|---|
| 44 | 44 | NHi-Pr | 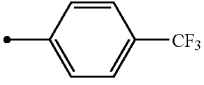 | OMe | H |
| 45 | 45 | NHi-Pr |  | OMe | H |
| 46 | 46 | NHi-Pr | 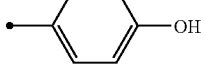 | OMe | H |
| 47 | 47 | NHi-Pr |  | OMe | H |
| 48 | 48 | NHi-Pr | 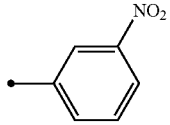 | OMe | H |
| 49 | 49 | NHi-Pr | 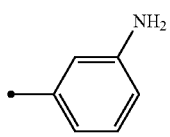 | OMe | H |
| 50 | 50 | NHi-Pr | 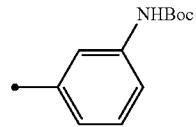 | OMe | H |
| 51 | 51 | NHi-Pr | 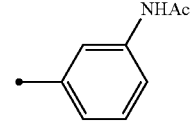 | OMe | H |
| 52 | 52 | NHi-Pr | 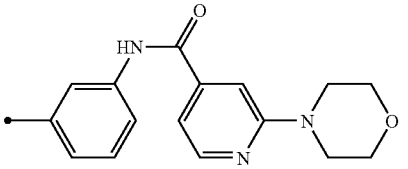 | OMe | H |
| 53 | 53 | NHi-Pr |  | OMe | H |

TABLE 5-continued

[Quinazoline structure with R⁵ at 8-position, R⁴ at 7, R³ at 6, and NR¹R² at 2-position]

| Example Number | Compound Number | NR¹R² | R³ | R⁴ | R⁵ |
|---|---|---|---|---|---|
| 54 | 54 | NHi-Pr | 3-(3-(dimethylamino)benzamido)phenyl | OMe | H |

TABLE 6

[Quinazoline structure with R⁵, R⁴, R³, NR¹R²]

| Example Number | Compound Number | NR¹R² | R³ | R⁴ | R⁵ |
|---|---|---|---|---|---|
| 55 | 55 | NHi-Pr | 2-nitrophenyl | OMe | H |
| 56 | 56 | NHi-Pr | 2-acetamidophenyl | OMe | H |
| 57 | 57 | NHi-Pr | 2-formylphenyl (OHC-) | OMe | H |

TABLE 6-continued

| Example Number | Compound Number | NR¹R² | R³ | R⁴ | R⁵ |
|---|---|---|---|---|---|
| 58 | 58 | NHi-Pr | 2-(HONHC-)phenyl | OMe | H |
| 59 | 59 | NHi-Pr | 2-(MeONHC-)phenyl | OMe | H |

TABLE 7

[Quinazoline structure with R⁵, R⁴, R³, NR¹R²]

| Example Number | Compound Number | NR¹R² | R³ | R⁴ | R⁵ |
|---|---|---|---|---|---|
| 60 | 60 | NHi-Pr | 2-chlorophenyl | OMe | Br |

TABLE 7-continued
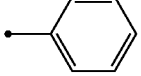
| Example Number | Compound Number | NR¹R² | R³ | R⁴ | R⁵ |
|---|---|---|---|---|---|
| 61 | 61 | NHi-Pr | 2-Cl-C₆H₄ | OMe | $CO_2Me$ |
| 62 | 62 | NHi-Pr | 2-Cl-C₆H₄ | OMe | $CO_2Pr$ |
| 63 | 63 | NHi-Pr | 2-Cl-C₆H₄ | OH | $CO_2Pr$ |
| 64 | 64 | NHi-Pr | 2-Cl-C₆H₄ | OMe | $CO_2H$ |
| 65 | 65 | NHi-Pr | 2-Cl-C₆H₄ | OH | $CO_2H$ |
| 66 | 66 | NHi-Pr | 2-Cl-C₆H₄ | OMe | CON(morpholino) |
| 67 | 67 | NHi-Pr | 2-Cl-C₆H₄ | OMe | CON(piperidino) |
| 68 | 68 | NHi-Pr | 2-Cl-C₆H₄ | OMe | $CONEt_2$ |
| 69 | 69 | NHi-Pr | 2-Cl-C₆H₄ | OMe | CONHPr |
| 70 | 70 | NHi-Pr | 2-Cl-C₆H₄ | OMe | $CONHCH_2Ph$ |

TABLE 7-continued

| Example Number | Compound Number | NR¹R² | R³ | R⁴ | R⁵ |
|---|---|---|---|---|---|
| 71 | 71 | NHi-Pr | 2-Cl-phenyl | OMe | CONMe(OMe) |
| 72 | 72 | NHi-Pr | 2-Cl-phenyl | OH | CONMe(OMe) |

TABLE 8

| Example Number | Compound Number | NR¹R² | R³ | R⁴ | R⁵ |
|---|---|---|---|---|---|
| 73 | 73 | NHi-Pr | 2-Cl-phenyl | OMe | CH=CHCO$_2$Et |
| 74 | 74 | NHi-Pr | 2-Cl-phenyl | OMe | CH=CHCO$_2$H |
| 75 | 75 | NHi-Pr | 2-Cl-phenyl | OMe | CH$_2$CH$_2$CO$_2$H |
| 76 | 76 | NHi-Pr | 2-Cl-phenyl | OMe | CH=CH$_2$ |
| 77 | 77 | NHi-Pr | 2-Cl-phenyl | OMe | COCH$_3$ |

TABLE 8-continued
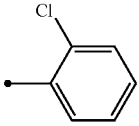
| Example Number | Compound Number | NR¹R² | R³ | R⁴ | R⁵ |
|---|---|---|---|---|---|
| 78 | 78 | NHi-Pr | 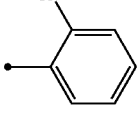 | OH | COCH$_3$ |
| 79 | 79 | NHi-Pr | 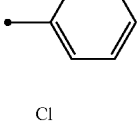 | OCH$_2$CO$_2$Et | COCH$_3$ |
| 80 | 80 | NHi-Pr | 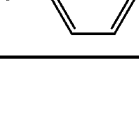 | OCH$_2$CO$_2$H | COCH$_3$ |
| 81 | 81 | NHi-Pr | 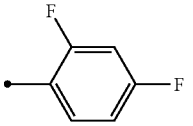 | OCH$_2$C(Me)$_2$OH | C(Me)$_2$OH |
TABLE 9
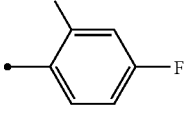
| Example Number | Compound Number | NR¹R² | R³ | R⁴ | R⁵ |
|---|---|---|---|---|---|
| 82 | 82 | NHi-Pr | 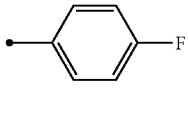 | OMe | Br |
| 83 | 83 | NHi-Pr | 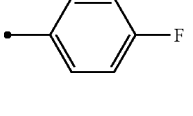 | OMe | 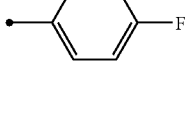 |
| 84 | 84 | NHi-Pr |  | OH |  |

TABLE 9-continued
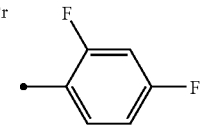
| Example Number | Compound Number | NR¹R² | R³ | R⁴ | R⁵ |
|---|---|---|---|---|---|
| 85 | 85 | NHi-Pr |  2,4-diF-phenyl | H | 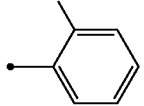 4-F-phenyl |
| 86 | 86 | NHi-Pr | 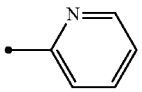 2-Cl-phenyl | OMe | 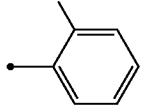 2-pyridyl |
| 87 | 87 | NHi-Pr | 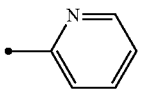 2-Cl-phenyl | OH | 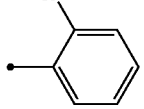 2-pyridyl |
| 88 | 88 | NHi-Pr | 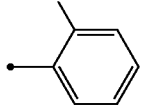 2-Cl-phenyl | OH | I |
| 89 | 89 | NHi-Pr | 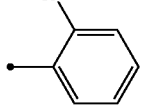 2-Cl-phenyl | OH | Br |
| 90 | 90 | NHi-Pr | 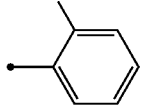 2-Cl-phenyl | OCH₂OMe | Br |
| 91 | 91 | NHi-Pr | 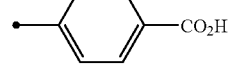 2-Cl-phenyl | OCH₂OMe | 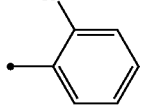 4-CO₂H-phenyl |
| 92 | 92 | NHi-Pr | 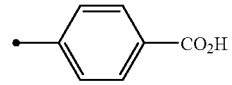 2-Cl-phenyl | OH | 4-CO₂H-phenyl |

TABLE 10

(structure: quinazoline with R³, R⁴, R⁵ on benzene ring and NR¹R² at 2-position)

| Example Number | Compound Number | NR¹R² | R³ | R⁴ | R⁵ |
|---|---|---|---|---|---|
| 93 | 93 | NHi-Pr | 2-Cl-phenyl | OCH₂OMe | 3-CO₂H-phenyl |
| 94 | 94 | NHi-Pr | 2-Cl-phenyl | OH | 3-CO₂H-phenyl |
| 95 | 95 | NHi-Pr | 2-Cl-phenyl | OH | 4-(CH₂CO₂H)-phenyl |
| 96 | 96 | NHi-Pr | 2-Cl-phenyl | OH | 3-(CH₂CO₂H)-phenyl |
| 97 | 97 | NHi-Pr | 2-Cl-phenyl | OCH₂OMe | 2-Cl-phenyl |
| 98 | 98 | NHi-Pr | 2-Cl-phenyl | OH | 2-Cl-phenyl |
| 99 | 99 | NHi-Pr | 2-Cl-phenyl | OCH₂OMe | 2-F-phenyl |
| 100 | 100 | NHi-Pr | 2-Cl-phenyl | OH | 2-F-phenyl |
| 101 | 101 | NHi-Pr | 2-Cl-phenyl | OCH₂OMe | 2,3-diF-phenyl |

TABLE 10-continued
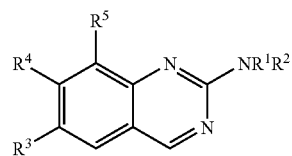
| Example Number | Compound Number | NR¹R² | R³ | R⁴ | R⁵ |
|---|---|---|---|---|---|
| 102 | 102 | NHi-Pr | 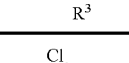 2-Cl-phenyl | OH | 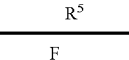 2,6-F₂-phenyl |
TABLE 11
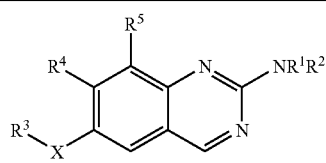
| Example Number | Compound Number | NR¹R² | R⁴ | XR³ | R⁵ |
|---|---|---|---|---|---|
| 103 | 103 | NHi-Pr | OMe |  | H |
| 104 | 104 | NHi-Pr | OMe |  | H |
| 105 | 105 | NHi-Pr | OMe |  | H |
| 106 | 106 | NHi-Pr | OMe |  | H |
| 107 | 107 | NHi-Pr | OMe |  | H |
| 108 | 108 | NH₂ | OMe |  | H |
| 109 | 109 | NHi-Pr | OMe |  | H |
| 110 | 110 | NHi-Pr | OH |  | H |
TABLE 12
| Example Number | Compound Number | |
|---|---|---|
| 111 | 111 |  |
| 112 | 112 | 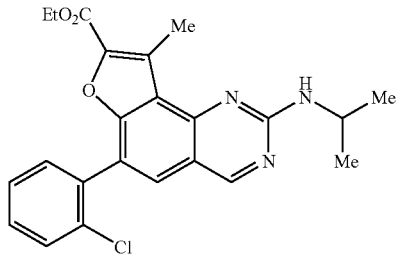 |
TABLE 13
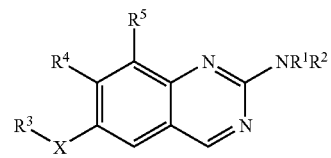
| Example Number | Compound Number | NR¹R² | R⁴ | XR³ | R⁵ |
|---|---|---|---|---|---|
| 113 | 113 | NHi-Pr | OMe | 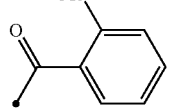 | H |

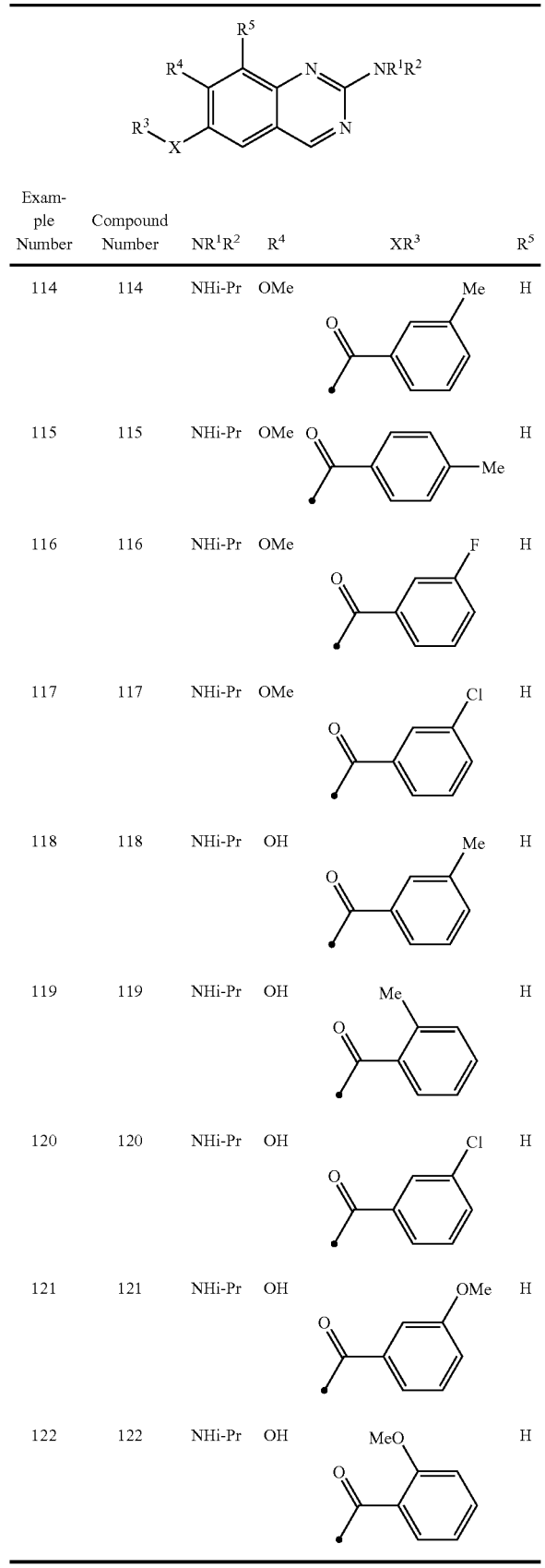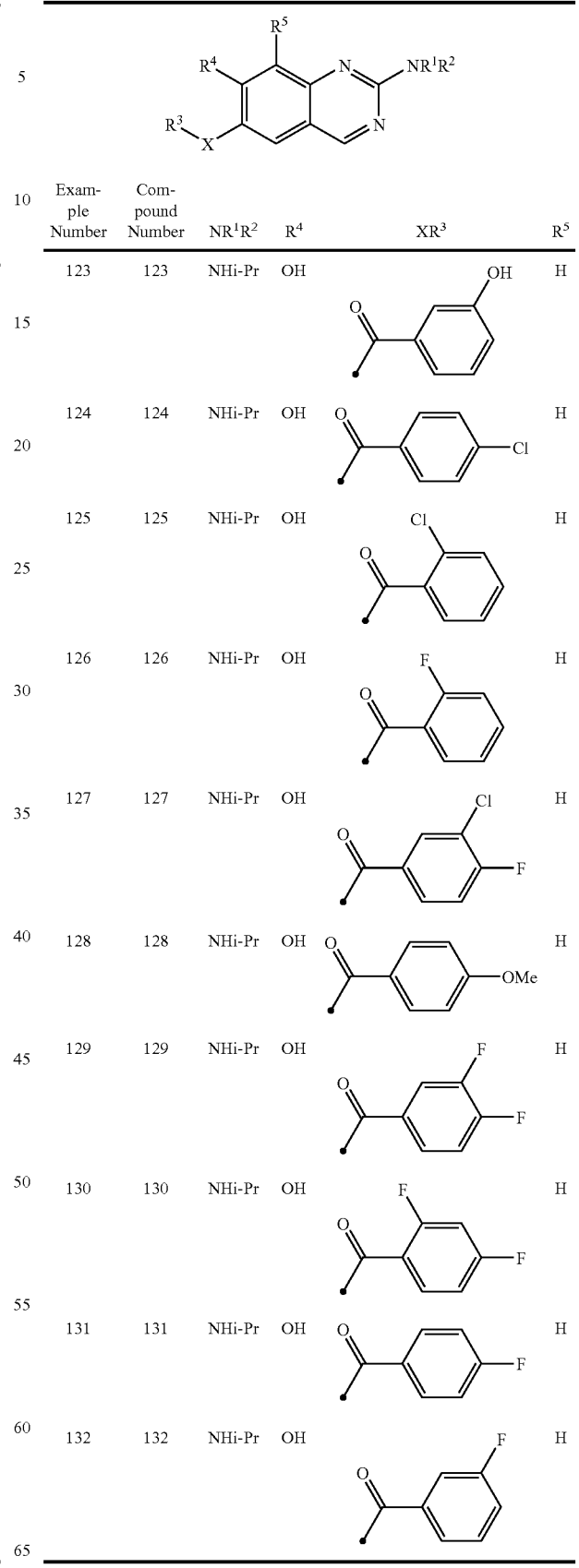

TABLE 15
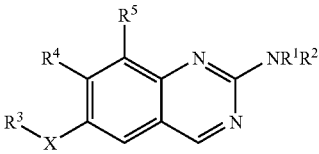
| Example Number | Compound Number | NR¹R² | R⁴ | XR³ | R⁵ |
|---|---|---|---|---|---|
| 133 | 133 | NHi-Pr | OH | 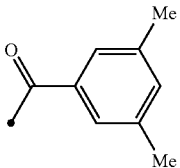 | H |
| 134 | 134 | NHi-Pr | OH | 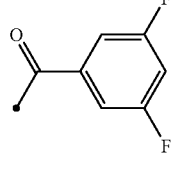 | H |
| 135 | 135 | 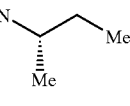 | OH | 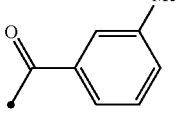 | H |
| 136 | 136 | 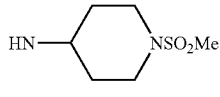 | OH | 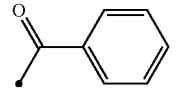 | H |
| 137 | 137 | 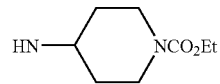 | OH | 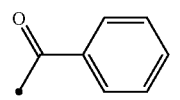 | H |
| 138 | 138 | 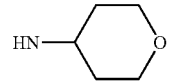 | OH | 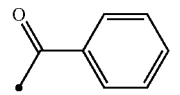 | H |
| 139 | 139 | 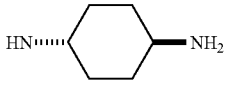 | OH | 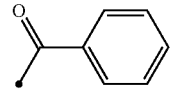 | H |
| 140 | 140 | 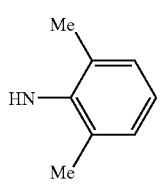 | OH | 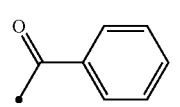 | H |
| 141 | 141 | 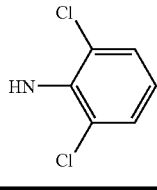 | OH | 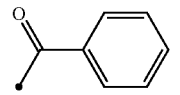 | H |

TABLE 16

[Structure: quinazoline core with R5 at 8-position, R4 at 7-position, R3 at 6-position, and NR1R2 at 2-position]

| Example Number | Compound Number | NR¹R² | R³ | R⁴ | R⁵ |
|---|---|---|---|---|---|
| 142 | 142 | HN–(piperidine)–NSO₂Et | 2-Cl-phenyl | OMe | H |
| 143 | 143 | HN–(piperidine)–NSO₂i-Pr | 2-Cl-phenyl | OMe | H |
| 144 | 144 | HN–CH₂–(piperidine)–NSO₂Me | 2-Cl-phenyl | OMe | H |
| 145 | 145 | HN–(pyrrolidine)–NSO₂Me | 2-Cl-phenyl | OMe | H |
| 146 | 146 | HN–(cyclohexane, trans)–NHSO₂Me | 2-Cl-phenyl | OMe | H |
| 147 | 147 | HN–(cyclohexane, trans)–NHSO₂Et | 2-Cl-phenyl | OMe | H |
| 148 | 148 | HN–(piperidine)–NSO₂Pr | 2-Cl-phenyl | OMe | H |
| 149 | 149 | HN–(piperidine)–NCO₂Et | 2-Cl-phenyl | OMe | H |
| 150 | 150 | HN–CH₂CH₂–NMe₂ | 2-Cl-phenyl | OMe | H |

TABLE 16-continued
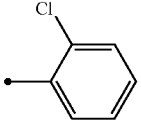
| Example Number | Compound Number | NR¹R² | R³ | R⁴ | R⁵ |
|---|---|---|---|---|---|
| 151 | 151 | HNCH₂CHMe₂ | 2-Cl-phenyl | OMe | H |
TABLE 17
| Example Number | Compound Number | NR¹R² | R³ | R⁴ | R⁵ |
|---|---|---|---|---|---|
| 152 | 152 | HN—(piperidin-4-yl)NH | 2-Cl-phenyl | OMe | H |
| 153 | 153 | HNCH₂CMe₃ | 2-Cl-phenyl | OMe | H |
| 154 | 154 | HN-C(O)-cyclopropyl | 2-Cl-phenyl | OMe | H |
| 155 | 155 | HN—CH(Me)—Me (S) | 2-Cl-phenyl | OMe | H |
| 156 | 156 | HN—(1-SO₂Me-piperidin-4-yl) | 2-Cl-phenyl | OH | H |
| 157 | 157 | HN—(1-CONH₂-piperidin-4-yl) | 2-Cl-phenyl | OH | H |

TABLE 17-continued

[Structure: quinazoline core with R⁵ at 8-position, R⁴ at 7-position, R³ at 6-position, and NR¹R² at 2-position]

| Example Number | Compound Number | NR¹R² | R³ | R⁴ | R⁵ |
|---|---|---|---|---|---|
| 158 | 158 | HN—(trans-cyclohexyl)—NH₂ | 2-Cl-phenyl | OH | H |
| 159 | 159 | HNCH₂CMe₃ | 2-Cl-phenyl | OH | H |
| 160 | 160 | HNCH₂CHMe₂ | 2-Cl-phenyl | OH | H |
| 161 | 161 | HN—(piperidin-4-yl)—NSO₂Et | 2-Cl-phenyl | OH | H |

TABLE 18

[Structure: quinazoline core with R⁵ at 8-position, R⁴ at 7-position, R³ at 6-position, and NR¹R² at 2-position]

| Example Number | Compound Number | NR¹R² | R³ | R⁴ | R⁵ |
|---|---|---|---|---|---|
| 162 | 162 | HN—(piperidin-4-yl)—NSO₂Pr | 2-Cl-phenyl | OH | H |
| 163 | 163 | HN—CH(Me)—CH₂Me (chiral) | 2-Cl-phenyl | OH | H |
| 164 | 164 | HN—(piperidin-4-yl)—NSO₂Me | 2-Me-phenyl | OMe | H |

TABLE 18-continued
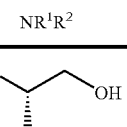
| Example Number | Compound Number | NR¹R² | R³ | R⁴ | R⁵ |
|---|---|---|---|---|---|
| 165 | 165 | 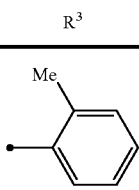 | 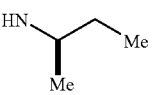 | OMe | H |
| 166 | 166 | 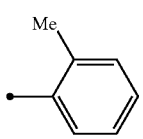 | 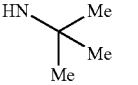 | OMe | H |
| 167 | 167 | 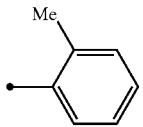 | 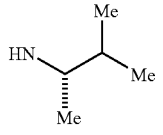 | OMe | H |
| 168 | 168 | 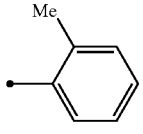 | 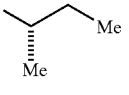 | OMe | H |
| 169 | 169 | 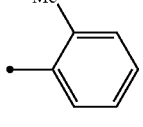 | 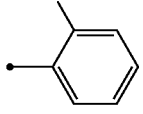 | OH | H |
| 170 | 170 | HNCH(Et)₂ |  | OH | H |
TABLE 19
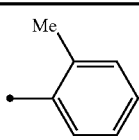
| Example Number | Compound Number | NR¹R² | R³ | R⁴ | R⁵ |
|---|---|---|---|---|---|
| 171 | 171 | HN-cyclohexyl | Me-phenyl | OH | H |

TABLE 19-continued
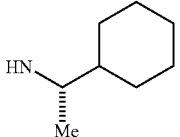
| Example Number | Compound Number | NR¹R² | R³ | R⁴ | R⁵ |
|---|---|---|---|---|---|
| 172 | 172 | 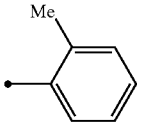 | 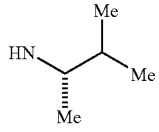 | OH | H |
| 173 | 173 | 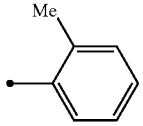 | 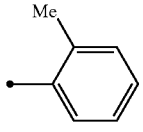 | OH | H |
| 174 | 174 | HNCH(Pr)₂ | 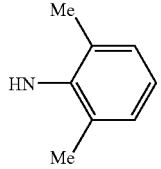 | OH | H |
| 175 | 175 | 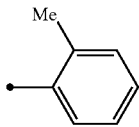 | 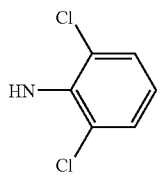 | OH | H |
| 176 | 176 | 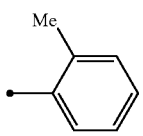 | 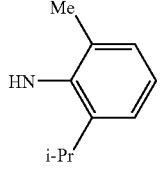 | OH | H |
| 177 | 177 | 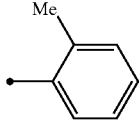 | 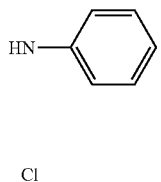 | OH | H |
| 178 | 178 | 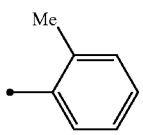 | 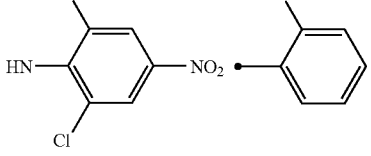 | OH | H |
| 179 | 179 | 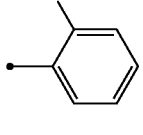 | Me | OH | H |

TABLE 19-continued

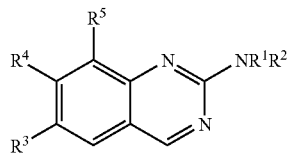

| Example Number | Compound Number | NR¹R² | R³ | R⁴ | R⁵ |
|---|---|---|---|---|---|
| 180 | 180 | 2-Me-6-Et-C₆H₃-NH | Me (2-methylphenyl) | OH | H |

TABLE 20

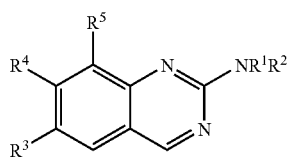

| Example Number | Compound Number | NR¹R² | R³ | R⁴ | R⁵ |
|---|---|---|---|---|---|
| 181 | 181 | NHi-Pr | 2-(EtONHC)-C₆H₄ | OMe | H |
| 182 | 182 | NHi-Pr | 2-(HOH₂C)-C₆H₄ | OMe | H |
| 183 | 183 | NHi-Pr | 2-NC-C₆H₄ | OMe | H |
| 184 | 184 | NHi-Pr | 2-(PhH₂CO)-C₆H₄ | OMe | H |
| 185 | 185 | NHi-Pr | 2-(HO₂C)-C₆H₄ | OMe | H |
| 186 | 186 | NHi-Pr | 2-HO-C₆H₄ | OMe | H |

TABLE 20-continued

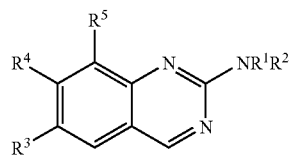

| Example Number | Compound Number | NR¹R² | R³ | R⁴ | R⁵ |
|---|---|---|---|---|---|
| 187 | 187 | NHi-Pr | 2-(MeOC)-C₆H₄ | OMe | H |
| 188 | 188 | NHi-Pr | 2-(morpholinyl-C(O))-C₆H₄ | OMe | H |
| 189 | 189 | NHi-Pr | 2-(MeHNOC)-C₆H₄ | OMe | H |
| 190 | 190 | NHi-Pr | 2-F-C₆H₄ | OMe | H |

TABLE 21

Structure: quinazoline with R5 at 8-position, R4 at 7-position, R3 at 6-position, and NR1R2 at 2-position.

| Example Number | Compound Number | NR¹R² | R³ | R⁴ | R⁵ |
|---|---|---|---|---|---|
| 191 | 191 | NHi-Pr | 2-Me-phenyl | OMe | H |
| 192 | 192 | NHi-Pr | 2-(F₃C)-phenyl | OMe | H |
| 193 | 193 | NHi-Pr | 2-MeO-phenyl | OMe | H |
| 194 | 194 | NHi-Pr | 3-[N(Ac)CH₂Ph]-phenyl | OMe | H |
| 195 | 195 | NHi-Pr | 3-(OCH₂Ph)-phenyl | OMe | H |
| 196 | 196 | NHi-Pr | 3-OH-phenyl | OMe | H |
| 197 | 197 | NHi-Pr | 3-CHO-phenyl | OMe | H |
| 198 | 198 | NHi-Pr | 3-CO₂H-phenyl | OMe | H |
| 199 | 199 | NHi-Pr | 3-COMe-phenyl | OMe | H |
| 200 | 200 | NHi-Pr | 3-OCF₃-phenyl | OMe | H |

TABLE 22

Structure: quinazoline with R5 at 8-position, R4 at 7-position, R3 at 6-position, and NR1R2 at 2-position.

| Example Number | Compound Number | NR¹R² | R³ | R⁴ | R⁵ |
|---|---|---|---|---|---|
| 201 | 201 | NHi-Pr | 3-OMe-phenyl | OMe | H |
| 202 | 202 | NHi-Pr | 3-OCOMe-phenyl | OMe | H |

TABLE 22-continued
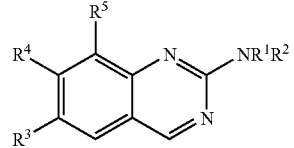
| Example Number | Compound Number | NR¹R² | R³ | R⁴ | R⁵ |
|---|---|---|---|---|---|
| 203 | 203 | NHi-Pr | 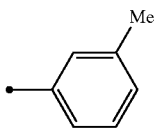 3-Me-phenyl | OMe | H |
| 204 | 204 | NHi-Pr | 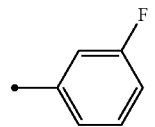 3-F-phenyl | OMe | H |
| 205 | 205 | NHi-Pr | 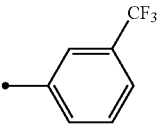 3-CF₃-phenyl | OMe | H |
| 206 | 206 | NHi-Pr | 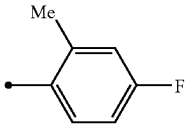 2-Me-4-F-phenyl | OMe | H |
| 207 | 207 | NHi-Pr | 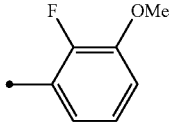 2-F-3-OMe-phenyl | OMe | H |
| 208 | 208 | NHi-Pr | 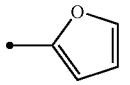 2-furyl | OMe | H |
| 209 | 209 | NHi-Pr | 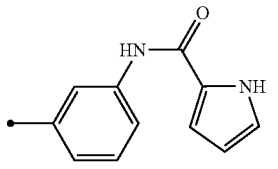 | OMe | H |
| 210 | 210 | NHi-Pr | 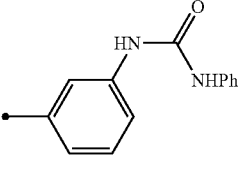 | OMe | H |

TABLE 23
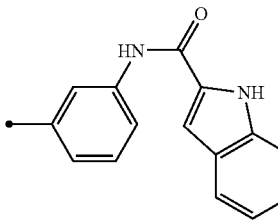
| Example Number | Compound Number | NR¹R² | R³ | R⁴ | R⁵ |
|---|---|---|---|---|---|
| 211 | 211 | NHi-Pr | 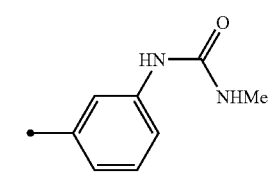 | OMe | H |
| 212 | 212 | NHi-Pr |  | OMe | H |
| 213 | 213 | NHi-Pr |  | OMe | H |
| 214 | 214 | NHi-Pr | 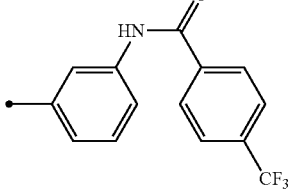 | OMe | H |
| 215 | 215 | NHi-Pr |  | OMe | H |
| 216 | 216 | NHi-Pr | 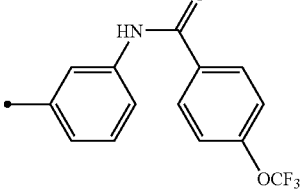 | OMe | H |
| 217 | 217 | NHi-Pr |  | OMe | H |

TABLE 23-continued

![Structure: quinazoline with R3, R4, R5 substituents and NR1R2 at 2-position]

| Example Number | Compound Number | NR¹R² | R³ | R⁴ | R⁵ |
|---|---|---|---|---|---|
| 218 | 218 | NHi-Pr | 3-(3,5-di-t-Bu-benzamido)phenyl | OMe | H |
| 219 | 219 | NHi-Pr | 3-(3-fluorobenzamido)phenyl | OMe | H |
| 220 | 220 | NHi-Pr | 3-(cyclopropanecarboxamido)phenyl | OMe | H |

TABLE 24

![Structure: quinazoline with R3, R4, R5 substituents and NR1R2 at 2-position]

| Example Number | Compound Number | NR¹R² | R³ | R⁴ | R⁵ |
|---|---|---|---|---|---|
| 221 | 221 | NHi-Pr | 3-(pyridine-3-carboxamido)phenyl | OMe | H |
| 222 | 222 | NHi-Pr | 3-(cyclobutanecarboxamido)phenyl | OMe | H |
| 223 | 223 | NHi-Pr | 2-(hydroxymethyl)-5-nitrophenyl | OMe | H |

TABLE 24-continued

[Structure: quinazoline core with R⁵ at 8-position, R⁴ at 7-position, R³ at 6-position, and NR¹R² at 2-position]

| Example Number | Compound Number | NR¹R² | R³ | R⁴ | R⁵ |
|---|---|---|---|---|---|
| 224 | 224 | NHi-Pr | phenyl with NH₂ (para) and CH₂OH (ortho to attachment) | OMe | H |
| 225 | 225 | NHi-Pr | phenyl with NHCOMe and CH₂OH | OMe | H |
| 226 | 226 | NHi-Pr | phenyl with NHCOMe and CO₂H | OMe | H |
| 227 | 227 | NHi-Pr | phenyl with NHCOMe and CN | OMe | H |
| 228 | 228 | NHi-Pr | phenyl with NH-CO-(1H-pyrrol-2-yl) and CH₂OH | OMe | H |
| 229 | 229 | NHi-Pr | phenyl with NH₂ and Me | OMe | H |
| 230 | 230 | NHi-Pr | phenyl with NHCOMe and Me | OMe | H |

TABLE 25
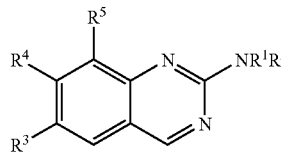
| Example Number | Compound Number | NR¹R² | R³ | R⁴ | R⁵ |
|---|---|---|---|---|---|
| 231 | 231 | NHi-Pr | 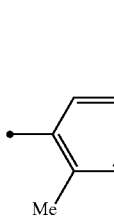 | OMe | H |
| 232 | 232 | NHi-Pr | 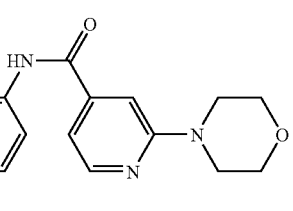 | OMe | H |
| 233 | 233 | NHi-Pr |  | OMe | H |
| 234 | 234 | NHi-Pr | 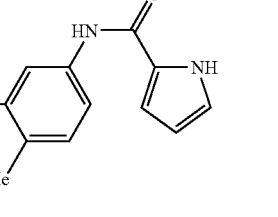 | OMe | H |
| 235 | 235 | NHi-Pr | 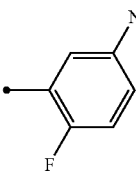 | OMe | H |
| 236 | 236 | NHi-Pr | 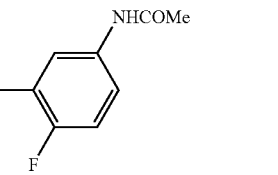 | OMe | H |
| 237 | 237 | 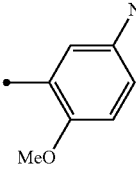 | 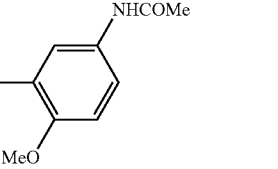 | OMe | H |

TABLE 25-continued

Structure: quinazoline core with R³, R⁴, R⁵ on benzene ring and NR¹R² at 2-position

| Example Number | Compound Number | NR¹R² | R³ | R⁴ | R⁵ |
|---|---|---|---|---|---|
| 238 | 238 | HN—(piperidine)—NSO₂Me | 3-NHCOMe-phenyl | OMe | H |
| 239 | 239 | HN—(piperidine)—NSO₂Me | 2-NHCOMe-phenyl | OMe | H |
| 240 | 240 | HN—(piperidine)—NSO₂Me | 3-OH-phenyl | OMe | H |

TABLE 26

| Example Number | Compound Number | NR¹R² | R³ | R⁴ | R⁵ |
|---|---|---|---|---|---|
| 241 | 241 | HN—(piperidine)—NSO₂Me | 2-OH-phenyl | OMe | H |
| 242 | 242 | HN—(piperidine)—NSO₂Me | 2-HO₂C-phenyl | OMe | H |
| 243 | 243 | HN—(tetrahydropyran-4-yl) | 3-NHCOMe-phenyl | OMe | H |
| 244 | 244 | NHi-Pr | 3-OH-phenyl | OH | H |

TABLE 26-continued
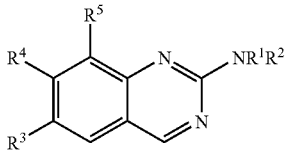
| Example Number | Compound Number | NR¹R² | R³ | R⁴ | R⁵ |
|---|---|---|---|---|---|
| 245 | 245 | NHi-Pr | 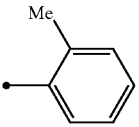 2-Me-phenyl | OH | H |
| 246 | 246 | NHi-Pr | 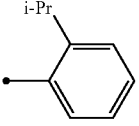 2-i-Pr-phenyl | OH | H |
| 247 | 247 | 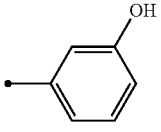 HN-(1-SO₂Me-piperidin-4-yl) | 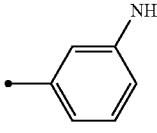 3-OH-phenyl | OH | H |
| 248 | 248 | NH₂ | 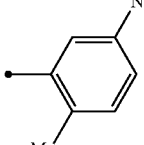 3-NHCOMe-phenyl | OMe | H |
| 249 | 249 | NH₂ | 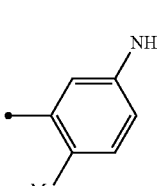 3-NHCOMe-4-Me-phenyl | OMe | H |
| 250 | 250 | NHMe | 3-NHCOMe-4-Me-phenyl | OMe | H |

TABLE 27

[Structure: quinazoline core with R⁵ at 8-position, R⁴ at 7-position, R³ at 6-position, and NR¹R² at 2-position]

| Example Number | Compound Number | NR¹R² | R³ | R⁴ | R⁵ |
|---|---|---|---|---|---|
| 251 | 251 | NHMe | 3-(1H-pyrrole-2-carboxamido)-4-methylphenyl | OMe | H |
| 252 | 252 | NHi-Pr | 3-(1H-pyrrole-2-carboxamido)-4-hydroxyphenyl | OMe | H |
| 253 | 253 | NHi-Pr | 3-(1H-pyrrole-2-carboxamido)-4-methylphenyl | H | H |
| 254 | 254 | NHi-Pr | 3-(NHCOMe)-4-methylphenyl | H | H |
| 255 | 255 | NHi-Pr | 3-(1H-pyrrole-2-carboxamido)-4-(hydroxymethyl)phenyl | H | H |
| 256 | 256 | NHi-Pr | 3-(2-morpholinoisonicotinamido)-4-methylphenyl | H | H |

TABLE 27-continued
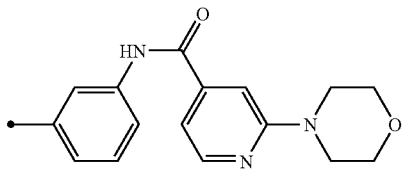
| Example Number | Compound Number | NR¹R² | R³ | R⁴ | R⁵ |
|---|---|---|---|---|---|
| 257 | 257 | NHi-Pr | 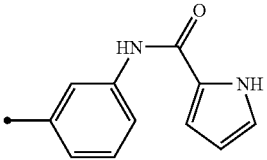 | H | H |
| 258 | 258 | NHi-Pr | 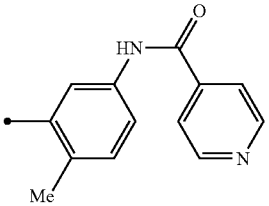 | H | H |
| 259 | 259 | NHi-Pr | 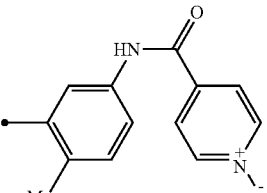 | H | H |
| 260 | 260 | NHi-Pr | 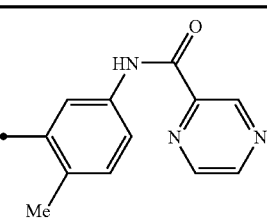 | H | H |
TABLE 28
| Example Number | Compound Number | NR¹R² | R³ | R⁴ | R⁵ |
|---|---|---|---|---|---|
| 261 | 261 | NHi-Pr | | H | H |

TABLE 28-continued
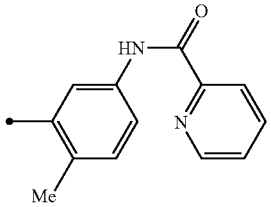
| Example Number | Compound Number | NR¹R² | R³ | R⁴ | R⁵ |
|---|---|---|---|---|---|
| 262 | 262 | NHi-Pr | 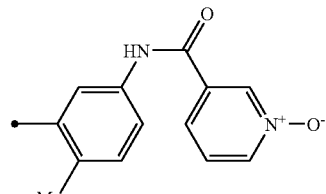 | H | H |
| 263 | 263 | NHi-Pr | 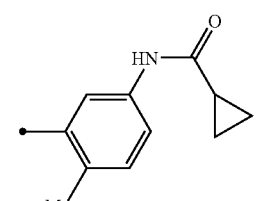 | H | H |
| 264 | 264 | NHi-Pr | 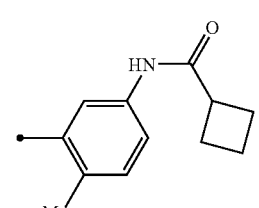 | H | H |
| 265 | 265 | NHi-Pr | 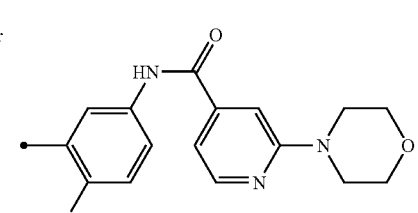 | H | H |
| 266 | 266 | NHi-Pr | 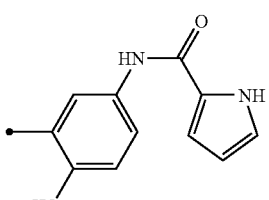 | H | H |
| 267 | 267 | NHi-Pr |  | H | H |

TABLE 28-continued
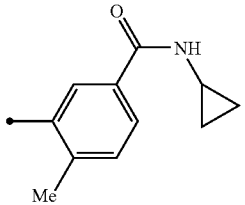
| Example Number | Compound Number | NR¹R² | R³ | R⁴ | R⁵ |
|---|---|---|---|---|---|
| 268 | 268 | NHi-Pr | 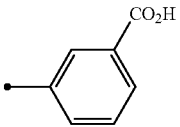 | H | H |
| 269 | 269 | NHi-Pr |  | H | H |
| 270 | 270 | NHi-Pr | 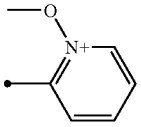 | H | H |
TABLE 29
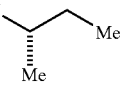
| Example Number | Compound Number | NR¹R² | R³ | R⁴ | R⁵ |
|---|---|---|---|---|---|
| 271 | 271 | NHi-Pr | 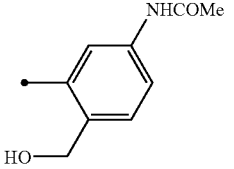 | H | H |
| 272 | 272 | 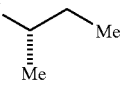 | 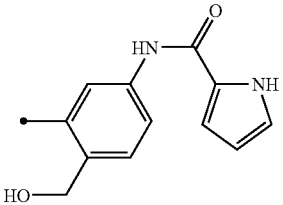 | H | H |
| 273 | 273 | | | H | H |

TABLE 29-continued
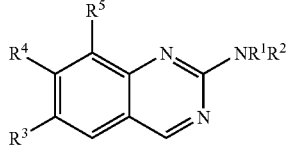
| Example Number | Compound Number | NR¹R² | R³ | R⁴ | R⁵ |
|---|---|---|---|---|---|
| 274 | 274 |  | 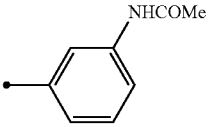 NHCOMe | H | H |
| 275 | 275 | 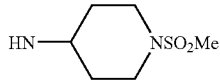 | 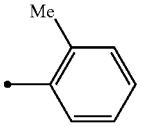 Me | H | H |
| 276 | 276 |  | 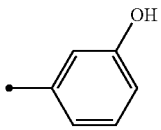 OH | H | H |
| 277 | 277 | NHi-Pr | 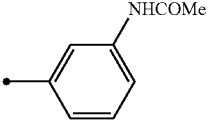 NHCOMe | Me | H |
| 278 | 278 | NHi-Pr | 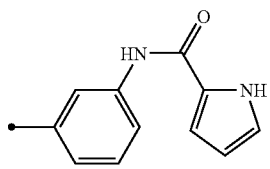 | Me | H |
| 279 | 279 | NHi-Pr | 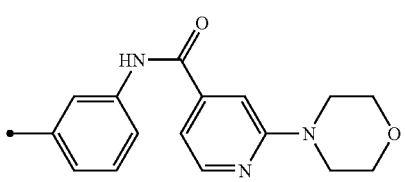 | Me | H |
| 280 | 280 | NHi-Pr | 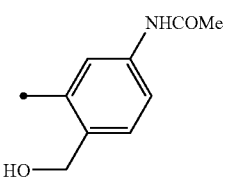 NHCOMe | Me | H |

TABLE 30
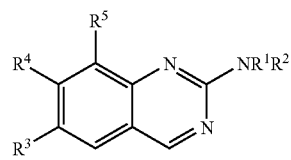
| Example Number | Compound Number | NR¹R² | R³ | R⁴ | R⁵ |
|---|---|---|---|---|---|
| 281 | 281 | NHi-Pr | 3-(pyrrole-2-carboxamido)-4-(hydroxymethyl)phenyl | Me | H |
| 282 | 282 | NHi-Pr | 3-nitrophenyl | OCH₂Ph | H |
| 283 | 283 | NHi-Pr | 3-nitrophenyl | OH | H |
| 284 | 284 | NHi-Pr | 3-aminophenyl | OCH₂Ph | H |
| 285 | 285 | NHi-Pr | 3-aminophenyl | OH | H |
| 286 | 286 | NHi-Pr | 3-(NHCOMe)phenyl | OCOMe | H |
| 287 | 287 | NHi-Pr | 3-(NHCOMe)phenyl | OH | H |
| 288 | 288 | NHi-Pr | 3-amino-4-methylphenyl | OCH₂Ph | H |

TABLE 30-continued

[Quinazoline core structure with R5 at 8-position, R4 at 7-position, R3 at 6-position, and NR¹R² at 2-position]

| Example Number | Compound Number | NR¹R² | R³ | R⁴ | R⁵ |
|---|---|---|---|---|---|
| 289 | 289 | NHi-Pr | 4-methyl-3-(NHCOMe)phenyl (attached at 3-position, Me at 4-position, NHCOMe at 5-position) | OH | H |

TABLE 31

[Quinazoline core structure with R5 at 8-position, R4 at 7-position, R3 at 6-position, and NR¹R² at 2-position]

| Example Number | Compound Number | NR¹R² | R³ | R⁴ | R⁵ |
|---|---|---|---|---|---|
| 290 | 290 | NHi-Pr | 3-[(2-morpholinopyridine-4-carbonyl)amino]phenyl | OH | H |
| 291 | 291 | NHi-Pr | 3-[(3-dimethylaminobenzoyl)amino]phenyl | OH | H |
| 292 | 292 | NHi-Pr | 3-[(1H-pyrrole-2-carbonyl)amino]phenyl | OH | H |
| 293 | 293 | NHi-Pr | 3-(cyclobutanecarbonylamino)-4-methylphenyl | OH | H |

TABLE 31-continued
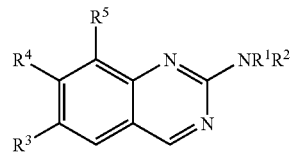
| Example Number | Compound Number | NR¹R² | R³ | R⁴ | R⁵ |
|---|---|---|---|---|---|
| 294 | 294 | NHi-Pr | 3-(cyclobutylcarbonylamino)phenyl | OH | H |
| 295 | 295 | NHi-Pr | 3-(cyclopropylcarbonylamino)-4-methylphenyl | OH | H |
| 296 | 296 | NHi-Pr | 3-(cyclopropylcarbonylamino)phenyl | OH | H |
| 297 | 297 | NHi-Pr | 3-(NHCOEt)phenyl | OH | H |
| 298 | 298 | NHi-Pr | 3-(NHCOt-Bu)phenyl | OH | H |
| 299 | 299 | NHi-Pr | 3-(1-methylcyclopropylcarbonylamino)phenyl | OH | H |

TABLE 32
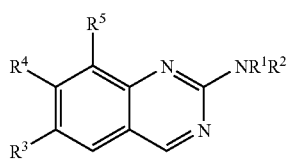
| Example Number | Compound Number | NR¹R² | R³ | R⁴ | R⁵ |
|---|---|---|---|---|---|
| 300 | 300 | HN-(2,4,6-trimethylphenyl) | 2-Me-phenyl | OH | H |
| 301 | 301 | HN-(2,6-dimethyl-4-t-Bu-phenyl) | 2-Me-phenyl | OH | H |
| 302 | 302 | HN-(2,6-dimethyl-4-OMe-phenyl) | 2-Me-phenyl | OH | H |
| 303 | 303 | HN-(2,6-dimethyl-4-OH-phenyl) | 2-Me-phenyl | OH | H |
| 304 | 304 | HN-(3,5-dichloro-4-NH₂-phenyl) | 2-Me-phenyl | OCH₂Ph | H |
| 305 | 305 | HN-(3,5-dichloro-4-NH₂-phenyl) | 2-Me-phenyl | OH | H |
| 306 | 306 | HN-(3,5-dichloro-4-NHSO₂Me-phenyl) | 2-Me-phenyl | OCH₂Ph | H |

TABLE 32-continued
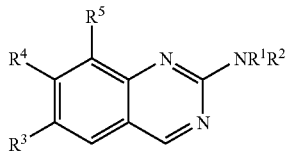
| Example Number | Compound Number | NR¹R² | R³ | R⁴ | R⁵ |
|---|---|---|---|---|---|
| 307 | 307 | 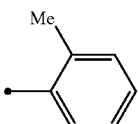 | 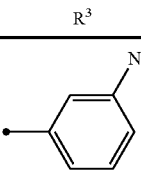 | OH | H |
TABLE 33
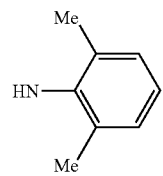
| Example Number | Compound Number | NR¹R² | R³ | R⁴ | R⁵ |
|---|---|---|---|---|---|
| 308 | 308 | $NH_2$ | 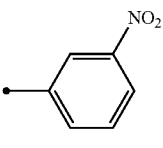 | $OCH_2Ph$ | H |
| 309 | 309 | 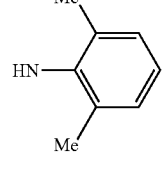 | 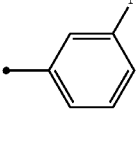 | $OCH_2Ph$ | H |
| 310 | 310 | 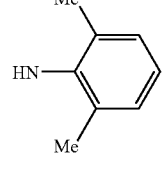 | 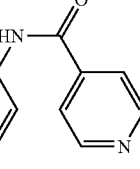 | $OCH_2Ph$ | H |
| 311 | 311 | 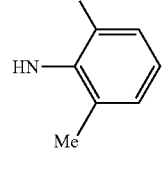 | 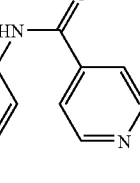 | $OCH_2Ph$ | H |
| 312 | 312 | 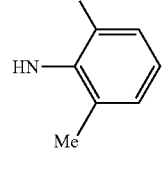 | 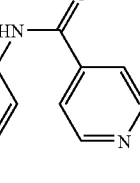 | OH | H |

TABLE 33-continued

| Example Number | Compound Number | NR¹R² | R³ | R⁴ | R⁵ |
|---|---|---|---|---|---|
| 313 | 313 | 2,6-dimethylphenyl-NH- | 3-[(3-(dimethylamino)benzoyl)amino]phenyl | OCH₂Ph | H |
| 314 | 314 | 2,6-dimethylphenyl-NH- | 3-[(3-(dimethylamino)benzoyl)amino]phenyl | OH | H |
| 315 | 315 | NH₂ | 3-(cyclopropylaminocarbonyl)-4-methylphenyl | OCH₂Ph | H |
| 316 | 316 | 2,6-dimethylphenyl-NH- | 3-(cyclopropylaminocarbonyl)-4-methylphenyl | OCH₂Ph | H |
| 317 | 317 | 2,6-dimethylphenyl-NH- | 3-(cyclopropylaminocarbonyl)-4-methylphenyl | OH | H |

TABLE 34

[Structure: quinazoline core with R⁵ at position 8, R⁴ at position 7, R³ at position 6, and NR¹R² at position 2]

| Example Number | Compound Number | NR¹R² | R³ | R⁴ | R⁵ |
|---|---|---|---|---|---|
| 318 | 318 | 2,6-dichlorophenyl-NH- | 4-methyl-3-(N-cyclopropylcarbamoyl)phenyl | OCH₂Ph | H |
| 319 | 319 | 2,6-dichlorophenyl-NH- | 4-methyl-3-(N-cyclopropylcarbamoyl)phenyl | OH | H |
| 320 | 320 | 3-amino-2,6-dichlorophenyl-NH- | 4-methyl-3-(N-cyclopropylcarbamoyl)phenyl | OH | H |
| 321 | 321 | NHi-Pr | 4-methyl-3-(N-cyclopropylcarbamoyl)phenyl | OCH₂Ph | H |
| 322 | 322 | NHi-Pr | 4-methyl-3-(N-cyclopropylcarbamoyl)phenyl | OH | H |
| 323 | 323 | NHi-Pr | 4-methyl-3-(N-(3-(dimethylamino)phenyl)carbamoyl)phenyl | OCH₂Ph | H |

TABLE 34-continued
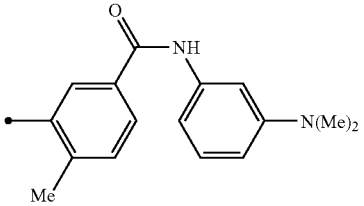
| Example Number | Compound Number | NR¹R² | R³ | R⁴ | R⁵ |
|---|---|---|---|---|---|
| 324 | 324 | NHi-Pr | 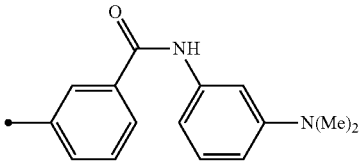 | OH | H |
| 325 | 325 | NHi-Pr | 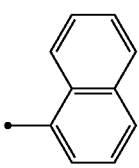 | OH | H |
| 326 | 326 | NHi-Pr | 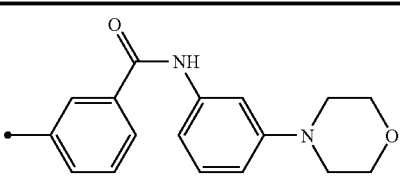 | OH | H |
TABLE 35
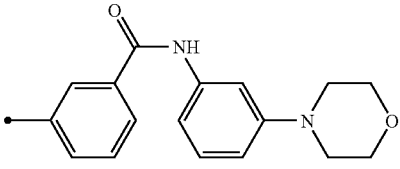
| Example Number | Compound Number | NR¹R² | R³ | R⁴ | R⁵ |
|---|---|---|---|---|---|
| 327 | 327 | NHi-Pr | 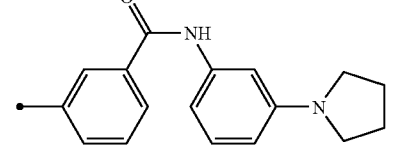 | OCH₂Ph | H |
| 328 | 328 | NHi-Pr | 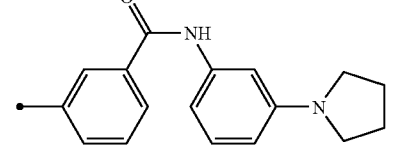 | OH | H |
| 329 | 329 | NHi-Pr | 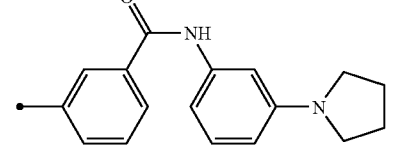 | OCH₂Ph | H |

TABLE 35-continued

![Structure: quinazoline core with R5 at 8-position, R4 at 7, R3 at 6, and NR1R2 at 2-position]

| Example Number | Compound Number | NR¹R² | R³ | R⁴ | R⁵ |
|---|---|---|---|---|---|
| 330 | 330 | NHi-Pr | 3-(3-pyrrolidin-1-yl-phenylcarbamoyl)phenyl | OH | H |
| 331 | 331 | NHi-Pr | 3-fluoro-5-morpholino-N-phenyl-benzamide linker | OCH₂Ph | H |
| 332 | 332 | NHi-Pr | 3-fluoro-5-morpholino-N-phenyl-benzamide linker | OH | H |
| 333 | 333 | NHi-Pr | 3-(cyclopropylcarbamoyl)phenyl | OCH₂Ph | H |
| 334 | 334 | NHi-Pr | 4-(cyclopropylcarbamoyl)phenyl | OH | H |
| 335 | 335 | NHi-Pr | N-phenyl-2-pyrrolidin-1-yl-isonicotinamide linker | OCH₂Ph | H |
| 336 | 336 | NHi-Pr | N-phenyl-2-pyrrolidin-1-yl-isonicotinamide linker | OH | H |

TABLE 36

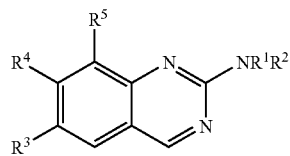

| Example Number | Compound Number | NR¹R² | R³ | R⁴ | R⁵ |
|---|---|---|---|---|---|
| 337 | 337 | NHi-Pr | 3-methyl-4-methylphenyl-C(O)NH-(2-OMe,5-CF₃-phenyl) | OCH₂Ph | H |
| 338 | 338 | NHi-Pr | 3-methyl-4-methylphenyl-C(O)NH-(2-OMe,5-CF₃-phenyl) | OH | H |
| 339 | 339 | NHi-Pr | 3-(NH-C(O)-(3-morpholinophenyl))phenyl | OCH₂Ph | H |
| 340 | 340 | NHi-Pr | 3-(NH-C(O)-(3-morpholinophenyl))phenyl | OH | H |
| 341 | 341 | NHi-Pr | 3-(C(O)NH-(2-morpholinopyridin-4-yl))phenyl | OCH₂Ph | H |
| 342 | 342 | NHi-Pr | 3-(C(O)NH-(2-morpholinopyridin-4-yl))phenyl | OH | H |
| 343 | 343 | NHi-Pr | 3-methyl-4-methyl-5-fluoro-phenyl-C(O)NH-cyclopropyl | OCH₂Ph | H |

TABLE 36-continued

| Example Number | Compound Number | NR¹R² | R³ | R⁴ | R⁵ |
|---|---|---|---|---|---|
| 344 | 344 | NHi-Pr | 3-F, 4-Me-benzamide N-cyclopropyl | OH | H |
| 345 | 345 | NHi-Pr | N-(3-methylphenyl)-2-morpholinopyridine-4-carboxamide | OCH₂Ph | H |
| 346 | 346 | NHi-Pr | N-(3-methylphenyl)-2-morpholinopyridine-4-carboxamide | OH | H |

TABLE 37

| Example Number | Compound Number | NR¹R² | R³ | R⁴ | R⁵ |
|---|---|---|---|---|---|
| 347 | 347 | NHi-Pr | N-(2-OMe, 4-t-Bu, 5-NHSO₂Me-phenyl)-4-methylbenzamide | OCH₂Ph | H |
| 348 | 348 | NHi-Pr | N-(2-OMe, 4-t-Bu, 5-NHSO₂Me-phenyl)-4-methylbenzamide | OH | H |

TABLE 37-continued

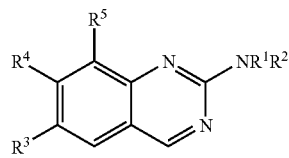

| Example Number | Compound Number | NR¹R² | R³ | R⁴ | R⁵ |
|---|---|---|---|---|---|
| 349 | 349 | NHi-Pr | 3-(2-piperidin-1-yl-pyridine-4-carboxamido)phenyl | OH | H |
| 350 | 350 | NHi-Pr | 3-(3-fluoro-5-pyrrolidin-1-yl-benzamido)phenyl | OCH₂Ph | H |
| 351 | 351 | NHi-Pr | 3-(3-fluoro-5-pyrrolidin-1-yl-benzamido)phenyl | OH | H |
| 352 | 352 | NHi-Pr | 3-CONH(OMe)-4-methylphenyl | OCH₂Ph | H |
| 353 | 353 | NHi-Pr | 3-CONH(OMe)-4-methylphenyl | OH | H |
| 354 | 354 | NHi-Pr | 3-(2-(4-fluorophenyl)pyridine-4-carboxamido)phenyl | OCH₂Ph | H |
| 355 | 355 | NHi-Pr | 3-(2-(4-fluorophenyl)pyridine-4-carboxamido)phenyl | OH | H |

TABLE 37-continued
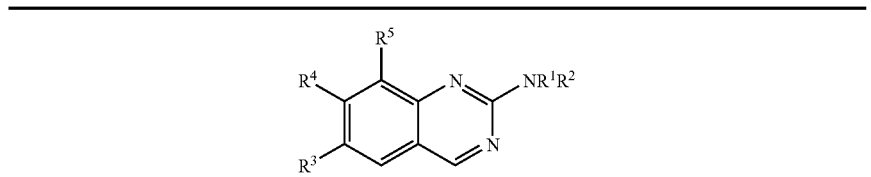
| Example Number | Compound Number | NR¹R² | R³ | R⁴ | R⁵ |
|---|---|---|---|---|---|
| 356 | 356 | NHi-Pr | ![structure] | Me | OCH₂Ph | H |
TABLE 38
| Example Number | Compound Number | NR¹R² | R³ | R⁴ | R⁵ |
|---|---|---|---|---|---|
| 357 | 357 | NHi-Pr | ![structure] | Me | OH | H |
| 358 | 358 | NHi-Pr | ![structure] | Me | OCH₂Ph | H |
| 359 | 359 | NHi-Pr | ![structure] | Me | OH | H |

TABLE 38-continued

[Structure: quinazoline core with R5 at position 8, R4 at position 7, R3 at position 6, and NR¹R² at position 2]

| Example Number | Compound Number | NR¹R² | R³ | R⁴ | R⁵ |
|---|---|---|---|---|---|
| 360 | 360 | HN–CH(Me)–CH₂Me (S) | 3-(N-cyclopropylcarbamoyl)-4-methylphenyl | OCH₂Ph | H |
| 361 | 361 | HN–CH(Me)–CH₂Me (S) | 3-(N-cyclopropylcarbamoyl)-4-methylphenyl | OH | H |
| 362 | 362 | HN–CH(Me)–CH₂Me (S) | 3-[(2-morpholinopyridin-4-yl)carbonylamino]phenyl | OCH₂Ph | H |
| 363 | 363 | HN–CH(Me)–CH₂Me (S) | 3-[(2-morpholinopyridin-4-yl)carbonylamino]phenyl | OH | H |
| 364 | 364 | HNCH(Et)₂ | 3-(N-cyclopropylcarbamoyl)-4-methylphenyl | OCH₂Ph | H |
| 365 | 365 | HNCH(Et)₂ | 3-(N-cyclopropylcarbamoyl)-4-methylphenyl | OH | H |

TABLE 38-continued

[Structure: quinazoline core with R⁵ at 8-position, R⁴ at 7-position, R³ at 6-position, and NR¹R² at 2-position]

| Example Number | Compound Number | NR¹R² | R³ | R⁴ | R⁵ |
|---|---|---|---|---|---|
| 366 | 366 | HNCH(Et)₂ | 3-(3-(NMe₂)benzamido)phenyl | OH | H |

TABLE 39

[Structure: quinazoline core with R⁵ at 8-position, R⁴ at 7-position, R³ at 6-position, and NR¹R² at 2-position]

| Example Number | Compound Number | NR¹R² | R³ | R⁴ | R⁵ |
|---|---|---|---|---|---|
| 367 | 367 | HNCH(Et)₂ | 3-(2-morpholinoisonicotinamido)phenyl | OCH₂Ph | H |
| 368 | 368 | HNCH(Et)₂ | 3-(2-morpholinoisonicotinamido)phenyl | OH | H |
| 369 | 369 | NHi-Pr | 3-(3-fluoro-5-piperidinobenzamido)phenyl | OCH₂Ph | H |
| 370 | 370 | NHi-Pr | 3-(3-fluoro-5-piperidinobenzamido)phenyl | OH | H |

TABLE 39-continued
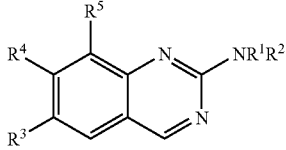
| Example Number | Compound Number | NR¹R² | R³ | R⁴ | R⁵ |
|---|---|---|---|---|---|
| 371 | 371 | NHi-Pr | 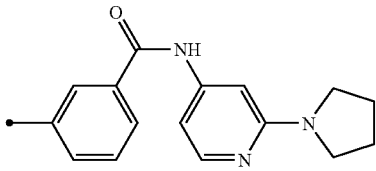 | OCH₂Ph | H |
| 372 | 372 | NHi-Pr | 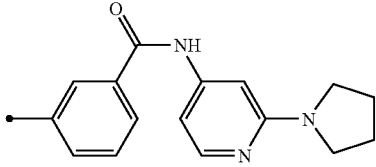 | OH | H |
| 373 | 373 | NHi-Pr | 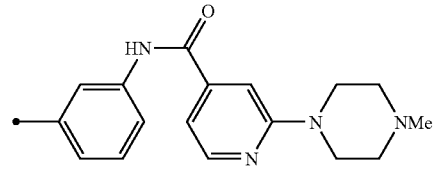 | OCH₂Ph | H |
| 374 | 374 | NHi-Pr | 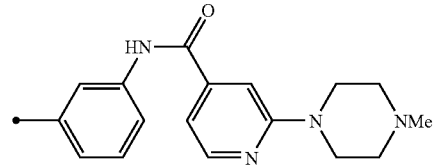 | OH | H |
| 375 | 375 | NHi-Pr | 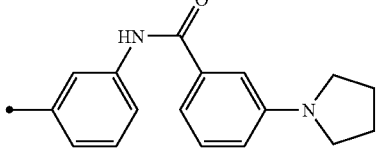 | OCH₂Ph | H |
| 376 | 376 | NHi-Pr | 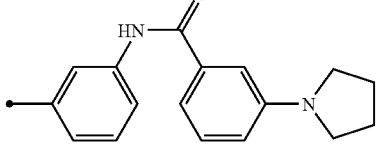 | OH | H |

TABLE 40
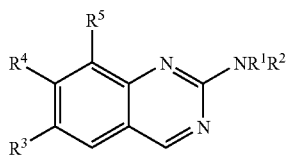
| Example Number | Compound Number | NR¹R² | R³ | R⁴ | R⁵ |
|---|---|---|---|---|---|
| 377 | 377 | NHi-Pr | 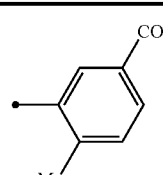 | OCH₂Ph | H |
| 378 | 378 | NHi-Pr | 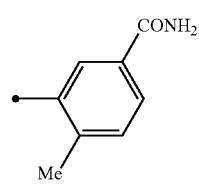 | OH | H |
| 379 | 379 | NHi-Pr | 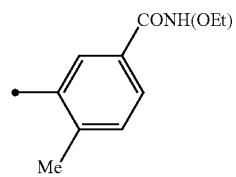 | OCH₂Ph | H |
| 380 | 380 | NHi-Pr | 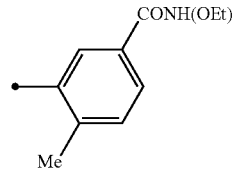 | OH | H |
| 381 | 381 | HNCH(Et)₂ | 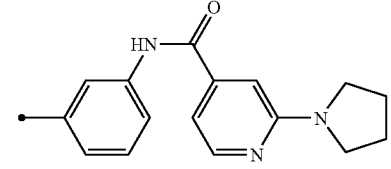 | OCH₂Ph | H |
| 382 | 382 | HNCH(Et)₂ | 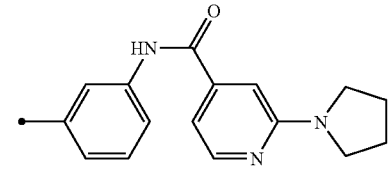 | OH | H |
| 383 | 383 | 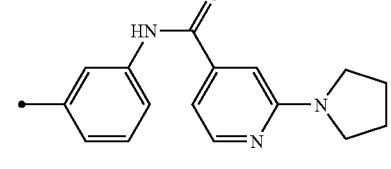 | | OCH₂Ph | H |

TABLE 40-continued

| Example Number | Compound Number | NR¹R² | R³ | R⁴ | R⁵ |
|---|---|---|---|---|---|
| 384 | 384 | (S)-sec-butylamino (HN-CH(Me)-CH₂Me) | 3-[(2-pyrrolidin-1-yl-pyridine-4-carbonyl)amino]phenyl | OH | H |
| 385 | 385 | NHi-Pr | 3-[(3-piperidin-1-yl-benzoyl)amino]phenyl | OCH₂Ph | H |
| 386 | 386 | NHi-Pr | 3-[(3-piperidin-1-yl-benzoyl)amino]phenyl | OH | H |

TABLE 41

| Example Number | Compound Number | NR¹R² | R³ | R⁴ | R⁵ |
|---|---|---|---|---|---|
| 387 | 387 | NHi-Pr | 3-{[2-(4-fluoro-2-methylphenyl)pyridine-4-carbonyl]amino}phenyl | OCH₂Ph | H |
| 388 | 388 | NHi-Pr | 3-{[2-(4-fluoro-2-methylphenyl)pyridine-4-carbonyl]amino}phenyl | OH | H |
| 389 | 389 | NHi-Pr | 3-[(2-piperidin-1-yl-pyridine-4-carbonyl)amino]phenyl | 3-hydroxyphenyl | H |

TABLE 41-continued

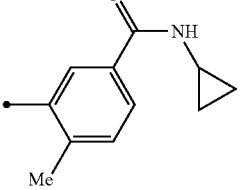

| Example Number | Compound Number | NR¹R² | R³ | R⁴ | R⁵ |
|---|---|---|---|---|---|
| 390 | 390 | NHi-Pr | 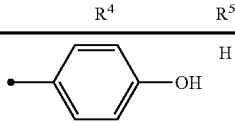 | 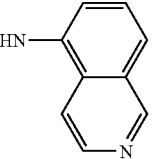 | H |
| 391 | 391 | 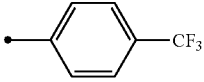 | 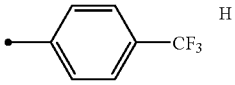 | 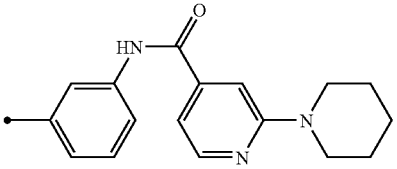 | H |
| 392 | 392 | NHi-Pr | 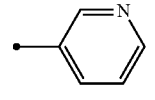 | (pyridyl) | H |

The pharmacological actions of the representative compound (I) will now be specifically described by experimental examples.

EXPERIMENTAL EXAMPLE p38MAP Kinase Inhibition Test

Activated human p38α was purchased from Upstate Biotechnology Inc. (Catalog No. 14-251). P38MAP kinase inhibitory activity was measured by the procedure described below with reference to the method by Whitmarsh A. J. and Davis R. J. [Methods in Enzymology (Method. Enzymol.), vol. 332, p. 319-336 (2001)]. As the substrate to be phosphorylated, a myelin basic protein (Catalog No. 133-13493, Wako Pure Chemical Industries, Ltd.) (20 μg/assay) was used. The reaction was carried out in a solution containing 3-[N-Morpholino]propanesulfonic acid (MOPS) (20 mmol/L, pH 7.2), β-glycerophosphoric acid (Sigma Corp.) (25 mmol/L), ethylenebis(oxyethylenenitrilo)tetraacetic acid (EGTA) (1 mmol/L), NaVO₄ (Sigma-Aldrich Corp.) (1 mmol/L), dithiothreitol (DTT, Wako Pure Chemical Industries, Ltd.) (1 mmol/L), adenosine 5'-triphosphate (ATP, Sigma Corp.) (20 μmol/L), and MgCl$_2$ (18.75 mmol/L) (total 40 μL/assay). The reaction was started by adding human p38α and [γ-$^{32}$P]ATP (1 μCi/assay), and incubation was performed at 30° C. for 15 minutes. The reaction was terminated by adding 4.5% v/v phosphoric acid (10 μL/well). Then, 45 μL of the reaction mixture was adsorbed onto phosphocellulose paper (p81 paper, Code No. 3698023, Whatman International, Maidstone, UK). The phosphocellulose paper was washed with 0.75% v/v phosphoric acid. Then, the radioactivity of the phosphorylated myelin basic protein ($[^{32}P]$) remaining on the phosphocellulose paper was measured with a scintillation counter (TRI-CARB2700TR, PerkinElmer, Boston, Mass., USA) using program No. 27 (data mode: cpm, measurement time: 1 min, Background substract: none, energy range measured: LL 0.0-UL 2000) or a scintillation counter (LS6500, BeckmanCoulter, Fullerton, Calif., USA) using program No. 17 (data mode: cpm, measurement time: 1 min, Background substract: none, energy range measured: high). The test compound was dissolved in DMSO before addition.

In this test, Compounds 3-17, 19-44, 47, 50, 52-63, 66-69, 71-74, 76-82, 84, 86-88, 91-96, 98-100, 102, 109-114, 116-123, 125-127, 129, 131, 132, 134-149, 151-153, 155-180, 182, 183, 185-188, 190-193, 195-197, 199, 201-204, 206-217, 219-225, 227-234, 236-245, 247, 249-268, 270-282, 285, 287, 289-303, 305, 307, 312, 314, 317, 319, 320, 322, 324-326, 328, 330, 332, 334, 336, 338, 340, 342, 344, 346, 348, 349, 351, 353, 355, 357, 359, 361, 363, 365, 366, and 368 showed enzyme inhibitory activity of 50% or higher at a concentration of 1 μmol/L.

Compounds (I), (IA), (IB), (IC), (ID) and (IE), or pharmaceutically acceptable salts thereof can be administered alone. However, usually, they are preferably provided in various pharmaceutical preparations. Such pharmaceutical preparations are used for animals and humans.

The pharmaceutical preparations according to the present invention may contain compound selected from Compound (I), (IA), (IB), (IC), (ID), and (IE), or a pharmaceutically acceptable salt thereof alone as an active ingredient, or as a mixture with any other effective ingredient. Furthermore, these pharmaceutical preparations are prepared by mixing the active ingredient with one or more pharmaceutically acceptable carriers and then subjecting the mixture to any method well-known in the technical field of pharmaceutics.

As for the administration route, it is preferable to select the most effective route of administration. Examples of the administration route include oral administration and parenteral administration such as intravenous administration.

Examples of the dosage form include tablets, powders, granules, syrups, injections, and the like.

With respect to preparations suitable for oral administration, for example, liquid preparations, such as syrups, can be prepared using water; saccharides such as sucrose, sorbitol, and fructose; glycols such as polyethylene glycol, and propylene glycol; oils such as sesame oil, olive oil, and soybean oil; antiseptics such as p-hydroxybenzoic acid esters; and flavors such as strawberry flavor, and peppermint. Tablets, powders, granules, and the like can be prepared using excipients such as lactose, glucose, sucrose, and mannitol; disintegrators such as starch and sodium alginate; lubricants such as magnesium stearate and talc; binders such as polyvinyl alcohol, hydroxypropyl cellulose, and gelatin; surfactants such as fatty acid esters; and plasticizers such as glycerin.

Preparations suitable for parenteral administration are made of a sterilized aqueous solution containing an active compound which is preferably isotonic with the blood of the recipient. For example, in the case of an injection, a solution for injection is prepared using a carrier such as a salt solution, a glucose solution, or a mixture of a brine and a glucose solution, etc.

In such parenteral preparations, one or more auxiliary components selected from the antiseptics, flavors, excipients, disintegrators, lubricants, binders, surfactants, plasticizers, and the like which are exemplified in the oral administration may be added.

The dosage and the dosage frequency of each of Compounds (I), (IA), (IB), (IC), (ID) and (IE), or a pharmaceutically acceptable salt thereof may vary depending upon dosage form, age and body weight of a patient, nature or seriousness of the symptom to be treated, and the like. In oral administration, in general, a dose of 0.01 mg to 1 g, preferably, 0.05 to 50 mg, is administered to an adult patient once or several times a day. In parenteral administration, such as intravenous administration, a dose of 0.001 to 100 mg, preferably, 0.01 to 10 mg, is administered to an adult patient once or several times a day. However, these dosages and dosage frequencies vary depending on the various conditions described above.

The embodiments of the present invention will be explained in the following Examples and Reference Examples. However, the scope of the present invention is not limited to them.

Reference Example 1

5-Bromo-2-fluoro-4-methoxybenzaldehyde

Compound A1

Potassium bromide (193 g, 1.62 mol) and bromine (33.0 mL, 649 mmol) were dissolved in water (1000 mL), and the solution was added with 2-fluoro-4-methoxybenzaldehyde (50.0 g, 324 mmol) under ice-cooling, followed by stirring at room temperature for 3 hours. The reaction mixture was added with water and the obtained crystals were collected by filtration to obtain Compound A1 (72.2 g, 95%).

$^1$H NMR (300 MHz, CDCl$_3$) δ (ppm) 3.98 (s, 3H), 6.78 (d, J=11.7 Hz, 1H), 8.06 (d, J=7.7 Hz, 1H), 10.17 (s, 1H).

Reference Example 2

2-Amino-6-bromo-7-methoxyquinazoline

Compound A2

Compound A1 (20.0 g, 85.8 mmol) was dissolved in DMA (300 mL) and the solution was added with guanidine carbonate (30.9 g, 172 mmol), followed by stirring at 140° C. for 2 hours. After adding ice water to the reaction mixture, the obtained crystal was collected by filtration to obtain Compound A2 (16.4 g, 75%).

$^1$H NMR (300 MHz, DMSO-d$_6$) δ (ppm) 4.00 (s, 3H), 5.24 (br s, 2H), 6.92 (s, 1H), 7.88 (s, 1H), 8.82 (s, 1H).

Reference Example 3

6-Bromo-2-iodo-7-methoxyquinazoline

Compound A3

Compound A2 (16.0 g, 65.3 mmol) was dissolved in THF (330 mL) and the solution was added with diiodomethane (53.0 mL, 658 mmol), isoamyl nitrite (26.3 mL, 196 mmol) and copper iodide (3.73 g, 19.6 mmol), followed by stirring at 60° C. for 8 hours. After removing the insoluble matter from the reaction mixture, the solvent was evaporated under reduced pressure. The residue was added with hexane and the obtained crystal was collected by filtration to obtain Compound A3 (13.7 g, 57%).

$^1$H NMR (300 MHz, DMSO-d$_6$) δ (ppm) 4.06 (s, 3H), 7.48 (s, 1H), 8.50 (s, 1H), 9.13 (s, 1H).

Reference Example 4

6-Bromo-2-isopropylamino-7-methoxyquinazoline

Compound A4

Compound A3 (6.84 g, 18.8 mmol) was dissolved in THF (140 mL) and the solution was added with triethylamine (7.80 mL, 56.3 mmol) and isopropylamine (16.9 mL, 188 mmol), followed by stirring at room temperature overnight. The reaction mixture was added with ethyl acetate and hydrochloric acid and the obtained crystal was collected by filtration. The filtrate was concentrated under reduced pressure and added with water. The obtained crystal was collected by filtration and the obtained crystals were combined and purified by silica gel column chromatography (ethyl acetate/hexane=1/4) to obtain Compound A4 (2.23 g, 40%).

$^1$H NMR (300 MHz, DMSO-d$_6$) δ (ppm) 1.19 (d, J=6.6 Hz, 6H), 3.96 (s, 3H), 4.11-4.23 (m, 1H), 6.93 (s, 1H), 7.27 (br s, 1H), 8.05 (s, 1H), 8.90 (s, 1H).

Reference Example 5

2-Morpholinoisonicotinic acid

Compound A5

Step 1

2-Chloroisonicotinic acid (300 mg, 1.91 mmol), potassium carbonate (790 mg, 5.72 mmol) and methyl iodide (360 µL, 5.72 mmol) was dissolved in DMF (4.5 mL) and the solution was stirred at room temperature for 4 hours. The reaction mixture was added with saturated brine and ethyl acetate, and the organic layer was separated, followed by washing with saturated brine. The organic layer was dried over anhydrous magnesium sulfate and the solvent was evaporated under reduced pressure to obtain methyl 2-chloroisonicotinate (320 mg, 98%).

$^1$H NMR (300 MHz, CDCl$_3$) δ (ppm) 3.98 (s, 3H), 7.77 (d, J=4.8 Hz, 1H), 7.89 (s, 1H), 8.55 (d, J=6.4 Hz, 1H).

Step 2

Methyl 2-chloroisonicotinate (320 mg, 1.89 mmol) was dissolved in morpholine (5 mL) and stirred at 90° C. for 4 hours. The reaction mixture was added with saturated brine and ethyl acetate, and the organic layer was separated, followed by washing with saturated brine. The organic layer was dried over anhydrous magnesium sulfate and the solvent was evaporated under reduced pressure. The residue was purified by silica gel column chromatography (ethyl acetate/hexane=1/4) to obtain methyl 2-morpholinoisonicotinate (50 mg, 98%).

$^1$H NMR (300 MHz, CDCl$_3$) δ (ppm) 3.55-3.58 (m, 4H), 3.82-3.85 (m, 4H), 3.93 (s, 3H), 7.16 (d, J=4.8 Hz, 1H), 7.18 (s, 1H), 8.30 (d, J=6.4 Hz, 1H).

Step 3

Methyl 2-morpholinoisonicotinate (462 mg, 2.08 mmol) was dissolved in methanol (6 mL) and the solution was added with 3 mol/L aqueous sodium hydroxide solution (2.1 mL, 6.2 mmol), followed by stirring at room temperature for 30 minutes. The reaction mixture was added with 1 mol/L hydrochloric acid to adjust the pH to 7, then the mixture was added with water and chloroform and the organic layer was separated, followed by washing with water. The organic layer was dried over anhydrous magnesium sulfate and the solvent was evaporated under reduced pressure to obtain Compound A5 (110 mg, 23%).

$^1$H NMR (300 MHz, CDCl$_3$) δ (ppm) 3.58-3.63 (m, 4H), 3.88-3.93 (m, 4H), 6.90 (d, J=4.8 Hz, 1H), 7.15 (s, 1H), 8.29 (d, J=6.4 Hz, 1H).

Reference Example 6

5-Benzoyl-2-fluoro-4-methoxybenzaldehyde

Compound A6

Step 1

5-Bromo-2-fluoro-4-methoxybenzaldehyde (1 g, 4.3 mmol), p-toluenesulfonic acid monohydrate (163 mg, 0.86 mmol) and trimethyl orthoformate (2.4 mL, 21 mmol) were dissolved in methanol (20 mL) and stirred under heating and reflux for 1 hour. After standing to cool the reaction mixture, triethylamine (2 mL) was added thereto and further stirred for 10 minutes. The mixture was added with saturated brine and ethyl acetate, and the organic layer was separated, followed by washing with saturated brine. The organic layer was dried over anhydrous magnesium sulfate and the solvent was evaporated under reduced pressure to obtain 5-bromo-2-fluoro-4-methoxybenzaldehyde dimethylacetal (1.19 g, 100%).

$^1$H NMR (300 MHz, CDCl$_3$) δ (ppm) 3.37 (s, 6H), 3.77 (s, 3H), 5.61 (s, 1H), 6.69 (d, J=11.7 Hz, 1H), 7.37 (d, J=8.4 Hz, 1H).

Step 2

5-Bromo-2-fluoro-4-methoxybenzaldehyde dimethylacetal (5 g, 18 mmol) was dissolved in THF (70 mL) and stirred at −70° C. for 20 minutes. The solution was added with n-butyllithium (1.53 mol/L hexane solution, 15 mL, 23 mmol) at −70° C. and further stirred for 10 minutes. At −70° C., a solution of N,N-dimethylbenzamide (8 g, 53 mmol) in THF (20 mL) was added dropwise to the reaction mixture and further stirred for 20 minutes. The reaction mixture was added with water and ethyl acetate, and the organic layer was separated, followed by washing with saturated brine. The organic layer was dried over anhydrous magnesium sulfate and then the solvent was evaporated under reduced pressure to obtain a syrupy residue. The residue was dissolved in acetone (20 mL) and the solution was added with p-toluene sulfonic acid monohydrate (1.7 g, 8.9 mmol), followed by stirring at room temperature for 30 minutes. The mixture was added with saturated aqueous sodium hydrogencarbonate solution and ethyl acetate, and the organic layer was separated, followed by washing with saturated aqueous sodium hydrogencarbonate solution and saturated brine. The organic layer was dried over anhydrous magnesium sulfate and the solvent was evaporated under reduced pressure. The residue was purified by silica gel column chromatography (ethyl acetate/hexane=1/4) to obtain Compound A6 (1.6 g, 35%).

$^1$H NMR (270 MHz, CDCl$_3$) δ (ppm) 3.84 (s, 3H), 6.76 (d, J=12.2 Hz, 1H), 7.43-7.48 (m, 2H), 7.56-7.62 (m, 1H), 7.75-7.78 (m, 2H), 7.91 (d, J=8.1 Hz, 1H), 10.2 (s, 1H).

Reference Example 7

2-Isopropylamino-7-methoxy-6-(4,4,5,5-tetramethyl-1,3,2-dioxaborolan-2-yl)quinazoline Compound A7

Compound A4 (600 mg, 2.02 mmol) was dissolved in dioxane (7 mL) and the solution was added with bis(pinacolate)diboron (564 mg, 2.22 mmol), [1,1'-bis(diphenylphosphino)ferrocene]dichloropalladium (132 mg, 0.16 mmol) and potassium acetate (892 mg, 9.09 mmol), followed by stirring at 100° C. for 1 hour. The reaction mixture was added with water and extracted with ethyl acetate. Then, the organic layer was washed with saturated brine and dried over anhydrous magnesium sulfate. The solvent was evaporated under reduced pressure to obtain Compound A7 (424 mg, 49%) as a crude product.

$^1$H NMR (300 MHz, CDCl$_3$) δ (ppm) 1.22-1.40 (m, 18H), 3.94 (s, 3H), 4.21-4.39 (m, 1H), 5.49 (br s, 1H), 6.82 (s, 1H), 8.01 (s, 1H), 8.79 (s, 1H).

Reference Example 8

2-Amino-6-bromoquinazoline

Compound A8

In a similar manner to Reference Example 2, Compound A8 was obtained using 5-bromo-2-fluorobenzaldehyde.

$^1$H NMR (300 MHz, CDCl$_3$) δ (ppm) 5.27 (s, 2H), 7.46 (d, J=9.0 Hz, 1H), 7.76 (dd, J=9.0, 2.1 Hz, 1H), 7.85 (d, J=2.1 Hz, 1H), 8.96 (s, 1H).

Reference Example 9

6-Bromo-2-iodoquinazoline

Compound A9

In a similar manner to Reference Example 3, Compound A9 was obtained using Compound A8.

¹H NMR (270 MHz, CDCl₃) δ (ppm) 7.86 (d, J=9.2 Hz, 1H), 7.99 (dd, J=9.2, 1.9 Hz, 1H), 8.08 (d, J=1.9 Hz, 1H), 9.03 (s, 1H).

Reference Example 10

6-Bromo-2-(isopropylamino)quinazoline

Compound A10

In a similar manner to Reference Example 4, Compound A10 was obtained using Compound A9.
¹H NMR (270 MHz, CDCl₃) δ (ppm) 1.29 (d, J=6.2 Hz, 6H), 4.19-4.37 (m, 1H), 5.15 (d, J=6.8 Hz, 1H), 7.44 (d, J=8.9 Hz, 1H), 7.70 (dd, J=8.9, 2.4 Hz, 1H), 7.77 (d, J=2.4 Hz, 1H), 8.87 (s, 1H).

Reference Example 11

6-Bromo-2-isopropylamino-7-methylquinazoline

Compound A11

Diisopropylamine (2.5 mL, 19.1 mmol) was dissolved in THF (24 mL) and the solution was cooled to −70° C., then the solution was added with n-butyllithium (1.57 mol/L hexane solution, 12 mL, 19.1 mmol), followed by stirring for 10 minutes. After warmed to room temperature, the mixture was cooled to −70° C. again and a solution of 2-methyl-4-fluoro-bromobenzene (3.0 g, 15.9 mmol) in THF (4 mL) was added dropwise thereto. After stirring for 15 minutes, the mixture was added with DMF (1.9 mL, 23.8 mmol) and warmed to 0° C., followed by stirring for 20 minutes. The reaction mixture was added with saturated aqueous ammonium chloride solution and extracted with ethyl acetate. The organic layer was washed with saturated brine and dried over anhydrous magnesium sulfate. The solvent was evaporated under reduced pressure to obtain 5-bromo-2-fluoro-4-methylbenzaldehyde as a crude product. In a similar manner to Reference Example 2, 2-amino-6-bromo-7-methylquinazoline (2.0 g, 50%) was obtained using the above-obtained 5-bromo-2-fluoro-4-methylbenzaldehyde. In a similar manner to Reference Example 3 and Reference Example 4, Compound A11 was obtained using the above-obtained 2-amino-6-bromo-7-methylquinazoline.
¹H NMR (300 MHz, CDCl₃) δ (ppm) 1.29 (d, J=6.6 Hz, 6H), 2.51 (s, 3H), 4.20-4.34 (m, 1H), 5.24 (d, J=6.9 Hz, 1H), 7.46 (s, 1H), 7.81 (s, 1H), 8.85 (s, 1H).

Reference Example 12

5-Bromo-2-fluoro-4-hydroxybenzaldehyde

Compound A12

Compound A1 (35.0 g, 150.4 mmol) was dissolved in DMF (250 mL) and the solution was added with lithium chloride (19.1 g, 451 mmol), followed by stirring at 140° C. for 3 hours. The reaction mixture was added with water and extracted with ethyl acetate. The aqueous layer was added with 2 mol/L hydrochloric acid to adjust the pH to about 4. The aqueous layer was extracted with ethyl acetate and the organic layer was washed with water and saturated brine, dried over anhydrous magnesium sulfate. The solvent was evaporated under reduced pressure to obtain Compound A12 (27.1 g, 82%).

¹H NMR (300 MHz, CDCl₃) δ (ppm) 6.85 (d, J=11.4 Hz, 1H), 7.42 (br s, 1H), 8.03 (d, J=6.9 Hz, 1H), 10.15 (s, 1H).

Reference Example 13

4-Benzyloxy-5-bromo-2-fluorobenzaldehyde

Compound A13

Compound A12 (13.5 g, 62 mmol) was dissolved in DMF (123 mL) and the solution was added with potassium carbonate (17.1 g, 124 mmol) and benzyl bromide (11 mL, 93 mmol), followed by stirring at room temperature for 2 hours. The reaction mixture was added with water and extracted with ethyl acetate. The organic layer was washed with water and saturated brine and dried over anhydrous magnesium sulfate. The solvent was evaporated under reduced pressure and the residue was reslurried with hexane to obtain Compound A13 (14.8 g, 78%).
¹H NMR (270 MHz, CDCl₃) δ (ppm) 5.22 (s, 2H), 6.72 (d, J=11.9 Hz, 1H), 7.32-7.50 (m, 5H), 8.08 (d, J=7.6 Hz, 1H), 10.15 (s, 1H).

Reference Example 14

7-Benzyloxy-6-bromo-2-aminoquinazoline

Compound A14

In a similar manner to Reference Example 2, Compound A14 was obtained using Compound A13.
¹H NMR (270 MHz, CDCl₃) δ (ppm) 5.13 (br s, 2H), 5.26 (s, 2H), 6.98 (s, 1H), 7.27-7.53 (m, 5H), 7.92 (s, 1H), 8.82 (s, 1H).

Reference Example 15

7-Benzyloxy-6-bromo-2-isopropylaminoquinazoline

Compound A15

Synthetic Method 1
In a similar manner to Reference Example 3 and Reference Example 4, Compound A15 was obtained using Compound A14.
Synthetic Method 2
Compound A14 (5.0 g, 15.1 mmol) was dissolved in DMF (150 mL), and the solution was cooled to 5° C., then was added with sodium hydride (60% in oil, 1.81 g, 41.5 mmol) under argon atmosphere, followed by stirring for 30 minutes. The reaction mixture was added with isopropyl iodide (3.02 mL, 30.2 mmol) and was stirred at 60° C. for 1.5 hours. After cooling to 0° C., the reaction mixture was added with sodium hydride (60% in oil, 1.81 g, 41.5 mmol) and stirred at room temperature for 30 minutes, followed by adding isopropyl iodide (3.02 mL, 30.2 mmol) and stirring at 60° C. for 1 hour. After repeating the same procedure, the reaction mixture was poured into ice-water (30 mL) and stirred at room temperature. The precipitated solid was collected by filtration to obtain Compound A15 (7.02 g, 100%).
¹H NMR (270 MHz, CDCl₃) δ (ppm) 1.29 (d, J=6.5 Hz, 6H), 4.18-4.33 (m, 1H), 5.00-5.20 (m, 1H), 5.25 (s, 2H), 6.99 (s, 1H), 7.30-7.57 (m, 5H), 7.85 (s, 1H), 8.77 (br s, 1H)
ESI m/z (M+H)⁺ 372. .

Reference Example 16

7-Benzyloxy-2-isopropylamino-6-(4,4,5,5-tetramethyl-1,3,2-dioxaborolan-2-yl)quinazoline Compound A16

In a similar manner to Reference Example 7, Compound A16 was obtained using Compound A15.
$^1$H NMR (270 MHz, CDCl$_3$) δ (ppm) 1.21-1.39 (m, 18H), 4.23-4.38 (m, 1H), 5.23 (s, 2H), 6.92 (s, 1H), 7.30-7.34 (m, 1H), 7.34-7.41 (m, 2H), 7.62-7.68 (m, 2H), 8.04 (s, 1H), 8.81 (s, 1H).

Reference Example 17

2-(4-Fluorophenyl)-N-[3-(4,4,5,5-tetramethyl-1,3,2-dioxaborolan-2-yl)phenyl]isonicotinamide Compound A17

Step 1

Methyl 2-chloroisonicotinate (300 mg, 1.75 mmol) obtained in Step 1 of Reference Example 5 was dissolved in toluene (3.5 mL), and the solution was added with palladium acetate (11.8 mg, 0.0525 mmol), 2,2'-bis(diphenylphosphino)-2,2'-binaphthyl (49.1 mg, 0.0788 mmol), cesium carbonate (798 mg, 2.45 mmol) and 4-fluorophenylboronic acid (294 mg, 2.10 mmol), followed by stirring at 100° C. for 1 hour under argon atmosphere. After an insoluble matter of the reaction mixture was filtered off, the solvent was evaporated under reduced pressure. The residue was purified by silica gel column chromatography (ethyl acetate/hexane=5/95 to 10/90) to obtain Methyl 2-(4-fluorophenyl)isonicotinate (284 mg, 70%).
$^1$H NMR (300 MHz, CDCl$_3$) δ (ppm) 3.99 (s, 3H), 7.15-7.21 (m, 1H), 7.77 (dd, J=5.0, 1.5 Hz, 1H), 8.02-8.08 (m, 2H), 8.25 (dd, J=1.5, 0.9 Hz, 1H), 8.82 (dd, J=5.0, 0.9 Hz, 1H).

Step 2

Methyl 2-(4-fluorophenyl)isonicotinate (278 mg, 1.20 mmol) was dissolved in methanol (2 mL) and the solution was added with 2 mol/L aqueous sodium hydroxide solution (2 mL, 4.0 mmol), followed by stirring at room temperature overnight. The solvent was evaporated under reduced pressure and the obtained reaction mixture was dissolved in water. The solution was washed with ethyl acetate, then was added with 1 mol/L hydrochloric acid, and the obtained crystal was collected by filtration to obtain 2-(4-fluorophenyl)isonicotinic acid (134 mg, 51%).

The obtained 2-(4-fluorophenyl)isonicotinic acid (126 mg, 0.582 mmol) was dissolved in DMF (2 mL) and the solution was added with 1-ethyl-3-(3-dimethylaminopropyl)carbodiimide hydrochloride (134 mg, 0.698 mmol), 1-hydroxybenzotriazole (89.0 mg, 0.582 mmol), and 3-(4,4,5,5-tetramethyl-1,3,2-dioxaborolan-2-yl)aniline (153 mg, 0.698 mmol), followed by stirring at room temperature for 1.5 hours and then at 50° C. for 3 hours. The reaction mixture was added with water, extracted with ethyl acetate, and the organic layer was washed with saturated aqueous sodium hydrogencarbonate solution, followed by drying over anhydrous sodium sulfate. The solvent was evaporated under reduced pressure to obtain Compound A17 (202 mg, 83%).
$^1$H NMR (300 MHz, CDCl$_3$) δ (ppm) 1.36 (s, 12H), 7.17-7.23 (m, 2H), 7.44 (dd, J=7.9, 7.4 Hz, 1H), 7.57 (dd, J=5.0, 1.7 Hz, 1H), 7.63-7.66 (m, 1H), 7.79 (d, J=1.7 Hz, 1H), 7.89 (br s, 1H), 8.04-8.12 (m, 4H), 8.84 (d, J=5.0 Hz, 1H).

Reference Example 18

N-(3-morpholinophenyl)-3-(4,4,5,5-tetramethyl-1,3,2-dioxaborolan-2-yl)benzamide

Compound A18

In a similar manner to Step 2 of Reference Example 17, Compound A18 was obtained by amidation using 3-morpholinoaniline and 3-(4,4,5,5-tetramethyl-1,3,2-dioxaborolan-2-yl)benzoic acid.
$^1$H NMR (300 MHz, CDCl$_3$) δ (ppm) 1.38 (s, 12H), 3.22 (t, J=4.8 Hz, 4H), 3.87 (t, J=4.8 Hz, 4H), 6.68-6.74 (m, 1H), 6.95-7.02 (m, 1H), 7.21-7.30 (m, 1H), 7.48-7.57 (m, 2H), 7.84 (br s, 1H), 7.95-8.02 (m, 1H), 8.04-8.10 (m, 1H), 8.20 (br s, 1H).

Reference Example 19

N-[3-(pyrrolidin-1-yl)phenyl]-3-(4,4,5,5-tetramethyl-1,3,2-dioxaborolan-2-yl)benzamide Compound A19

In a similar manner to Step 2 of Reference Example 17, Compound A19 was obtained by amidation using 3-(pyrrolidin-1-yl)aniline and 3-(4,4,5,5-tetramethyl-1,3,2-dioxaborolan-2-yl)benzoic acid.
$^1$H NMR (300 MHz, CDCl$_3$) δ (ppm) 1.38 (s, 12H), 1.97-2.05 (m, 4H), 3.23-3.37 (m, 4H), 6.33-6.40 (m, 1H), 6.78-6.84 (m, 1H), 7.07-7.10 (m, 1H), 7.19 (t, J=8.1 Hz, 1H), 7.51 (t, J=7.8 Hz, 1H), 7.82 (br s, 1H), 7.95-8.00 (m, 1H), 8.03-8.10 (m, 1H), 8.21 (br s, 1H).

Reference Example 20

3-Fluoro-5-morpholino-N-[3-(4,4,5,5-tetramethyl-1,3,2-dioxaborolan-2-yl)phenyl]benzamide Compound A20

In a similar manner to Step 2 of Reference Example 17, Compound A20 was obtained by amidation using 3-fluoro-5-morpholinobenzoic acid (WO04/089929).
$^1$H NMR (270 MHz, CDCl$_3$) δ (ppm) 1.35 (s, 12H), 3.21-3.25 (m, 4H), 3.84-3.88 (m, 4H), 6.69-6.75 (m, 1H), 6.91-6.95 (m, 1H), 7.20 (s, 1H), 7.41 (dd, J=7.9, 7.6 Hz, 1H), 7.58-7.61 (m, 1H), 7.73-7.74 (m, 1H), 7.78 (br d, J=4.4 Hz, 1H), 8.04-8.08 (m, 1H).

Reference Example 21

N-cyclopropyl-3-(4,4,5,5-tetramethyl-1,3,2-dioxaborolan-2-yl)benzamide

Compound A21

In a similar manner to Step 2 of Reference Example 17, Compound A21 was obtained by amidation using cyclopropylamine and 3-(4,4,5,5-tetramethyl-1,3,2-dioxaborolan-2-yl)benzoic acid.

¹H NMR (270 MHz, CDCl₃) δ (ppm) 0.60-0.66 (m, 2H), 0.84-0.91 (m, 2H), 1.36 (s, 12H), 2.86-2.95 (m, 1H), 6.32 (br s, 1H), 7.45 (dd, J=7.4, 7.4 Hz, 1H), 7.92 (d, J=7.4, 1H), 7.96-8.00 (m, 2H).

Reference Example 22

3-Morpholino-N-[3-(4,4,5,5-tetramethyl-1,3,2-dioxaborolan-2-yl)phenyl]benzamide

Compound A22

In a similar manner to Step 2 of Reference Example 17, Compound A22 was obtained by amidation using 3-morpholinobenzoic acid.

¹H NMR (300 MHz, CDCl₃) δ (ppm) 1.35 (s, 12H), 3.22-3.25 (m, 4H), 3.86-3.90 (m, 4H), 7.05-7.09 (m, 1H), 7.13-7.23 (m, 1H), 7.37 (dd, J=8.1, 7.7 Hz, 1H), 7.41 (dd, J=7.9, 7.5 Hz, 1H), 7.46-7.47 (m, 1H), 7.57-7.60 (m, 1H), 7.73-7.74 (m, 1H), 7.83 (br s, 1H), 8.07-8.11 (m, 1H).

Reference Example 23

2-Morpholino-N-[2-methyl-3-(4,4,5,5-tetramethyl-1,3,2-dioxaborolan-2-yl)phenyl]isonicotinamide Compound A23

In a similar manner to Step 2 of Reference Example 17, Compound A23 was obtained by amidation using Compound A5 and 2-methyl-3-(4,4,5,5-tetramethyl-1,3,2-dioxaborolan-2-yl)aniline.

¹H NMR (270 MHz, CDCl₃) δ (ppm) 1.35 (s, 12H), 2.53 (s, 3H), 3.57-3.61 (m, 4H), 3.81-3.85 (m, 4H), 6.90 (dd, J=5.3, 1.0 Hz, 1H), 7.11 (s, 1H), 7.20 (d, J=8.1 Hz, 1H), 7.64 (d, J=2.2 Hz, 1H), 7.78 (s, 1H), 7.95 (dd, J=8.1, 2.2 Hz, 1H), 8.3 (d, J=5.1 Hz, 1H).

Reference Example 24

N-(3-iodophenyl)-2-(piperidino)isonicotinamide

Compound A24

In a similar manner to Step 2 of Reference Example 17, N-(3-iodophenyl)-2-chloroisonicotinamide was obtained by amidation using 2-chloroisonicotinic acid and 3-iodoaniline. In a similar manner to Step 2 of Reference Example 5, Compound A24 was obtained using the above-obtained N-(3-iodophenyl)-2-chloroisonicotinamide and piperidine.

¹H NMR (270 MHz, DMSO-d₆) δ (ppm) 1.55-1.62 (m, 6H), 3.56-3.61 (m, 4H), 6.97-6.99 (m, 1H), 7.14-7.20 (m, 2H), 7.45-7.50 (m, 1H), 7.75-7.76 (m, 1H), 8.20-8.23 (m, 2H), 10.36 (br s, 1H).

Reference Example 25

N-(3-iodophenyl)-2-(pyrrolidin-1-yl)isonicotinamide

Compound A25

In a similar manner to Reference Example 24, Compound A25 was obtained using pyrrolidine.

¹H NMR (270 MHz, CDCl₃) δ (ppm) 2.02-2.07 (m, 4H), 3.49-3.54 (m, 4H), 6.74-6.77 (m, 1H), 6.80 (s, 1H), 7.10 (dd, J=8.1, 7.8 Hz, 1H), 7.51 (ddd, J=7.8, 0.8, 0.7 Hz, 1H), 7.63 (ddd, J=8.1, 1.2, 0.8, 1H), 7.82 (br s, 1H), 8.06-8.07 (m, 1H), 8.26-8.28 (m, 1H).

Reference Example 26

3-Fluoro-5-(pyrrolidin-1-yl)-N-[3-(4,4,5,5-tetramethyl-1,3,2-dioxaborolan-2-yl)phenyl]benzamide Compound A26

In a similar manner to Step 2 of Reference Example 17, Compound A26 was obtained by amidation using 3-fluoro-5-(pyrrolidin-1-yl)benzoic acid (WO06/010082).

¹H NMR (300 MHz, CDCl₃) δ (ppm) 1.35 (s, 12H), 2.02-2.07 (m, 4H), 3.30-3.35 (m, 4H), 6.34-6.39 (m, 1H), 6.69-6.73 (m, 1H), 6.81-6.83 (m, 1H), 7.38-7.43 (m, 1H), 7.57-7.60 (m, 1H), 7.73-7.74 (m, 2H), 8.06-8.10 (m, 1H).

Reference Example 27

N-[3-(4,4,5,5-tetramethyl-1,3,2-dioxaborolan-2-yl)phenyl]-5-(tert-butyl)-2-(4-methylphenyl)-2H-pyrazol-3-ylcarboxamide Compound A27

In a similar manner to Step 2 of Reference Example 17, Compound A27 was obtained using 5-(tert-butyl)-2-(4-methylphenyl)-2H-pyrazole-3-carboxylic acid ethyl ester (WO05/023761) and ethanol.

¹H NMR (270 MHz, CDCl₃) δ (ppm) 1.33 (s, 12H), 1.38 (s, 9H), 2.40 (s, 3H), 6.70 (s, 1H), 7.24-7.43 (m, 6H), 7.51-7.56 (m, 2H), 7.84 (m, 1H).

Reference Example 28

2-Morpholino-N-[3-(4,4,5,5-tetramethyl-1,3,2-dioxaborolan-2-yl)phenyl]isonicotinamide Compound A28

In a similar manner to Step 2 of Reference Example 17, Compound A28 was obtained by amidation using Compound A5.

¹H NMR (300 MHz, CDCl₃) δ (ppm) 1.35 (s, 12H), 3.59-3.62 (m, 4H), 3.82-3.86 (m, 4H), 6.90 (dd, J=5.1, 1.3 Hz, 1H), 7.12 (s, 1H), 7.42 (dd, J=8.1, 7.4 Hz, 1H), 7.60-7.63 (m, 1H), 7.73-7.74 (m, 1H), 7.77 (br s, 1H), 8.06-8.09 (m, 1H), 8.32 (dd, J=5.1, 0.6 Hz, 1H).

Reference Example 29

3-Fluoro-5-piperidino-N-[3-(4,4,5,5-tetramethyl-1,3,2-dioxaborolan-2-yl)phenyl]benzamide Compound A29

In a similar manner to Step 2 of Reference Example 17, Compound A29 was obtained by amidation using 3-fluoro-5-piperidinobenzoic acid (WO06/010082).

¹H NMR (300 MHz, CDCl₃) δ (ppm) 1.35 (s, 12H), 1.60-1.74 (m, 6H), 3.24-3.28 (m, 4H), 6.72 (ddd, J=11.9, 2.4, 2.2 Hz, 1H), 6.83-6.87 (m, 1H), 7.18-7.19 (m, 1H), 7.41 (dd, J=7.9, 7.5 Hz, 1H), 7.59 (ddd, J=7.5, 1.1, 0.9 Hz, 1H), 7.72-7.73 (m, 2H), 8.07 (ddd, J=7.9, 2.2, 0.9 Hz, 1H).

Reference Example 30

2-(4-Methylpiperazin-1-yl)-N-[3-(4,4,5,5-tetramethyl-1,3,2-dioxaborolan-2-yl)phenyl]isonicotinamide Compound A30

In a similar manner to Step 2 of Reference Example 17, Compound A30 was obtained using ethyl 2-(4-methylpiperazin-1-yl)isonicotinate (WO00/50401) and ethanol.
$^1$H NMR (300 MHz, CDCl$_3$) δ (ppm) 1.35 (s, 12H), 2.36 (s, 3H), 2.52-2.55 (m, 4H), 3.64-3.68 (m, 4H), 6.86 (dd, J=5.1, 1.1 Hz, 1H), 7.12 (s, 1H), 7.42 (dd, J=7.9, 7.7 Hz, 1H), 7.60-7.62 (m, 1H), 7.73-7.74 (m, 1H), 7.80 (s, 1H), 8.05-8.08 (m, 1H), 8.30 (d, J=5.1 Hz, 1H).

Reference Example 31

3-Dimethylamino-N-[3-(4,4,5,5-tetramethyl-1,3,2-dioxaborolan-2-yl)phenyl]benzamide Compound A31

In a similar manner to Step 2 of Reference Example 17, Compound A31 was obtained by amidation using 3-(dimethylamino)benzoic acid.
$^1$H NMR (270 MHz, CDCl$_3$) δ (ppm) 1.35 (s, 12H), 3.02 (s, 6H), 6.86-6.90 (m, 1H), 7.05-7.08 (m, 1H), 7.32 (dd, J=8.3, 7.8 Hz, 1H), 7.40 (dd, J=7.8, 7.4 Hz, 1H), 7.56-7.59 (m, 1H), 7.73-7.74 (m, 1H), 7.82 (br s, 1H), 8.09-8.13 (m, 1H).

Reference Example 32

3-(Pyrrolidin-1-yl)-N-[3-(4,4,5,5-tetramethyl-1,3,2-dioxaborolan-2-yl)phenyl]benzamide Compound A32

In a similar manner to Step 2 of Reference Example 17, Compound A32 was obtained by amidation using 3-(pyrrolidin-1-yl)benzoic acid.
$^1$H NMR (270 MHz, CDCl$_3$) δ (ppm) 1.35 (s, 12H), 2.01-2.06 (m, 4H), 3.32-3.37 (m, 4H), 6.71 (dd, 8.6, 1.9 Hz, 1H), 7.01 (d, J=7.8 Hz, 1H), 7.07-7.08 (m, 1H), 7.31 (d, J=8.1 Hz, 1H), 7.37-7.43 (m, 1H), 7.56-7.59 (m, 1H), 7.74-7.75 (m, 1H), 7.83 (br s, 1H), 8.09-8.12 (m, 1H).

Reference Example 33

(5-Methoxycarbamoyl-2-methyl)iodobenzene

Compound A33

3-Iodo-4-methylbenzoic acid (750 mg, 2.80 mmol) was dissolved in DMF (4.7 mL) and the solution was added with 1-ethyl-3-(3-dimethylaminopropyl)carbodiimide hydrochloride (590 mg, 3.08 mmol) and 1-hydroxybenzotriazole (470 mg, 3.08 mmol), followed by stirring at room temperature for 0.5 hours. Then, the mixture was added with methoxyamine hydrochloride (257 mg, 3.08 mmol) and stirred at room temperature for 10 minutes. The reaction mixture was ice-cooled and added with N,N-diisopropylethylamine (1.1 mL, 6.44 mmol), followed by stirring at room temperature overnight. The reaction mixture was added with water and extracted with ethyl acetate, the organic layer was washed with saturated aqueous sodium hydrogencarbonate solution and dried over anhydrous sodium sulfate. The solvent was evaporated under reduced pressure to obtain Compound A33 (775 mg, 95%).
$^1$H NMR (300 MHz, CDCl$_3$) δ (ppm) 2.45 (s, 3H), 3.87 (s, 3H), 7.26-7.28 (m, 1H), 7.62 (dd, J=7.9, 1.7 Hz, 1H), 8.18 (d, J=1.7 Hz, 1H).

Reference Example 34

(5-Ethoxycarbamoyl-2-methyl)iodobenzene

Compound A34

In a similar manner to Reference Example 33, Compound A34 was obtained using ethoxyamine hydrochloride.
$^1$H NMR (300 MHz, CDCl$_3$) δ (ppm) 1.34 (t, J=7.0 Hz, 3H), 2.47 (s, 3H), 4.09 (q, J=7.0 Hz, 2H), 7.29 (d, J=7.9 Hz, 1H), 7.62 (dd, J=7.9, 1.6 Hz, 1H), 8.17 (d, J=1.6 Hz, 1H), 8.51 (br s, 1H).

Reference Example 35

4-Methyl-N-[5-methyl-2-(p-tolyl)-2H-pyrazol-3-yl]-3-(4,4,5,5-tetramethyl-1,3,2-dioxaborolan-2-yl)benzamide Compound A35

Step 1
3-Iodo-4-methylbenzoic acid (1.00 g, 3.89 mmol) was dissolved in thionyl chloride (12.5 mL) and was stirred at 80° C. for 1.75 hours, then thionyl chloride was evaporated under reduced pressure. The reaction mixture was dissolved in methylene chloride (10.0 mL) and the solution was added with a solution of 5-amino-3-methyl-1-(p-tolyl)pyrazole (0.728 g, 3.89 mmol) and N,N-diisopropylethylamine (0.678 mL, 3.89 mmol) in methylene chloride (10.0 mL), followed by stirring at room temperature overnight. After the reaction mixture was added with water and extracted with ethyl acetate, the organic layer was washed with saturated aqueous sodium hydrogencarbonate solution, saturated aqueous ammonium chloride solution and water, followed by drying over anhydrous sodium sulfate. The solvent was evaporated under reduced pressure and the residue was purified by silica gel column chromatography (ethyl acetate/hexane=1/4) to obtain 3-iodo-4-methyl-N-[5-methyl-2-(p-tolyl)-2H-pyrazol-3-yl]benzamide (1.44 g, 86%).
$^1$H NMR (270 MHz, CDCl$_3$) δ (ppm) 2.34 (s, 3H), 2.43 (s, 3H), 2.47 (s, 3H), 6.61 (s, 1H), 7.27-7.41 (m, 5H), 7.53 (dd, J=7.9, 1.9 Hz, 1H), 7.85 (br s, 1H), 8.19 (d, J=1.9 Hz, 1H).
Step 2
3-Iodo-4-methyl-N-[5-methyl-2-(p-tolyl)-2H-pyrazol-3-yl]benzamide (1.54 g, 3.57 mmol) and bis(pinacolate)diboron was dissolved in DMF (11.9 mL) and the solution was added with potassium acetate (1.05 g, 10.7 mmol) and [1,1'-bis(diphenylphosphino)ferrocene]dichloropalladium (197 mg, 0.241 mmol), followed by stirring at 95° C. overnight under argon atmosphere. The reaction mixture was added with ethyl acetate and water and an insoluble matter was filtered off using Celite, followed by extracting with ethyl acetate. The organic layer was washed with water and was dried over anhydrous sodium sulfate. The solvent was evaporated under reduced pressure and the residue was purified by silica gel column chromatography (ethyl acetate/hexane=1/4 to 1/3) to obtain Compound A35 (1.20 g, 78%).

¹H NMR (270 MHz, CDCl₃) δ (ppm) 1.35 (s, 12H), 2.35 (s, 3H), 2.42 (s, 3H), 2.57 (s, 3H), 6.67 (s, 1H), 7.25-7.44 (m, 5H), 7.80 (dd, J=7.9, 2.1 Hz, 1H), 8.03 (d, J=2.0 Hz, 1H), 8.05 (br s, 1H).

Reference Example 36

N-(2-methoxy-5-trifluoromethylphenyl)-4-methyl-3-(4,4,5,5-tetramethyl-1,3,2-dioxaborolan-2-yl)benzamide Compound A36

In a similar manner to Reference Example 35, Compound A36 was obtained using 2-methoxy-5-trifluoroaniline.

¹H NMR (300 MHz, CDCl₃) δ (ppm) 1.37 (s, 12H), 2.61 (s, 3H), 3.99 (s, 3H), 6.97 (d, J=8.5 Hz, 1H), 7.30 (d, J=7.9 Hz, 1H), 7.33-7.37 (m, 1H), 7.85 (dd, J=7.9, 2.2 Hz, 1H), 8.27 (d, J=2.0 Hz, 1H), 8.57 (br s, 1H), 8.88 (d, J=2.2 Hz, 1H).

Reference Example 37

N-[5-tert-butyl-2-methoxy-3-(methylsulfonylamino)phenyl]-4-methyl-3-(4,4,5,5-tetramethyl-1,3,2-dioxaborolan-2-yl)benzamide Compound A37

In a similar manner to Reference Example 35, Compound A37 was obtained using N-(3-amino-5-tert-butyl-2-methoxyphenyl)methanesulfonamide (WO05/023761).

¹H NMR (270 MHz, CDCl₃) δ (ppm) 1.35 (s, 9H), 1.36 (s, 12H), 2.61 (s, 3H), 3.08 (s, 3H), 3.83 (s, 3H), 6.74 (br s, 1H), 7.30-7.33 (m, 2H), 7.87 (dd, J=8.1, 2.3 Hz, 1H), 8.24-8.27 (m, 2H).

Reference Example 38

4-Methyl-3-(4,4,5,5-tetramethyl-1,3,2-dioxaborolan-2-yl)benzamide

Compound A38

In a similar manner to Reference Example 35, Compound A38 was obtained using ammonia-methanol solution (7 mmol/L).

¹H NMR (270 MHz, CDCl₃) δ (ppm) 1.36 (s, 12H), 2.58 (s, 3H), 5.70-6.10 (m, 2H), 7.24-7.26 (m, 1H), 7.84 (dd, J=8.1, 1.9 Hz, 1H), 8.12 (d, J=1.9 Hz, 1H).

Reference Example 39

3-Iodo-N-(2-morpholinopyridin-4-yl)benzamide

Compound A39

In a similar manner to Step 1 of Reference Example 35, Compound A39 was obtained using 2-morpholinopyridin-4-ylamine (WO05/023761) and 3-iodobenzoic acid.

¹H NMR (300 MHz, CDCl₃) δ (ppm) 3.52-3.55 (m, 4H), 3.80-3.84 (m, 4H), 6.69 (dd, J=5.6, 1.8 Hz, 1H), 7.21-7.26 (m, 1H), 7.33-7.34 (m, 1H), 7.81 (ddd, J=7.9, 1.7, 1.5 Hz, 1H), 7.87 (br s, 1H), 7.90 (ddd, J=8.1, 1.5, 1.5 Hz, 1H), 8.13 (d, J=5.6 Hz, 1H), 8.18 (dd, J=1.8, 1.7 Hz, 1H).

Reference Example 40

3-Iodo-N-[2-(pyrrolidin-1-yl)pyridin-4-yl]benzamide

Compound A40

Step 1
2-Chloro-4-nitropyridine (2.0 g, 12.2 mmol) was dissolved in THF (30 mL) and the solution was added with pyrrolidine (3.25 mL, 38.9 mmol), followed by stirring at 80° C. overnight. After an insoluble matter of the reaction mixture was filtered off, the solvent was evaporated under reduced pressure. The residue was purified by silica gel column chromatography (ethyl acetate/hexane=20/80) to obtain 4-nitro-2-(pyrrolidin-1-yl)pyridine (560 mg, 24%).

¹H NMR (270 MHz, CDCl₃) δ (ppm) 2.04-2.09 (m, 4H), 3.50-3.54 (m, 4H), 7.02 (d, J=1.8 Hz, 1H), 7.15 (dd, J=5.4, 1.6 Hz, 1H), 8.33 (d, J=5.4 Hz, 1H).

Step 2
4-Nitro-2-(pyrrolidin-1-yl)pyridine (560 mg, 2.90 mmol) was dissolved in methanol (21 mL) and methylene chloride (8.3 mL) and the solution was added with palladium carbon (50% aqueous, 560 mg), followed by stirring at room temperature for 1 hour under hydrogen atmosphere. After filtering off the insoluble matter of the reaction mixture, the solvent was evaporated under reduced pressure to obtain 2-(pyrrolidin-1-yl)pyridin-4-ylamine (474 mg, 91%).

¹H NMR (300 MHz, CDCl₃) δ (ppm) 1.94-1.99 (m, 4H), 3.38-3.43 (m, 4H), 3.96 (br s, 2H), 5.58 (d, J=1.9 Hz, 1H), 5.92 (dd, J=5.7, 1.9 Hz, 1H), 7.85 (d, J=5.7 Hz, 1H).

Step 3
In a similar manner to Step 1 of Reference Example 35, Compound A40 was obtained using 2-(pyrrolidin-1-yl)pyridin-4-ylamine and 3-iodobenzoic acid.

¹H NMR (270 MHz, CDCl₃) δ (ppm) 1.97-2.02 (m, 4H), 3.46-3.51 (m, 4H), 6.60 (dd, J=5.8, 1.8 Hz, 1H), 7.04 (d, J=1.6 Hz, 1H), 7.19-7.25 (m, 1H), 7.83-7.90 (m, 2H), 8.04 (d, J=5.8, 1H), 8.08 (br s, 1H), 8.21-8.23 (m, 1H).

Reference Example 41

N-(3-dimethylaminophenyl)-4-methyl-3-(4,4,5,5-tetramethyl-1,3,2-dioxaborolan-2-yl)benzamide Compound A41

In a similar manner to Reference Example 33 and Step 2 of Reference Example 35, Compound A41 was obtained using 3-dimethylaminoaniline dihydrochloride.

¹H NMR (300 MHz, CDCl₃) δ (ppm) 1.37 (s, 12H), 2.60 (s, 3H), 2.98 (s, 6H), 6.50-6.57 (m, 1H), 6.82-6.88 (m, 1H), 7.21 (t, J=8.1 Hz, 1H), 7.25-7.33 (m, 2H), 7.79 (br s, 1H), 7.90 (dd, J=8.1, 2.1 Hz, 1H), 8.18 (d, J=2.1 Hz, 1H).

Reference Example 42

N-(3-dimethylaminophenyl)-3-(4,4,5,5-tetramethyl-1,3,2-dioxaborolan-2-yl)benzamide Compound A42

In a similar manner to Step 2 of Reference Example 17, Compound A42 was obtained by amidation using 3-dimethylaminoaniline dihydrochloride and 3-(4,4,5,5-tetramethyl-1,3,2-dioxaborolan-2-yl)benzoic acid.

$^1$H NMR (300 MHz, CDCl$_3$) δ (ppm) 1.38 (s, 12H), 2.98 (s, 6H), 6.50-6.80 (m, 1H), 6.85-6.92 (m, 1H), 7.22 (t, J=8.1 Hz, 1H), 7.25-7.29 (m, 1H), 7.51 (t, J=7.5 Hz, 1H), 7.82 (br s, 1H), 7.76-8.00 (m, 1H), 8.03-8.09 (m, 1H), 8.18-8.22 (m, 1H).

Reference Example 43

2-(Pyrrolidin-1-yl)-N-[3-(4,4,5,5-tetramethyl-1,3,2-dioxaborolan-2-yl)phenyl]isonicotinamide Compound A43

In a similar manner to Step 2 of Reference Example 17, Compound A43 was obtained by amidation using 2-(pyrrolidin-1-yl)isonicotinic acid.

$^1$H NMR (270 MHz, CDCl$_3$) δ (ppm) 1.35 (s, 12H), 2.02-2.07 (m, 4H), 3.49-3.54 (m, 4H), 6.75-6.81 (m, 1H), 7.13-7.20 (m, 1H), 7.41-7.44 (m, 1H), 7.59-7.61 (m, 1H), 7.74-7.75 (m, 1H), 7.80 (br s, 1H), 8.05-8.08 (m, 1H), 8.26 (d, J=5.1 Hz, 1H).

Reference Example 44

3-Piperidino-N-[3-(4,4,5,5-tetramethyl-1,3,2-dioxaborolan-2-yl)phenyl]benzamide

Compound A44

In a similar manner to Step 2 of Reference Example 17, Compound A44 was obtained by amidation using 3-piperidinobenzoic acid.

$^1$H NMR (270 MHz, CDCl$_3$) δ (ppm) 1.35 (s, 12H), 1.61-1.73 (m, 6H), 3.23-3.27 (m, 4H), 7.09 (dd, J=8.4, 2.4 Hz, 1H), 7.16-7.19 (m, 1H), 7.31 (d, J=7.8 Hz, 1H), 7.43-7.46 (m, 2H), 7.57-7.59 (m, 1H), 7.73-7.74 (m, 1H), 7.80 (br s, 1H), 8.09-8.12 (m, 1H).

Reference Example 45

2-(4-Fluoro-2-methylphenyl)-N-[3-(4,4,5,5-tetramethyl-1,3,2-dioxaborolan-2-yl)phenyl]isonicotinamide Compound A45

In a similar manner to Reference Example 17, Compound A45 was obtained using 4-fluoro-2-methylphenylboronic acid.

$^1$H NMR (270 MHz, CDCl$_3$) δ (ppm) 1.35 (s, 12H), 2.39 (s, 3H), 7.01-7.04 (m, 2H), 7.14-7.10 (m, 2H), 7.39-7.46 (m, 2H), 7.62-7.64 (m, 2H), 7.78-7.85 (m, 2H), 8.05-8.07 (m, 1H), 8.86 (d, J=5.4 Hz, 1H).

Example 1

2-Amino-6-(2,4-difluorophenyl)-7-methoxyquinazoline

Compound 1

In a similar manner to Example 4, Compound 1 was obtained by using Compound A2 and 2,4-difluorophenylboronic acid.

$^1$H NMR (300 MHz, CDCl$_3$) δ (ppm) 3.91 (s, 3H), 5.19 (br s, 2H), 6.88-6.98 (m, 2H), 6.99 (s, 1H), 7.30-7.37 (m, 1H), 7.55 (s, 1H), 8.88 (s, 1H).

APCI m/z (M+H)$^+$ 288.

Example 2

2-Amino-6-(2-chlorophenyl)-7-methoxyquinazoline

Compound 2

In a similar manner to Example 4, Compound 2 was obtained using Compound A2.

$^1$H NMR (300 MHz, CDCl$_3$) δ (ppm) 3.89 (s, 3H), 5.18 (s, 2H), 6.99 (s, 1H), 7.30-7.37 (m, 3H), 7.44-7.51 (m, 1H), 7.51 (s, 1H), 8.81 (s, 1H).

Example 3

6-(2,4-Difluorophenyl)-2-isopropylamino-7-methoxyquinazoline

Compound 3

In a similar manner to Example 4, Compound 3 was obtained using Compound A4 and 2,4-difluorophenylboronic acid.

$^1$H NMR (300 MHz, CDCl$_3$) δ (ppm) 1.30 (d, J=6.4 Hz, 6H), 3.90 (s, 3H), 4.28-4.35 (m, 1H), 5.09 (d, J=6.4 Hz, 1H), 6.86-6.97 (m, 2H), 6.98 (s, 1H), 7.29-7.35 (m, 1H), 7.58 (s, 1H), 8.80 (s, 1H).

APCI m/z (M+H)$^+$ 330.

Example 4

6-(2-Chlorophenyl)-2-isopropylamino-7-methoxyquinazoline

Compound 4

Compound A4 (1.20 g, 4.05 mmol) was dissolved in dioxane (20 mL) and water (20 mL), and the solution was added with 2-chlorophenylboronic acid (0.900 g, 5.76 mmol), sodium carbonate (1.03 g, 9.72 mmol) and [1,1'-bis(diphenylphosphino)ferrocene]dichloropalladium (197 mg, 0.241 mmol), followed by stirring for 2 hours under heating and reflux. After the insoluble matter was filtered off using Celite, the mixture was added with ethyl acetate and water, and the organic layer was separated. The organic layer was washed with water and dried over anhydrous magnesium sulfate. The solvent was evaporated under reduced pressure and the residue was purified by silica gel column chromatography (ethyl acetate/hexane=1/5) to obtain Compound 4 (873 mg, 66%).

$^1$H NMR (270 MHz, CDCl$_3$) δ (ppm) 1.31 (d, J=6.4 Hz, 6H), 3.89 (s, 3H), 4.33 (sep, J=6.4 Hz, 1H), 5.25 (br s, 1H), 6.99 (s, 1H), 7.31-7.34 (m, 3H), 7.45-7.49 (m, 2H), 8.81 (s, 1H).

Example 5

2-(trans-4-Aminocyclohexylamino)-6-(2-chlorophenyl)-7-methoxyquinazoline

Compound 5

In a similar manner to Reference Example 3,6-(2-chlorophenyl)-2-iodo-7-methoxyquinazoline was obtained using Compound 2. The obtained 6-(2-chlorophenyl)-2-iodo-7- methoxyquinazoline (113.2 mg, 0.285 mmol) was dissolved in DMF (1.4 mL) and the solution was added with triethylamine (60.0 µL, 0.430 mmol) and trans-1,4-diaminocyclohexane (97.8 mg, 0.856 mmol), followed by stirring at room temperature overnight. The reaction mixture was added with water and was extracted with ethyl acetate, then the organic layer was washed with water and saturated brine, followed by drying over anhydrous magnesium sulfate. The solvent was evaporated under reduced pressure and the residue was purified by preparative thin-layer chromatography (chloroform/methanol/ammonia water=90/9/1) to obtain Compound 5 (96.4 mg, 88%).

$^1$H NMR (270 MHz, CDCl$_3$) δ (ppm) 1.20-1.45 (m, 4H), 1.90-2.02 (m, 2H), 2.13-2.30 (m, 2H), 2.65-2.82 (m, 1H), 3.89 (s, 3H), 3.90-4.03 (m, 1H), 5.08 (d, J=8.4 Hz, 1H), 6.98 (s, 1H), 7.30-7.36 (m, 3H), 7.43 (s, 1H), 7.43-7.50 (m, 1H), 8.80 (s, 1H).

APCI m/z (M+H)$^+$ 383.

Example 6

6-(2-Chlorophenyl)-2-(cyclopentylamino)-7-methoxyquinazoline

Compound 6

In a similar manner to Example 5, Compound 6 was obtained using cyclopentylamine.

$^1$H NMR (300 MHz, CDCl$_3$) δ (ppm) 1.47-1.85 (m, 6H), 2.05-2.20 (m, 2H), 3.89 (s, 3H), 4.36-4.51 (m, 1H), 5.30 (d, J=7.5 Hz, 1H), 6.99 (s, 1H), 7.30-7.35 (m, 3H), 7.44 (s, 1H), 7.42-7.50 (m, 1H), 8.80 (s, 1H).

APCI m/z (M+H)$^+$ 354.

Example 7

(R)-6-(2-Chlorophenyl)-2-(2-hydroxy-1,2-dimethylpropylamino)-7-methoxyquinazoline Compound 7

In a similar manner to Example 5, Compound 7 was obtained using (R)-3-amino-2-methylbutan-2-ol.

$^1$H NMR (300 MHz, CDCl$_3$) δ (ppm) 1.26 (s, 3H), 1.32 (d, J=7.2 Hz, 3H), 1.33 (s, 3H), 3.87 (s, 3H), 4.05-4.20 (m, 1H), 5.48 (d, J=6.9 Hz, 1H), 6.97 (s, 1H), 7.29-7.37 (m, 3H), 7.46 (s, 1H), 7.42-7.51 (m, 1H), 8.81 (s, 1H).

APCI m/z (M+H)$^+$ 372.

Example 8

(R)-6-(2-Chlorophenyl)-7-methoxy-2-[(1-phenylethyl)amino]quinazoline

Compound 8

In a similar manner to Example 5, Compound 8 was obtained using (R)-(+)-1-phenylethylamine.

$^1$H NMR (300 MHz, CDCl$_3$) δ (ppm) 1.63 (d, J=6.9 Hz, 3H), 3.87 (s, 3H), 5.33-5.45 (m, 1H), 5.59-5.73 (m, 1H), 6.96 (s, 1H), 7.20-7.50 (m, 10H), 8.78 (s, 1H)

ESI m/z (M+H)$^+$ 390. .

Example 9

(S)-6-(2-Chlorophenyl)-7-methoxy-2-[(1-phenylethyl)amino]quinazoline

Compound 9

In a similar manner to Example 5, Compound 9 was obtained using (S)-(−)-1-phenylethylamine.

$^1$H NMR (300 MHz, CDCl$_3$) δ (ppm) 1.63 (d, J=6.6 Hz, 3H), 3.87 (s, 3H), 5.32-5.45 (m, 1H), 5.59-5.73 (m, 1H), 6.96 (s, 1H), 7.20-7.50 (m, 10H), 8.78 (s, 1H).

ESI m/z (M+H)$^+$ 390.

Example 10

6-(2-Chlorophenyl)-2-(trans-4-hydroxycyclohexylamino)-7-methoxyquinazoline

Compound 10

In a similar manner to Example 5, Compound 10 was obtained using trans-4-hydroxycyclohexylamine.

$^1$H NMR (270 MHz, CDCl$_3$) δ (ppm) 1.26-1.40 (m, 2H), 1.46-1.61 (m, 2H), 2.02-2.08 (m, 2H), 2.20-2.26 (m, 2H), 3.62-3.76 (m, 1H), 3.89 (s, 3H), 3.94-4.05 (m, 1H), 5.20 (m, 1H), 6.08-6.19 (br s, 1H), 6.99 (s, 1H), 7.30-7.34 (m, 3H), 7.42 (s, 1H), 7.45-7.49 (m, 1H), 8.79 (s, 1H).

ESI m/z (M+H)$^+$ 384.

Example 11

6-(2-Chlorophenyl)-7-methoxy-2-(4-tetrahydropyranylamino)quinazoline

Compound 11

In a similar manner to Example 5, Compound 11 was obtained using 4-aminotetrahydropyrane.

$^1$H NMR (270 MHz, CDCl$_3$) δ (ppm) 1.52-1.70 (m, 2H), 2.08-2.20 (m, 2H), 3.61 (dt, J=11.7, 2.2 Hz, 2H), 3.90 (s, 3H), 4.03 (dt, J=11.6, 3.2 Hz, 2H), 4.15-4.32 (m, 1H), 5.16 (d, J=8.1 Hz, 1H), 6.98 (s, 1H), 7.29-7.37 (m, 3H), 7.46 (s, 1H), 7.42-7.51 (m, 1H), 8.82 (s, 1H).

APCI m/z (M+H)$^+$ 370.

Example 12

6-(2-Chlorophenyl)-2-[1-(methylsulfonyl)piperidin-4-ylamino]-7-methoxyquinazoline Compound 12

In a similar manner to Example 5, Compound 12 was obtained using 1-(methylsulfonyl)piperidin-4-ylamine.

$^1$H NMR (270 MHz, CDCl$_3$) δ (ppm) 1.62-1.81 (m, 2H), 2.21-2.34 (m, 2H), 2.83 (s, 3H), 2.94-3.10 (m, 2H), 3.71-3.84 (m, 2H), 3.88 (s, 3H), 4.09-4.24 (m, 1H), 5.15 (d, J=7.6 Hz, 1H), 6.98 (s, 1H), 7.29-7.38 (m, 3H), 7.47 (s, 1H), 7.43-7.52 (m, 1H), 8.82 (s, 1H).

APCI m/z (M+H)$^+$ 447.

Example 13

6-(2-Chlorophenyl)-7-methoxy-2-[1-(trifluoromethylsulfonyl)piperidin-4-ylamino]quinazoline

Compound 13

In a similar manner to Example 5, Compound 13 was obtained using 1-(trifluoromethylsulfonyl)piperidin-4-ylamine.

$^1$H NMR (270 MHz, CDCl$_3$) δ (ppm) 1.60-1.77 (m, 2H), 2.22-2.35 (m, 2H), 3.27-3.41 (m, 2H), 3.90 (s, 3H), 3.92-4.05 (m, 2H), 4.15-4.32 (m, 1H), 5.14 (d, J=7.8 Hz, 1H), 6.98 (s, 1H), 7.29-7.37 (m, 3H), 7.48 (s, 1H), 7.43-7.52 (m, 1H), 8.83 (s, 1H).

APCI m/z (M+H)$^+$ 501.

Example 14

6-(2-Chlorophenyl)-7-methoxy-2-[1-(2,2,2-trifluoroethylsulfonyl)piperidin-4-ylamino]quinazoline

Compound 14

In a similar manner to Example 5, Compound 14 was obtained using 1-(2,2,2-trifluoroethylsulfonyl)piperidin-4-ylamine.

$^1$H NMR (270 MHz, CDCl$_3$) δ (ppm) 1.57-1.75 (m, 2H), 2.20-2.32 (m, 2H), 3.10-3.24 (m, 2H), 3.74 (dd, J=18.9, 9.2 Hz, 2H), 3.82-3.95 (m, 2H), 3.90 (s, 3H), 4.10-4.27 (m, 1H), 5.13 (d, J=7.8 Hz, 1H), 6.98 (s, 1H), 7.29-7.37 (m, 3H), 7.46 (s, 1H), 7.43-7.51 (m, 1H), 8.83 (s, 1H).

ESI m/z (M+H)$^+$ 515.

Example 15

2-(1-Carbamoylpiperidin-4-ylamino)-6-(2-chlorophenyl)-7-methoxyquinazoline

Compound 15

In a similar manner to Example 5, Compound 15 was obtained using 1-carbamoylpiperidin-4-ylamine.

$^1$H NMR (270 MHz, CDCl$_3$) δ (ppm) 1.45-1.65 (m, 2H), 2.11-2.26 (m, 2H), 3.03-3.21 (m, 2H), 3.90 (s, 3H), 3.85-4.00 (m, 2H), 4.11-4.33 (m, 1H), 4.46 (s, 2H), 5.16 (d, J=7.6 Hz, 1H), 6.99 (s, 1H), 7.30-7.39 (m, 3H), 7.46 (s, 1H), 7.43-7.52 (m, 1H), 8.82 (s, 1H).

APCI m/z (M+H)$^+$ 412.

Example 16

6-(2-Chlorophenyl)-2-(2,6-difluoroanilino)-7-methoxyquinazoline

Compound 16

6-(2-Chlorophenyl)-2-iodo-7-methoxyquinazoline (91.1 mg, 0.230 mmol) obtained in Example 5 was dissolved in toluene (2.3 mL) and the solution was added with 2,6-difluoroaniline (99.0 μL, 0.919 mmol), palladium acetate (5.2 mg, 0.023 mmol), 2,2'-bis(diphenylphosphino)-1,1'-binaphthyl (22 mg, 0.034 mmol) and cesium carbonate (112 mg, 0.345 mmol), followed by stirring at 100° C. for 20 hours. The reaction mixture was added with water and was extracted with ethyl acetate, then the organic layer was washed with saturated brine and dried over anhydrous magnesium sulfate. The solvent was evaporated under reduced pressure and the residue was purified by preparative thin-layer chromatography (ethyl acetate/hexane=3/7) to obtain Compound 16 (48.8 mg, 53%).

$^1$H NMR (300 MHz, CDCl$_3$) δ (ppm) 3.88 (s, 3H), 6.75 (br s, 1H), 6.97-7.10 (m, 3H), 7.15-7.25 (m, 1H), 7.30-7.40 (m, 3H), 7.43-7.52 (m, 1H), 7.55 (s, 1H), 8.95 (s, 1H).

APCI m/z (M+H)$^+$ 398.

Example 17

6-(2-Chlorophenyl)-2-(2,6-dichloroanilino)-7-methoxyquinazoline

Compound 17

In a similar manner to Example 16, Compound 17 was obtained using 2,6-dichloroaniline.

$^1$H NMR (300 MHz, CDCl$_3$) δ (ppm) 3.88 (s, 3H), 6.91 (br s, 1H), 7.04 (s, 1H), 7.20 (t, J=8.1 Hz, 1H), 7.30-7.37 (m, 3H), 7.45 (d, J=8.1 Hz, 2H), 7.45-7.51 (m, 1H), 7.55 (s, 1H), 8.95 (s, 1H).

APCI m/z (M+H)$^+$ 430.

Example 18

2-(N-Carbamoyl-2,6-dichloroanilino)-6-(2-chlorophenyl)-7-methoxyquinazoline

Compound 18

Compound 17 (98.1 mg, 0.228 mmol) was dissolved in THF (35.0 mL) and the solution was added with 4-(dimethylamino)pyridine (2.8 mg, 0.023 mmol), triethylamine (0.64 mL, 4.56 mmol) and triphosgene (337.9 mg, 1.14 mmol), followed by stirring at room temperature for 2 hours. The reaction mixture was added with 28% aqueous ammonia (6.0 mL) and further stirred at room temperature for 0.5 hour. The reaction mixture was poured into saturated brine and extracted with ethyl acetate, followed by drying over anhydrous magnesium sulfate. The solvent was evaporated under reduced pressure and the residue was purified by preparative thin-layer chromatography (ethyl acetate/hexane=4/6) to obtain Compound 18 (18.2 mg, 17%).

$^1$H NMR (270 MHz, CDCl$_3$) δ (ppm) 3.95 (s, 3H), 5.56 (br s, 1H), 7.16 (s, 1H), 7.25-7.40 (m, 4H), 7.43-7.52 (m, 3H), 7.63 (s, 1H), 8.97 (s, 1H), 10.37 (br s, 1H).

ESI m/z (M+H)$^+$ 473.

Example 19

6-(2-Chlorophenyl)-7-hydroxy-2-isopropylaminoquinazoline

Compound 19

Compound 4 (2.50 g, 7.63 mmol) was dissolved in dichloroethane (140 mL) and the solution was added with boron tribromide (7.20 mL, 76.3 mmol), then was heated under reflux overnight. The reaction mixture was added with ethyl acetate and water, and the organic layer was separated. The organic layer was washed with water and dried over anhydrous magnesium sulfate. The solvent was evaporated under reduced pressure to obtain Compound 19 (1.27 g, 53%).

$^1$H NMR (270 MHz, CDCl$_3$) δ (ppm) 1.19 (d, J=6.4 Hz, 6H), 4.16-4.30 (m, 1H), 5.22 (br s, 1H), 6.65 (br s, 1H), 7.06 (s, 1H), 7.29-7.34 (m, 3H), 7.40 (s, 1H), 7.47-7.50 (m, 1H), 8.73 (s, 1H).

APCI m/z (M+H)$^+$ 314.

Example 20

7-Benzoyloxy-6-(2-chlorophenyl)-2-isopropylaminoquinazoline

Compound 20

Compound 19 (126 mg, 0.40 mmol) was dissolved in methylene chloride (4 mL) and the solution was added with triethylamine (83 µL, 0.60 mmol) and benzoyl chloride (51 µL, 0.44 mmol) at 0° C., followed by stirring at room temperature for 1 hour. The reaction mixture was added with water and chloroform, then the organic layer was separated. The organic layer was washed with water and dried over anhydrous magnesium sulfate. The solvent was evaporated under reduced pressure and the precipitated solid was reslurried with diethylether. The solid was collected by filtration and was dried to obtain Compound 20 (89 mg, 53%).

$^1$H NMR (300 MHz, CDCl$_3$) δ (ppm) 1.31 (d, J=6.4 Hz, 6H), 4.27-4.38 (m, 1H), 5.20 (d, J=6.4 Hz, 1H), 7.22-7.26 (m, 2H), 7.34-7.42 (m, 4H), 7.52-7.56 (m, 1H), 7.57 (s, 1H), 7.64 (s, 1H), 7.90-7.93 (m, 2H), 8.96 (s, 1H).

ESI m/z (M+H)$^+$ 418.

Example 21

6-(2-Chlorophenyl)-7-cyanomethyloxy-2-isopropylaminoquinazoline

Compound 21

Compound 19 (40 mg, 0.13 mmol) was dissolved in DMF (1 mL) and the solution was added with chloroacetonitrile (8.9 µL, 0.14 mmol) and potassium carbonate (44 mg, 0.32 mmol), followed by stirring at room temperature for 24 hours. After the reaction mixture was added with water and ethyl acetate, the organic layer was separated and washed with water. The organic layer was dried over anhydrous magnesium sulfate. Under reduced pressure, the solvent was evaporated and the precipitated solid was reslurried with diethylether, the solid collected by filtration was dried to obtain Compound 21 (27 mg, 64%).

$^1$H NMR (300 MHz, CDCl$_3$) δ (ppm) 1.23 (d, J=6.4 Hz, 6H), 4.28-4.35 (m, 1H), 4.85 (s, 2H), 5.15 (m, 1H), 6.91 (s, 1H), 7.31-7.37 (m, 2H), 7.33 (s, 1H), 7.47-7.49 (m, 1H), 7.50 (s, 1H), 8.85 (s, 1H).

APCI m/z (M+H)$^+$ 353.

Example 22

7-(2-Acetyloxyethyloxy)-6-(2-chlorophenyl)-2-isopropylaminoquinazoline

Compound 22

In a similar manner to Example 21, Compound 22 was obtained using 2-bromoethylacetate.

$^1$H NMR (300 MHz, CDCl$_3$) δ (ppm) 1.30 (d, J=6.4 Hz, 6H), 2.01 (s, 3H), 4.25-4.35 (m, 5H), 5.07 (m, 1H), 6.91 (s, 1H), 7.29-7.35 (m, 3H), 7.43-7.48 (m, 1H), 7.46 (s, 1H), 8.81 (s, 1H).

APCI m/z (M+H)$^+$ 400.

Example 23

6-(2-Chlorophenyl)-7-(2-hydroxyethyloxy)-2-isopropylaminoquinazoline

Compound 23

Compound 22 (150 mg, 0.275 mmol) was dissolved in ethanol (1 mL) and the solution was added with 3 mol/L aqueous sodium hydroxide solution (440 µL, 1.32 mmol), followed by stirring at room temperature for 30 minutes. The reaction mixture was added with 1 mol/L hydrochloric acid to adjust the pH to 7, and was added with water and ethyl acetate, then the organic layer was separated. The organic layer was washed with water and dried over anhydrous magnesium sulfate, then the solvent was evaporated under reduced pressure. Then, the mixture was purified by preparative thin-layer chromatography (ethyl acetate/hexane=1/1) to obtain Compound 23 (88.0 mg, 63%).

$^1$H NMR (300 MHz, CDCl$_3$) δ (ppm) 1.38 (d, J=6.4 Hz, 6H), 3.87-3.95 (m, 2H), 4.25-4.28 (m, 2H), 4.34-4.52 (m, 1H), 7.12 (s, 1H), 7.28-7.31 (m, 1H), 7.34-7.41 (m, 2H), 7.48-7.52 (m, 1H), 7.64 (s, 1H), 9.00 (s, 1H).

APCI m/z (M+H)$^+$ 358.

Example 24

6-(2-Chlorophenyl)-7-(3-hydroxypropyloxy)-2-isopropylaminoquinazoline

Compound 24

Compound 19 (95.0 mg, 0.303 mmol) was dissolved in DMF (2 mL) and the solution was added with (3-bromopropoxy)-tert-butyldimethylsilane (0.14 mL, 0.61 mmol) and potassium carbonate (84 mg, 0.61 mmol), followed by stirring at room temperature overnight. The reaction mixture was added with water and ethyl acetate, then the organic layer was separated and washed with water. The organic layer was dried over anhydrous magnesium sulfate, then the organic solvent was evaporated under reduced pressure. The residue was dissolved in THF (3 mL), and the solution was added with 1 mol/L tetrabutylammonium fluoride-THF solution (0.3 mL), followed by stirring at 60° C. The reaction mixture was added with water and extracted with ethyl acetate. The organic layer was washed with water and dried over anhydrous magnesium sulfate, and the solvent was evaporated under reduced pressure. The residue was purified by silica gel column chromatography (ethyl acetate/hexane=1/2) to obtain Compound 24 (44.0 mg, 39%).

$^1$H NMR (270 MHz, DMSO-d$_6$) δ (ppm) 1.21 (d, J=6.4 Hz, 6H), 1.70-1.80 (m, 2H), 3.33-3.34 (m, 2H), 4.11-4.26 (m, 3H), 4.45 (t, J=5.3 Hz, 1H), 6.90 (s, 1H), 7.15 (d, J=7.9 Hz, 1H), 7.34-7.43 (m, 3H), 7.51-7.56 (m, 2H), 8.92 (s, 1H).

APCI m/z (M+H)$^+$ 372.

Example 25

6-(2-Chlorophenyl)-7-(4-hydroxybutyloxy)-2-isopropylaminoquinazoline

Compound 25

Compound 19 (95.0 mg, 0.303 mmol) was dissolved in DMF (2 mL) and the solution was added with 4-bromobutylacetate (0.088 mL, 0.61 mmol) and potassium carbonate (84 mg, 0.61 mmol) followed by stirring at 50° C. for 3 hours. The reaction mixture was added with water and ethyl acetate, then the organic layer was separated and washed with water. The organic layer was dried over anhydrous magnesium sulfate. The organic solvent was evaporated under reduced pressure and the residue was dissolved in THF (2 mL). The solution was added with 2 mol/L aqueous sodium hydroxide solution (0.75 mL), followed by stirring at 60° C. The reaction mixture was added with water and diluted hydrochloric acid, and was extracted with ethyl acetate. The organic layer was washed with water and dried over anhydrous magnesium sulfate and the solvent was evaporated under reduced pressure. The residue was purified by silica gel column chromatography (ethyl acetate/hexane=1/2) to obtain Compound 25 (43.0 mg, 37%).

$^1$H NMR (270 MHz, DMSO-$d_6$) δ (ppm) 1.21 (d, J=6.4 Hz, 6H), 1.37-1.49 (m, 2H), 1.58-1.70 (m, 2H), 3.35 (t, J=6.4 Hz, 2H), 4.08 (t, J=6.2 Hz, 2H), 4.20 (sep, J=6.4 Hz, 1H), 6.91 (s, 1H), 7.34-7.43 (m, 3H), 7.52-7.57 (m, 2H), 8.93 (s, 1H).

APCI m/z (M+H)$^+$ 386.

Example 26

6-(2-Chlorophenyl)-2-isopropylamino-7-methoxymethyloxyquinazoline

Compound 26

Compound 90 (100 mg, 0.229 mmol) was dissolved in DMF (2 mL) and the solution was added with sodium formate (31 mg, 0.023 mmol) and tetrakis(triphenylphosphine)palladium (27 mg, 0.023 mmol), followed by stirring at 100° C. for 2 hours. The insoluble matter was filtered off using Celite, and the mixture was added with ethyl acetate and water. The organic layer was separated and dried over anhydrous magnesium sulfate. The solvent was evaporated under reduced pressure and the residue was purified by silica gel column chromatography (ethyl acetate/hexane=1/2) to obtain Compound 26 (57.8 mg, 71%).

$^1$H NMR (270 MHz, DMSO-$d_6$) δ (ppm) 1.19 (d, J=6.6 Hz, 6H), 3.32 (s, 3H), 4.10-4.25 (m, 1H), 5.26 (s, 2H), 7.05 (s, 1H), 7.19 (d, J=7.6H, 1H), 7.30-7.45 (m, 3H), 7.50-7.56 (m, 1H), 7.58 (s, 1H), 8.74 (s, 1H).

APCI m/z (M+H)$^+$ 358.

Example 27

7-Benzyloxy-6-(2-chlorophenyl)-2-isopropylaminoquinazoline

Compound 27

In a similar manner to Example 21, Compound 27 was obtained using benzyl bromide.

$^1$H NMR (270 MHz, DMSO-$d_6$) δ (ppm) 1.17 (d, J=6.6 Hz, 6H), 4.13-4.27 (m, 1H), 5.24 (s, 2H), 7.01 (s, 1H), 7.18-7.35 (m, 6H), 7.39-7.44 (m, 3H), 7.52-7.58 (m, 1H), 7.60 (s, 1H), 8.94 (s, 1H).

ESI m/z (M+H)$^+$ 404.

Example 28

7-(4-Carboxyphenylmethyloxy)-6-(2-chlorophenyl)-2-isopropylaminoquinazoline

Compound 28

In a similar manner to Example 25, Compound 28 was obtained using methyl 4-bromomethylbenzoate.

$^1$H NMR (270 MHz, DMSO-$d_6$) δ (ppm) 1.21 (d, J=6.4 Hz, 6H), 4.12-4.26 (m, 1H), 5.34 (s, 2H), 7.02 (s, 1H), 7.25 (br s, 1H), 7.37-7.46 (m, 5H), 7.54-7.60 (m, 1H), 7.63 (s, 1H), 7.91 (d, J=8.1 Hz, 2H), 8.96 (s, 1H).

APCI m/z (M+H)$^+$ 448.

Example 29

7-(3-Carboxyphenylmethyloxy)-6-(2-chlorophenyl)-2-isopropylaminoquinazoline

Compound 29

In a similar manner to Example 25, Compound 29 was obtained using methyl 3-bromomethylbenzoate.

$^1$H NMR (270 MHz, DMSO-$d_6$) δ (ppm) 1.21 (d, J=6.4 Hz, 6H), 4.13-4.27 (m, 1H), 5.34 (s, 2H), 7.02 (s, 1H), 7.21 (d, J=7.8 Hz, 1H), 7.38-7.49 (m, 4H), 7.52-7.58 (m, 2H), 7.62 (s, 1H), 7.85 (d, J=7.6 Hz, 2H), 7.96 (s, 1H), 8.95 (s, 1H).

APCI m/z (M+H)$^+$ 448.

Example 30

7-(2-Carboxyethyloxy)-6-(2-chlorophenyl)-2-isopropylaminoquinazoline

Compound 30

Compound 19 (200 mg, 0.637 mmol) was dissolved in DMF (4 mL) and the solution was added with β-propiolactone (0.160 mL, 2.55 mmol) and potassium carbonate (352 mg, 2.55 mmol), followed by stirring overnight. The reaction mixture was added with water and extracted with ethyl acetate. The organic layer was washed with water and dried over anhydrous magnesium sulfate. The solvent was evaporated under reduced pressure and the residue was purified by silica gel column chromatography (ethyl acetate/hexane=1/2) to obtain Compound 30 (45.7 mg, 20%).

$^1$H NMR (270 MHz, DMSO-$d_6$) δ (ppm) 1.21 (d, J=6.4 Hz, 6H), 2.58 (t, J=6.0 Hz, 2H), 4.14-4.26 (m, 1H), 4.30 (t, J=6.0 Hz, 2H), 6.93 (s, 1H), 7.18 (d, J=7.9 Hz, 1H), 7.32-7.42 (m, 3H), 7.48-7.51 (m, 1H), 7.57 (s, 1H), 8.93 (s, 1H).

APCI m/z (M+H)$^+$ 386.

Example 31

7-(3-Carboxypropyloxy)-6-(2-chlorophenyl)-2-isopropylaminoquinazoline

Compound 31

In a similar manner to Example 25, Compound 31 was obtained using 4-bromobutylate.

$^1$H NMR (270 MHz, DMSO-$d_6$) δ (ppm) 1.20 (d, J=6.6 Hz, 6H), 1.81 (tt, J=7.1, 6.2 Hz, 2H), 2.20 (t, J=7.1 Hz, 2H), 4.09 (t, J=6.2 Hz, 2H), 4.14-4.26 (m, 1H), 6.90 (s, 1H), 7.16 (d, J=7.2 Hz, 1H), 7.34-7.44 (m, 3H), 7.50-7.58 (m, 1H), 7.56 (s, 1H), 8.92 (s, 1H).

ESI m/z (M+H)$^+$ 400.

Example 32

6-(2-Chlorophenyl)-7-(ethoxycarbonylmethyloxy)-2-isopropylaminoquinazoline

Compound 32

Compound 19 (0.94 g, 3.0 mmol) was dissolved in DMF (20 mL) and the solution was added with ethyl bromoacetate (0.70 mL, 6.0 mmol) and potassium carbonate (0.83 g, 6.0 mmol), followed by stirring at room temperature. The reaction mixture was added with water and ethyl acetate, then the organic layer was separated. The organic layer was washed with water and dried over anhydrous magnesium sulfate. The solvent was evaporated under reduced pressure and the residue was purified by silica gel column chromatography (ethyl acetate/hexane=1/2) to obtain Compound 32 (0.52 g, 45%).

$^1$H NMR (270 MHz, DMSO-$d_6$) δ (ppm) 1.15-1.21 (m, 9H), 4.10-4.30 (m, 3H), 4.91 (s, 2H), 6.83 (s, 1H), 7.22 (d, J=7.7 Hz, 1H), 7.34-7.41 (m, 3H), 7.52-7.56 (m, 1H), 7.61 (s, 1H), 8.95 (s, 1H).

APCI m/z (M+H)$^+$ 400.

Example 33

7-(Carboxymethyloxy)-6-(2-chlorophenyl)-2-isopropylaminoquinazoline

Compound 33

Compound 32 (0.45 g, 1.4 mmol) was dissolved in THF (10 mL) and the solution was added with 2 mol/L aqueous sodium hydroxide solution (3.5 mL), followed by stirring at room temperature for 1 hour. The reaction mixture was added with water and then washed with ether. The aqueous layer was added with diluted hydrochloric acid, then the obtained crystal was collected by filtration to obtain Compound 33 (0.36 g, 86%).

$^1$H NMR (270 MHz, DMSO-$d_6$) δ (ppm) 1.20 (d, J=6.4 Hz, 6H), 4.12-4.26 (m, 1H), 4.80 (s, 2H), 6.78 (s, 1H), 7.22 (d, J=7.9 Hz, 1H), 7.38-7.45 (m, 3H), 7.51-7.56 (m, 1H), 7.60 (s, 1H), 8.95 (s, 1H).

APCI m/z (M+H)$^+$ 372.

Example 34

6-(2-Chlorophenyl)-7-(2-hydroxy-2-methylpropyloxy)-2-isopropylaminoquinazoline

Compound 34

Compound 32 (70 mg, 0.18 mmol) was dissolved in THF (1.4 mL) and was cooled to 0° C., then the solution was added with methylmagnesium bromide (0.93 mol/L THF solution, 0.77 mL, 0.72 mmol), followed by stirring at room temperature for 2 hours. The mixture was further cooled to 0° C. and added with methylmagnesium bromide (0.93 mol/L THF solution, 0.77 mL, 0.72 mmol), followed by stirring at room temperature for 30 minutes. The reaction mixture was added with aqueous ammonium chloride solution and extracted with ethyl acetate. The organic layer was dried over anhydrous magnesium sulfate and the solvent was evaporated under reduced pressure to obtain Compound 34 (28 mg, 40%).

$^1$H NMR (270 MHz, CDCl$_3$) δ (ppm) 1.15 (br s, 6H), 1.31 (d, J=6.4 Hz, 6H), 3.90 (br s, 2H), 4.23-4.36 (m, 1H), 5.12 (d, J=7.8 Hz, 1H), 6.95 (s, 1H), 7.30-7.36 (m, 3H), 7.45-7.50 (m, 2H), 8.81 (s, 1H).

APCI m/z (M+H)$^+$ 386.

Example 35

7-(Carbamoylmethyloxy)-6-(2-chlorophenyl)-2-isopropylaminoquinazoline

Compound 35

In a similar manner to Example 38, Compound 35 was obtained using 28% aqueous ammonia.

$^1$H NMR (270 MHz, DMSO-$d_6$) δ (ppm) 1.20 (d, J=6.4 Hz, 6H), 4.12-4.26 (m, 1H), 4.58 (s, 2H), 6.82 (s, 1H), 6.92 (br s, 1H), 7.22 (d, J=7.5 Hz, 1H), 7.39-7.50 (m, 4H), 7.53-7.58 (m, 1H), 7.61 (s, 1H), 8.95 (s, 1H).

APCI m/z (M+H)$^+$ 371.

Example 36

6-(2-Chlorophenyl)-2-isopropylamino-7-(N-methylcarbamoylmethyloxy)quinazoline

Compound 36

In a similar manner to Example 38, Compound 36 was obtained using methylamine hydrochloride.

$^1$H NMR (270 MHz, DMSO-$d_6$) δ (ppm) 1.20 (d, J=6.4 Hz, 6H), 2.62 (d, J=4.4 Hz, 3H), 4.12-4.26 (m, 1H), 4.61 (s, 2H), 6.81 (s, 1H), 7.22 (d, J=7.6 Hz, 1H), 7.38-7.62 (m, 5H), 7.61 (s, 1H), 8.95 (s, 1H).

APCI m/z (M+H)$^+$ 385.

Example 37

6-(2-Chlorophenyl)-7-(N,N-dimethylcarbamoylmethyloxy)-2-isopropylaminoquinazoline Compound 37

In a similar manner to Example 38, Compound 37 was obtained using dimethylamine.

$^1$H NMR (270 MHz, DMSO-$d_6$) δ (ppm) 1.20 (d, J=6.5 Hz, 6H), 2.81 (s, 3H), 2.93 (s, 3H), 4.14-4.26 (m, 1H), 4.97 (s, 2H), 6.85 (s, 1H), 7.17 (d, J=7.8 Hz, 1H), 7.37-7.56 (m, 4H), 7.58 (s, 1H), 8.93 (s, 1H).

APCI m/z (M+H)$^+$ 399.

Example 38

6-(2-Chlorophenyl)-2-isopropylamino-7-[(piperidinocarbonyl)methyloxy]quinazoline Compound 38

Compound 33 (70 mg, 0.19 mmol) was dissolved in DMF (1 mL) and was cooled to 0° C., then the solution was added with piperidine (0.058 mL, 0.58 mmol), 1-ethyl-3-(3-dimethylaminopropyl)carbodiimide hydrochloride (112 mg, 0.58 mmol), 1-hydroxybenzotriazole (90 mg, 0.58 mmol) and triethylamine (0.080 mL, 0.58 mmol), followed by stirring at room temperature overnight. The reaction mixture was added with water and aqueous sodium hydrogencarbonate solution and the obtained crystal was collected by filtration to obtain Compound 38 (44 mg, 51%).

$^1$H NMR (270 MHz, DMSO-$d_6$) δ (ppm) 1.20 (d, J=6.5 Hz, 6H), 1.32-1.44 (m, 4H), 1.48-1.58 (m, 2H), 3.30-3.42 (m, 4H), 4.12-4.18 (m, 1H), 4.93 (s, 2H), 6.86 (s, 1H), 7.18 (d, J=8.1 Hz, 1H), 7.38-7.46 (m, 3H), 7.50-7.55 (m, 1H), 7.58 (s, 1H), 8.93 (s, 1H).

APCI m/z (M+H)$^+$ 439.

Example 39

6-(2-Chlorophenyl)-2-isopropylamino-7-[(morpholinocarbonyl)methyloxy]quinazoline Compound 39

In a similar manner to Example 38, Compound 39 was obtained using morpholine.

¹H NMR (270 MHz, DMSO-d₆) δ (ppm) 1.20 (d, J=6.4 Hz, 6H), 3.34-3.42 (m, 4H), 3.43-3.54 (m, 4H), 4.12-4.18 (m, 1H), 4.97 (s, 2H), 6.90 (s, 1H), 7.19 (d, J=8.0 Hz, 1H), 7.38-7.47 (m, 3H), 7.51-7.56 (m, 1H), 7.59 (s, 1H), 8.94 (s, 1H).

APCI m/z (M+H)⁺ 441.

Example 40

6-(2-Chlorophenyl)-2-isopropylamino-7-[(4-methylpiperazin-1-ylcarbonyl)methyloxy]quinazoline Compound 40

In a similar manner to Example 38, Compound 40 was obtained using 1-methylpiperazine.

¹H NMR (270 MHz, DMSO-d₆) δ (ppm) 1.20 (d, J=6.6 Hz, 6H), 2.12-3.22 (m, 4H), 2.14 (s, 3H), 3.30-3.44 (m, 4H), 4.10-4.30 (m, 1H), 4.94 (s, 2H), 6.88 (s, 1H), 7.19 (d, J=8.0 Hz, 1H), 7.36-7.46 (m, 3H), 7.52-7.55 (m, 1H), 7.59 (s, 1H), 8.94 (s, 1H).

APCI m/z (M+H)⁺ 454.

Example 41

7-(4-Carboxyphenyl)-6-(2-chlorophenyl)-2-isopropylaminoquinazoline

Compound 41

Step 1

Compound 19 (560 mg, 1.78 mmol) was dissolved in pyridine (6 mL) and was cooled to 0° C., then the solution was added with trifluoromethanesulfonic anhydride (0.928 mL, 5.35 mmol), followed by stirring at room temperature overnight. The reaction mixture was concentrated under reduced pressure. The residue was added with ethyl acetate and water, and extracted. The organic layer was washed with diluted hydrochloric acid and dried over anhydrous magnesium sulfate, then the solvent was evaporated under reduced pressure. The residue was purified by silica gel column chromatography (ethyl acetate/hexane=1/2) to obtain 6-(2-chlorophenyl)-2-isopropylamino-7-(trifluoromethanesulfonyloxy)quinazoline quantitatively.

Step 2

In a similar manner to Example 91, Compound 41 was obtained using 6-(2-chlorophenyl)-2-isopropylamino-7-(trifluoromethanesulfonyloxy)quinazoline obtained in Step 1.

¹H NMR (300 MHz, DMSO-d₆) δ (ppm) 1.22 (d, J=6.4 Hz, 6H), 4.14-4.28 (m, 1H), 7.25-7.44 (m, 8H), 7.76-7.79 (m, 3H), 9.18 (s, 1H), 12.96 (br s, 1H).

APCI m/z (M+H)⁺ 418.

Example 42

7-(3-Carboxyphenyl)-6-(2-chlorophenyl)-2-isopropylaminoquinazoline

Compound 42

In a similar manner to Example 91, Compound 42 was obtained using 6-(2-chlorophenyl)-2-isopropylamino-7-(trifluoromethanesulfonyloxy)quinazoline obtained in Step 1 of Example 41 and 3-carboxyphenylboronic acid.

¹H NMR (270 MHz, DMSO-d₆) δ (ppm) 1.23 (d, J=6.4 Hz, 6H), 4.14-4.30 (m, 1H), 7.27-7.52 (m, 8H), 7.74-7.82 (m, 3H), 9.18 (s, 1H).

APCI m/z (M+H)⁺ 418.

Example 43

6-(2-Chlorophenyl)-7-(3-chlorophenyl)-2-isopropylaminoquinazoline

Compound 43

In a similar manner to Example 91, Compound 43 was obtained using 6-(2-chlorophenyl)-2-isopropylamino-7-(trifluoromethanesulfonyloxy)quinazoline obtained in Step 1 of Example 41 and 3-chlorophenylboronic acid.

¹H NMR (270 MHz, DMSO-d₆) δ (ppm) 1.22 (d, J=6.4 Hz, 6H), 4.16-4.28 (m, 1H), 7.15-7.48 (m, 10H), 7.76 (s, 1H), 9.17 (s, 1H).

APCI m/z (M+H)⁺ 409.

Example 44

2-Isopropylamino-7-methoxy-6-phenylquinazoline

Compound 44

In a similar manner to Example 4, Compound 44 was obtained using phenylboronic acid.

¹H NMR (300 MHz, CDCl₃) δ (ppm) 1.31 (d, J=6.6 Hz, 6H), 3.93 (s, 3H), 4.26-4.35 (m, 1H), 5.07 (d, J=6.6 Hz, 1H), 6.99 (s, 1H), 7.33-7.46 (m, 3H), 7.52-7.55 (m, 2H), 7.54 (s, 1H), 8.82 (s, 1H).

APCI m/z (M+H)⁺ 294.

Example 45

2-Isopropylamino-7-methoxy-6-(4-trifluoromethylphenyl)quinazoline

Compound 45

In a similar manner to Example 4, Compound 45 was obtained using 4-(trifluoromethyl)phenylboronic acid.

¹H NMR (300 MHz, DMSO-d₆) δ (ppm) 1.21 (d, J=6.6 Hz, 6H), 3.91 (s, 3H), 4.18-4.25 (m, 1H), 6.97 (s, 1H), 7.23-7.28 (m, 1H), 7.72-7.80 (m, 4H), 7.76 (s, 1H), 8.96 (s, 1H).

APCI m/z (M+H)⁺ 362.

Example 46

6-(4-Carboxyphenyl)-2-isopropylamino-7-methoxyquinazoline

Compound 46

In a similar manner to Example 4, Compound 46 was obtained using 4-carboxyphenylboronic acid.

¹H NMR (300 MHz, DMSO-d₆) δ (ppm) 1.21 (d, J=6.4 Hz, 6H), 3.91 (s, 3H), 4.18-4.25 (m, 1H), 7.01 (s, 1H), 7.64 (d, J=8.4 Hz, 2H), 7.79 (s, 1H), 7.99 (d, J=8.4 Hz, 2H), 9.00 (s, 1H).

APCI m/z (M+H)⁺ 338.

Example 47

6-(4-Hydroxyphenyl)-2-isopropylamino-7-methoxyquinazoline

Compound 47

In a similar manner to Example 4, Compound 47 was obtained using 4-hydroxyphenylboronic acid.

¹H NMR (300 MHz, DMSO-d₆) δ (ppm) 1.19 (d, J=6.4 Hz, 6H), 3.87 (s, 3H), 4.15-4.22 (m, 1H), 6.79 (d, J=8.4 Hz, 2H), 6.89 (s, 1H), 7.06 (m, 1H), 7.31 (d, J=8.4 Hz, 2H), 7.59 (s, 1H), 8.91 (s, 1H), 9.47 (br s, 1H).
APCI m/z (M+H)⁺ 310.

Example 48

2-Isopropylamino-7-methoxy-6-(4-methylphenyl)quinazoline

Compound 48

In a similar manner to Example 4, Compound 48 was obtained using 4-methylphenylboronic acid.
¹H NMR (300 MHz, CDCl₃) δ (ppm) 1.29 (d, J=6.4 Hz, 6H), 2.40 (s, 3H), 3.90 (s, 3H), 4.25-4.36 (m, 1H), 5.17 (m, 1H), 6.98 (s, 1H), 7.23 (d, J=8.4 Hz, 2H), 7.42 (d, J=8.4 Hz, 2H), 7.50 (s, 1H), 8.80 (s, 1H).
APCI m/z (M+H)⁺ 308.

Example 49

2-Isopropylamino-7-methoxy-6-(3-nitrophenyl)quinazoline

Compound 49

In a similar manner to Example 4, Compound 49 was obtained using 3-nitrophenylboronic acid.
¹H NMR (270 MHz, CDCl₃) δ (ppm) 1.31 (d, J=6.4 Hz, 6H), 3.95 (s, 3H), 4.26-4.38 (m, 1H), 5.13 (br s, 1H), 7.02 (s, 1H), 7.57 (s, 1H), 7.58 (dd, J=8.0, 8.0 Hz, 1H), 7.87 (ddd, J=8.0, 1.9, 1.4 Hz, 1H), 8.22 (ddd, J=8.0, 1.9, 1.4 Hz, 1H), 8.42 (dd, J=1.9, 1.9 Hz, 1H), 8.85 (s, 1H).
APCI m/z (M+H)⁺ 339.

Example 50

6-(3-Aminophenyl)-2-isopropylamino-7-methoxyquinazoline

Compound 50

Compound 49 (188 mg, 0.556 mmol), ammonium formate (350 mg, 5.55 mmol) and 10% palladium carbon (12 mg) were suspended in methanol (6 mL) and the suspension was stirred at room temperature for 3 hours. The reaction mixture was added with saturated brine and ethyl acetate. The organic layer was separated and washed with saturated brine. The organic layer was dried over anhydrous magnesium sulfate and the solvent was evaporated under reduced pressure. The residue was reslurried with hexane/diethylether (1/1) and was collected by filtration, then was dried to obtain Compound 50 (170 mg, 99%).
¹H NMR (270 MHz, CDCl₃) δ (ppm) 1.30 (d, J=6.4 Hz, 6H), 3.72 (br s, 2H), 3.92 (s, 3H), 4.27-4.35 (m, 1H), 5.03-5.06 (m, 1H), 6.69 (ddd, J=7.2, 2.2, 1.4 Hz, 1H), 6.86 (dd, J=2.2, 2.2 Hz, 1H), 6.92 (ddd, J=7.2 Hz, 2.2, 1.4 Hz, 1H), 6.96 (s, 1H), 7.21 (dd, J=7.4 Hz, 1H), 7.52 (s, 1H), 8.80 (s, 1H)
APCI m/z (M+H)⁺ 309. .

Example 51

6-[3-(tert-Butoxycarbonylamino)phenyl]-2-isopropylamino-7-methoxyquinazoline

Compound 51

Compound 50 (46 mg, 0.15 mmol), di-tert-butyldicarbonate (51 μL, 0.22 mmol) and dimethylaminopyridine (6 mg, 0.04 mmol) were dissolved in THF (1.5 mL), and the solution was stirred at room temperature for 30 minutes. The reaction mixture was added with saturated brine and ethyl acetate, and the organic layer was separated. The organic layer was washed with saturated brine and dried over anhydrous magnesium sulfate, then the solvent was evaporated under reduced pressure. The residue was purified by preparative thin-layer chromatography (ethyl acetate/hexane=1/1) to obtain Compound 51 (32 mg, 53%).
¹H NMR (300 MHz, CDCl₃) δ (ppm) 1.30 (d, J=6.4 Hz, 6H), 1.47 (s, 9H), 3.89 (s, 3H), 4.25-4.36 (m, 1H), 5.13 (br s, 1H), 6.95 (s, 1H), 7.21-7.23 (m, 1H), 7.35-7.49 (m, 3H), 7.50 (s, 1H), 8.79 (s, 1H).
APCI m/z (M+H)⁺ 409.

Example 52

6-[(3-Acetylamino)phenyl]-2-isopropylamino-7-methoxyquinazoline

Compound 52

Compound 50 (92 mg, 0.29 mmol) and acetic anhydride (56 μL, 0.59 mmol) were dissolved in methylene chloride (2 mL) and the solution was stirred at room temperature for 10 minutes. The reaction mixture was added with saturated brine and chloroform, and the organic layer was separated. The organic layer was washed with saturated brine and dried over anhydrous magnesium sulfate, then the solvent was evaporated under reduced pressure. The residue was purified by preparative thin-layer chromatography (ethyl acetate/hexane=1/1) to obtain Compound 52 (35 mg, 34%).
¹H NMR (270 MHz, CDCl₃) δ (ppm) 1.31 (d, J=6.4 Hz, 6H), 2.19 (s, 3H), 3.93 (s, 3H), 4.27-4.35 (m, 1H), 5.07 (br s, 1H), 6.98 (s, 1H), 7.19-7.40 (m, 3H), 7.51-7.53 (m, 1H), 7.54 (s, 1H), 7.65 (s, 1H), 8.81 (s, 1H).
APCI m/z (M+H)⁺ 351.

Example 53

2-Isopropylamino-7-methoxy-6-{3-[(2-morpholinopyridin-4-yl)carbonylamino]phenyl}quinazoline Compound 53

Step 1
Compound A5 (60 mg, 0.38 mmol) was dissolved in THF (2 mL) and the solution was added with thionyl chloride (25 μL, 1.2 mmol), followed by stirring at room temperature for 15 minutes. Then, the solution was concentrated by azeotropic distillation using toluene to obtain 2-morpholinoisonicotinoyl chloride. This compound was used to the next reaction without purification.
Step 2
Compound 50 (94 mL, 0.27 mmol) was dissolved in THF (2 mL) and the solution was added with a solution of 2-morpholinoisonicotinoyl chloride (0.38 mmol) prepared in the Step 1 in THF (2 mL) and triethylamine (52 μL, 0.38 mmol), followed by stirring at room temperature for 2 hours. The reaction mixture was added with saturated brine and ethyl acetate, and the organic layer was separated. The organic layer was washed with saturated brine and dried over anhydrous magnesium sulfate, then the solvent was evaporated under reduced pressure. The residue was purified by preparative thin-layer chromatography (ethyl acetate/hexane=1/4) to obtain Compound 53 (20 mg, 15%).

$^1$H NMR (300 MHz, CDCl$_3$) δ (ppm) 1.31 (d, J=6.4 Hz, 6H), 3.58-3.62 (m, 4H), 3.82-3.85 (m, 4H), 3.95 (s, 3H), 4.24-4.33 (m, 1H), 5.06 (br s, 1H), 6.94 (d, J=5.1 Hz, 1H), 6.99 (s, 1H), 7.15 (s, 1H), 7.35-7.47 (m, 2H), 7.57 (s, 1H), 7.65-7.67 (m, 1H), 7.80 (br s, 1H), 7.88 (s, 1H), 8.33 (d, J=5.1 Hz, 1H), 8.83 (s, 1H).

ESI m/z (M+H)$^+$ 499.

Example 54

2-Isopropylamino-7-methoxy-6-{3-[(3-dimethylaminophenyl)carbonylamino]phenyl}quinazoline Compound 54

In a similar manner to Step 2 of Example 53, Compound 54 was obtained using 3-(dimethylamino)benzoic acid.

$^1$H NMR (300 MHz, CDCl$_3$) δ (ppm) 1.31 (d, J=6.4 Hz, 6H), 3.02 (s, 6H), 3.94 (s, 3H), 4.28-4.35 (m, 1H), 5.07 (br s, 1H), 6.87-6.90 (m, 1H), 6.99 (s, 1H), 7.08-7.10 (m, 1H), 7.28-7.45 (m, 4H), 7.58 (s, 1H), 7.65-7.68 (m, 1H), 7.82 (br s, 1H), 7.83-7.86 (m, 1H), 8.83 (s, 1H).

APCI m/z (M+H)$^+$ 456.

Example 55

2-Isopropylamino-7-methoxy-6-(2-nitrophenyl)quinazoline

Compound 55

In a similar manner to Example 4, Compound 55 was obtained using 2-nitrophenylboronic acid.

$^1$H NMR (270 MHz, CDCl$_3$) δ (ppm) 1.30 (d, J=6.4 Hz, 6H), 3.80 (s, 3H), 4.27-4.35 (m, 1H), 5.09-5.12 (m, 1H), 6.92 (s, 1H), 7.44-7.54 (m, 2H), 7.55 (s, 1H), 7.64-7.70 (m, 1H), 7.98-8.01 (m, 1H), 8.84 (s, 1H).

APCI m/z (M+H)$^+$ 339.

Example 56

6-[2-(Acetylamino)phenyl]-2-isopropylamino-7-methoxyquinazoline

Compound 56

In a similar manner Example 50 and Example 52, Compound 56 was obtained using Compound 55.

$^1$H NMR (270 MHz, CDCl$_3$) δ (ppm) 1.32 (d, J=6.4 Hz, 6H), 2.20 (s, 3H), 3.93 (s, 3H), 4.28-4.36 (m, 1H), 5.09 (br s, 1H), 6.98 (s, 1H), 7.20-7.40 (m, 3H), 7.52-7.55 (m, 1H), 7.54 (s, 1H), 7.65 (s, 1H), 8.81 (s, 1H).

APCI m/z (M+H)$^+$ 351.

Example 57

6-(2-Formylphenyl)-2-isopropylamino-7-methoxyquinazoline

Compound 57

In a similar manner to Example 4, Compound 57 was obtained using 2-formylphenylboronic acid.

$^1$H NMR (270 MHz, CDCl$_3$) δ (ppm) 1.31 (d, J=6.4 Hz, 6H), 3.86 (s, 3H), 4.26-4.38 (m, 1H), 5.15 (m, 1H), 6.99 (s, 1H), 7.39 (d, J=7.8 Hz, 1H), 7.52 (t, J=7.8 Hz, 1H), 7.53 (s, 1H), 7.67 (d, J=7.8 Hz, 1H), 8.01 (d, J=7.8 Hz, 1H), 8.84 (s, 1H), 9.80 (s, 1H).

APCI m/z (M+H)$^+$ 322.

Example 58

6-[2-(Hydroxyimino)phenyl]-2-isopropylamino-7-methoxyquinazoline

Compound 58

Compound 57 (300 mg, 0.934 mmol), sodium acetate (115 mg, 1.40 mmol) and hydroxyamine hydrochloride (78.0 mg, 1.12 mmol) were dissolved in methylene chloride (4.5 mL) and the solution was stirred at room temperature for 3 hours. The reaction mixture was added with saturated brine and ethyl acetate, and the organic layer was separated. The organic layer was washed with saturated brine and dried over anhydrous magnesium sulfate, then the solvent was evaporated under reduced pressure. The residue was purified by silica gel column chromatography (ethyl acetate/hexane=1/1) and then reslurried with hexane/diethylether (1/1). The obtained solid was collected by filtration to obtain Compound 58 (296 mg, 94%).

$^1$H NMR (270 MHz, CDCl$_3$) δ (ppm) 1.31 (d, J=6.4 Hz, 6H), 3.86 (s, 3H), 4.27-4.38 (m, 1H), 5.37 (br s, 1H), 6.99 (s, 1H), 7.28-7.47 (m, 3H), 7.42 (s, 1H), 7.91 (s, 1H), 7.92-7.95 (m, 1H), 8.81 (s, 1H).

APCI m/z (M+H)$^+$ 337.

Example 59

2-Isopropylamino-7-methoxy-6-[2-(methoxyimino)phenyl]quinazoline

Compound 59

Compound 58 (86 mg, 0.26 mmol), sodium hydride (60% in oil, 31 mg, 0.77 mmol) and methyl iodide (48 μL, 0.77 mmol) were dissolved in DMF (1.5 mL) and the solution was stirred at room temperature for 15 minutes. The reaction mixture was added with water and further stirred for 10 minutes. The mixture was added with saturated brine and ethyl acetate, and the organic layer was separated. The organic layer was washed with saturated brine and dried over anhydrous magnesium sulfate, then the solvent was evaporated under reduced pressure. The residue was purified by silica gel column chromatography (ethyl acetate/hexane=1/1) and then reslurried with hexane/diethylether (1/1). The obtained solid was collected by filtration to obtain Compound 59 (36 mg, 40%).

$^1$H NMR (270 MHz, CDCl$_3$) δ (ppm) 1.31 (d, J=6.4 Hz, 6H), 3.86 (s, 3H), 3.90 (s, 3H), 4.30-4.33 (m, 1H), 5.07 (br s, 1H), 6.97 (s, 1H), 7.29-7.44 (m, 3H), 7.40 (s, 1H), 7.82 (s, 1H), 7.95-7.98 (m, 1H), 8.79 (s, 1H).
APCI m/z (M+H)+ 351.

Example 60

8-Bromo-6-(2-chlorophenyl)-2-isopropylamino-7-methoxyquinazoline

Compound 60

Compound 4 (3.67 g, 11.2 mmol) was dissolved in acetic acid (140 mL) and the solution was added with bromine (2.01 mL, 39.2 mmol), followed by stirring at 60° C. for 2 hours. The reaction mixture was added with aqueous ammonia solution and the obtained crystal was collected by filtration. The crystal was dissolved in ethyl acetate and washed with water, followed by drying over anhydrous magnesium sulfate. The solvent was evaporated under reduced pressure to obtain Compound 60 (4.21 g, 93%).
$^1$H NMR (270 MHz, DMSO-$d_6$) δ (ppm) 1.24 (d, J=6.4 Hz, 6H), 3.48 (s, 3H), 4.20-4.32 (m, 1H), 7.43-7.50 (m, 3H), 7.57-7.65 (m, 2H), 7.70 (s, 1H), 9.05 (s, 1H).

Example 61

6-(2-Chlorophenyl)-2-isopropylamino-7-methoxy-8-(methoxycarbonyl)quinazoline

Compound 61

In a similar manner to Example 62, Compound 61 was obtained using methanol in place of propanol.
$^1$H NMR (270 MHz, CDCl$_3$) δ (ppm) 1.30 (d, J=6.4 Hz, 6H), 3.64 (s, 3H), 4.03 (s, 3H), 4.14-4.26 (m, 1H), 5.24 (d, J=6.4 Hz, 1H), 7.31-7.38 (m, 3H), 7.47-7.51 (m, 1H), 7.55 (s, 1H), 8.84 (s, 1H).
APCI m/z (M+H)+ 386.

Example 62

6-(2-Chlorophenyl)-2-isopropylamino-7-methoxy-8-(propoxycarbonyl)quinazoline

Compound 62

Compound 60 (540 mg, 1.33 mmol), palladium acetate (30 mg, 0.13 mmol), 1,3-bis(diphenylphosphino)propane (55 mg, 0.13 mmol) and potassium carbonate (277 mg, 2.00 mmol) were dissolved in propanol (5 mL) and DMF (4 mL), and the atmosphere of the reaction vessel was substituted with carbon monoxide, followed by stirring at 90° C. for 23 hours. The reaction mixture was added with saturated brine and ethyl acetate, and the organic layer was separated. The organic layer was washed with saturated brine and dried over anhydrous magnesium sulfate, then the solvent was evaporated under reduced pressure. The residue was purified by silica gel column chromatography (ethyl acetate/hexane=1/6) to obtain Compound 62 (470 mg, 85%).
$^1$H NMR (300 MHz, CDCl$_3$) δ (ppm) 1.05 (t, J=7.5 Hz, 3H), 1.24 (d, J=6.4 Hz, 6H), 1.84 (qt, J=7.5 Hz, 6.6 Hz, 2H), 3.64 (s, 3H), 4.16-4.27 (m, 1H), 4.41 (t, J=6.6 Hz, 2H), 5.23 (m, 1H), 7.31-7.37 (m, 3H), 7.48-7.51 (m, 1H), 7.55 (s, 1H), 8.84 (s, 1H).
APCI m/z (M+H)+ 414.

Example 63

6-(2-Chlorophenyl)-7-hydroxy-2-isopropylamino-8-(propoxycarbonyl)quinazoline

Compound 63

In a similar manner to Example 62, Compound 63 was obtained using Compound 90.
$^1$H NMR (300 MHz, CDCl$_3$) δ (ppm) 1.09 (t, J=7.5 Hz, 3H), 1.32 (d, J=6.4 Hz, 6H), 1.92 (qt, J=7.5 Hz, 6.6 Hz, 2H), 4.33-4.47 (m, 1H), 4.45 (t, J=6.6 Hz, 2H), 5.20-5.27 (m, 1H), 7.32-7.36 (m, 3H), 7.48-7.52 (m, 1H), 7.59 (s, 1H), 8.72 (s, 1H), 13.3 (br s, 1H).
APCI m/z (M+H)+ 400.

Example 64

8-Carboxy-6-(2-chlorophenyl)-2-isopropylamino-7-methoxyquinazoline

Compound 64

In a similar manner to Example 33, Compound 64 was obtained using Compound 61.
$^1$H NMR (270 MHz, CDCl$_3$) δ (ppm) 1.39 (d, J=6.4 Hz, 6H), 3.79 (s, 3H), 4.13 (br s, 1H), 5.67 (br s, 1H), 7.33-7.40 (m, 3H), 7.50-7.53 (m, 1H), 7.74 (s, 1H), 8.96 (s, 1H).
APCI m/z (M+H)+ 372.

Example 65

8-Carboxy-6-(2-chlorophenyl)-7-hydroxy-2-(isopropylamino)quinazoline

Compound 65

In a similar manner to Example 19, Compound 65 was obtained using Compound 61.
$^1$H NMR (300 MHz, DMSO-$d_6$) δ (ppm) 1.30 (d, J=6.4 Hz, 6H), 4.17-4.21 (m, 1H), 7.35-7.41 (m, 3H), 7.49-7.52 (m, 1H), 7.79 (s, 1H), 9.01 (s, 1H).
APCI m/z (M+H)+ 358.

Example 66

6-(2-Chlorophenyl)-2-isopropylamino-8-(morpholinocarbonyl)-7-methoxyquinazoline

Compound 66

Compound 62 (98 mg, 0.24 mmol) and morpholine (186 μL, 2.14 mmol) were dissolved in THF (2.5 mL) and the solution was stirred at −78° C. for 10 minutes. Then, n-BuLi (1.65 mol/L hexane solution, 1.3 mL, 2.14 mmol) was added dropwise thereto and further stirred at −78° C. for 5 minutes. The reaction mixture was added with water and ethyl acetate and the organic layer was separated. The organic layer was washed with water and dried over anhydrous magnesium sulfate, then the solvent was evaporated under reduced pressure. The residue was purified by silica gel column chromatography (ethyl acetate/hexane=1/3) to obtain Compound 66 (70 mg, 67%).
$^1$H NMR (300 MHz, CDCl$_3$) δ (ppm) 1.29 (d, J=6.4 Hz, 6H), 3.30-3.33 (m, 2H), 3.57-3.70 (m, 2H), 3.62 (s, 3H), 3.75-3.92 (m, 4H), 4.23-4.29 (m, 1H), 5.14-5.16 (m, 1H), 7.30-7.37 (m, 3H), 7.46-7.48 (m, 1H), 7.49 (s, 1H), 8.83 (s, 1H).
APCI m/z (M+H)$^+$ 441.

Example 67

6-(2-Chlorophenyl)-2-isopropylamino-7-methoxy-8-(piperidinocarbonyl)quinazoline

Compound 67

In a similar manner to Example 66, Compound 67 was obtained using piperidine.
$^1$H NMR (270 MHz, CDCl$_3$) δ (ppm) 1.28 (d, J=6.4 Hz, 6H), 1.49-1.57 (m, 2H), 1.61-1.77 (m, 4H), 3.20-3.29 (m, 2H), 3.62 (s, 3H), 3.79-3.90 (m, 2H), 4.15-4.31 (m, 1H), 5.05-5.15 (m, 1H), 7.28-7.36 (m, 3H), 7.42-7.51 (m, 1H), 7.45 (s, 1H), 8.80 (s, 1H).
APCI m/z (M+H)$^+$ 439.

Example 68

6-(2-Chlorophenyl)-8-(N,N-diethylaminocarbonyl)-2-isopropylamino-7-methoxyquinazoline Compound 68

In a similar manner to Example 66, Compound 68 was obtained using diethylamine.
$^1$H NMR (300 MHz, CDCl$_3$) δ (ppm) 1.08 (t, J=6.9 Hz, 3H), 1.28 (d, J=6.4 Hz, 6H), 1.34 (t, J=6.9 Hz, 3H), 3.22 (q, J=6.9 Hz, 2H), 3.48-3.56 (m, 1H), 3.61 (s, 3H), 3.79-3.86 (m, 1H), 4.19-4.26 (m, 1H), 5.09-5.12 (m, 1H), 7.29-7.37 (m, 3H), 7.46-7.49 (m, 1H), 7.47 (s, 1H), 8.81 (s, 1H).
APCI m/z (M+H)$^+$ 427.

Example 69

6-(2-Chlorophenyl)-2-isopropylamino-7-methoxy-8-(N-propylaminocarbonyl)quinazoline Compound 69

In a similar manner to Example 66, Compound 69 was obtained using propylamine.
$^1$H NMR (300 MHz, CDCl$_3$) δ (ppm) 1.04 (t, J=7.5 Hz, 3H), 1.29 (d, J=6.4 Hz, 6H), 1.73 (qt, J=7.5, 6.6 Hz, 2H), 3.52 (q, J=6.6 Hz, 2H), 3.71 (s, 3H), 4.20-4.27 (m, 1H), 5.20-5.23 (m, 1H), 6.65-6.70 (br s, 1H), 7.26-7.35 (m, 3H), 7.47-7.52 (m, 1H), 7.53 (s, 1H), 8.84 (s, 1H).
APCI m/z (M+H)$^+$ 413.

Example 70

8-(N-benzylaminocarbonyl)-6-(2-chlorophenyl)-2-isopropylamino-7-methoxyquinazoline Compound 70

In a similar manner to Example 66, Compound 70 was obtained using benzylamine.
$^1$H NMR (270 MHz, CDCl$_3$) δ (ppm) 1.19 (d, J=6.4 Hz, 6H), 3.72 (s, 3H), 3.85-4.17 (m, 1H), 4.76 (d, J=5.4 Hz, 2H), 5.14-5.17 (m, 1H), 7.31-7.39 (m, 6H), 7.47-7.51 (m, 3H), 7.54 (s, 1H), 8.83 (s, 1H).
APCI m/z (M+H)$^+$ 461.

Example 71

6-(2-Chlorophenyl)-2-isopropylamino-7-methoxy-8-(N-methoxy-N-methylaminocarbonyl)quinazoline Compound 71

In a similar manner to Example 66, Compound 71 was obtained using N-methoxy-N-methylamine.
$^1$H NMR (270 MHz, DMSO-d$_6$) δ (ppm) 1.22 (d, J=6.4 Hz, 6H), 3.24 (br s, 3H), 3.53 (s, 3H), 3.59 (br s, 3H), 4.03-4.16 (m, 1H), 7.06 (br s, 1H), 7.40-7.44 (m, 3H), 7.52-7.57 (m, 1H), 7.64 (s, 1H), 9.00 (s, 1H).
APCI m/z (M+H)$^+$ 415.

Example 72

6-(2-Chlorophenyl)-7-hydroxy-2-isopropylamino-8-(N-methoxy-N-methylaminocarbonyl)quinazoline Compound 72

In a similar manner to Example 19, Compound 72 was obtained using Compound 71.
$^1$H NMR (300 MHz, DMSO-d$_6$) δ (ppm) 1.22 (d, J=6.4 Hz, 6H), 3.21 (s, 3H), 3.62 (s, 3H), 4.03-4.14 (m, 1H), 6.68 (br s, 1H), 7.36-7.40 (m, 3H), 7.47-7.52 (m, 1H), 7.50 (s, 1H), 8.84 (s, 1H).
APCI m/z (M+H)$^+$ 401.

Example 73

6-(2-Chlorophenyl)-8-[(E)-2-(ethoxycarbonyl)ethenyl]-7-methoxy-2-(isopropylamino)quinazoline Compound 73

Compound 60 (122 mg, 0.30 mmol), palladium acetate (7 mg, 0.03 mmol), 1,1'-bis(diphenylphosphino)ferrocene (33 mg, 0.06 mmol), ethyl acrylate (325 μL, 3.00 mmol) and triethylamine (208 μL, 1.50 mmol) were dissolved in DMF (4 mL) and the solution was stirred at 100° C. for 18 hours. The reaction mixture was added with water and ethyl acetate, and the organic layer was separated. The organic layer was washed with saturated brine and dried over anhydrous magnesium sulfate, then the solvent was evaporated under reduced pressure. The residue was purified by silica gel column chromatography (ethyl acetate/hexane=1/2) to obtain Compound 73 (49 mg, 38%).
$^1$H NMR (300 MHz, CDCl$_3$) δ (ppm) 1.36 (d, J=6.4 Hz, 6H), 1.36 (t, J=7.0 Hz, 3H), 3.49 (s, 3H), 4.27-4.38 (m, 1H), 4.29 (q, J=7.0 Hz, 2H), 5.31 (d, J=6.4 Hz, 1H), 7.33-7.41 (m, 3H), 7.51-7.54 (m, 1H), 7.55 (s, 1H), 7.61 (d, J=16 Hz, 1H), 8.49 (d, J=16 Hz, 1H), 8.87 (s, 1H).
APCI m/z (M+H)$^+$ 426.

Example 74

8-[(E)-2-carboxyethenyl]-6-(2-chlorophenyl)-7-methoxy-2-(isopropylamino)quinazoline Compound 74

In a similar manner to Example 33, Compound 74 was obtained using Compound 73.

¹H NMR (300 MHz, CDCl₃) δ (ppm) 1.38 (d, J=6.6 Hz, 6H), 3.50 (s, 3H), 4.27-4.38 (m, 1H), 5.60 (d, J=6.6 Hz, 1H), 7.34-7.42 (m, 3H), 7.51-7.57 (m, 1H), 7.61 (s, 1H), 7.80 (d, J=16 Hz, 1H), 8.55 (d, J=16 Hz, 1H), 8.88 (s, 1H).
APCI m/z (M+H)⁺ 398.

Example 75

8-(2-Carboxyethyl)-6-(2-chlorophenyl)-7-methoxy-2-(isopropylamino)quinazoline

Compound 75

Compound 73 (95 mg, 0.22 mmol) was dissolved in ethanol (10 mL) and the solution was added with 10% palladium carbon (50% aqueous, 20 mg), followed by stirring at 40° C. for 6 hours under hydrogen atmosphere. After filtering off using Celite, the solvent was evaporated under reduced pressure. The residue was dissolved in chloroform (10 mL) and the solution was added with manganese dioxide (194 mg, 2.23 mmol), followed by stirring at 40° C. for 20 hours. After filtering off using Celite, the solvent was evaporated under reduced pressure. The residue was dissolved in THF (2 mL) and methanol (2 mL) and the solution was added with 1 mol/L lithium hydroxide solution (2 mL), followed by stirring at room temperature for 3 hours. The reaction mixture was added with diluted hydrochloric acid to adjust the pH to 5. Then, the obtained crystal was collected by filtration to obtain Compound 75 (45 mg, 60%).
¹H NMR (300 MHz, DMSO-d₆) δ (ppm) 1.22 (d, J=6.4 Hz, 6H), 2.40-2.44 (m, 2H), 3.14-3.19 (m, 2H), 3.34 (s, 3H), 4.17 (br s, 1H), 7.22-7.28 (m, 1H), 7.38-7.62 (m, 5H), 9.00 (s, 1H).
APCI m/z (M+H)⁺ 400.

Example 76

6-(2-Chlorophenyl)-2-isopropylamino-7-methoxy-8-vinylquinazoline

Compound 76

Compound 60 (80 mg, 0.20 mmol), tributyl(vinyl)tin (67 mg, 0.22 mmol) and tetrakis(triphenylphosphine)palladium (11 mg, 0.0098 mmol) were dissolved in DMF (2.4 mL) and the solution was stirred at 100° C. for 3 hours. The reaction mixture was added with 10% aqueous potassium fluoride solution and further stirred for 10 minutes. The mixture was added with saturated brine and chloroform, and the organic layer was separated. The organic layer was washed with saturated brine and dried over anhydrous magnesium sulfate, then the solvent was evaporated under reduced pressure. The residue was purified by preparative thin-layer chromatography (ethyl acetate/hexane=1/3) to obtain Compound 76 (22 mg, 34%).
¹H NMR (270 MHz, DMSO-d₆) δ (ppm) 1.30 (d, J=6.4 Hz, 6H), 3.49 (s, 3H), 4.07-4.19 (m, 1H), 5.61 (dd, J=12.6 Hz, 2.4 Hz, 1H), 6.70 (dd, J=19.5 Hz, 2.4 Hz, 1H), 7.31 (dd, J=19.5, 12.6 Hz, 1H), 7.43-7.46 (m, 4H), 7.71 (s, 1H), 9.04 (s, 1H).
ESI m/z (M+H)⁺ 354.

Example 77

8-Acetyl-6-(2-chlorophenyl)-2-isopropylamino-7-methoxyquinazoline

Compound 77

Compound 60 (358 mg, 0.88 mmol), tributyl(1-ethoxyvinyl)tin (357 μL, 1.06 mmol) and tetrakis(triphenylphosphine) palladium (51 mg, 0.044 mmol) were dissolved in DMF (4 mL) and the solution was stirred at 120° C. for 2 hours. After standing to cool, the reaction mixture was added with 10% aqueous potassium fluoride solution and further stirred for 10 minutes. The mixture was added with water and ethyl acetate and the organic layer was separated. The organic layer was washed with saturated brine and dried over anhydrous magnesium sulfate, then the solvent was evaporated under reduced pressure. The residue was dissolved in THF (8 mL) and added with 1 mol/L hydrochloric acid (2 mL), followed by stirring at room temperature for 4 hours. The reaction mixture was added with water and ethyl acetate and the organic layer was separated. The organic layer was washed with saturated brine and dried over anhydrous magnesium sulfate, then the solvent was evaporated under reduced pressure. The residue was purified by silica gel column chromatography (ethyl acetate/hexane=1/3) to obtain Compound 77 (132 mg, 41%).
¹H NMR (270 MHz, CDCl₃) δ (ppm) 1.28 (d, J=6.4 Hz, 6H), 2.74 (s, 3H), 3.51 (s, 3H), 4.15-4.27 (m, 1H), 5.21 (d, J=6.4 Hz, 1H), 7.32-7.40 (m, 3H), 7.49-7.52 (m, 1H), 7.54 (s, 1H), 8.86 (s, 1H).
APCI m/z (M+H)⁺ 370.

Example 78

8-Acetyl-6-(2-chlorophenyl)-7-hydroxy-2-(isopropylamino)quinazoline

Compound 78

In a similar manner to Example 19, Compound 78 was obtained using Compound 77.
¹H NMR (300 MHz, CDCl₃) δ (ppm) 1.41 (d, J=6.6 Hz, 6H), 3.10 (s, 3H), 4.25-4.35 (m, 1H), 7.31-7.45 (m, 3H), 7.51-7.54 (m, 1H), 7.78 (s, 1H), 8.22 (d, J=6.6 Hz, 1H), 8.86 (s, 1H).
APCI m/z (M+H)⁺ 356.

Example 79

8-Acetyl-6-(2-chlorophenyl)-7-(ethoxycarbonylmethyloxy)-2-(isopropylamino)quinazoline

Compound 79

In a similar manner to Example 32, Compound 79 was obtained using Compound 78.
¹H NMR (300 MHz, CDCl₃) δ (ppm) 1.19 (t, J=7.2 Hz, 3H), 1.33 (d, J=6.4 Hz, 6H), 2.77 (s, 3H), 4.07 (q, J=7.2 Hz, 2H), 4.13-4.20 (m, 3H), 5.24 (m, 1H), 7.32-7.41 (m, 3H), 7.49-7.53 (m, 1H), 7.57 (s, 1H), 8.88 (s, 1H).
APCI m/z (M+H)⁺ 442.

Example 80

8-Acetyl-7-(carboxymethyloxy)-6-(2-chlorophenyl)-2-(isopropylamino)quinazoline

Compound 80

In a similar manner to Example 33, Compound 80 was obtained using Compound 79.
¹H NMR (300 MHz, CDCl₃) δ (ppm) 1.30 (d, J=6.4 Hz, 6H), 2.86 (s, 3H), 4.17-4.28 (m, 3H), 6.09 (br s, 1H), 7.35-7.41 (m, 3H), 7.51-7.55 (m, 1H), 7.65 (s, 1H), 8.87 (s, 1H).
APCI m/z (M+H)⁺ 414.

Example 81

6-(2-Chlorophenyl)-8-(1-hydroxy-1-methylethyl)-7-(2-hydroxy-2-methylpropyloxy)-2-(isopropylamino)quinazoline

Compound 81

Compound 79 (30 mg, 0.068 mmol) was dissolved in THF (1 mL), and the solution was added with methylmagnesium bromide (1.4 mol/L toluene/THF solution, 250 μL, 0.39 mmol), followed by stirring at room temperature for 30 minutes. The reaction mixture was added with saturated aqueous ammonium chloride solution and ethyl acetate, and the organic layer was separated. The organic layer was washed with saturated brine and dried over anhydrous magnesium sulfate, then the solvent was evaporated under reduced pressure. The residue was purified by preparative thin-layer chromatography (ethyl acetate/hexane=1/1) to obtain Compound 81 (12 mg, 43%).

$^1$H NMR (300 MHz, CDCl$_3$) δ (ppm) 0.93 (s, 6H), 1.33 (d, J=6.4 Hz, 6H), 1.87 (s, 3H), 1.88 (s, 3H), 3.41 (d, J=9.0 Hz, 1H), 3.45 (d, J=9.0 Hz, 1H), 4.11-4.22 (m, 1H), 5.34 (br s, 1H), 7.33-7.40 (m, 3H), 7.45 (s, 1H), 7.49-7.52 (m, 1H), 8.88 (s, 1H).

APCI m/z (M+H)$^+$ 444.

Example 82

8-Bromo-6-(2,4-difluorophenyl)-2-isopropylamino-7-methoxyquinazoline

Compound 82

In a similar manner to Example 60, Compound 82 was obtained using Compound 3.

$^1$H NMR (300 MHz, CDCl$_3$) δ (ppm) 1.35 (d, J=6.6 Hz, 6H), 3.62 (s, 3H), 4.33-4.44 (m, 1H), 5.37 (br s, 1H), 6.91-7.01 (m, 2H), 7.38-7.46 (m, 1H), 7.55 (s, 1H), 8.86 (s, 1H).

APCI m/z (M+H)$^+$ 408, 410.

Example 83

6-(2,4-Difluorophenyl)-8-(4-fluorophenyl)-2-isopropylamino-7-methoxyquinazoline

Compound 83

In a similar manner to Example 91, Compound 83 was obtained using Compound 82 and 4-fluorophenylboronic acid.

$^1$H NMR (270 MHz, CDCl$_3$) δ (ppm) 1.19 (d, J=6.4 Hz, 6H), 3.22 (s, 3H), 3.98 (br s, 1H), 5.10 (d, J=6.4 Hz, 1H), 6.89-7.01 (m, 2H), 7.11-7.19 (m, 2H), 7.37-7.46 (m, 1H), 7.54-7.60 (m, 2H), 7.59 (s, 1H), 8.90 (s, 1H).

APCI m/z (M+H)$^+$ 424.

Example 84

6-(2,4-Difluorophenyl)-8-(4-fluorophenyl)-2-isopropylamino-7-hydroxyquinazoline

Compound 84

In a similar manner to Example 19, Compound 84 was obtained using Compound 83.

$^1$H NMR (300 MHz, CDCl$_3$) δ (ppm) 1.16 (d, J=6.4 Hz, 6H), 3.93 (br s, 1H), 5.09 (br s, 1H), 6.90-7.01 (m, 2H), 7.19-7.25 (m, 2H), 7.39-7.54 (m, 3H), 7.55 (s, 1H), 8.80 (s, 1H).

APCI m/z (M+H)$^+$ 410.

Example 85

6-(2,4-Difluorophenyl)-8-(4-fluorophenyl)-2-(isopropylamino)quinazoline

Compound 85

Compound 84 (50 mg, 0.12 mmol) was dissolved in pyridine (1 mL) and the solution was added with trifluoromethanesulfonic anhydride (27 μL, 0.16 mmol) at 0° C., followed by stirring at room temperature for 1 hour. The reaction mixture was added with water and ethyl acetate, and the organic layer was separated. The organic layer was washed with water and dried over anhydrous magnesium sulfate, then the solvent was evaporated under reduced pressure. The residue was dissolved in DMF (1 mL) and the solution was added with sodium formate (50 mg, 0.74 mmol) and tetrakis(triphenylphosphine)palladium (14 mg, 0.012 mmol), followed by stirring at 100° C. for 2 hours. After standing to cool, the reaction mixture was added with water and ethyl acetate, and the organic layer was separated. The organic layer was washed with saturated brine and dried over anhydrous magnesium sulfate, then the solvent was evaporated under reduced pressure. The residue was purified by silica gel column chromatography (ethyl acetate/hexane=1/5) to obtain Compound 85 (23 mg, 49%).

$^1$H NMR (270 MHz, CDCl$_3$) δ (ppm) 1.26 (d, J=6.6 Hz, 6H), 4.07-4.19 (m, 1H), 5.19 (d, J=6.6 Hz, 1H), 6.91-7.03 (m, 2H), 7.12-7.20 (m, 2H), 7.45-7.54 (m, 1H), 7.75-7.80 (m, 3H), 7.84-7.86 (m, 1H), 9.02 (s, 1H).

APCI m/z (M+H)$^+$ 394.

Example 86

6-(2-Chlorophenyl)-2-isopropylamino-7-methoxy-8-(2-pyridyl)quinazoline

Compound 86

In a similar manner to Example 76, Compound 86 was obtained using tributyl(2-pyridyl)tin.

$^1$H NMR (300 MHz, CDCl$_3$) δ (ppm) 1.14 (d, J=6.4 Hz, 6H), 3.28 (s, 3H), 3.87 (br s, 1H), 5.08 (d, J=6.4 Hz, 1H), 7.26-7.35 (m, 3H), 7.40-7.44 (m, 1H), 7.47-7.51 (m, 1H), 7.55-7.58 (m, 1H), 7.60 (s, 1H), 7.76-7.82 (m, 1H), 8.77-8.78 (m, 1H), 8.89 (s, 1H).

APCI m/z (M+H)$^+$ 405.

Example 87

6-(2-Chlorophenyl)-2-isopropylamino-7-hydroxy-8-(2-pyridyl)quinazoline

Compound 87

In a similar manner to Example 19, Compound 87 was obtained using Compound 86.

$^1$H NMR (300 MHz, DMSO-d$_6$) δ (ppm) 1.30 (d, J=6.6 Hz, 6H), 4.18-4.29 (m, 1H), 7.08 (d, J=6.6 Hz, 1H), 7.38-7.46 (m, 4H), 7.51-7.54 (m, 1H), 7.62 (s, 1H), 8.04-8.10 (m, 1H), 8.57-8.60 (m, 1H), 8.89 (s, 1H), 9.80-9.83 (m, 1H).

APCI m/z (M+H)$^+$ 391.

Example 88

6-(2-Chlorophenyl)-7-hydroxy-8-iodo-2-(isopropylamino)quinazoline

Compound 88

Compound 19 (52 mg, 0.17 mmol), sodium iodide (28 mg, 0.18 mmol), sodium hydroxide (8 mg, 0.18 mmol) and sodium chlorite (275 µL, 0.18 mmol) were dissolved in methanol (0.6 mL), and the atmosphere of the reaction vessel was substituted with argon, followed by stirring at 0° C. for 50 minutes. The reaction mixture was sequentially added with water, 20% aqueous sodium thiosulfate solution and 1 mol/L hydrochloric acid and the precipitated crystal was filtered off to obtain Compound 88 (72 mg, 98%).

$^1$H NMR (270 MHz, CDCl$_3$) δ (ppm) 1.36 (d, J=6.4 Hz, 6H), 4.34-4.41 (m, 1H), 5.25 (br s, 1H), 7.26-7.38 (m, 3H), 7.45 (s, 1H), 7.50-7.60 (m, 1H), 8.71 (s, 1H).

Example 89

8-Bromo-6-(2-chlorophenyl)-7-hydroxy-2-(isopropylamino)quinazoline

Compound 89

Compound 60 (4.21 g, 10.4 mmol) was dissolved in dichloroethane (90 mL) and the solution was added with boron tribromide (9.80 mL, 104 mmol), followed by heating under reflux for 5 hours. The reaction mixture was added with 28% aqueous ammonia and the obtained crystal was collected by filtration. The reaction mixture was poured into ice water, and was added with aqueous sodium hydrogencarbonate solution and chloroform, and the organic layer was separated. The organic layer was dried over anhydrous magnesium sulfate and the solvent was evaporated under reduced pressure to obtain Compound 89 (2.12 g, 52%).

$^1$H NMR (270 MHz, DMSO-d$_6$) δ (ppm) 1.24 (d, J=6.4 Hz, 6H), 4.20-4.32 (m, 1H), 7.36-7.48 (m, 4H), 7.53-7.60 (m, 2H), 8.91 (s, 1H), 9.87 (s, 1H).

ESI m/z (M+H)$^+$ 392.

Example 90

8-Bromo-6-(2-chlorophenyl)-2-isopropylamino-7-(methoxymethyloxy)quinazoline

Compound 90

Compound 89 (2.11 g, 5.40 mmol) was dissolved in methylene chloride (40 mL), and the solution was cooled to 0° C., then the solution was added with triethylamine (2.26 mL, 16.2 mmol) and methoxymethyl chloride (1.23 mL, 16.2 mmol), followed by stirring at room temperature for 2 hours. The reaction mixture was added with aqueous sodium hydrogencarbonate solution and methylene chloride, and the organic layer was separated. The organic layer was washed with water and dried over anhydrous magnesium sulfate, then the solvent was evaporated under reduced pressure. The residue was reslurried with ether to obtain Compound 90 (1.82 g, 78%).

$^1$H NMR (270 MHz, CDCl$_3$) δ (ppm) 1.35 (d, J=6.6 Hz, 6H), 3.02 (s, 3H), 4.32-4.44 (m, 1H), 4.92 (s, 2H), 5.35 (s, 1H), 7.30-7.42 (m, 3H), 7.48-7.54 (m, 2H), 8.87 (s, 1H).

Example 91

8-(4-Carboxyphenyl)-6-(2-chlorophenyl)-2-isopropylamino-7-(methoxymethyloxy)quinazoline

Compound 91

Compound 90 (100 mg, 0.230 mmol), 4-carboxyphenylboronic acid (46 mg, 0.28 mmol), sodium carbonate (49 mg, 0.46 mmol) and tetrakis(triphenylphosphine)palladium (13 mg, 0.012 mmol) were added with dioxane (1.5 mL) and water (1.5 mL) under argon atmosphere. Then, the mixture was heated under reflux for 3 hours. An insoluble matter was filtered off using Celite, and the mixture was added with diluted hydrochloric acid to neutralized, then was extracted with ethyl acetate. The organic layer was washed with water and dried over anhydrous magnesium sulfate, then the solvent was evaporated under reduced pressure. The residue was purified by silica gel column chromatography (ethyl acetate/hexane=2/1) to obtain Compound 91 (75.1 mg, 69%).

$^1$H NMR (270 MHz, DMSO-d$_6$) δ (ppm) 1.08 (d, J=5.0 Hz, 6H), 3.32 (s, 3H), 3.65-3.85 (m, 1H), 4.27 (s, 2H), 7.30-7.66 (m, 7H), 7.75 (s, 1H), 7.99 (d, J=8.2 Hz, 2H), 9.09 (s, 1H).

ESI m/z (M+H)$^+$ 478.

Example 92

8-(4-Carboxyphenyl)-6-(2-chlorophenyl)-7-hydroxy-2-(isopropylamino)quinazoline

Compound 92

Compound 91 (45.0 mg, 0.0945 mmol) was dissolved in dioxane (1 mL) and the solution was added with 6 mol/L hydrochloric acid (0.010 mL), followed by stirring at room temperature for 2 hours. The reaction mixture was added with water and extracted with ethyl acetate. The organic layer was washed with water and dried over anhydrous magnesium sulfate, then the solvent was evaporated under reduced pressure. The residue was reslurried with ether to obtain Compound 92 (34.0 mg, 83%).

$^1$H NMR (270 MHz, DMSO-d$_6$) δ (ppm) 1.08 (d, J=6.4 Hz, 6H), 3.60-3.85 (m, 1H), 7.05 (br s, 1H), 7.40-7.47 (m, 3H), 7.52-7.61 (m, 4H), 7.99 (d, J=8.2 Hz, 2H), 8.93 (s, 1H), 9.20 (br s, 1H).

ESI m/z (M+H)$^+$ 434.

Example 93

8-(3-Carboxyphenyl)-6-(2-chlorophenyl)-2-isopropylamino-7-(methoxymethyloxy)quinazoline

Compound 93

In a similar manner to Example 91, Compound 93 was obtained using 3-carboxyphenylboronic acid.

$^1$H NMR (270 MHz, DMSO-d$_6$) δ (ppm) 1.07 (d, J=4.6 Hz, 6H), 3.32 (s, 3H), 3.65-3.85 (m, 1H), 4.28 (s, 2H), 7.33 (br s, 1H), 7.41-7.47 (m, 2H), 7.52-7.60 (m, 3H), 7.72-7.80 (m, 2H), 7.92 (d, J=7.6 Hz, 1H), 8.15 (s, 1H), 9.09 (s, 1H), 12.90 (br s, 1H).

ESI m/z (M+H)$^+$ 478.

Example 94

8-(3-Carboxyphenyl)-6-(2-chlorophenyl)-7-hydroxy-2-(isopropylamino)quinazoline

Compound 94

In a similar manner to Example 92, Compound 94 was obtained using Compound 93.

$^1$H NMR (270 MHz, DMSO-d$_6$) δ (ppm) 1.06 (d, J=6.4 Hz, 6H), 3.60-3.90 (m, 1H), 7.00 (br s, 1H), 7.40-7.49 (m, 3H), 7.51-7.58 (m, 3H), 7.69 (d, J=7.7 Hz, 1H), 7.91 (d, J=7.7 Hz, 1H), 8.07 (s, 1H), 8.93 (s, 1H).

APCI m/z (M+H)$^+$ 434.

Example 95

8-[4-(Carboxymethyl)phenyl]-6-(2-chlorophenyl)-7-hydroxy-2-(isopropylamino)quinazoline

Compound 95

After carrying out the coupling reaction in a similar manner to Example 91 using 4-(carboxymethyl)phenylboronic acid, Compound 95 was obtained by demethoxymethylation in a similar manner to Example 92.

$^1$H NMR (300 MHz, DMSO-d$_6$) δ (ppm) 1.09 (d, J=6.5 Hz, 6H), 3.61 (s, 2H), 3.65-3.90 (m, 1H), 6.95 (br s, 1H), 7.32 (d, J=8.1 Hz, 2H), 7.36-7.46 (m, 5H), 7.52-7.58 (m, 2H), 8.92 (s, 1H), 12.33 (br s, 1H).

APCI m/z (M+H)$^+$ 448.

Example 96

8-[3-(Carboxymethyl)phenyl]-6-(2-chlorophenyl)-7-hydroxy-2-(isopropylamino)quinazoline

Compound 96

After carrying out the coupling reaction in a similar manner to Example 91 using 3-(carboxymethyl)phenylboronic acid, Compound 95 was obtained by demethoxymethylation in a similar manner to Example 92.

$^1$H NMR (300 MHz, DMSO-d$_6$) δ (ppm) 1.08 (d, J=6.6 Hz, 6H), 3.59 (s, 2H), 3.70-3.95 (m, 1H), 6.98 (br s, 1H), 7.22-7.47 (m, 7H), 7.52-7.58 (m, 2H), 8.91 (s, 1H).

APCI m/z (M+H)$^+$ 448.

Example 97

6,8-Di(2-chlorophenyl)-2-isopropylamino-7-(methoxymethyloxy)quinazoline

Compound 97

Compound 90 (70.0 mg, 0.161 mmol), 2-chlorophenylboronic acid (50.0 mg, 0.322 mmol), tripotassium phosphate (103 mg, 0.483 mmol), tris(dibenzylideneacetone)dipalladium (15.0 mg, 0.0161 mmol) and 2-(dicyclohexylphenylphosphino)biphenyl (23.0 mg, 0.0644 mmol) were added with dioxane (1 mL) and water (1 mL) under argon atmosphere, and the mixture was heated under reflux for 1.5 hours. The reaction mixture was added with water and ethyl acetate, and the organic layer was separated. The organic layer was washed with water and dried over anhydrous magnesium sulfate, then the solvent was evaporated under reduced pressure. The residue was purified by silica gel column chromatography (ethyl acetate/hexane=1/9) to obtain Compound 97 (60.0 mg, 80%).

$^1$H NMR (270 MHz, CDCl$_3$) δ (ppm) 1.02-1.20 (m, 6H), 2.66 (s, 3H), 3.70-4.00 (m, 1H), 4.40-4.48 (m, 2H), 5.17 (s, 1H), 7.28-7.36 (m, 4H), 7.40-7.62 (m, 4H), 7.68 (s, 1H), 8.92 (s, 1H).

APCI m/z (M+H)$^+$ 468.

Example 98

6,8-Di(2-chlorophenyl)-7-hydroxy-2-(isopropylamino)quinazoline

Compound 98

In a similar manner to Example 92, Compound 98 was obtained using Compound 97.

$^1$H NMR (270 MHz, CDCl$_3$) δ (ppm) 1.10-1.18 (m, 6H), 3.78-3.98 (m, 1H), 5.20 (br s, 1H), 7.32-7.64 (m, 10H), 8.80 (s, 1H).

APCI m/z (M+H)$^+$ 424.

Example 99

6-(2-Chlorophenyl)-8-(2-fluorophenyl)-2-isopropylamino-7-(methoxymethyloxy)quinazoline

Compound 99

In a similar manner to Example 97, Compound 99 was obtained using 2-fluorophenylboronic acid.

$^1$H NMR (270 MHz, CDCl$_3$) δ (ppm) 1.08-1.20 (m, 6H), 2.66 (s, 3H), 3.80-4.00 (m, 1H), 4.44 (s, 2H), 5.23 (br s, 1H), 7.13-7.25 (m, 2H), 7.30-7.41 (m, 3H), 7.45-7.53 (m, 3H), 7.62 (s, 1H), 8.92 (s, 1H).

APCI m/z (M+H)$^+$ 452.

Example 100

6-(2-Chlorophenyl)-8-(2-fluorophenyl)-7-hydroxy-2-(isopropylamino)quinazoline

Compound 100

In a similar manner to Example 92, Compound 100 was obtained using Compound 99.

$^1$H NMR (270 MHz, CDCl$_3$) δ (ppm) 1.12-1.22 (m, 6H), 3.80-4.20 (m, 1H), 7.22-7.57 (m, 10H), 8.80 (s, 1H).

ESI m/z (M+H)$^+$ 408.

Example 101

6-(2-Chlorophenyl)-8-(2,6-difluorophenyl)-2-isopropylamino-7-(methoxymethyloxy)quinazoline

Compound 101

In a similar manner to Example 97, Compound 101 was obtained using 2,6-difluorophenylboronic acid and 2-(dicyclohexylphosphino)-2'-dimethylaminobiphenyl as a ligand.

$^1$H NMR (270 MHz, CDCl$_3$) δ (ppm) 1.16 (d, J=6.4 Hz, 6H), 2.72 (s, 3H), 3.80-4.00 (m, 1H), 4.49 (s, 2H), 5.12 (d, J=7.6 Hz, 1H), 7.01 (t, J=7.8 Hz, 2H), 7.31-7.42 (m, 3H), 7.45-7.53 (m, 2H), 7.67 (s, 1H), 8.92 (s, 1H).

Example 102

6-(2-Chlorophenyl)-8-(2,6-difluorophenyl)-7-hydroxy-2-(isopropylamino)quinazoline

Compound 102

In a similar manner to Example 92, Compound 102 was obtained using Compound 101.
$^1$H NMR (270 MHz, DMSO-$d_6$) δ (ppm) 1.02-1.08 (m, 6H), 3.54-3.66 (m, 1H), 7.08 (br s, 1H), 7.13 (t, J=8.1 Hz, 2H), 7.40-7.51 (m, 4H), 7.52-7.60 (m, 1H), 7.63 (s, 1H), 8.93 (s, 1H), 9.45 (s, 1H).
APCI m/z (M+H)$^+$ 426.

Example 103

2-Isopropylamino-7-methoxy-6-(propyloxycarbonyl)quinazoline

Compound 103

In a similar manner to Example 62, Compound 103 was obtained using Compound A4.
$^1$H NMR (300 MHz, CDCl$_3$) δ (ppm) 1.05 (t, J=7.5 Hz, 3H), 1.30 (d, J=6.4 Hz, 6H), 1.80 (qt, J=7.5, 6.6 Hz, 2H), 3.51 (s, 3H), 4.26-4.32 (m, 1H), 4.28 (t, J=6.6 Hz, 2H), 5.19-5.22 (m, 1H), 6.92 (s, 1H), 8.16 (s, 1H), 8.83 (s, 1H).
APCI m/z (M+H)$^+$ 304.

Example 104

2-Isopropylamino-7-methoxy-6-(4-methylpiperadinocarbonyl)quinazoline

Compound 104

In a similar manner to Example 66, Compound 104 was obtained using Compound 103 and N-methylpiperazine.
$^1$H NMR (300 MHz, CDCl$_3$) δ (ppm) 1.29 (d, J=6.4 Hz, 6H), 2.31 (s, 3H), 2.26-2.51 (m, 4H), 3.26-3.28 (m, 2H), 3.81-3.98 (m, 2H), 3.94 (s, 3H), 4.25-4.32 (m, 1H), 5.11-5.14 (m, 1H), 6.91 (s, 1H), 7.52 (s, 1H), 8.78 (s, 1H).
APCI m/z (M+H)$^+$ 344.

Example 105

2-Isopropylamino-7-methoxy-6-(morpholinocarbonyl)quinazoline

Compound 105

In a similar manner to Example 66, Compound 105 was obtained using Compound 103.
$^1$H NMR (270 MHz, CDCl$_3$) δ (ppm) 1.29 (d, J=6.4 Hz, 6H), 3.23-3.31 (m, 2H), 3.55-3.64 (m, 2H), 3.74-3.84 (m, 4H), 3.95 (s, 3H), 4.28-4.32 (m, 1H), 5.11-5.15 (m, 1H), 6.91 (s, 1H), 7.54 (s, 1H), 8.79 (s, 1H).
APCI m/z (M+H)$^+$ 331.

Example 106

2-Isopropylamino-7-methoxy-6-(piperidinocarbonyl)quinazoline

Compound 106

In a similar manner to Example 66, Compound 106 was obtained using Compound 103 and piperidine.
$^1$H NMR (270 MHz, CDCl$_3$) δ (ppm) 1.29 (d, J=6.4 Hz, 6H), 1.45-1.60 (m, 6H), 3.17-3.21 (m, 2H), 3.66-3.78 (m, 2H), 3.93 (s, 3H), 4.25-4.35 (m, 1H), 5.09-5.12 (m, 1H), 6.90 (s, 1H), 7.50 (s, 1H), 8.78 (s, 1H).
APCI m/z (M+H)$^+$ 329.

Example 107

2-Isopropylamino-7-methoxy-6-(pyrrolidin-1-ylcarbonyl)quinazoline

Compound 107

In a similar manner to Example 66, Compound 107 was obtained using Compound 103 and pyrrolidine.
$^1$H NMR (270 MHz, CDCl$_3$) δ (ppm) 1.29 (d, J=6.4 Hz, 6H), 1.82-2.00 (m, 4H), 3.22 (t, J=6.6 Hz, 2H), 3.66 (t, J=6.6 Hz, 2H), 3.94 (s, 3H), 4.23-4.34 (m, 1H), 5.10-5.13 (m, 1H), 6.92 (s, 1H), 7.55 (s, 1H), 8.78 (s, 1H).
APCI m/z (M+H)$^+$ 315.

Example 108

2-Amino-6-benzoyl-7-methoxyquinazoline

Compound 108

Guanidine carbonate (1.6 g, 8.6 mmol) was dissolved in DMA (35 mL) and the solution was stirred at 160° C. for 20 minutes. The solution was added with Compound A6 (1.6 g, 6.2 mmol) and further stirred for 50 minutes. After standing to cool, the reaction mixture was added with water and ethyl acetate, and the organic layer was separated. The organic layer was washed with water and dried over anhydrous magnesium sulfate, then the solvent was evaporated under reduced pressure. The obtained solid was reslurried with hexane/diethylether (1/1). The solid was collected by filtration to obtain Compound 108 (965 mg, 56%).
$^1$H NMR (300 MHz, CDCl$_3$) δ (ppm) 3.84 (s, 3H), 5.27 (br s, 2H), 6.97 (s, 1H), 7.43-7.48 (m, 2H), 7.56-7.61 (m, 1H), 7.73 (s, 1H), 7.81-7.83 (m, 2H), 8.90 (s, 1H).

Example 109

6-Benzoyl-2-isopropylamino-7-methoxyquinazoline

Compound 109

Compound 108 (965 mg, 3.4 mmol), copper iodide (394 mg, 2.1 mmol), diiodomethane (2.8 mL, 34 mmol) and isoamyl nitrite (1.4 mL, 10 mmol) were dissolved in THF (20 mL) and the solution was stirred at 70° C. for 4 hours. After standing to cool, the reaction mixture was added with hexane (100 mL) and the precipitate was collected by filtration. The obtained precipitate was dissolved in DMF (10 mL) and the solution was added with isopropylamine (0.88 mL, 10 mmol) and triethylamine (0.96 mL, 6.9 mmol), followed by stirring at room temperature for 30 minutes. The mixture was added with water and ethyl acetate, and the organic layer was separated. The organic layer was washed with water and dried over anhydrous magnesium sulfate, then the solvent was evaporated under reduced pressure. The residue was purified by silica gel column chromatography (ethyl acetate/hexane=1/1) to obtain Compound 109 (394 mg, 35%).
$^1$H NMR (300 MHz, CDCl$_3$) δ (ppm) 1.32 (d, J=6.4 Hz, 6H), 3.83 (s, 3H), 4.28-4.36 (m, 1H), 5.34 (br s, 1H), 6.96 (s, 1H), 7.41-7.47 (m, 2H), 7.54-7.60 (m, 1H), 7.68 (s, 1H), 7.79-7.83 (m, 2H), 8.81 (s, 1H).
APCI m/z (M+H)$^+$ 322.

Example 110

6-Benzoyl-7-hydroxy-2-(isopropylamino)quinazoline

Compound 110

Compound 109 (114 mg, 0.35 mmol) and boron tribromide (1 mol/L methylene chloride solution, 1.8 mL, 1.7 mmol) were dissolved in methylene chloride (2 mL) and stirred at room temperature for 1 hour. After cooling to 0° C., the reaction mixture was added with saturated aqueous sodium hydrogencarbonate solution. The mixture was added with chloroform and the organic layer was separated. The organic layer was washed with saturated aqueous sodium hydrogencarbonate solution and dried over anhydrous magnesium sulfate, then the solvent was evaporated under reduced pressure. The obtained solid was reslurried with hexane/diethylether (1/1) and the solid was collected by filtration to obtain Compound 110 (65 mg, 60%).
$^1$H NMR (270 MHz, CDCl$_3$) δ (ppm) 1.30 (d, J=6.4 Hz, 6H), 4.29-4.40 (m, 1H), 5.34 (br s, 1H), 7.00 (s, 1H), 7.52-7.58 (m, 2H), 7.61-7.72 (m, 3H), 7.95 (s, 1H), 8.74 (s, 1H), 12.0 (br s, 1H).
ESI m/z (M+H)$^+$ 308.

Example 111

6-(2-Chlorophenyl)-8-ethoxycarbonyl-2-isopropylamino-9-methylfuro[2,3-h]quinazoline Compound 111

Compound 79 (10 mg, 0.02 mmol) was dissolved in ethanol and the solution was added with sodium ethoxide (4 mg, 0.06 mmol) at 0° C., followed by stirring at room temperature for 1 hour. The reaction mixture was added with 1 mol/L hydrochloric acid and further stirred for 10 minutes. The mixture was added with saturated brine and ethyl acetate, and the organic layer was separated. The organic layer was washed with saturated brine and dried over anhydrous magnesium sulfate, then the solvent was evaporated under reduced pressure. The precipitated solid was collected by filtration to obtain Compound 111 (2 mg, 19%).
$^1$H NMR (300 MHz, CDCl$_3$) δ (ppm) 1.22 (t, J=7.2 Hz, 3H), 1.36 (d, J=6.4 Hz, 6H), 3.07 (s, 3H), 4.28-4.38 (m, 1H), 4.40 (q, J=7.2 Hz, 2H), 5.37 (br s, 1H), 7.26-7.40 (m, 2H), 7.51-7.60 (m, 2H), 7.62 (s, 1H), 8.96 (s, 1H).
APCI m/z (M+H)$^+$ 424.

Example 112

6-(2-Chlorophenyl)-8-(1-hydroxy-1-methylethyl)-2-(isopropylamino)furo[2,3-h]quinazoline Compound 112

Compound 88 (71 mg, 0.16 mmol), tetrakis(triphenylphosphine)palladium (11 mg, 0.016 mmol), copper iodide (3 mg, 0.016 mmol), tetramethylguanidine (202 μL, 1.65 mmol) and 2-methyl-3-butyn-2-ol (78 μL, 0.81 mmol) were dissolved in DMF (0.5 mL) and the atmosphere of the reaction vessel was substituted with argon, followed by stirring at room temperature for 7 hours. The reaction mixture was added with water and the precipitated crystal was filtered off. The filtrate was concentrated under reduced pressure and the residue was purified by silica gel column chromatography (ethyl acetate/hexane=1/6) to obtain Compound 112 (10 mg, 15%).
$^1$H NMR (270 MHz, CDCl$_3$) δ (ppm) 1.33 (d, J=6.4 Hz, 6H), 1.69 (s, 6H), 4.34-4.46 (m, 1H), 5.24 (br s, 1H), 7.19 (s, 1H), 7.37-7.40 (m, 2H), 7.48 (s, 1H), 7.49-7.57 (m, 2H), 8.98 (s, 1H).
ESI m/z (M+H)$^+$ 396.

Example 113

2-Isopropylamino-7-methoxy-6-(2-methylbenzoyl)quinazoline

Compound 113

Compound A4 (101 mg, 0.34 mmol) was dissolved in anisole (2 mL) and the solution was added with 2-methylphenylboronic acid (51 mg, 0.38 mmol), [1,1'-bis(diphenylphosphino)ferrocene]dichloropalladium (27.9 mg, 0.034 mmol), potassium iodide (171 mg, 1.03 mmol) and potassium carbonate (142 mg, 1.03 mmol), followed by stirring at 80° C. overnight under carbon monoxide atmosphere. The reaction mixture was added with water and extracted with ethyl acetate. The organic layer was washed with saturated brine and dried over anhydrous magnesium sulfate, then the solvent was evaporated under reduced pressure. The residue was purified by preparative thin-layer chromatography (ethyl acetate/hexane=3/7) to obtain Compound 113 (34 mg, 29%).
$^1$H NMR (300 MHz, CDCl$_3$) δ (ppm) 1.31 (d, J=6.6 Hz, 6H), 2.47 (s, 3H), 3.81 (s, 3H), 4.25-4.38 (m, 1H), 5.17-5.27 (m, 1H), 6.91 (s, 1H), 7.15-7.23 (m, 1H), 7.25-7.41 (m, 3H), 7.74 (s, 1H), 8.80 (s, 1H).
APCI m/z (M+H)$^+$ 336.

Example 114

2-Isopropylamino-7-methoxy-6-(3-methylbenzoyl)quinazoline

Compound 114

In a similar manner to Example 113, Compound 114 was obtained using 3-methylphenylboronic acid.
$^1$H NMR (300 MHz, CDCl$_3$) δ (ppm) 1.32 (d, J=6.3 Hz, 6H), 2.39 (s, 3H), 3.84 (s, 3H), 4.26-4.39 (m, 1H), 5.15-5.25 (m, 1H), 6.96 (s, 1H), 7.32 (t, J=7.8 Hz, 1H), 7.39 (br d, J=7.8 Hz, 1H), 7.57 (br d, J=7.8 Hz, 1H), 7.66 (s, 1H), 7.66 (s, 1H), 8.82 (s, 1H).
APCI m/z (M+H)$^+$ 336.

Example 115

2-Isopropylamino-7-methoxy-6-(4-methylbenzoyl)quinazoline

Compound 115

In a similar manner to Example 113, Compound 115 was obtained using 4-methylphenylboronic acid.
$^1$H NMR (300 MHz, CDCl$_3$) δ (ppm) 1.32 (d, J=6.6 Hz, 6H), 2.43 (s, 3H), 3.84 (s, 3H), 4.26-4.39 (m, 1H), 5.15-5.23 (m, 1H), 6.96 (s, 1H), 7.24 (d, J=8.4 Hz, 2H), 7.65 (s, 1H), 7.72 (d, J=8.4 Hz, 2H), 8.81 (s, 1H).
APCI m/z (M+H)$^+$ 336.

Example 116

6-(3-Fluorobenzoyl)-2-isopropylamino-7-methoxyquinazoline

Compound 116

In a similar manner to Example 113, Compound 116 was obtained using 3-fluorophenylboronic acid.
$^1$H NMR (300 MHz, CDCl$_3$) δ (ppm) 1.32 (d, J=6.6 Hz, 6H), 3.83 (s, 3H), 4.26-4.40 (m, 1H), 5.27 (br s, 1H), 6.96 (s, 1H), 7.22-7.32 (m, 1H), 7.36-7.47 (m, 1H), 7.47-7.59 (m, 1H), 7.71 (s, 1H), 8.83 (s, 1H).
APCI m/z (M+H)$^+$ 340.

Example 117

6-(3-Chlorobenzoyl)-2-isopropylamino-7-methoxyquinazoline

Compound 117

In a similar manner to Example 113, Compound 117 was obtained using 3-chlorophenylboronic acid.
$^1$H NMR (300 MHz, CDCl$_3$) δ (ppm) 1.32 (d, J=6.6 Hz, 6H), 3.83 (s, 3H), 4.26-4.40 (m, 1H), 5.26 (br s, 1H), 6.97 (s, 1H), 7.38 (t, J=7.8 Hz, 1H), 7.51-7.57 (m, 1H), 7.65 (ddd, J=7.8, 1.8, 1.2 Hz, 1H), 7.71 (s, 1H), 7.77 (t, J=1.8 Hz, 1H), 8.84 (s, 1H).
APCI m/z (M+H)$^+$ 356.

Example 118

7-Hydroxy-2-isopropylamino-6-(3-methylbenzoyl)quinazoline

Compound 118

In a similar manner to Example 110, Compound 118 was obtained using Compound 114.
$^1$H NMR (300 MHz, CDCl$_3$) δ (ppm) 1.30 (d, J=6.3 Hz, 6H), 2.47 (s, 3H), 4.28-4.42 (m, 1H), 5.35 (br s, 1H), 7.01 (s, 1H), 7.39-7.57 (m, 4H), 7.96 (s, 1H), 8.74 (s, 1H), 12.07 (s, 1H).
APCI m/z (M+H)$^+$ 322.

Example 119

7-Hydroxy-2-isopropylamino-6-(2-methylbenzoyl)quinazoline

Compound 119

In a similar manner to Example 110, Compound N119 was obtained using Compound 113.
$^1$H NMR (300 MHz, CDCl$_3$) δ (ppm) 1.30 (d, J=6.6 Hz, 6H), 2.33 (s, 3H), 4.27-4.41 (m, 1H), 5.35 (br s, 1H), 6.99 (s, 1H), 7.28-7.38 (m, 3H), 7.41-7.50 (m, 1H), 7.67 (s, 1H), 8.67 (s, 1H), 12.24 (s, 1H).
APCI m/z (M+H)$^+$ 322.

Example 120

6-(3-Chlorobenzoyl)-7-hydroxy-2-(isopropylamino)quinazoline

Compound 120

In a similar manner to Example 110, Compound 120 was obtained using Compound 117.
$^1$H NMR (300 MHz, CDCl$_3$) δ (ppm) 1.31 (d, J=6.6 Hz, 6H), 4.28-4.42 (m, 1H), 5.30-5.45 (m, 1H), 7.01 (s, 1H), 7.45-7.65 (m, 3H), 7.68-7.71 (m, 1H), 7.90 (s, 1H), 8.75 (s, 1H), 11.85 (s, 1H).
APCI m/z (M+H)$^+$ 342.

Example 121

7-Hydroxy-2-isopropylamino-6-(3-methoxybenzoyl)quinazoline

Compound 121

In a similar manner to Example 113 and Example 110, Compound 121 was obtained using 3-methoxyphenylboronic acid. In this example, Compound 123, in which 3-methoxybenzoyl in 6$^{th}$ position of quinazoline is converted to 3-hydroxybenzoyl, was also obtained.
$^1$H NMR (300 MHz, CDCl$_3$) δ (ppm) 1.31 (d, J=6.6 Hz, 6H), 3.89 (s, 3H), 4.29-4.42 (m, 1H), 5.35 (br s, 1H), 7.01 (s, 1H), 7.14-7.25 (m, 3H), 7.46 (t, J=7.8 Hz, 1H), 7.99 (s, 1H), 8.75 (s, 1H), 12.01 (s, 1H).
APCI m/z (M+H)$^+$ 338.

Example 122

7-Hydroxy-2-isopropylamino-6-(2-methoxybenzoyl)quinazoline

Compound 122

In a similar manner to Example 113 and Example 110, Compound 122 was obtained using 2-methoxyphenylboronic acid.
$^1$H NMR (300 MHz, CDCl$_3$) δ (ppm) 1.32 (d, J=6.6 Hz, 6H), 3.88 (s, 3H), 4.26-4.39 (m, 1H), 5.24 (br s, 1H), 6.77-6.85 (m, 1H), 6.99 (s, 1H), 7.02-7.08 (m, 1H), 7.32-7.37 (m, 1H), 7.45-7.53 (m, 1H), 7.60 (s, 1H), 8.83 (s, 1H), 12.10 (s, 1H).
APCI m/z (M+H)$^+$ 338.

Example 123

7-Hydroxy-6-(3-hydroxybenzoyl)-2-(isopropylamino)quinazoline

Compound 123

Compound 123 was obtained together with Compound 121 in Example 121.
$^1$H NMR (270 MHz, CDCl$_3$) δ (ppm) 1.30 (d, J=6.8 Hz, 6H), 4.28-4.43 (m, 1H), 7.00 (s, 1H), 7.09-7.17 (m, 2H), 7.20-7.30 (m, 1H), 7.37-7.47 (m, 1H), 7.97 (s, 1H), 8.74 (s, 1H), 11.99 (br s, 1H).
APCI m/z (M+H)$^+$ 324.

Example 124

6-(4-Chlorobenzoyl)-7-hydroxy-2-(isopropylamino)quinazoline

Compound 124

In a similar manner to Example 113 and Example 110, Compound 124 was obtained using 4-chlorophenylboronic acid.

$^1$H NMR (300 MHz, CDCl$_3$) δ (ppm) 1.31 (d, J=6.3 Hz, 6H), 4.28-4.42 (m, 1H), 5.37 (br s, 1H), 7.01 (s, 1H), 7.50-7.57 (m, 2H), 7.63-7.70 (m, 2H), 7.91 (s, 1H), 8.74 (s, 1H), 11.88 (s, 1H).

APCI m/z (M+H)$^+$ 342.

Example 125

6-(2-Chlorobenzoyl)-7-hydroxy-2-(isopropylamino)quinazoline

Compound 125

In a similar manner to Example 113 and Example 110, Compound 125 was obtained using 2-chlorophenylboronic acid.

$^1$H NMR (300 MHz, CDCl$_3$) δ (ppm) 1.29 (d, J=6.3 Hz, 6H), 4.27-4.41 (m, 1H), 5.35 (br s, 1H), 6.99 (s, 1H), 7.37-7.57 (m, 4H), 7.61 (s, 1H), 8.67 (s, 1H), 11.92 (s, 1H).

APCI m/z (M+H)$^+$ 342.

Example 126

6-(2-Fluorobenzoyl)-7-hydroxy-2-(isopropylamino)quinazoline

Compound 126

In a similar manner to Example 113 and Example 110, Compound 126 was obtained using 2-fluorophenylboronic acid.

$^1$H NMR (300 MHz, CDCl$_3$) δ (ppm) 1.30 (d, J=6.3 Hz, 6H), 4.27-4.41 (m, 1H), 5.37 (br s, 1H), 6.99 (s, 1H), 7.20-7.37 (m, 2H), 7.47-7.65 (m, 2H), 7.79 (s, 1H), 8.72 (s, 1H), 11.94 (s, 1H).

APCI m/z (M+H)$^+$ 326.

Example 127

6-(3-Chloro-4-fluorobenzoyl)-7-hydroxy-2-(isopropylamino)quinazoline

Compound 127

In a similar manner to Example 113 and Example 110, Compound 127 was obtained using 3-chloro-4-fluorophenylboronic acid.

$^1$H NMR (300 MHz, CDCl$_3$) δ (ppm) 1.31 (d, J=6.6 Hz, 6H), 4.28-4.42 (m, 1H), 5.38 (br s, 1H), 7.02 (s, 1H), 7.29-7.37 (m, 1H), 7.57-7.67 (m, 1H), 7.77-7.84 (m, 1H), 7.89 (s, 1H), 8.76 (s, 1H), 11.73 (s, 1H).

APCI m/z (M+H)$^+$ 360.

Example 128

7-Hydroxy-2-isopropylamino-6-(4-methoxybenzoyl)quinazoline

Compound 128

In a similar manner to Example 113 and Example 110, Compound 128 was obtained using 4-methoxyphenylboronic acid.

$^1$H NMR (270 MHz, CDCl$_3$) δ (ppm) 1.31 (d, J=6.5 Hz, 6H), 3.93 (s, 3H), 4.27-4.42 (m, 1H), 5.35 (br s, 1H), 7.00 (s, 1H), 7.01-7.08 (m, 2H), 7.70-7.77 (m, 2H), 7.99 (s, 1H), 8.76 (s, 1H), 12.01 (s, 1H).

APCI m/z (M+H)$^+$ 338.

Example 129

6-(3,4-Difluorobenzoyl)-7-hydroxy-2-(isopropylamino)quinazoline

Compound 129

In a similar manner to Example 113 and Example 110, Compound 129 was obtained using 3,4-difluorophenylboronic acid.

$^1$H NMR (270 MHz, CDCl$_3$) δ (ppm) 1.31 (d, J=6.5 Hz, 6H), 4.27-4.42 (m, 1H), 5.40 (br s, 1H), 7.01 (s, 1H), 7.29-7.41 (m, 1H), 7.45-7.53 (m, 1H), 7.53-7.63 (m, 1H), 7.90 (s, 1H), 8.76 (s, 1H), 11.72 (s, 1H).

APCI m/z (M+H)$^+$ 344.

Example 130

6-(2,4-Difluorobenzoyl)-7-hydroxy-2-(isopropylamino)quinazoline

Compound 130

In a similar manner to Example 113 and Example 110, Compound 130 was obtained using 2,4-difluorophenylboronic acid.

$^1$H NMR (270 MHz, CDCl$_3$) δ (ppm) 1.30 (d, J=6.5 Hz, 6H), 4.27-4.42 (m, 1H), 5.39 (br s, 1H), 6.93-7.13 (m, 3H), 7.49-7.60 (m, 1H), 7.72-7.80 (m, 1H), 8.73 (s, 1H), 11.82 (s, 1H).

APCI m/z (M+H)$^+$ 344.

Example 131

6-(4-Fluorobenzoyl)-7-hydroxy-2-(isopropylamino)quinazoline

Compound 131

In a similar manner to Example 113 and Example 110, Compound 131 was obtained using 4-fluorophenylboronic acid.

$^1$H NMR (270 MHz, CDCl$_3$) δ (ppm) 1.31 (d, J=6.5 Hz, 6H), 4.28-4.42 (m, 1H), 5.30-5.42 (m, 1H), 7.01 (s, 1H), 7.20-7.30 (m, 2H), 7.70-7.80 (m, 2H), 7.92 (s, 1H), 8.75 (s, 1H), 11.89 (s, 1H).

APCI m/z (M+H)$^+$ 326.

Example 132

6-(3-Fluorobenzoyl)-7-hydroxy-2-(isopropylamino)quinazoline

Compound 132

In a similar manner to Example 113 and Example 110, Compound 132 was obtained using 3-fluorophenylboronic acid.

$^1$H NMR (270 MHz, CDCl$_3$) δ (ppm) 1.31 (d, J=6.5 Hz, 6H), 4.27-4.42 (m, 1H), 5.31-5.43 (m, 1H), 7.01 (s, 1H), 7.20-7.60 (m, 4H), 7.92 (s, 1H), 8.75 (s, 1H), 11.85 (s, 1H).
APCI m/z (M+H)$^+$ 326.

Example 133

6-(3,5-Dimethylbenzoyl)-7-hydroxy-2-(isopropylamino)quinazoline

Compound 133

In a similar manner to Example 113 and Example 110, Compound 133 was obtained using 3,5-dimethylphenylboronic acid.

$^1$H NMR (270 MHz, CDCl$_3$) δ (ppm) 1.30 (d, J=6.5 Hz, 6H), 2.42 (s, 6H), 4.28-4.42 (m, 1H), 5.28-5.40 (m, 1H), 6.99 (s, 1H), 7.24-7.31 (m, 3H), 7.96 (s, 1H), 8.75 (s, 1H), 12.07 (s, 1H).
APCI m/z (M+H)$^+$ 336.

Example 134

6-(3,5-Difluorobenzoyl)-7-hydroxy-2-(isopropylamino)quinazoline

Compound 134

In a similar manner to Example 113 and Example 110, Compound 134 was obtained using 3,5-difluorophenylboronic acid.

$^1$H NMR (270 MHz, CDCl$_3$) δ (ppm) 1.31 (d, J=6.5 Hz, 6H), 4.28-4.42 (m, 1H), 5.34-5.47 (m, 1H), 7.01 (s, 1H), 7.05-7.14 (m, 1H), 7.20-7.25 (m, 2H), 7.89 (s, 1H), 8.77 (s, 1H), 11.67 (s, 1H).
APCI m/z (M+H)$^+$ 344.

Example 135

(S)-2-(sec-Butylamino)-7-hydroxy-6-(3-methylbenzoyl)quinazoline

Compound 135

In a similar manner to Reference Example 4, (S)-6-bromo-2-(sec-butylamino)-7-methoxyquinazoline was obtained using (S)-(+)-sec-butylamine. In a similar manner to Example 113 and Example 110, Compound 135 was obtained using the above-obtained (S)-6-bromo-2-(sec-butylamino)-7-methoxyquinazoline and 3-methylphenylboronic acid.

$^1$H NMR (300 MHz, CDCl$_3$) δ (ppm) 0.99 (t, J=7.2 Hz, 3H), 1.27 (d, J=6.6 Hz, 3H), 1.57-1.70 (m, 2H), 2.47 (s, 3H), 4.13-4.28 (m, 1H), 5.30 (br s, 1H), 7.00 (s, 1H), 7.39-7.55 (m, 4H), 7.96 (s, 1H), 8.74 (s, 1H), 12.07 (s, 1H).
APCI m/z (M+H)$^+$ 336.

Example 136

6-Benzoyl-7-hydroxy-2-[1-(methylsulfonyl)piperidin-4-ylamino]quinazoline

Compound 136

In a similar manner to Example 109 and Example 110, Compound 136 was obtained using Compound 108 and 1-(methylsulfonyl)piperidin-4-ylamine.

$^1$H NMR (300 MHz, CDCl$_3$) δ (ppm) 1.60-1.79 (m, 2H), 2.18-2.33 (m, 2H), 2.84 (s, 3H), 2.92-3.05 (m, 2H), 3.74-3.83 (m, 2H), 4.13-4.29 (m, 1H), 5.42 (br s, 1H), 7.02 (s, 1H), 7.52-7.79 (m, 5H), 8.00 (s, 1H), 8.80 (s, 1H), 12.06 (s, 1H).
ESI m/z (M+H)$^+$ 427.

Example 137

6-Benzoyl-2-[1-(ethoxycarbonyl)piperidin-4-ylamino]-7-hydroxyquinazoline

Compound 137

In a similar manner to Example 109 and Example 110, Compound 137 was obtained using Compound 108 and 1-(ethoxycarbonyl)piperidin-4-ylamine.

$^1$H NMR (300 MHz, CDCl$_3$) δ (ppm) 1.28 (t, J=7.2 Hz, 3H), 1.40-1.53 (m, 2H), 2.03-2.21 (m, 2H), 2.97-3.14 (m, 2H), 4.16 (q, J=7.2 Hz, 2H), 4.06-4.20 (m, 2H), 4.18-4.30 (m, 1H), 5.39 (br s, 1H), 7.03 (s, 1H), 7.50-7.75 (m, 5H), 7.99 (s, 1H), 8.76 (s, 1H), 12.05 (s, 1H).
ESI m/z (M+H)$^+$ 421.

Example 138

6-Benzoyl-7-hydroxy-2-(4-tetrahydropyranylamino)quinazoline

Compound 138

In a similar manner to Example 109 and Example 110, Compound 138 was obtained using Compound 108 and 4-aminotetrahydropyrane.

$^1$H NMR (300 MHz, CDCl$_3$) δ (ppm) 1.60-1.70 (m, 2H), 2.01-2.21 (m, 2H), 3.52-3.69 (m, 2H), 3.97-4.10 (m, 2H), 4.18-4.37 (m, 1H), 5.41 (br s, 1H), 7.02 (s, 1H), 7.51-7.76 (m, 5H), 7.98 (s, 1H), 8.76 (s, 1H), 12.05 (s, 1H).
ESI m/z (M+H)$^+$ 350.

Example 139

2-(trans-4-Aminocyclohexylamino)-6-benzoyl-7-hydroxyquinazoline

Compound 139

In a similar manner to Example 109 and Example 110, Compound 139 was obtained using Compound 108 and trans-1,4-diaminocyclohexane.

$^1$H NMR (300 MHz, DMSO-d$_6$) δ (ppm) 1.29-1.51 (m, 4H), 1.90-2.07 (m, 4H), 2.88-3.00 (m, 1H), 3.75-3.90 (m, 1H), 6.78 (s, 1H), 7.50-7.60 (m, 2H), 7.60-7.70 (m, 1H), 7.71-7.78 (m, 2H), 7.89 (s, 1H), 8.96 (s, 1H).
ESI m/z (M+H)$^+$ 363.

Example 140

6-Benzoyl-2-(2,6-dimethylanilino)-7-hydroxyquinazoline

Compound 140

Compound 108 (201 mg, 0.72 mmol) was dissolved in dioxane (7.2 mL) and the solution was added with 2,6-dimethyliodobenzene (110 μL, 0.79 mmol), tris(dibenzylideneacetone)dipalladium (32.9 mg, 0.036 mmol), 9,9-dimethyl-4,5-bis(diphenylphosphino)xanthene (46 mg, 0.079 mmol) and cesium carbonate (328 mg, 1.01 mmol), followed by stirring at 100° C. for 22 hours. The reaction mixture was added with water and extracted with ethyl acetate. The organic layer was washed with saturated brine and dried over anhydrous magnesium sulfate, then the solvent was evaporated under reduces pressure. The residue was purified by preparative thin-layer chromatography (ethyl acetate/hexane=4/6) to obtain 6-benzoyl-2-(2,6-dimethylanilino)-7-methoxyquinazoline (161 mg, 59%). In a similar manner to Example 110, Compound 140 was obtained using the above-obtained 6-benzoyl-2-(2,6-dimethylanilino)-7-methoxyquinazoline.

$^1$H NMR (300 MHz, CDCl$_3$) δ (ppm) 2.28 (s, 6H), 6.88 (br s, 1H), 7.02 (s, 1H), 7.16-7.20 (m, 3H), 7.52-7.76 (m, 5H), 8.02 (s, 1H), 8.84 (s, 1H), 11.97 (s, 1H).

ESI m/z (M+H)$^+$ 370.

Example 141

6-Benzoyl-2-(2,6-dichloroanilino)-7-hydroxyquinazoline

Compound 141

In a similar manner to Example 140, Compound 141 was obtained using 2,6-dichloroiodobenzene.

$^1$H NMR (300 MHz, CDCl$_3$) δ (ppm) 7.01 (br s, 1H), 7.10 (s, 1H), 7.19-7.28 (m, 1H), 7.44 (d, J=7.8 Hz, 2H), 7.53-7.61 (m, 2H), 7.62-7.75 (m, 3H), 8.08 (s, 1H), 8.90 (s, 1H), 11.93 (s, 1H).

APCI m/z (M+H)$^+$ 410.

Example 142

6-(2-Chlorophenyl)-2-[1-(ethylsulfonyl)piperidin-4-ylamino]-7-methoxyquinazoline

Compound 142

In a similar manner to Example 5, Compound 142 was obtained using 1-(ethylsulfonyl)piperidin-4-ylamine.

$^1$H NMR (270 MHz, CDCl$_3$) δ (ppm) 1.37 (t, J=7.6 Hz, 3H), 1.55-1.73 (m, 2H), 2.11-2.32 (m, 2H), 2.97 (q, J=7.6 Hz, 2H), 3.00-3.17 (m, 2H), 3.75-3.85 (m, 2H), 3.87 (s, 3H), 4.07-4.23 (m, 1H), 5.07-5.18 (m, 1H), 6.95 (s, 1H), 7.23-7.37 (m, 3H), 7.44 (s, 1H), 7.40-7.50 (m, 1H), 8.79 (s, 1H).

APCI m/z (M+H)$^+$ 461.

Example 143

6-(2-Chlorophenyl)-2-[1-(isopropylsulfonyl)piperidin-4-ylamino]-7-methoxyquinazoline

Compound 143

In a similar manner to Example 5, Compound 143 was obtained using 1-(isopropylsulfonyl)piperidin-4-ylamine.

$^1$H NMR (270 MHz, CDCl$_3$) δ (ppm) 1.37 (d, J=7.0 Hz, 6H), 1.55-1.71 (m, 2H), 2.11-2.30 (m, 2H), 3.07-3.28 (m, 3H), 3.75-3.92 (m, 2H), 3.90 (s, 3H), 4.10-4.27 (m, 1H), 5.07-5.21 (m, 1H), 6.98 (s, 1H), 7.27-7.39 (m, 3H), 7.42-7.52 (m, 1H), 7.46 (s, 1H), 8.82 (s, 1H).

APCI m/z (M+H)$^+$ 475.

Example 144

6-(2-Chlorophenyl)-7-methoxy-2-[1-(methylsulfonyl)piperidin-4-ylmethylamino]quinazoline

Compound 144

In a similar manner to Example 5, Compound 144 was obtained using 1-(methylsulfonyl)piperidin-4-ylmethylamine.

$^1$H NMR (270 MHz, CDCl$_3$) δ (ppm) 1.38-1.57 (m, 2H), 1.75-1.90 (m, 1H), 1.89-2.00 (m, 2H), 2.62-2.73 (m, 2H), 2.78 (s, 3H), 3.47-3.55 (m, 2H), 3.80-3.90 (m, 2H), 3.90 (s, 3H), 5.34 (br s, 1H), 6.99 (s, 1H), 7.30-7.37 (m, 3H), 7.42-7.50 (m, 1H), 7.46 (s, 1H), 8.81 (s, 1H).

APCI m/z (M+H)$^+$ 461.

Example 145

6-(2-Chlorophenyl)-7-methoxy-2-[1-(methylsulfonyl)pyrrolidin-3-ylamino]quinazoline

Compound 145

In a similar manner to Example 5, Compound 145 was obtained using 1-(methylsulfonyl)pyrrolidin-3-ylamine.

$^1$H NMR (270 MHz, CDCl$_3$) δ (ppm) 1.99-2.15 (m, 1H), 2.33-2.50 (m, 1H), 2.87 (s, 3H), 3.40-3.63 (m, 3H), 3.79-3.88 (m, 1H), 3.91 (s, 3H), 4.66-4.78 (m, 1H), 5.29 (d, J=6.5 Hz, 1H), 7.01 (s, 1H), 7.29-7.37 (m, 3H), 7.43-7.51 (m, 1H), 7.49 (s, 1H), 8.84 (s, 1H).

APCI m/z (M+H)$^+$ 433.

Example 146

6-(2-Chlorophenyl)-7-methoxy-2-[trans-4-(methylsulfonylamino)cyclohexylamino]quinazoline

Compound 146

Compound 5 (50 mg, 0.13 mmol) was dissolved in methylene chloride (1.3 mL) and the solution was added with triethylamine (36 μL, 0.26 mmol) and methanesulfonyl chloride (13 μL, 0.17 mmol), followed by stirring at room temperature overnight. The reaction mixture was added with water and extracted with ethyl acetate. The organic layer was washed with saturated aqueous sodium hydrogencarbonate solution and saturated brine, and dried over anhydrous magnesium sulfate, then the solvent was evaporated under reduced pressure. The residue was purified by preparative thin-layer chromatography (chloroform/methanol=95/5) to obtain Compound 146 (33 mg, 56%).

$^1$H NMR (270 MHz, CDCl$_3$) δ (ppm) 1.30-1.60 (m, 4H), 2.10-2.35 (m, 4H), 3.01 (s, 3H), 3.30-3.49 (m, 1H), 3.90 (s, 3H), 3.90-4.05 (m, 1H), 4.10-4.22 (m, 1H), 5.02-5.18 (m, 1H), 6.98 (s, 1H), 7.28-7.37 (m, 3H), 7.45 (s, 1H), 7.42-7.52 (m, 1H), 8.81 (s, 1H).

APCI m/z (M+H)$^+$ 461.

Example 147

6-(2-Chlorophenyl)-2-[trans-4-(ethylsulfonylamino)cyclohexylamino]-7-methoxyquinazoline Compound 147

In a similar manner to Example 146, Compound 147 was obtained using ethanesulfonyl chloride.

$^1$H NMR (270 MHz, CDCl$_3$) δ (ppm) 1.40 (t, J=7.6 Hz, 3H), 1.31-1.59 (m, 4H), 2.10-2.33 (m, 4H), 3.07 (q, J=7.6 Hz, 2H), 3.30-3.47 (m, 1H), 3.90 (s, 3H), 3.90-4.03 (m, 1H), 3.96-4.02 (m, 1H), 5.00-5.20 (m, 1H), 6.97 (s, 1H), 7.29-7.37 (m, 3H), 7.45 (s, 1H), 7.43-7.50 (m, 1H), 8.81 (s, 1H).

APCI m/z (M+H)$^+$ 475.

Example 148

6-(2-Chlorophenyl)-7-methoxy-2-[1-(1-propylsulfonyl)piperidin-4-ylamino]quinazoline Compound 148

In a similar manner to Example 5, Compound 148 was obtained using 1-(1-propylsulfonyl)piperidin-4-ylamine.

$^1$H NMR (270 MHz, CDCl$_3$) δ (ppm) 1.08 (t, J=7.6 Hz, 3H), 1.59-1.75 (m, 2H), 1.80-1.95 (m, 2H), 2.18-2.30 (m, 2H), 2.88-2.96 (m, 2H), 3.02-3.14 (m, 2H), 3.73-3.85 (m, 2H), 3.89 (s, 3H), 4.16 (br s, 1H), 5.11-5.22 (m, 1H), 6.98 (s, 1H), 7.30-7.37 (m, 3H), 7.47 (s, 1H), 7.42-7.50 (m, 1H), 8.82 (s, 1H).

APCI m/z (M+H)$^+$ 475.

Example 149

6-(2-Chlorophenyl)-2-[1-(ethoxycarbonyl)piperidin-4-ylamino]-7-methoxyquinazoline Compound 149

In a similar manner to Example 5, Compound 149 was obtained using 1-(ethoxycarbonyl)piperidin-4-ylamine.

$^1$H NMR (300 MHz, CDCl$_3$) δ (ppm) 1.26 (t, J=7.2 Hz, 3H), 1.40-1.58 (m, 2H), 2.06-2.18 (m, 2H), 2.99-3.14 (m, 2H), 3.88 (s, 3H), 4.14 (q, J=7.2 Hz, 2H), 4.01-4.27 (m, 2H), 4.01-4.27 (m, 1H), 6.98 (s, 1H), 7.27-7.37 (m, 3H), 7.46 (s, 1H), 7.40-7.50 (m, 1H), 8.82 (s, 1H).

APCI m/z (M+H)$^+$ 441.

Example 150

6-(2-Chlorophenyl)-2-[2-(dimethylamino)ethylamino]-7-methoxyquinazoline dihydrochloride Compound 150

In a similar manner to Example 5, 6-(2-chlorophenyl)-2-[2-(dimethylamino)ethylamino]-7-methoxyquinazoline was obtained using N,N-dimethylethylenediamine. This was dissolved in ethanol and the solution was added with 4 mol/L hydrogen chloride-ethyl acetate solution, followed by concentrating under reduced pressure. The residue was recrystallized from ethanol to obtain Compound 150.

$^1$H NMR (300 MHz, DMSO-d$_6$) δ (ppm) 2.87 (s, 6H), 3.32-3.42 (m, 2H), 3.79-3.90 (m, 2H), 3.88 (s, 3H), 7.18 (s, 1H), 7.35-7.48 (m, 3H), 7.52-7.60 (m, 1H), 7.75 (s, 1H), 9.13 (s, 1H), 10.01 (br s, 1H).

ESI m/z (M+H)$^+$ 357.

Example 151

6-(2-Chlorophenyl)-2-isobutylamino-7-methoxyquinazoline

Compound 151

In a similar manner to Example 5, Compound 151 was obtained using isobutylamine.

$^1$H NMR (300 MHz, CDCl$_3$) δ (ppm) 1.01 (d, J=6.6 Hz, 6H), 1.88-2.02 (m, 1H), 3.38 (t, J=6.6 Hz, 2H), 3.87 (s, 3H), 6.98 (s, 1H), 7.27-7.37 (m, 3H), 7.44 (s, 1H), 7.44-7.55 (m, 1H), 8.80 (s, 1H).

ESI m/z (M+H)$^+$ 342.

Example 152

6-(2-Chlorophenyl)-7-methoxy-2-(piperidin-4-ylamino)quinazoline

Compound 152

Compound 149 (71 mg, 0.16 mmol) was added with 48% hydrobromic acid (4.0 mL) and stirred at 80° C. for 7 hours. The reaction mixture was poured into ice-water and 5 mol/L aqueous sodium hydroxide solution was added thereto to neutralize. The mixture was extracted with chloroform/2-propanol (4/1). The organic layer was washed with water and saturated brine, and dried over anhydrous magnesium sulfate, then the solvent was evaporated under reduced pressure to obtain Compound 152 (18 mg, 30%).

$^1$H NMR (270 MHz, DMSO-d$_6$) δ (ppm) 1.62-1.82 (m, 2H), 2.01-2.17 (m, 2H), 2.93-3.07 (m, 2H), 3.35-3.45 (m, 2H), 3.84 (s, 3H), 4.06-4.20 (m, 1H), 6.91 (s, 1H), 7.32-7.47 (m, 3H), 7.50-7.59 (m, 1H), 7.60 (s, 1H), 8.98 (s, 1H).

APCI m/z (M+H)$^+$ 369.

Example 153

6-(2-Chlorophenyl)-2-[2,2-(dimethylpropyl)amino]-7-methoxyquinazoline

Compound 153

In a similar manner to Example 5, Compound 153 was obtained using 2,2-dimethylpropylamine.

$^1$H NMR (300 MHz, CDCl$_3$) δ (ppm) 1.01 (s, 9H), 3.41 (d, J=6.3 Hz, 2H), 3.87 (s, 3H), 6.97 (s, 1H), 7.28-7.35 (m, 3H), 7.44 (s, 1H), 7.42-7.50 (m, 1H), 8.81 (s, 1H).

ESI m/z (M+H)$^+$ 356.

Example 154

6-(2-Chlorophenyl)-2-(cyclopropylcarbonylamino)-7-methoxyquinazoline

Compound 154

Compound 2 (160 mg, 0.56 mmol) was dissolved in THF (5.6 mL) and the solution was added with cyclopropanecarbonyl chloride (61 μL, 0.67 mmol) and triethylamine (0.19 mL, 1.4 mmol), followed by stirring under heating and reflux overnight. The reaction mixture was added with water and extracted with ethyl acetate. The organic layer was washed with water and saturated brine, and dried over anhydrous magnesium sulfate, then the solvent was evaporated under reduced pressure. The residue was purified by preparative thin-layer chromatography (ethyl acetate/hexane=7/3) to obtain Compound 154 (20 mg, 10%).

$^1$H NMR (300 MHz, CDCl$_3$) δ (ppm) 0.93-1.01 (m, 2H), 1.20-1.30 (m, 2H), 2.51 (br s, 1H), 3.93 (s, 3H), 7.29 (s, 1H), 7.31-7.40 (m, 3H), 7.45-7.52 (m, 1H), 7.64 (s, 1H), 9.12 (s, 1H).

APCI m/z (M+H)$^+$ 354.

Example 155

(S)-2-(sec-Butylamino)-6-(2-chlorophenyl)-7-methoxyquinazoline

Compound 155

In a similar manner to Example 5, Compound 155 was obtained using (S)-(+)-sec-butylamine.

$^1$H NMR (270 MHz, CDCl$_3$) δ (ppm) 1.00 (t, J=7.4 Hz, 3H), 1.27 (d, J=6.5 Hz, 3H), 1.57-1.70 (m, 2H), 3.89 (s, 3H), 4.09-4.23 (m, 1H), 5.01-5.13 (m, 1H), 6.97 (s, 1H), 7.29-7.36 (m, 3H), 7.43 (s, 1H), 7.42-7.50 (m, 1H), 8.80 (s, 1H).

APCI m/z (M+H)$^+$ 342.

Example 156

6-(2-Chlorophenyl)-7-hydroxy-2-[1-(methylsulfonyl)piperidin-4-ylamino]quinazoline Compound 156

In a similar manner to Example 19, Compound 156 was obtained using Compound 12.

$^1$H NMR (300 MHz, DMSO-d$_6$) δ (ppm) 1.52-1.70 (m, 2H), 1.94-2.08 (m, 2H), 2.89 (s, 3H), 2.87-3.01 (m, 2H), 3.48-3.61 (m, 2H), 3.91-4.13 (m, 1H), 6.83 (s, 1H), 7.27 (d, J=8.4 Hz, 1H), 7.38 (s, 1H), 7.33-7.43 (m, 2H), 7.50-7.57 (m, 1H), 7.53 (s, 1H), 8.89 (s, 1H) 10.53 (br s, 1H).

APCI m/z (M+H)$^+$ 433.

m.p. 268-271° C.

Example 157

2-(1-Carbamoylpiperidin-4-ylamino)-6-(2-chlorophenyl)-7-hydroxyquinazoline

Compound 157

In a similar manner to Example 19, Compound 157 was obtained using Compound 15.

$^1$H NMR (300 MHz, DMSO-d$_6$) δ (ppm) 1.29-1.46 (m, 2H), 1.78-1.92 (m, 2H), 2.77-2.92 (m, 2H), 3.85-3.97 (m, 2H), 3.93-4.12 (m, 1H), 5.91 (s, 2H), 6.82 (s, 1H), 7.20 (d, J=7.8 Hz, 1H), 7.38 (s, 1H), 7.33-7.45 (m, 2H), 7.52 (s, 1H), 7.47-7.57 (m, 1H), 8.87 (s, 1H) 10.50 (s, 1H).

APCI m/z (M+H)$^+$ 398.

Example 158

2-(trans-4-Aminocyclohexylamino)-6-(2-chlorophenyl)-7-hydroxyquinazoline

Compound 158

In a similar manner to Example 19, Compound 158 was obtained using Compound 5.

$^1$H NMR (300 MHz, DMSO-d$_6$) δ (ppm) 1.10-1.40 (m, 4H), 1.78-2.00 (m, 4H), 3.00-3.10 (m, 1H), 3.70-3.83 (m, 1H), 6.79 (s, 1H), 6.99-7.06 (m, 1H), 7.34-7.42 (m, 3H), 7.49 (s, 1H), 7.50-7.55 (m, 1H), 8.84 (s, 1H).

APCI m/z (M+H)$^+$ 369.

Example 159

6-(2-Chlorophenyl)-2-[2,2-(dimethyl)propylamino]-7-hydroxyquinazoline

Compound 159

In a similar manner to Example 19, Compound 159 was obtained using Compound 153.

$^1$H NMR (300 MHz, CDCl$_3$) δ (ppm) 0.86 (s, 9H), 3.27 (d, J=6.3 Hz, 2H), 7.06 (s, 1H), 7.22-7.32 (m, 3H), 7.40 (s, 1H), 7.37-7.46 (m, 1H), 8.70 (s, 1H).

ESI m/z (M+H)$^+$ 342.

Example 160

6-(2-Chlorophenyl)-7-hydroxy-2-isobutylaminoquinazoline

Compound 160

In a similar manner to Example 19, Compound 160 was obtained using Compound 151.

$^1$H NMR (300 MHz, CDCl$_3$) δ (ppm) 0.87 (d, J=6.6 Hz, 6H), 1.70-1.90 (m, 1H), 3.26 (t, J=6.3 Hz, 2H), 7.11 (s, 1H), 7.24-7.33 (m, 3H), 7.43 (s, 1H), 7.40-7.47 (m, 1H), 8.70 (s, 1H).

ESI m/z (M+H)$^+$ 328.

Example 161

6-(2-Chlorophenyl)-2-[1-(ethylsulfonyl)piperidin-4-ylamino]-7-hydroxyquinazoline Compound 161

In a similar manner to Example 19, Compound 161 was obtained using Compound 142.

$^1$H NMR (270 MHz, CDCl$_3$) δ (ppm) 1.39 (t, J=7.6 Hz, 3H), 1.55-1.73 (m, 2H), 2.15-2.27 (m, 2H), 2.98 (q, J=7.6 Hz, 2H), 3.03-3.13 (m, 2H), 3.73-3.84 (m, 2H), 4.07-4.25 (m, 1H), 5.18 (d, J=8.1 Hz, 1H), 7.06 (s, 1H), 7.37-7.45 (m, 3H), 7.50 (s, 1H), 7.51-7.57 (m, 1H), 8.83 (s, 1H).

APCI m/z (M+H)$^+$ 447.

m.p. 251-253° C.

Example 162

6-(2-Chlorophenyl)-7-hydroxy-2-[1-(1-propylsulfonyl)piperidin-4-ylamino]quinazoline Compound 162

In a similar manner to Example 19, Compound 162 was obtained using Compound 148.
¹H NMR (300 MHz, DMSO-d₆) δ (ppm) 1.01 (t, J=7.2 Hz, 3H), 1.47-1.63 (m, 2H), 1.65-1.77 (m, 2H), 1.92-2.05 (m, 2H), 2.95-3.07 (m, 4H), 3.53-3.67 (m, 2H), 3.97-4.10 (m, 1H), 6.81 (s, 1H), 7.21-7.30 (m, 1H), 7.35-7.42 (m, 3H), 7.53 (s, 1H), 7.49-7.56 (m, 1H), 8.87 (s, 1H).
APCI m/z (M+H)⁺ 461.

Example 163

(S)-2-(sec-Butylamino)-6-(2-chlorophenyl)-7-hydroxyquinazoline

Compound 163

In a similar manner to Example 19, Compound 163 was obtained using Compound 155.
¹H NMR (270 MHz, CDCl₃) δ (ppm) 0.97 (t, J=7.3 Hz, 3H), 1.24 (d, J=6.5 Hz, 3H), 1.52-1.64 (m, 2H), 4.08-4.24 (m, 1H), 5.20 (br s, 1H), 7.06 (s, 1H), 7.33-7.42 (m, 3H), 7.47 (s, 1H), 7.50-7.57 (m, 1H), 8.80 (s, 1H).
APCI m/z (M+H)⁺ 328.
m.p. 173-175° C.

Example 164

7-Methoxy-6-(2-methylphenyl)-2-[1-(methylsulfonyl)piperidin-4-ylamino]quinazoline Compound 164

Compound A3 (509 mg, 1.39 mmol) was dissolved in DMF (7.0 mL) and the solution was added with 1-(methylsulfonyl)piperidin-4-ylamine (497 mg, 2.79 mmol) and triethylamine (0.29 mL, 2.09 mmol), followed by stirring at 100° C. for 3 hours. The reaction mixture was added with water and the obtained crystal was collected by filtration to obtain 6-bromo-7-methoxy-2-[1-(methylsulfonyl)piperidin-4-ylamino]quinazoline (471 mg, 81%). In a similar manner to Example 4, Compound 164 was obtained using the above-obtained 6-bromo-7-methoxy-2-[1-(methylsulfonyl)piperidin-4-ylamino]quinazoline and 2-methylphenylboronic acid.
¹H NMR (300 MHz, DMSO-d₆) δ (ppm) 1.53-1.71 (m, 2H), 1.98-2.10 (m, 2H), 2.06 (s, 3H), 2.89-3.00 (m, 2H), 2.90 (s, 3H), 3.51-3.62 (m, 2H), 3.83 (s, 3H), 3.98-4.13 (m, 1H), 6.92 (s, 1H), 7.11-7.18 (m, 1H), 7.19-7.30 (m, 3H), 7.32-7.40 (m, 1H), 7.51 (s, 1H), 8.95 (s, 1H).
APCI m/z (M+H)⁺ 427.

Example 165

(S)-2-(1-Hydroxy-2-propylamino)-7-methoxy-6-(2-methylphenyl)quinazoline

Compound 165

In a similar manner to Example 164, Compound 165 was obtained using (S)-(+)-2-amino-1-propanol.
¹H NMR (300 MHz, CDCl₃) δ (ppm) 1.33 (d, J=6.6 Hz, 3H), 2.12 (s, 3H), 3.72 (dd, J=11.1, 7.5 Hz, 1H), 3.85 (dd, J=11.1, 2.4 Hz, 1H), 3.87 (s, 3H), 4.19-4.32 (m, 1H), 5.29-5.40 (m, 1H), 6.96 (s, 1H), 7.16-7.33 (m, 4H), 7.42 (s, 1H), 8.81 (s, 1H).
APCI m/z (M+H)⁺ 324.

Example 166

(R)-2-(sec-Butylamino)-7-methoxy-6-(2-methylphenyl)quinazoline

Compound 166

In a similar manner to Example 164, Compound 166 was obtained using (R)-(−)-sec-butylamine.
¹H NMR (300 MHz, CDCl₃) δ (ppm) 1.00 (t, J=7.5 Hz, 3H), 1.28 (d, J=6.3 Hz, 3H), 1.57-1.70 (m, 2H), 2.13 (s, 3H), 3.88 (s, 3H), 4.10-4.23 (m, 1H), 5.05 (br s, 1H), 6.97 (s, 1H), 7.17-7.33 (m, 4H), 7.39 (s, 1H), 8.79 (s, 1H).
APCI m/z (M+H)⁺ 322.

Example 167

2-(tert-Butylamino)-7-methoxy-6-(2-methylphenyl)quinazoline

Compound 167

In a similar manner to Example 164, Compound 167 was obtained using tert-butylamine.
¹H NMR (300 MHz, CDCl₃) δ (ppm) 1.55 (s, 9H), 2.13 (s, 3H), 3.88 (s, 3H), 5.24 (br s, 1H), 6.97 (s, 1H), 7.17-7.32 (m, 4H), 7.37 (s, 1H), 8.77 (s, 1H).
APCI m/z (M+H)⁺ 322.

Example 168

(S)-2-(3-methyl-2-butylamino)-7-methoxy-6-(2-methylphenyl)quinazoline

Compound 168

In a similar manner to Example 164, Compound 168 was obtained using (S)-(+)-3-methyl-2-butylamine.
¹H NMR (300 MHz, CDCl₃) δ (ppm) 0.99 (d, J=6.9 Hz, 3H), 1.02 (d, J=6.9 Hz, 3H), 1.22 (d, J=6.6 Hz, 3H), 1.82-1.96 (m, 1H), 2.13 (s, 3H), 3.88 (s, 3H), 4.08-4.20 (m, 1H), 5.03-5.17 (m, 1H), 6.96 (s, 1H), 7.16-7.35 (m, 4H), 7.38 (s, 1H), 8.79 (s, 1H).
APCI m/z (M+H)⁺ 336.

Example 169

(S)-2-(sec-Butylamino)-7-hydroxy-6-(2-methylphenyl)quinazoline

Compound 169

In a similar manner to Example 164 and Example 19, Compound 169 was obtained using (S)-(+)-sec-butylamine.
¹H NMR (300 MHz, CDCl₃) δ (ppm) 0.98 (t, J=7.5 Hz, 3H), 1.25 (d, J=6.6 Hz, 3H), 1.55-1.68 (m, 2H), 2.19 (s, 3H), 4.10-4.23 (m, 1H), 5.03-5.15 (m, 1H), 7.06 (s, 1H), 7.23-7.39 (m, 4H), 7.41 (s, 1H), 8.79 (s, 1H).
APCI m/z (M+H)⁺ 308.
m.p. 165° C.

Example 170

2-(3-Pentylamino)-7-hydroxy-6-(2-methylphenyl)quinazoline

Compound 170

In a similar manner to Example 164 and Example 19, Compound 170 was obtained using 3-pentylamine.

$^1$H NMR (300 MHz, CDCl$_3$) δ (ppm) 0.96 (t, J=7.5 Hz, 6H), 1.46-1.76 (m, 4H), 2.19 (s, 3H), 4.02-4.15 (m, 1H), 5.07 (br s, 1H), 7.05 (s, 1H), 7.22-7.37 (m, 4H), 7.41 (s, 1H), 8.79 (s, 1H).

APCI m/z (M+H)$^+$ 322.

m.p. 198-200° C.

Example 171

2-(Cyclohexylamino)-7-hydroxy-6-(2-methylphenyl)quinazoline

Compound 171

In a similar manner to Example 164 and Example 19, Compound 171 was obtained using cyclohexylamine.

$^1$H NMR (270 MHz, CDCl$_3$) δ (ppm) 1.15-1.87 (m, 8H), 2.02-2.16 (m, 2H), 2.18 (s, 3H), 3.92-4.10 (m, 1H), 5.23 (br s, 1H), 7.06 (s, 1H), 7.26-7.39 (m, 4H), 7.40 (s, 1H), 8.79 (s, 1H).

APCI m/z (M+H)$^+$ 334.

m.p. 158° C.

Example 172

(S)-2-(1-cyclohexylethylamino)-7-hydroxy-6-(2-methylphenyl)quinazoline

Compound 172

In a similar manner to Example 164 and Example 19, Compound 172 was obtained using (S)-(+)-1-cyclohexylethylamine.

$^1$H NMR (270 MHz, CDCl$_3$) δ (ppm) 0.97-1.31 (m, 6H), 1.20 (d, J=6.8 Hz, 3H), 1.37-1.52 (m, 1H), 1.60-1.90 (m, 4H), 2.19 (s, 3H), 4.07-4.21 (m, 1H), 5.19 (br s, 1H), 7.05 (s, 1H), 7.22-7.37 (m, 4H), 7.40 (s, 1H), 8.78 (s, 1H).

APCI m/z (M+H)$^+$ 362.

Example 173

(S)-2-(3-methyl-2-butylamino)-7-hydroxy-6-(2-methylphenyl)quinazoline

Compound 173

In a similar manner to Example 19, Compound 173 was obtained using Compound 168.

$^1$H NMR (300 MHz, CDCl$_3$) δ (ppm) 0.96 (d, J=6.9 Hz, 3H), 0.99 (d, J=6.9 Hz, 3H), 1.19 (d, J=6.9 Hz, 3H), 1.80-1.92 (m, 1H), 2.19 (s, 3H), 4.09-4.21 (m, 1H), 5.19 (br s, 1H), 7.05 (s, 1H), 7.22-7.39 (m, 4H), 7.41 (s, 1H), 8.79 (s, 1H).

APCI m/z (M+H)$^+$ 322.

Example 174

7-Hydroxy-6-(2-methylphenyl)-2-(4-heptylamino)quinazoline

Compound 174

In a similar manner to Example 4, 2-amino-7-methoxy-6-(2-methylphenyl)quinazoline was obtained using Compound A2 and 2-methylphenylboronic acid. The obtained 2-amino-7-methoxy-6-(2-methylphenyl)quinazoline (4.38 g, 16.5 mmol) was dissolved in DME (165 mL) and the solution was added with iodine (1.05 g, 8.3 mmol), cesium iodide (4.3 g, 16.5 mmol), isoamyl nitrite (13.3 mL, 99 mmol) and copper iodide (3.1 g, 16.5 mmol), followed by stirring at 80° C. for 7 hours. After an insoluble matter was filtered off from the reaction mixture, the solvent was evaporated under reduced pressure. The residue was added with aqueous saturated sodium thiosulfate solution and 28% aqueous ammonia and the obtained crystal was collected by filtration to obtain 2-iodo-7-methoxy-6-(2-methylphenyl)quinazoline (5.76 g, 93%) as a crude product. In a similar manner to Reference Example 4 and Example 19, Compound 174 was obtained using the above-obtained 2-iodo-7-methoxy-6-(2-methylphenyl)quinazoline and 4-heptylamine.

$^1$H NMR (300 MHz, CDCl$_3$) δ (ppm) 0.92 (t, J=7.0 Hz, 6H), 1.28-1.64 (m, 8H), 2.19 (s, 3H), 4.17-4.31 (m, 1H), 7.06 (s, 1H), 7.20-7.37 (m, 4H), 7.40 (s, 1H), 8.77 (s, 1H).

APCI m/z (M+H)$^+$ 350.

Example 175

2-(2,6-Dimethylanilino)-7-hydroxy-6-(2-methylphenyl)quinazoline

Compound 175

In a similar manner to Example 16 and Example 19, Compound 175 was obtained using 2-iodo-7-methoxy-6-(2-methylphenyl)quinazoline obtained in Example 174 and 2,6-dimethylaniline.

$^1$H NMR (270 MHz, CDCl$_3$) δ (ppm) 2.19 (s, 3H), 2.26 (s, 6H), 6.79 (br s, 1H), 7.08 (s, 1H), 7.15 (s, 3H), 7.20-7.37 (m, 4H), 7.46 (s, 1H), 8.84 (s, 1H).

APCI m/z (M+H)$^+$ 356.

m.p. 220-222° C.

Example 176

2-(2,6-Dichloroanilino)-7-hydroxy-6-(2-methylphenyl)quinazoline

Compound 176

In a similar manner to Example 16 and Example 19, Compound 176 was obtained using 2-iodo-7-methoxy-6-(2-methylphenyl)quinazoline obtained in Example 174 and 2,6-dichloroaniline.

$^1$H NMR (270 MHz, CDCl$_3$) δ (ppm) 2.19 (s, 3H), 7.14 (s, 1H), 7.19 (t, J=8.1 Hz, 1H), 7.23-7.39 (m, 4H), 7.43 (d, J=8.1 Hz, 2H), 7.52 (s, 1H), 8.93 (s, 1H).

ESI m/z (M+H)$^+$ 396.

m.p. 226-227° C.

Example 177

7-Hydroxy-2-(2-isopropyl-6-methylanilino)-6-(2-methylphenyl)quinazoline

Compound 177

In a similar manner to Example 16 and Example 19, Compound 177 was obtained using 2-iodo-7-methoxy-6-(2-methylphenyl)quinazoline obtained in Example 174 and 2-isopropyl-6-methylaniline.

$^1$H NMR (300 MHz, CDCl$_3$) δ (ppm) 1.20 (d, J=6.9 Hz, 6H), 2.19 (s, 3H), 2.27 (s, 3H), 3.18-3.31 (m, 1H), 7.05-7.41 (m, 8H), 7.48 (s, 1H), 8.88 (s, 1H).

APCI m/z (M+H)$^+$ 384.

Example 178

2-Anilino-7-hydroxy-6-(2-methylphenyl)quinazoline

Compound 178

2-Amino-7-methoxy-6-(2-methylphenyl)quinazoline (150 mg, 0.565 mmol) obtained in Example 174 was dissolved in dioxane (5.7 mL) and the solution was added with iodobenzene (70 μL, 0.622 mmol), tris(dibenzylideneacetone)dipalladium (25.9 mg, 0.028 mmol), 9,9-dimethyl-4,5-bis(diphenylphosphino)xanthene (36 mg, 0.062 mmol) and cesium carbonate (258 mg, 0.791 mmol), followed by stirring at 100° C. for 20 hours. The reaction mixture was added with water and extracted with ethyl acetate. The organic layer was washed with saturated brine and dried over anhydrous magnesium sulfate, then the solvent was evaporated under reduced pressure. The residue was purified by preparative thin-layer chromatography (ethyl acetate/hexane=3/7) to obtain 2-anilino-7-methoxy-6-(2-methylphenyl)quinazoline (164 mg, 85%). In a similar manner to Example 19, Compound 178 was obtained using the above-obtained 2-anilino-7-methoxy-6-(2-methylphenyl)quinazoline.

$^1$H NMR (270 MHz, CDCl$_3$) δ (ppm) 2.20 (s, 3H), 7.02-7.11 (m, 1H), 7.24 (s, 1H), 7.25-7.44 (m, 6H), 7.51 (s, 1H), 7.78-7.86 (m, 2H), 8.93 (s, 1H).

APCI m/z (M+H)$^+$ 328.

m.p. 234-236° C.

Example 179

2-(2,6-Dichloro-4-nitroanilino)-7-hydroxy-6-(2-methylphenyl)quinazoline

Compound 179

In a similar manner to Example 178, Compound 179 was obtained using 3,5-dichloro-4-iodonitrobenzene.

$^1$H NMR (270 MHz, CDCl$_3$) δ (ppm) 2.19 (s, 3H), 7.16 (s, 1H), 7.24-7.29 (m, 1H), 7.30-7.43 (m, 3H), 7.58 (s, 1H), 8.33 (s, 2H), 8.98 (s, 1H).

APCI m/z (M+H)$^+$ 441.

Example 180

2-(2-Ethyl-6-methylanilino)-7-hydroxy-6-(2-methylphenyl)quinazoline

Compound 180

In a similar manner to Example 178, Compound 180 was obtained using 2-ethyl-6-methyliodobenzene.

$^1$H NMR (300 MHz, CDCl$_3$) δ (ppm) 1.18 (t, J=7.5 Hz, 3H), 2.19 (s, 3H), 2.27 (s, 3H), 2.67 (q, J=7.5 Hz, 2H), 7.12 (s, 1H), 7.15-7.38 (m, 7H), 7.48 (s, 1H), 8.87 (s, 1H).

ESI m/z (M+H)$^+$ 370.

m.p. 130-133° C.

Example 181

6-[2-(Ethoxyiminomethyl)phenyl]-2-isopropylamino-7-methoxyquinazoline

Compound 181

In a similar manner to Example 58, Compound 181 was obtained using ethoxyamine hydrochloride.

$^1$H NMR (270 MHz, CDCl$_3$) δ (ppm) 1.25 (t, J=7.0 Hz, 3H), 1.31 (d, J=6.5 Hz, 6H), 3.85 (s, 3H), 4.15 (q, J=7.0 Hz, 2H), 4.24-4.40 (m, 1H), 5.04-5.11 (m, 1H), 6.97 (s, 1H), 7.21-7.29 (m, 1H), 7.33-7.45 (m, 3H), 7.83 (s, 1H), 7.92-8.00 (m, 1H), 8.79 (s, 1H).

ESI m/z (M+H)$^+$ 365.

Example 182

6-[2-(Hydroxymethyl)phenyl]-2-isopropylamino-7-methoxyquinazoline

Compound 182

Compound 57 (162 mg, 0.504 mmol) was dissolved in THF (3 mL) and the solution was added with sodium borohydride (38 mg, 1.01 mmol), followed by stirring at room temperature for 1 hour. The reaction mixture was added with water and extracted with ethyl acetate. The organic layer was washed with saturated brine and dried over anhydrous magnesium sulfate, then the solvent was evaporated under reduced pressure. The residue was purified by silica gel column chromatography (ethyl acetate/hexane=1/1) to obtain Compound 182 (42 mg, 35%).

$^1$H NMR (270 MHz, CDCl$_3$) δ (ppm) 1.31 (d, J=6.5 Hz, 6H), 3.87 (s, 3H), 4.24-4.37 (m, 1H), 4.47 (s, 2H), 5.09 (d, J=7.8 Hz, 1H), 6.98 (s, 1H), 7.23 (dd, J=7.3 Hz, 1.6 Hz, 1H), 7.36 (dt, J=7.3 Hz, 1.6 Hz, 1H), 7.42 (s, 1H), 7.44 (dt, J=7.3 Hz, 1.6 Hz, 1H), 7.59 (dd, J=7.3 Hz, 1.6 Hz, 1H), 8.79 (s, 1H).

ESI m/z (M+H)$^+$ 324.

Example 183

6-(2-Cyanophenyl)-2-isopropylamino-7-methoxyquinazoline

Compound 183

Compound 58 (160 mg, 0.48 mmol) was dissolved in THF (2.5 mL), and the solution was cooled to 0° C., then added with thionyl chloride (104 μL, 1.43 mmol), followed by stirring for 15 minutes. The reaction mixture was poured into saturated aqueous sodium hydrogencarbonate solution, followed by extracting with ethyl acetate. The organic layer was washed with saturated brine and dried over anhydrous magnesium sulfate, then the solvent was evaporated under reduced pressure. The residue was purified by silica gel column chromatography (ethyl acetate/hexane=1/1) to obtain Compound 183 (100 mg, 66%).

$^1$H NMR (300 MHz, CDCl$_3$) δ (ppm) 1.31 (d, J=6.6 Hz, 6H), 3.93 (s, 3H), 4.26-4.37 (m, 1H), 5.12 (d, J=7.8 Hz, 1H), 7.03 (s, 1H), 7.45 (dt, J=7.5, 1.5 Hz, 1H), 7.50 (dd, J=7.5, 1.5

Hz, 1H), 7.53 (s, 1H), 7.65 (dt, J=7.5, 1.5 Hz, 1H), 7.75 (dd, J=7.5, 1.5 Hz, 1H), 8.83 (s, 1H).
ESI m/z (M+H)+ 319.

Example 184

6-[2-(Benzyloxy)phenyl]-2-isopropylamino-7-methoxyquinazoline

Compound 184

In a similar manner to Example 4, Compound 184 was obtained using 2-(benzyloxy)phenylboronic acid.
$^1$H NMR (300 MHz, CDCl$_3$) δ (ppm) 1.29 (d, J=6.6 Hz, 6H), 3.70 (s, 3H), 4.28-4.35 (m, 1H), 5.02 (bs, 1H), 5.07 (s, 2H), 6.95 (s, 1H), 7.01-7.04 (m, 2H), 7.21-7.35 (m, 7H), 7.49 (s, 1H), 8.78 (s, 1H).
ESI m/z (M+H)+ 400.

Example 185

6-(2-Carboxyphenyl)-2-isopropylamino-7-methoxyquinazoline

Compound 185

Compound 57 (100 mg, 0.31 mmol) was suspended in a mixed solvent of acetonitrile (2 mL) and water (1 mL), and the suspension was added with DMSO (20 μL, 0.31 mmol) and NaH$_2$PO$_4$ (110 mg, 0.93 mmol). The mixture was cooled to 0° C., then added with NaClO$_2$ (43 mg, 0.46 mmol) and stirred at 60° C. for 1 hour. The reaction mixture was added with 1 mol/L hydrochloric acid and chloroform, and the organic layer was separated. The organic layer was washed with 1 mol/L hydrochloric acid and dried over anhydrous magnesium sulfate, then the solvent was evaporated under reduced pressure. The residue was reslurried with diethylether to obtain Compound 185 (91 mg, 85%).
$^1$H NMR (300 MHz, CDCl$_3$) δ (ppm) 1.38 (d, J=6.6 Hz, 6H), 3.81 (s, 3H), 4.38-4.47 (m, 1H), 7.01 (s, 1H), 7.31 (dd, J=7.2, 1.2 Hz, 1H), 7.52 (dt, J=7.2, 1.2 Hz, 1H), 7.64 (s, 1H), 7.65 (dt, J=7.2, 1.2 Hz, 1H), 8.08 (dd, J=7.2, 1.2 Hz, 1H), 8.78 (d, J=8.4 Hz, 1H), 9.03 (s, 1H).
ESI m/z (M+H)+ 338.

Example 186

6-(2-Hydroxyphenyl)-2-isopropylamino-7-methoxyquinazoline

Compound 186

Compound 184 (100 mg, 0.25 mmol) was dissolved in methylene chloride (2 mL) and the solution was added with 1 mol/L boron tribromide-methylene chloride solution (750 uL, 0.75 mmol), followed by stirring at room temperature for 20 minutes. The reaction mixture was added with saturated aqueous sodium hydrogen carbonate solution and ethyl acetate, and the organic layer was separated. The organic layer was washed with saturated aqueous sodium hydrogencarbonate solution and dried over anhydrous magnesium sulfate, then the solvent was evaporated under reduced pressure. The residue was reslurried with diethylether to obtain Compound 186 (70 mg, 90%).
$^1$H NMR (300 MHz, CDCl$_3$) δ (ppm) 1.30 (d, J=6.6 Hz, 6H), 3.98 (s, 3H), 4.24-4.36 (m, 1H), 5.14 (br s, 1H), 6.99- 7.04 (m, 3H), 7.22 (dd, J=5.4, 1.8 Hz, 1H), 7.32 (dt, J=5.4, 1.8 Hz, 1H), 7.55 (s, 1H), 8.80 (s, 1H).
ESI m/z (M+H)+ 310.

Example 187

6-(2-Acetylphenyl)-2-isopropylamino-7-methoxyquinazoline

Compound 187

In a similar manner to Example 4, Compound 187 was obtained using 2-acetylphenylboronic acid.
$^1$H NMR (270 MHz, CDCl$_3$) δ (ppm) 1.31 (d, J=6.5 Hz, 6H), 2.26 (s, 3H), 3.84 (s, 3H), 4.30-4.35 (m, 1H), 5.10 (br s, 1H), 6.94 (s, 1H), 7.35-7.68 (m, 5H), 8.82 (s, 1H).
APCI m/z (M+H)+ 336

Example 188

2-Isopropylamino-7-methoxy-6-[2-(morpholinocarbonyl)phenyl]quinazoline

Compound 188

Compound 185 (100 mg, 0.30 mmol) was dissolved in DMF (2 mL) and the solution was added with 1-ethyl-3-(3-dimethylaminopropyl)carbodiimide hydrochloride (170 mg, 0.89 mmol), 1-hydroxybenzotriazole (120 mg, 0.89 mmol) and morpholine (40 μL, 0.44 mmol), followed by stirring at room temperature for 2 hours. The reaction mixture was added with water and extracted with ethyl acetate. The organic layer was washed with saturated aqueous sodium hydrogencarbonate solution and saturated brine, and dried over anhydrous magnesium sulfate, then the solvent was evaporated under reduced pressure. The residue was purified by preparative thin-layer chromatography (ethyl acetate/hexane=2/1) to obtain Compound 188 (25 mg, 21%).
$^1$H NMR (300 MHz, CDCl$_3$) δ (ppm) 1.32 (d, J=6.3 Hz, 6H), 2.28-3.10 (m, 8H), 3.88 (s, 3H), 4.13-4.35 (m, 1H), 5.27 (br s, 1H), 6.99 (s, 1H), 7.38-7.45 (m, 4H), 7.55 (s, 1H), 8.82 (s, 1H).
ESI m/z (M+H)+ 407.

Example 189

2-Isopropylamino-7-methoxy-6-[2-(N-methylcarbamoyl)phenyl]quinazoline

Compound 189

In a similar manner to Example 188, Compound 189 was obtained using methylamine.
$^1$H NMR (270 MHz, CDCl$_3$) δ (ppm) 1.35 (d, J=6.2 Hz, 6H), 2.72 (d, J=4.9 Hz, 3H), 3.88 (s, 3H), 4.26-4.45 (m, 1H), 5.50-5.63 (m, 1H), 7.03 (s, 1H), 7.28-7.85 (m, 6H), 8.86 (s, 1H).
ESI m/z (M+H)+ 351.

Example 190

6-(2-Fluorophenyl)-2-isopropylamino-7-methoxyquinazoline

Compound 190

In a similar manner to Example 4, Compound 190 was obtained using 2-fluorophenylboronic acid.

¹H NMR (270 MHz, CDCl₃) δ (ppm) 1.31 (d, J=6.2 Hz, 6H), 3.91 (s, 3H), 4.27-4.35 (m, 1H), 5.06 (d, J=7.6 Hz, 1H), 6.98 (s, 1H), 7.10-7.23 (m, 2H), 7.32-7.39 (m, 2H), 7.51 (s, 1H), 8.81 (s, 1H).
ESI m/z (M+H)⁺ 312.

Example 191

2-Isopropylamino-7-methoxy-6-(2-methylphenyl)quinazoline

Compound 191

In a similar manner to Example 4, Compound 191 was obtained using 2-methylphenylboronic acid.
¹H NMR (270 MHz, CDCl₃) δ (ppm) 1.31 (d, J=6.8 Hz, 6H), 2.13 (s, 3H), 3.88 (s, 3H), 4.28-4.35 (m, 1H), 5.05 (d, J=8.1 Hz, 1H), 6.98 (s, 1H), 7.19-7.30 (m, 4H), 7.38 (s, 1H), 8.79 (s, 1H).
ESI m/z (M+H)⁺ 308.

Example 192

2-Isopropylamino-7-methoxy-6-(2-trifluoromethylphenyl)quinazoline

Compound 192

In a similar manner to Example 4, Compound 192 was obtained using 2-trifluoromethylphenylboronic acid.
¹H NMR (270 MHz, CDCl₃) δ (ppm) 1.31 (d, J=6.2 Hz, 6H), 3.83 (s, 3H), 4.30 (m, 1H), 5.07 (d, J=8.1 Hz, 1H), 6.95 (s, 1H), 7.31 (d, J=7.6 Hz, 1H), 7.39 (s, 1H), 7.46-7.60 (m, 2H), 7.74 (d, J=7.6 Hz, 1H), 8.78 (s, 1H).
ESI m/z (M+H)⁺ 362.

Example 193

2-Isopropylamino-7-methoxy-6-(2-methoxyphenyl)quinazoline

Compound 193

In a similar manner to Example 4, Compound 193 was obtained using 2-methoxyphenylboronic acid.
¹H NMR (300 MHz, CDCl₃) δ (ppm) 1.30 (d, J=6.3 Hz, 6H), 3.77 (s, 3H), 3.88 (s, 3H), 4.25-4.34 (m, 1H), 5.03 (d, J=7.5 Hz, 1H), 6.97 (s, 1H), 7.00 (dt, J=7.2, 1.8 Hz, 1H), 7.03 (dd, J=7.2, 1.8 Hz, 1H), 7.25 (dt, J=7.2, 1.8 Hz, 1H), 7.36 (dt, J=7.2, 1.8 Hz, 1H), 7.48 (s, 1H), 8.79 (s, 1H).
ESI m/z (M+H)⁺ 324.

Example 194

6-[3-(N-Acetyl-N-benzylamino)phenyl]-2-isopropylamino-7-methoxyquinazoline

Compound 194

Compound 52 (200 mg, 0.57 mmol) was dissolved in DMF (4 mL) and the solution was added with sodium hydride (60% in oil, 57 mg, 1.43 mmol) and benzyl bromide (170 μL, 1.43 mmol), followed by stirring at room temperature for 2 hours. The reaction mixture was added with water and extracted with ethyl acetate. The organic layer was washed with water and saturated brine, and dried over anhydrous magnesium sulfate, then the solvent was evaporated under reduced pressure. The residue was purified by silica gel column chromatography (ethyl acetate/hexane=1/1) to obtain Compound 194 (240 mg, 96%).
¹H NMR (300 MHz, CDCl₃) δ (ppm) 1.30 (d, J=6.6 Hz, 6H), 1.95 (s, 3H), 3.86 (s, 3H), 4.24-4.38 (m, 1H), 4.92 (s, 2H), 6.93-7.03 (m, 2H), 7.15 (s, 1H), 7.18-7.32 (m, 5H), 7.33-7.50 (m, 3H), 8.81 (s, 1H).
ESI m/z (M+H)⁺ 341.

Example 195

6-[3-(Benzyloxy)phenyl]-2-isopropylamino-7-methoxyquinazoline

Compound 195

In a similar manner to Example 4, Compound 195 was obtained using 3-(benzyloxy)phenylboronic acid.
¹H NMR (300 MHz, CDCl₃) δ (ppm) 1.30 (d, J=6.6 Hz, 6H), 3.90 (s, 3H), 4.25-4.37 (m, 1H), 5.11 (s, 2H), 5.15 (bs, 1H), 6.97-7.00 (m, 2H), 7.12-7.17 (m, 2H), 7.30-7.47 (m, 6H), 7.53 (s, 1H), 8.82 (s, 1H).
ESI m/z (M+H)⁺ 400.

Example 196

6-(3-Hydroxyphenyl)-2-isopropylamino-7-methoxyquinazoline

Compound 196

In a similar manner to Example 186, Compound 196 was obtained using Compound 195.
¹H NMR (300 MHz, CDCl₃) δ (ppm) 1.30 (d, J=6.6 Hz, 6H), 3.89 (s, 3H), 4.26-4.37 (m, 1H), 5.09 (d, J=8.1 Hz, 1H), 5.87 (bs, 1H), 6.86 (ddd, J=8.1, 2.4, 0.9 Hz, 1H), 6.98 (s, 1H), 7.02 (d, J=2.4 Hz, 2H), 7.09 (ddd, J=8.1, 2.4, 0.9 Hz, 1H), 7.29 (t, J=8.1 Hz, 1H), 7.52 (s, 1H).
ESI m/z (M+H)⁺ 310.

Example 197

6-(3-Formylphenyl)-2-isopropylamino-7-methoxyquinazoline

Compound 197

In a similar manner to Example 4, Compound 197 was obtained using 3-formylphenylboronic acid.
¹H NMR (300 MHz, CDCl₃) δ (ppm) 1.31 (d, J=6.6 Hz, 6H), 3.95 (s, 3H), 4.26-4.36 (m, 1H), 5.10 (br s, 1H), 7.01 (s, 1H), 7.56 (s, 1H), 7.59 (t, J=8.1 Hz, 1H), 7.82 (dt, J=8.1, 1.2 Hz, 1H), 7.88 (dt, J=8.1, 1.2 Hz, 1H), 8.05 (t, J=1.2 Hz, 1H), 8.84 (s, 1H), 10.08 (s, 1H).
ESI m/z (M+H)⁺ 322.

Example 198

6-(3-Carboxyphenyl)-2-isopropylamino-7-methoxyquinazoline

Compound 198

In a similar manner to Example 185, Compound 198 was obtained using Compound 197.

¹H NMR (270 MHz, DMSO-d₆) δ (ppm) 1.29 (d, J=6.6 Hz, 6H), 3.69 (br s, 1H), 3.97 (s, 3H), 4.34-4.47 (m, 1H), 7.57-7.63 (m, 1H), 7.77-7.80 (m, 1H), 7.96-8.08 (m, 4H), 9.26 (s, 1H).
ESI m/z (M+H)⁺ 338.

Example 199

6-(3-Acetylphenyl)-2-isopropylamino-7-methoxyquinazoline

Compound 199

In a similar manner to Example 4, Compound 199 was obtained using 3-acetylphenylboronic acid.
¹H NMR (300 MHz, CDCl₃) δ (ppm) 1.31 (d, J=6.6 Hz, 6H), 2.65 (s, 3H), 3.94 (s, 3H), 4.26-4.38 (m, 1H), 5.10 (d, J=8.1 Hz, 1H), 7.00 (s, 1H), 7.52 (t, J=7.8 Hz, 1H), 7.56 (s, 1H), 7.75 (dd, J=7.8, 0.9 Hz, 1H), 7.95 (dd, J=7.8, 0.9 Hz, 1H), 8.12 (s, 1H), 8.84 (s, 1H).
ESI m/z (M+H)⁺ 336.

Example 200

2-Isopropylamino-7-methoxy-6-(3-trifluoromethoxyphenyl)quinazoline

Compound 200

In a similar manner to Example 4, Compound 200 was obtained using 3-trifluoromethoxyphenylboronic acid.
¹H NMR (300 MHz, CDCl₃) δ (ppm) 1.31 (d, J=6.6 Hz, 6H), 3.94 (s, 3H), 4.28-4.35 (m, 1H), 5.09 (d, J=8.4 Hz, 1H), 6.99 (s, 1H), 7.20-7.22 (m, 1H), 7.41-7.45 (m, 3H), 7.54 (m, 1H), 8.83 (s, 1H).
APCI m/z (M+H)⁺ 378.

Example 201

2-Isopropylamino-7-methoxy-6-(3-methoxyphenyl)quinazoline

Compound 201

In a similar manner to Example 4, Compound 201 was obtained using 3-methoxyphenylboronic acid.
¹H NMR (300 MHz, CDCl₃) δ (ppm) 1.31 (d, J=6.3 Hz, 6H), 3.86 (s, 3H), 3.93 (s, 3H), 4.28-4.35 (m, 1H), 5.05 (d, J=7.5 Hz, 1H), 6.90 (ddd, J=8.1, 2.4, 1.5 Hz, 1H), 6.98 (s, 1H), 7.08 (t, J=1.5 Hz, 1H), 7.12 (ddd, J=8.1, 2.4, 1.5 Hz, 1H), 7.34 (t, J=8.1 Hz, 1H), 7.54 (s, 1H), 8.82 (t, J=8.1 Hz, 1H).
ESI m/z (M+H)⁺ 324.

Example 202

6-(3-Acetoxyphenyl)-2-isopropylamino-7-methoxyquinazoline

Compound 202

Compound 196 (100 mg, 0.32 mmol) was dissolved in methylene chloride (4 mL) and the solution was added with acetic anhydride (92 μL, 0.97 mmol) and triethylamine (180 μL, 1.29 mmol), followed by stirring at room temperature for 10 minutes. The reaction mixture was added with water and extracted with ethyl acetate. The organic layer was washed with water and saturated brine, and dried over anhydrous magnesium sulfate, then the solvent was evaporated under reduced pressure. The residue was purified by silica gel column chromatography (ethyl acetate/hexane=1/1) to obtain Compound 202 (42 mg, 37%).
¹H NMR (300 MHz, CDCl₃) δ (ppm) 1.31 (d, J=6.6 Hz, 6H), 2.31 (s, 3H), 3.93 (s, 3H), 4.28-4.35 (m, 1H), 5.12 (d, J=7.5 Hz, 1H), 6.98 (s, 1H), 7.07-7.09 (m, 1H), 7.25-7.28 (m, 1H), 7.41-7.43 (m, 2H), 7.55 (s, 1H), 8.82 (s, 1H).
APCI m/z (M+H)⁺ 352.

Example 203

2-Isopropylamino-7-methoxy-6-(3-methylphenyl)quinazoline

Compound 203

In a similar manner to Example 4, Compound 203 was obtained using 3-methylphenylboronic acid.
¹H NMR (270 MHz, CDCl₃) δ (ppm) 1.31 (d, J=6.5 Hz, 6H), 2.42 (s, 3H), 3.93 (s, 3H), 4.27-4.35 (m, 1H), 5.05 (d, J=7.6 Hz, 1H), 6.98 (s, 1H), 7.16-7.18 (m, 1H), 7.31-7.33 (m, 2H), 7.33 (s, 1H), 7.52 (s, 1H), 8.81 (s, 1H).
ESI m/z (M+H)⁺ 308.

Example 204

6-(3-Fluorophenyl)-2-isopropylamino-7-methoxyquinazoline

Compound 204

In a similar manner to Example 4, Compound 204 was obtained using 3-fluorophenylboronic acid.
¹H NMR (270 MHz, CDCl₃) δ (ppm) 1.31 (d, J=6.5 Hz, 6H), 3.94 (s, 3H), 4.25-4.37 (m, 1H), 5.08 (d, J=8.1 Hz, 1H), 6.99 (s, 1H), 7.01-7.08 (m, 1H), 7.28-7.42 (m, 3H), 7.54 (s, 1H), 8.82 (s, 1H).
ESI m/z (M+H)⁺ 312.

Example 205

2-Isopropylamino-7-methoxy-6-(3-trifluoromethylphenyl)quinazoline

Compound 205

In a similar manner to Example 4, Compound 205 was obtained using 3-trifluoromethylphenylboronic acid.
¹H NMR (270 MHz, CDCl₃) δ (ppm) 1.31 (d, J=6.5 Hz, 6H), 3.94 (s, 3H), 4.25-4.38 (m, 1H), 5.10 (d, J=7.3 Hz, 1H), 7.00 (s, 1H), 7.54 (d, J=7.6 Hz, 1H), 7.55 (s, 1H), 7.59 (br s, 1H), 7.72 (d, J=7.6 Hz, 1H), 7.79 (br s, 1H), 8.84 (s, 1H).
ESI m/z (M+H)⁺ 362.

Example 206

6-(4-Fluoro-2-methylphenyl)-2-isopropylamino-7-methoxyquinazoline

Compound 206

In a similar manner to Example 4, Compound 206 was obtained using 4-fluoro-2-methylphenylboronic acid.
¹H NMR (300 MHz, CDCl₃) δ (ppm) 1.31 (d, J=6.3 Hz, 6H), 2.11 (s, 3H), 3.88 (s, 3H), 4.28-4.35 (m, 1H), 5.06 (d, J=7.5 Hz, 1H), 6.91-6.98 (m, 3H), 7.14 (dd, J=8.4, 5.7 Hz, 1H), 7.36 (s, 1H), 8.79 (s, 1H).
ESI m/z (M+H)⁺ 326.

Example 207

6-(2-Fluoro-3-methoxyphenyl)-2-isopropylamino-7-methoxyquinazoline

Compound 207

In a similar manner to Example 4, Compound 207 was obtained using 2-fluoro-3-methoxyphenylboronic acid.
¹H NMR (270 MHz, CDCl₃) δ (ppm) 1.31 (d, J=6.5 Hz, 6H), 3.91 (s, 3H), 3.93 (s, 3H), 4.25-4.37 (m, 1H), 5.07 (d, J=8.1 Hz, 1H), 6.90-6.97 (m, 2H), 6.98 (s, 1H), 7.13 (td, J=8.1, 1.0 Hz, 1H), 7.51 (s, 1H), 8.80 (s, 1H).
ESI m/z (M+H)⁺ 342.

Example 208

6-(2-Furyl)-2-isopropylamino-7-methoxyquinazoline

Compound 208

In a similar manner to Example 76, Compound 208 was obtained using Compound A4 and 2-(tributylstannyl)furane.
¹H NMR (300 MHz, DMSO-d₆) δ (ppm) 1.29 (d, J=6.3 Hz, 6H), 4.03 (s, 3H), 4.26-4.33 (m, 1H), 5.33 (br s, 1H), 6.48 (dd, J=3.3, 1.8 Hz, 1H), 6.92 (d, J=3.3 Hz, 1H), 6.96 (s, 1H), 7.46 (d, J=1.8 Hz, 1H), 8.06 (s, 1H), 8.86 (s, 1H).
ESI m/z (M+H)⁺ 284.

Example 209

2-Isopropylamino-7-methoxy-6-{3-[(1H-pyrrol-2-yl)carbonylamino]phenyl}quinazoline Compound 209

1H-Pyrrol-2-carboxylic acid (72 mg, 0.65 mmol) was dissolved in DMF (2 mL) and the solution was added with 1-ethyl-3-(3-dimethylaminopropyl)carbodiimide hydrochloride (187 mg, 0.97 mmol), 1-hydroxybenzotriazole (132 mg, 0.97 mmol) and Compound 50 (100 mg, 0.32 mmol), followed by stirring at 70° C. for 30 minutes. The reaction mixture was added with water and extracted with ethyl acetate. The organic layer was washed with saturated aqueous sodium hydrogencarbonate solution and saturated brine, and dried over anhydrous magnesium sulfate, then the solvent was evaporated under reduced pressure. The residue was purified by preparative thin-layer chromatography (ethyl acetate/hexane=2/1) to obtain Compound 209 (35 mg, 27%).
¹H NMR (270 MHz, CDCl₃) δ (ppm) 1.31 (d, J=6.5 Hz, 6H), 3.94 (s, 3H), 4.28-4.36 (m, 1H), 5.09 (br s, 1H), 6.30-6.32 (m, 1H), 6.69-6.72 (m, 1H), 6.99 (s, 1H), 6.98-7.00 (m, 1H), 7.29 (dt, J=7.8, 2.0 Hz, 1H), 7.41 (t, J=7.8 Hz, 1H), 7.57 (s, 1H), 7.58 (br s, 1H), 7.63 (dt, J=7.8, 2.0 Hz, 1H), 7.74 (t, J=2.0 Hz, 1H), 8.83 (s, 1H), 9.40 (br s, 1H).
ESI m/z (M+H)⁺ 402.

Example 210

2-Isopropylamino-7-methoxy-6-[3-(3-phenylureido)phenyl]quinazoline

Compound 210

Compound 50 (100 mg, 0.32 mmol) was dissolved in DMF (1.5 mL) and the solution was added with triethylamine (64 µL, 0.45 mmol) and phenyl isocyanate (42 µL, 0.39 mmol), followed by stirring at room temperature for 40 minutes. The reaction mixture was added with water. The obtained crystal was collected by filtration and purified by silica gel column chromatography (ethyl acetate/hexane=4/1) to obtain Compound 210 (68 mg, 49%).
¹H NMR (270 MHz, CDCl₃) δ (ppm) 1.23 (d, J=6.5 Hz, 6H), 3.91 (s, 3H), 4.15-4.29 (m, 1H), 6.83-6.86 (m, 1H), 6.95-6.99 (m, 2H), 7.09-7.13 (m, 1H), 7.24-7.32 (m, 3H), 7.43-7.47 (m, 3H), 7.59 (br s, 1H), 7.65 (s, 1H), 8.57 (br s, 1H), 8.64 (br s, 1H), 8.94 (s, 1H).
ESI m/z (M+H)⁺ 428.

Example 211

6-{3-[(1H-indol-2-yl)carbonylamino]phenyl}-2-isopropylamino-7-methoxyquinazoline Compound 211

In a similar manner to Example 209, Compound 211 was obtained using 1H-indole-2-carboxylic acid.
¹H NMR (270 MHz, CDCl₃) δ (ppm) 1.32 (d, J=6.4 Hz, 6H), 3.96 (s, 3H), 4.25-4.40 (m, 1H), 5.06-5.15 (m, 1H), 5.31-5.39 (m, 1H), 6.98-7.04 (m, 2H), 7.14-7.21 (m, 1H), 7.29-7.37 (m, 1H), 7.40-7.49 (m, 2H), 7.59 (s, 1H), 7.65-7.74 (m, 2H), 7.80 (s, 1H), 7.87 (s, 1H), 8.84 (s, 1H), 9.18 (s, 1H).
ESI m/z (M+H)⁺ 452.

Example 212

2-Isopropylamino-7-methoxy-6-[3-(3-methylureido)phenyl]quinazoline

Compound 212

Compound 50 (150 mg, 0.49 mmol) was dissolved in THF (2 mL) and the solution was added with phenyl chloroformate (122 µL, 0.97 mmol), triethylamine (150 µL, 1.07 mmol) and 4-dimethylaminopyridine (6 mg, 0.05 mmol), followed by stirring at room temperature for 1.5 hours. The reaction mixture was added with water and extracted with ethyl acetate. The organic layer was washed with water and saturated brine, and dried over anhydrous magnesium sulfate, then the solvent was evaporated under reduced pressure. The residue was purified by preparative thin-layer chromatography (ethyl acetate/hexane=1/1) to obtain 2-isopropylamino-7-methoxy-6-[3-(phenoxycarbonylamino)phenyl]quinazoline (60 mg, 29%). The obtained 2-isopropylamino-7-methoxy-6-[3-(phenoxycarbonylamino)phenyl]quinazoline (60 mg, 0.14 mmol) was dissolved in THF (1.5 mL) and the solution was added with 2 mol/L methylamine-THF solution (690 µL, 1.26 mmol), followed by stirring at room temperature for 3 nights. The reaction mixture was added with water and extracted with ethyl acetate. The organic layer was washed with water and saturated brine, and dried over anhydrous magnesium sulfate, then the solvent was evaporated under reduced pressure. The residue was purified by preparative thin-layer chromatography (ethyl acetate/hexane=2/1) to obtain Compound 212 (25 mg, 49%).
¹H NMR (300 MHz, CDCl₃) δ (ppm) 1.31 (d, J=6.3 Hz, 6H), 2.85 (s, 3H), 3.93 (s, 3H), 4.28-4.35 (m, 1H), 4.74 (br s, 1H), 5.08 (br s, 1H), 6.29 (s, 1H), 6.98 (s, 1H), 7.26-7.38 (m, 3H), 7.46 (s, 1H), 7.53 (s, 1H), 8.81 (s, 1H).
APCI m/z (M+H)⁺ 366.

Example 213

2-Isopropylamino-7-methoxy-6-{3-[(4-trifluoromethylphenyl)carbonylamino]phenyl}quinazoline Compound 213

In a similar manner to Example 209, Compound 213 was obtained using 4-trifluoromethylbenzoic acid.
$^1$H NMR (270 MHz, CDCl$_3$) δ (ppm) 1.35 (d, J=6.5 Hz, 6H), 3.98 (s, 3H), 4.30-4.37 (m, 1H), 7.07 (s, 1H), 7.35 (dt, J=7.8, 1.6 Hz, 1H), 7.46 (t, J=7.8 Hz, 1H), 7.60 (s, 1H), 7.65 (dt, J=7.8, 1.6 Hz, 1H), 7.71 (d, J=8.0 Hz, 1H), 7.77 (d, J=8.0 Hz, 1H), 7.84 (d, J=1.6 Hz, 1H), 7.90 (br s, 1H), 7.99 (s, 1H), 8.01 (d, J=8.0 Hz, 1H), 8.24 (d, J=8.0 Hz, 1H), 8.87 (s, 1H).
APCI m/z (M+H)$^+$ 481.

Example 214

2-Isopropylamino-7-methoxy-6-{3-[(4-trifluoromethoxyphenyl)carbonylamino]phenyl}quinazoline Compound 214

In a similar manner to Example 209, Compound 214 was obtained using 4-trifluoromethoxybenzoic acid.
$^1$H NMR (300 MHz, CDCl$_3$) δ (ppm) 1.32 (d, J=6.6 Hz, 6H), 3.95 (s, 3H), 4.28-4.36 (m, 1H), 7.01 (s, 1H), 7.31 (d, J=8.7 Hz, 1H), 7.35 (s, 1H), 7.44 (t, J=8.1 Hz, 1H), 7.58 (s, 1H), 7.65 (dt, J=8.1, 1.2 Hz, 1H), 7.79 (t, J=1.2 Hz, 1H), 7.84 (br s, 1H), 7.94 (d, J=8.7 Hz, 2H), 8.84 (s, 1H).
ESI m/z (M+H)$^+$ 497.

Example 215

2-Isopropylamino-7-methoxy-6-{3-[(4-pyridyl)carbonylamino]phenyl}quinazoline

Compound 215

In a similar manner to Example 209, Compound 215 was obtained using isonicotinic acid.
$^1$H NMR (300 MHz, CDCl$_3$) δ (ppm) 1.35 (d, J=6.3 Hz, 6H), 3.95 (s, 3H), 4.33-4.39 (m, 1H), 7.05 (s, 1H), 7.32 (d, J=8.4 Hz, 1H), 7.46 (t, J=7.8 Hz, 1H), 7.59 (s, 1H), 7.65 (d, J=7.8 Hz, 1H), 7.70 (d, J=7.8 Hz, 1H), 7.76 (d, J=6.0 Hz, 1H), 7.83 (br s, 1H), 8.16 (br s, 1H), 8.79 (d, J=6.0 Hz, 2H), 8.87 (s, 1H).
APCI m/z (M+H)$^+$ 414.

Example 216

2-Isopropylamino-7-methoxy-6-{3-[(3-trifluoromethylphenyl)carbonylamino]phenyl}quinazoline Compound 216

In a similar manner to Example 209, Compound 216 was obtained using 3-trifluoromethylbenzoic acid.
$^1$H NMR (300 MHz, CDCl$_3$) δ (ppm) 1.35 (d, J=6.6 Hz, 6H), 3.99 (s, 3H), 4.32-4.39 (m, 1H), 7.06 (s, 1H), 7.37 (d, J=7.8 Hz, 1H), 7.47 (t, J=7.8 Hz, 1H), 7.57-7.69 (m, 4H), 7.84 (m, 2H), 7.92 (br s, 1H), 8.10 (d, J=7.8 Hz, 1H), 8.16 (s, 1H), 8.88 (s, 1H).
APCI m/z (M+H)$^+$ 481.

Example 217

2-Isopropylamino-7-methoxy-6-{3-[(2-trifluoromethylphenyl)carbonylamino]phenyl}quinazoline Compound 217

In a similar manner to Example 209, Compound 217 was obtained using 2-trifluoromethylbenzoic acid.
$^1$H NMR (300 MHz, CDCl$_3$) δ (ppm) 1.31 (d, J=6.3 Hz, 6H), 3.94 (s, 3H), 4.28-4.37 (m, 1H), 5.21 (br s, 1H), 6.99 (s, 1H), 7.37 (d, J=7.8 Hz, 1H), 7.44 (d, J=7.8 Hz, 1H), 7.51 (br s, 1H), 7.58 (s, 1H), 7.61-7.70 (m, 3H), 7.67 (d, J=8.4 Hz, 1H), 7.76 (s, 1H), 7.78 (d, J=8.4 Hz, 1H), 8.84 (s, 1H).
ESI m/z (M+H)$^+$ 481.

Example 218

6-{3-[(3,5-Di-tert-butylphenyl)carbonylamino]phenyl}-2-isopropylamino-7-methoxyquinazoline Compound 218

In a similar manner to Example 209, Compound 218 was obtained using 3,5-di-tert-butylbenzoic acid.
$^1$H NMR (270 MHz, CDCl$_3$) δ (ppm) 1.31 (d, J=6.5 Hz, 6H), 1.40 (s, 18H), 3.94 (s, 3H), 4.27-4.35 (m, 1H), 5.09 (br s, 1H), 6.99 (s, 1H), 7.31-7.79 (m, 9H), 8.83 (s, 1H).
APCI m/z (M+H)$^+$ 525.

Example 219

6-{3-[(3-Fluorophenyl)carbonylamino]phenyl}-2-isopropylamino-7-methoxyquinazoline Compound 219

In a similar manner to Example 209, Compound 219 was obtained using 3-fluorobenzoic acid.
$^1$H NMR (300 MHz, CDCl$_3$) δ (ppm) 1.31 (d, J=6.2 Hz, 6H), 3.95 (s, 3H), 4.28-4.33 (m, 1H), 5.11 (br s, 1H), 6.99 (s, 1H), 7.33-7.79 (m, 10H), 8.83 (s, 1H).
APCI m/z (M+H)$^+$ 431.

Example 220

6-[3-(Cyclopropylcarbonylamino)phenyl]-2-isopropylamino-7-methoxyquinazoline

Compound 220

In a similar manner to Example 209, Compound 220 was obtained using cyclopropanecarboxylic acid.
$^1$H NMR (300 MHz, CDCl$_3$) δ (ppm) 0.82-0.89 (m, 2H), 1.08-1.13 (m, 2H), 1.31 (d, J=6.5 Hz, 6H), 1.51-1.54 (m, 1H), 3.93 (s, 3H), 4.27-4.35 (m, 1H), 5.10 (d, J=7.8 Hz, 1H), 6.97 (s, 1H), 7.27 (d, J=7.8 Hz, 1H), 7.36 (t, J=7.8 Hz, 1H), 7.41 (br s, 1H), 7.51 (d, J=7.8 Hz, 1H), 7.54 (s, 1H), 7.69 (br s, 1H), 8.81 (s, 1H).
APCI m/z (M+H)$^+$ 377.

Example 221

2-Isopropylamino-7-methoxy-6-{3-[(3-pyridyl)carbonylamino]phenyl}quinazoline

Compound 221

In a similar manner to Example 209, Compound 221 was obtained using nicotinic acid.
$^1$H NMR (300 MHz, CDCl$_3$) δ (ppm) 1.31 (d, J=6.6 Hz, 6H), 3.95 (s, 3H), 4.28-4.35 (m, 1H), 5.10 (d, J=8.1 Hz, 1H), 6.99 (s, 1H), 7.37 (dt, J=8.1, 1.4 Hz, 1H), 7.46 (t, J=8.1 Hz, 1H), 7.47 (dd, J=8.1, 4.8 Hz, 1H), 7.58 (s, 1H), 7.67 (d, J=8.1 Hz, 1H), 7.81 (br s, 1H), 7.89 (br s, 1H), 8.24 (dt, J=8.1, 1.4 Hz, 1H), 8.79 (dd, J=4.8, 1.8 Hz, 1H), 8.83 (s, 1H), 9.12 (d, J=1.8 Hz, 1H).
APCI m/z (M+H)$^+$ 414.

Example 222

6-[3-(Cyclobutylcarbonylamino)phenyl]-2-isopropylamino-7-methoxyquinazoline

Compound 222

In a similar manner to Example 209, Compound 222 was obtained using cyclobutanecarboxylic acid.
$^1$H NMR (270 MHz, CDCl$_3$) δ (ppm) 1.31 (d, J=6.5 Hz, 6H), 1.95-2.05 (m, 2H), 2.19-2.26 (m, 2H), 2.34-2.45 (m, 2H), 3.14-3.20 (m, 1H), 3.93 (s, 3H), 4.27-4.35 (m, 1H), 5.10 (d, J=8.4 Hz, 1H), 6.98 (s, 1H), 7.05 (br s, 1H), 7.27 (d, J=8.1 Hz, 1H), 7.37 (t, J=8.1 Hz, 1H), 7.52 (d, J=8.1 Hz, 1H), 7.55 (s, 1H), 7.70 (s, 1H), 8.81 (s, 1H).
APCI m/z (M+H)$^+$ 391.

Example 223

6-(2-Hydroxymethyl-5-nitrophenyl)-2-isopropylamino-7-methoxyquinazoline

Compound 223

In a similar manner to Example 4, Compound 223 was obtained using anhydrous 2-hydroxymethyl-5-nitrophenylboronic acid.
$^1$H NMR (270 MHz, CDCl$_3$) δ (ppm) 1.32 (d, J=6.5 Hz, 6H), 3.88 (s, 3H), 4.51-4.61 (m, 3H), 5.15 (d, J=8.6 Hz, 1H), 7.00 (s, 1H), 7.43 (s, 1H), 7.82 (d, J=8.6 Hz, 1H), 8.10 (d, J=2.7 Hz, 1H), 8.28 (dd, J=8.6, 2.7 Hz, 1H), 8.81 (s, 1H).
APCI m/z (M+H)$^+$ 369.

Example 224

6-[5-Amino-2-(hydroxymethyl)phenyl]-2-isopropylamino-7-methoxyquinazoline

Compound 224

In a similar manner to Example 50, Compound 224 was obtained using Compound 223.
$^1$H NMR (300 MHz, CDCl$_3$) δ (ppm) 1.30 (d, J=6.6 Hz, 6H), 3.87 (s, 3H), 4.24-4.33 (m, 3H), 5.11 (d, J=8.1 Hz, 1H), 6.55 (d, J=7.4 Hz, 1H), 6.73 (dd, J=8.1, 2.4 Hz, 1H), 6.97 (s, 1H), 7.33 (d, J=8.1 Hz, 1H), 7.41 (s, 1H), 8.76 (s, 1H).
APCI m/z (M+H)$^+$ 339.

Example 225

6-[5-Acetylamino-2-(hydroxymethyl)phenyl]-2-isopropylamino-7-methoxyquinazoline

Compound 225

In a similar manner to Example 52, Compound 225 was obtained using Compound 224.
$^1$H NMR (270 MHz, CDCl$_3$) δ (ppm) 1.31 (d, J=6.5 Hz, 6H), 2.18 (s, 3H), 3.87 (s, 3H), 4.27-4.42 (m, 3H), 5.09 (d, J=8.4 Hz, 1H), 6.98 (s, 1H), 7.20 (br s, 1H), 7.42 (s, 2H), 7.53 (s, 2H), 8.78 (s, 1H).
APCI m/z (M+H)$^+$ 381.

Example 226

6-(5-Acetylamino-2-carboxyphenyl)-2-isopropylamino-7-methoxyquinazoline

Compound 226

Compound 225 (150 mg, 0.49 mmol) was dissolved in DMF (2 mL) and the solution was added with manganese dioxide (6 mg, 0.05 mmol), followed by stirring at 60° C. overnight. After filtering off using Celite, the reaction mixture was extracted with ethyl acetate. The organic layer was washed with water and saturated brine, and dried over anhydrous magnesium sulfate, then the solvent was evaporated under reduced pressure to obtain 6-(5-acetylamino-2-formylphenyl)-2-isopropylamino-7-methoxyquinazoline. In a similar manner to Example 185, Compound 226 was obtained using the above-obtained 6-(5-acetylamino-2-formylphenyl)-2-isopropylamino-7-methoxyquinazoline.
$^1$H NMR (300 MHz, DMSO-d$_6$) δ (ppm) 1.28 (d, J=6.0 Hz, 6H), 2.08 (s, 3H), 3.82 (s, 3H), 4.21-4.32 (m, 1H), 7.62-7.65 (m, 2H), 7.64 (s, 1H), 7.75 (br s, 1H), 7.84 (s, 1H), 7.87 (s, 1H), 9.19 (br s, 1H), 10.3 (s, 1H).
APCI m/z (M+H)$^+$ 395.

Example 227

6-(5-Acetylamino-2-cyanophenyl)-2-isopropylamino-7-methoxyquinazoline

Compound 227

In a similar manner to Example 226, 6-(5-amino-2-formylphenyl)-2-isopropylamino-7-methoxyquinazoline was obtained using Compound 224. In a similar manner to Example 58, Example 183 and Example 52, Compound 227 was obtained using the above-obtained 6-(5-amino-2-formylphenyl)-2-isopropylamino-7-methoxyquinazoline.
$^1$H NMR (300 MHz, CDCl$_3$) δ (ppm) 1.31 (d, J=6.6 Hz, 6H), 2.22 (s, 3H), 3.93 (s, 3H), 4.28-4.35 (m, 1H), 5.13 (d, J=7.5 Hz, 1H), 7.01 (s, 1H), 7.35 (s, 1H), 7.52 (s, 1H), 7.63-7.67 (m, 3H), 8.81 (s, 1H).
APCI m/z (M+H)$^+$ 376.

Example 228

6-{2-Hydroxymethyl-5-[(1H-pyrrol-2-yl)carbonylamino]phenyl}-2-isopropylamino-7-methoxyquinazoline Compound 228

In a similar manner to Example 209, Compound 228 was obtained using Compound 224 and 1H-pyrrole-2-carboxylic acid.
$^1$H NMR (300 MHz, CDCl$_3$) δ (ppm) 1.31 (d, J=6.3 Hz, 6H), 3.88 (s, 3H), 4.27-4.35 (m, 1H), 4.43 (d, J=11.1 Hz, 1H), 5.14 (d, J=7.5 Hz, 1H), 6.28-6.31 (m, 1H), 6.68-6.70 (m, 1H), 6.98-7.00 (m, 1H), 6.99 (s, 1H), 7.46 (s, 1H), 7.51 (d, J=2.4 Hz, 1H), 7.57 (t, J=8.4 Hz, 1H), 7.61 (s, 1H), 7.66 (dd, J=8.4, 2.4 Hz, 1H), 8.79 (s, 1H), 9.41 (br s, 1H).
APCI m/z (M+H)$^+$ 432.

Example 229

6-(5-Amino-2-methylphenyl)-2-isopropylamino-7-methoxyquinazoline

Compound 229

In a similar manner to Example 4, Compound 229 was obtained using 4-methyl-3-(4,4,5,5-tetramethyl-1,3,2-dioxaboran-2-yl)aniline.
$^1$H NMR (270 MHz, CDCl$_3$) δ (ppm) 1.31 (d, J=6.5 Hz, 6H), 1.99 (s, 3H), 3.56 (br s, 1H), 3.88 (s, 3H), 4.25-4.32 (m, 1H), 5.06 (br s, 1H), 6.58 (d, J=2.7 Hz, 1H), 6.65 (dd, J=7.8, 2.7 Hz, 1H), 6.96 (s, 1H), 7.04 (d, J=7.8 Hz, 1H), 7.37 (s, 1H), 8.78 (s, 1H).
ESI m/z (M+H)$^+$ 323.

Example 230

6-(5-Acetylamino-2-methylphenyl)-2-isopropylamino-7-methoxyquinazoline

Compound 230

In a similar manner to Example 52, Compound 230 was obtained using Compound 229.
$^1$H NMR (270 MHz, CDCl$_3$) δ (ppm) 1.31 (d, J=6.5 Hz, 6H), 2.07 (s, 3H), 2.16 (s, 3H), 3.87 (s, 3H), 4.28-4.35 (m, 1H), 5.07 (br s, 1H), 6.96 (s, 1H), 7.10 (br s, 1H), 7.20 (d, J=8.1 Hz, 1H), 7.30 (d, J=2.4 Hz, 1H), 7.38 (s, 1H), 7.45 (dd, J=8.1 Hz, 2.4 Hz, 1H), 8.78 (s, 1H).
ESI m/z (M+H)$^+$ 365.

Example 231

2-Isopropylamino-7-methoxy-6-{2-methyl-5-[(2-morpholinopyridin-4-yl)carbonylamino]phenyl}quinazoline Compound 231

In a similar manner to Example 209, Compound 231 was obtained using Compound 229 and Compound A5.
$^1$H NMR (270 MHz, CDCl$_3$) δ (ppm) 1.32 (d, J=6.2 Hz, 6H), 2.11 (s, 3H), 3.56-3.60 (m, 4H), 3.80-3.84 (m, 4H), 3.88 (s, 3H), 4.28-4.36 (m, 1H), 5.32 (br s, 1H), 6.89 (dd, J=5.1, 1.4 Hz, 1H), 6.99 (s, 1H), 7.11 (s, 1H), 7.27 (d, J=8.1 Hz, 1H), 7.42 (s, 1H), 7.46 (d, J=2.2 Hz, 1H), 7.59 (dd, J=8.1, 2.2 Hz, 1H), 7.76 (br s, 1H), 8.30 (dd, J=5.1, 0.8 Hz, 1H), 8.80 (s, 1H).
APCI m/z (M+H)$^+$ 513.

Example 232

2-Isopropylamino-7-methoxy-6-{2-methyl-5-[(1H-pyrrol-2-yl)carbonylamino]phenyl}quinazoline Compound 232

In a similar manner to Example 209, Compound 232 was obtained using Compound 229.
$^1$H NMR (300 MHz, CDCl$_3$) δ (ppm) 1.31 (d, J=6.3 Hz, 6H), 2.09 (s, 3H), 3.88 (s, 3H), 4.28-4.35 (m, 1H), 5.09 (d, J=8.1 Hz, 1H), 6.29 (m, 1H), 6.66 (m, 1H), 6.97 (s, 2H), 7.25 (d, J=8.1 Hz, 1H), 7.41 (s, 1H), 7.42 (d, J=2.4 Hz, 1H), 7.54 (br s, 1H), 7.57 (dd, J=8.1, 2.4 Hz, 1H), 8.79 (s, 1H), 9.44 (br s, 1H).
APCI m/z (M+H)$^+$ 416.

Example 233

6-(5-Acetylamino-2-fluorophenyl)-2-isopropylamino-7-methoxyquinazoline

Compound 233

In a similar manner to Example 4, Example 50 and Example 52, Compound 233 was obtained using 2-fluoro-5-nitrophenylboronic acid.
$^1$H NMR (300 MHz, CDCl$_3$) δ (ppm) 1.29 (d, J=4.5 Hz, 6H), 2.18 (s, 3H), 3.91 (s, 3H), 4.29-4.33 (m, 1H), 5.08 (br s, 1H), 6.98 (s, 1H), 7.06-7.14 8 m, 2H), 7.47-7.51 8 m, 2H), 7.52 (s, 1H), 8.80 (s, 1H).
APCI m/z (M+H)$^+$ 369.

Example 234

6-(5-Acetylamino-2-methoxyphenyl)-2-isopropylamino-7-methoxyquinazoline

Compound 234

In a similar manner to Example 4, Example 50 and Example 52, Compound 234 was obtained using Compound A7 and 2-methoxy-5-nitrobromobenzene.
$^1$H NMR (270 MHz, CDCl$_3$) δ (ppm) 1.31 (d, J=6.5 Hz, 6H), 2.05 (s, 3H), 3.74 (s, 3H), 3.88 (s, 3H), 4.26-4.34 (m, 1H), 6.93 (d, J=8.7 Hz, 1H), 6.95 (s, 1H), 7.09 (br s, 1H), 7.29 (d, J=2.7 Hz, 1H), 7.41 (s, 1H), 7.54 (dd, J=8.7, 2.7 Hz, 1H), 8.77 (s, 1H).
ESI m/z (M+H)$^+$ 381.

Example 235

6-(3-Acetylamino-2-methylphenyl)-2-isopropylamino-7-methoxyquinazoline

Compound 235

In a similar manner to Example 4 and Example 52, Compound 235 was obtained using 2-methyl-3-(4,4,5,5-tetramethyl-1,3,2-dioxaboran-2-yl)aniline.
$^1$H NMR (300 MHz, CDCl$_3$) δ (ppm) 1.32 (d, J=6.6 Hz, 6H), 1.96 (s, 3H), 2.25 (s, 3H), 3.87 (s, 3H), 4.29-4.34 (m, 1H), 5.30 (br s, 1H), 6.99 (s, 1H), 7.01 (br s, 1H), 7.05 (d, J=7.5 Hz, 1H), 7.24 (t, J=7.5 Hz, 1H), 7.41 (s, 1H), 7.80 (d, J=7.5 Hz, 1H), 8.82 (s, 1H).

ESI m/z (M+H)$^+$ 365.

Example 236

6-(5-Cyclopropylcarbamoyl-2-methylphenyl)-2-isopropylamino-7-methoxyquinazoline

Compound 236

In a similar manner to Example 4, Compound 236 was obtained using N-cyclopropyl-4-methyl-3-(4,4,5,5-tetramethyl-1,3,2-dioxaboran-2-yl)benzamide (WO03/093248).

$^1$H NMR (270 MHz, CDCl$_3$) δ (ppm) 0.56-0.64 (m, 2H), 0.81-0.90 (m, 2H), 1.31 (d, J=6.5 Hz, 6H), 2.15 (s, 3H), 2.83-2.95 (m, 1H), 3.86 (s, 3H), 4.24-4.38 (m, 1H), 5.08 (d, J=8.1 Hz, 1H), 6.20 (br s, 1H), 6.97 (s, 1H), 7.31 (d, J=7.8 Hz, 1H), 7.39 (s, 1H), 7.55 (d, J=2.2 Hz, 1H), 7.68 (dd, J=7.8, 2.2 Hz, 1H), 8.80 (s, 1H).

ESI m/z (M+H)$^+$ 391.

m.p. 122-125° C.

Example 237

6-(2-Formylphenyl)-7-methoxy-2-[1-(methylsulfonyl)piperidin-4-ylamino]quinazoline

Compound 237

In a similar manner to Example 4, Compound 237 was obtained using 6-bromo-7-methoxy-2-[1-(methylsulfonyl)piperidin-4-ylamino]quinazoline obtained in Example 164 and 2-formylphenylboronic acid.

$^1$H NMR (270 MHz, CDCl$_3$) δ (ppm) 1.65-1.82 (m, 2H), 2.20-2.35 (m, 2H), 2.83 (s, 3H), 2.95-3.10 (m, 2H), 3.71-3.85 (m, 2H), 3.86 (s, 3H), 4.18 (br s, 1H), 5.23 (br s, 1H), 6.98 (s, 1H), 7.37-7.45 (m, 1H), 7.50-7.60 (m, 1H), 7.56 (s, 1H), 7.62-7.71 (m, 1H), 7.78-8.06 (m, 1H), 8.86 (s, 1H), 9.80 (s, 1H).

APCI m/z (M+H)$^+$ 441.

Example 238

6-(3-Acetylaminophenyl)-7-methoxy-2-[1-(methylsulfonyl)piperidin-4-ylamino]quinazoline

Compound 238

In a similar manner to Example 4, Compound 238 was obtained using 6-bromo-7-methoxy-2-[1-(methylsulfonyl)piperidin-4-ylamino]quinazoline obtained in Example 164 and 3-acetylaminophenylboronic acid.

$^1$H NMR (300 MHz, DMSO-d$_6$) δ (ppm) 1.52-1.71 (m, 2H), 1.97-2.08 (m, 2H), 2.05 (s, 3H), 2.90 (s, 3H), 2.87-2.98 (m, 2H), 3.51-3.63 (m, 2H), 3.89 (s, 3H), 3.97-4.12 (m, 1H), 6.93 (s, 1H), 7.12-7.19 (m, 1H), 7.29-7.37 (m, 1H), 7.33-7.42 (m, 1H), 7.55-7.61 (m, 1H), 7.66 (s, 1H), 7.69-7.72 (m, 1H), 8.98 (s, 1H), 9.97 (s, 1H).

APCI m/z (M+H)$^+$ 470.

Example 239

6-(2-Acetylaminophenyl)-7-methoxy-2-[1-(methylsulfonyl)piperidin-4-ylamino]quinazoline

Compound 239

In a similar manner to Example 4, Compound 239 was obtained using 6-bromo-7-methoxy-2-[1-(methylsulfonyl)piperidin-4-ylamino]quinazoline obtained in Example 164 and 2-acetylaminophenylboronic acid.

$^1$H NMR (300 MHz, DMSO-d$_6$) δ (ppm) 1.53-1.70 (m, 2H), 1.84 (s, 3H), 1.98-2.10 (m, 2H), 2.90 (s, 3H), 2.89-3.00 (m, 2H), 3.51-3.62 (m, 2H), 3.80 (s, 3H), 3.99-4.13 (m, 1H), 6.90 (s, 1H), 7.14-7.29 (m, 2H), 7.29-7.40 (m, 2H), 7.56 (s, 1H), 7.59-7.65 (m, 1H), 8.76 (s, 1H), 8.96 (s, 1H).

APCI m/z (M+H)$^+$ 470.

Example 240

6-(3-Hydroxyphenyl)-7-methoxy-2-[1-(methylsulfonyl)piperidin-4-ylamino]quinazoline

Compound 240

In a similar manner to Example 4 and Example 186, Compound 240 was obtained using 6-bromo-7-methoxy-2-[1-(methylsulfonyl)piperidin-4-ylamino]quinazoline obtained in Example 164 and 3-(benzyloxy)phenylboronic acid.

$^1$H NMR (300 MHz, DMSO-d$_6$) δ (ppm) 1.52-1.70 (m, 2H), 1.96-2.11 (m, 2H), 2.89 (s, 3H), 2.90-3.00 (m, 2H), 3.50-3.62 (m, 2H), 3.89 (s, 3H), 4.06 (br s, 1H), 6.71-6.78 (m, 1H), 6.88-6.95 (m, 3H), 7.21 (t, J=8.1 Hz, 1H), 7.31-7.42 (m, 1H), 7.66 (s, 1H), 8.97 (s, 1H), 9.41 (s, 1H).

APCI m/z (M+H)$^+$ 429.

Example 241

6-(2-Hydroxyphenyl)-7-methoxy-2-[1-(methylsulfonyl)piperidin-4-ylamino]quinazoline

Compound 241

In a similar manner to Example 4 and Example 186, Compound 241 was obtained using 6-bromo-7-methoxy-2-[1-(methylsulfonyl)piperidin-4-ylamino]quinazoline obtained in Example 164 and 2-(benzyloxy)phenylboronic acid.

$^1$H NMR (300 MHz, DMSO-d$_6$) δ (ppm) 1.52-1.70 (m, 2H), 1.97-2.10 (m, 2H), 2.89 (s, 3H), 2.87-3.00 (m, 2H), 3.50-3.62 (m, 2H), 3.82 (s, 3H), 3.96-4.12 (m, 1H), 6.79-6.92 (m, 3H), 7.08-7.20 (m, 2H), 7.23-7.34 (m, 1H), 7.54 (s, 1H), 8.93 (s, 1H), 9.19 (s, 1H).

APCI m/z (M+H)$^+$ 429.

Example 242

6-(2-Carboxyphenyl)-7-methoxy-2-[1-(methylsulfonyl)piperidin-4-ylamino]quinazoline

Compound 242

In a similar manner to Example 4 and Example 185, Compound 242 was obtained using 6-bromo-7-methoxy-2-[1-(methylsulfonyl)piperidin-4-ylamino]quinazoline obtained in Example 164 and 2-formylphenylboronic acid.

¹H NMR (300 MHz, DMSO-d₆) δ (ppm) 1.52-1.70 (m, 2H), 1.98-2.10 (m, 2H), 2.90 (s, 3H), 2.88-2.97 (m, 2H), 3.51-3.61 (m, 2H), 3.76 (s, 3H), 3.97-4.12 (m, 1H), 6.82 (s, 1H), 7.29-7.40 (m, 1H), 7.32-7.38 (m, 1H), 7.41-7.49 (m, 1H), 7.54-7.62 (m, 1H), 7.59 (s, 1H), 7.75-7.83 (m, 1H), 8.95 (s, 1H).
ESI m/z (M+H)⁺ 457.

Example 243

6-(3-Acetylaminophenyl)-7-methoxy-2-(4-tetrahydropyranylamino)quinazoline

Compound 243

In a similar manner to Example 164, Compound 243 was obtained using 4-aminotetrahydropyrane and 3-acetylaminophenylboronic acid.
¹H NMR (300 MHz, DMSO-d₆) δ (ppm) 1.48-1.65 (m, 2H), 1.83-1.94 (m, 2H), 2.05 (s, 3H), 3.37-3.50 (m, 2H), 3.89 (s, 3H), 3.85-3.96 (m, 2H), 4.05-4.20 (m, 1H), 6.94 (s, 1H), 7.12-7.20 (m, 1H), 7.29-7.39 (m, 2H), 7.55-7.61 (m, 1H), 7.65 (s, 1H), 7.68-7.73 (m, 1H), 8.97 (s, 1H), 9.98 (s, 1H).
APCI m/z (M+H)⁺ 393.

Example 244

7-Hydroxy-6-(3-hydroxyphenyl)-2-(isopropylamino)quinazoline

Compound 244

In a similar manner to Example 19, Compound 244 was obtained using Compound 196.
¹H NMR (270 MHz, CDCl₃) δ (ppm) 1.27 (d, J=6.2 Hz, 6H), 4.25 (m, 1H), 6.77 (dd, J=7.8, 1.4 Hz, 1H), 6.97 (dd, J=7.8, 1.4 Hz, 1H), 6.98 (s, 1H), 7.14 (s, 1H), 7.22 (t, J=7.8 Hz, 1H), 7.86 (s, 1H), 9.13 (s, 1H).
APCI m/z (M+H)⁺ 296.

Example 245

7-Hydroxy-2-isopropylamino-6-(2-methylphenyl)quinazoline

Compound 245

In a similar manner to Example 19, Compound 245 was obtained using Compound 191.
¹H NMR (300 MHz, CDCl₃) δ (ppm) 1.36 (d, J=6.6 Hz, 6H), 2.18 (s, 3H), 4.39-4.45 (m, 1H), 7.20 (s, 1H), 7.29-7.37 (m, 2H), 7.59 (s, 1H), 7.72 (s, 1H), 8.53 (br s, 1H), 8.96 (s, 1H).
APCI m/z (M+H)⁺ 294.

Example 246

7-Hydroxy-2-isopropylamino-6-(2-isopropylphenyl)quinazoline

Compound 246

In a similar manner to Example 4 and Example 19, Compound 246 was obtained using 2-isopropylphenylboronic acid.
¹H NMR (270 MHz, CDCl₃) δ (ppm) 1.09 (d, J=7.0 Hz, 3H), 1.20 (d, J=6.8 Hz, 3H), 1.28 (d, J=6.5 Hz, 6H), 2.74-2.89 (m, 1H), 4.23-4.40 (m, 1H), 5.10-5.25 (m, 1H), 7.07 (s, 1H), 7.18-7.24 (m, 1H), 7.26-7.34 (m, 1H), 7.41 (s, 1H), 7.42-7.48 (m, 2H), 8.78 (s, 1H).
APCI m/z (M+H)⁺ 322.

Example 247

7-Hydroxy-6-(3-hydroxyphenyl)-2-[1-(methylsulfonyl)piperidin-4-ylamino]quinazoline

Compound 247

In a similar manner to Example 19, Compound 247 was obtained using Compound 240.
¹H NMR (300 MHz, DMSO-d₆) δ (ppm) 1.51-1.68 (m, 2H), 1.95-2.06 (m, 2H), 2.89 (s, 3H), 2.86-2.99 (m, 2H), 3.48-3.60 (m, 2H), 3.92-4.08 (m, 1H), 6.70-6.76 (m, 1H), 6.83 (s, 1H), 6.93-7.02 (m, 2H), 7.20 (t, J=7.9 Hz, 1H), 7.19-7.25 (m, 1H), 7.64 (s, 1H), 8.90 (s, 1H).
APCI m/z (M+H)⁺ 415.
m.p. 285-290° C.

Example 248

6-(3-Acetylaminophenyl)-2-amino-7-methoxyquinazoline

Compound 248

In a similar manner to Example 4, Compound 248 was obtained using Compound A2 and 3-acetylaminophenylboronic acid.
¹H NMR (270 MHz, CDCl₃) δ (ppm) 2.20 (s, 3H), 3.93 (s, 3H), 5.15 (br s, 2H), 6.98 (s, 1H), 7.23 (s, 1H), 7.27 (d, J=7.6 Hz, 1H), 7.39 (t, J=7.6 Hz, 1H), 7.52 (d, J=7.6 Hz, 1H), 7.60 (s, 1H), 7.68 (br s, 1H), 8.86 (s, 1H).
APCI m/z (M+H)⁺ 309.

Example 249

6-(5-Acetylamino-2-methylphenyl)-2-amino-7-methoxyquinazoline

Compound 249

In a similar manner to Example 4 and Example 52, Compound 249 was obtained using Compound A2 and 4-methyl-3-(4,4,5,5-tetramethyl-1,3,2-dioxaboran-2-yl)aniline.
¹H NMR (300 MHz, CDCl₃) δ (ppm) 2.01 (s, 3H), 2.08 (s, 3H), 3.87 (s, 3H), 5.31 (br s, 2H), 6.97 (s, 1H), 7.11-7.15 (m, 1H), 7.21 (d, J=8.1 Hz, 1H), 7.33 (d, J=2.4 Hz, 1H), 7.44 (dd, J=8.1, 2.4 hz, 1H), 7.45 (s, 1H), 8.85 (s, 1H).
APCI m/z (M+H)⁺ 323.

Example 250

6-(5-Acetylamino-2-methylphenyl)-7-methoxy-2-(methylamino)quinazoline

Compound 250

In a similar manner to Reference Example 4, 6-bromo-7-methoxy-2-methylaminoquinazoline was obtained using methylamine (2 mol/L THF solution). In a similar manner to Example 4 and Example 52, Compound 250 was obtained using the above-obtained 6-bromo-7-methoxy-2-methylaminoquinazoline and 4-methyl-3-(4,4,5,5-tetramethyl-1,3,2-dioxaboran-2-yl)aniline.

$^1$H NMR (300 MHz, CDCl$_3$) δ (ppm) 2.07 (s, 3H), 2.16 (s, 3H), 3.13 (d, J=5.1 Hz, 3H), 3.87 (s, 3H), 5.26 (d, J=5.1 Hz, 1H), 7.02 (s, 1H), 7.16 (br s, 1H), 7.21 (d, J=8.1 Hz, 1H), 7.32 (d, J=2.4 Hz, 1H), 7.40 (s, 1H), 7.45 (dd, J=8.1, 2.4 Hz, 1H), 8.79 (s, 1H).

APCI m/z (M+H)$^+$ 337.

Example 251

7-Methoxy-2-methylamino-6-{2-methyl-5-[(1H-pyrrol-2-yl)carbonylamino]phenyl}quinazoline Compound 251

In a similar manner to Example 4 and Example 209, Compound 251 was obtained using 6-bromo-7-methoxy-2-methylaminoquinazoline obtained in Example 250 and 4-methyl-3-(4,4,5,5-tetramethyl-1,3,2-dioxaboran-2-yl)aniline.

$^1$H NMR (300 MHz, CDCl$_3$) δ (ppm) 2.09 (s, 3H), 3.14 (d, J=5.1 Hz, 3H), 3.89 (s, 3H), 3.30 (d, J=5.1 Hz, 1H), 6.27-6.30 (m, 1H), 6.66-6.68 (m, 1H), 6.96-6.99 (m, 1H), 7.03 (s, 1H), 7.44 (s, 2H), 7.55-7.61 (m, 2H), 8.02 (s, 1H), 8.80 (s, 1H), 9.52 (br s, 1H).

APCI m/z (M+H)$^+$ 388.

Example 252

6-{2-Hydroxy-5-[(1H-pyrrol-2-yl)carbonylamino]phenyl}-2-isopropylamino-7-methoxyquinazoline Compound 252

In a similar manner to Example 186 and Example 209, Compound 252 was obtained using 6-(5-amino-2-methoxyphenyl)-2-isopropylamino-7-methoxyquinazoline obtained in Example 234.

$^1$H NMR (300 MHz, CDCl$_3$) δ (ppm) 1.31 (d, J=6.6 Hz, 6H), 3.99 (s, 3H), 4.27-4.34 (m, 1H), 5.17 (d, J=8.4 Hz, 1H), 6.28-6.31 (m, 1H), 6.68 (s, 1H), 6.96-6.99 (m, 1H), 7.03 (d, J=8.7 Hz, 1H), 7.05 (s, 1H), 7.46 (dd, J=8.7, 2.7 Hz, 1H), 7.51 (br s, 1H), 7.55 (d, J=2.7 Hz, 1H), 7.61 (s, 1H), 8.83 (s, 1H), 9.42 (br s, 1H).

APCI m/z (M+H)$^+$ 418.

Example 253

2-Isopropylamino-6-{2-methyl-5-[(1H-pyrrol-2-yl)carbonylamino]phenyl}quinazoline Compound 253

In a similar manner to Example 4 and Example 209, Compound 253 was obtained using Compound A10 and 4-methyl-3-(4,4,5,5-tetramethyl-1,3,2-dioxaboran-2-yl)aniline.

$^1$H NMR (300 MHz, CDCl$_3$) δ (ppm) 1.32 (d, J=6.3 Hz, 6H), 2.27 (s, 3H), 4.30-4.37 (m, 1H), 5.21 (d, J=6.9 Hz, 1H), 6.28-6.31 (m, 1H), 6.69 (br s, 1H), 6.97-6.99 (m, 1H), 7.52 (s, 1H), 7.54-7.69 (m, 6H), 8.97 (s, 1H), 9.48 (br s, 1H).

APCI m/z (M+H)$^+$ 386.

Example 254

6-(5-Acetylamino-2-methylphenyl)-2-(isopropylamino)quinazoline

Compound 254

In a similar manner to Example 52, Compound 254 was obtained using 6-(5-amino-2-methylphenyl)-2-(isopropylamino)quinazoline obtained in Example 253.

$^1$H NMR (300 MHz, CDCl$_3$) δ (ppm) 1.31 (d, J=6.3 Hz, 6H), 2.18 (s, 3H), 2.25 (s, 3H), 4.29-4.39 (m, 1H), 5.14 (d, J=8.1 Hz, 1H), 7.16 (br s, 1H), 7.24 (d, J=8.4 Hz, 1H), 7.41 (s, 1H), 7.43 (d, J=9.6 Hz, 1H), 7.57 (d, J=2.1 Hz, 1H), 7.59 (d, J=9.6 Hz, 1H), 7.64 (dd, J=8.4, 2.1 Hz, 1H), 8.96 (s, 1H).

APCI m/z (M+H)$^+$ 335.

Example 255

6-{2-Hydroxymethyl-5-[(1H-pyrrol-2-yl)carbonylamino]phenyl}-2-(isopropylamino)quinazoline Compound 255

In a similar manner to Example 4 and Example 209, Compound 255 was obtained using Compound A10 and anhydrous (5-amino-2-hydroxymethyl)phenylboronic acid.

$^1$H NMR (270 MHz, CDCl$_3$) δ (ppm) 1.31 (d, J=6.2 Hz, 6H), 4.28-4.37 (m, 1H), 4.60 (s, 2H), 5.20 (d, J=8.1 Hz, 1H), 6.28-6.30 (m, 1H), 6.72-6.73 (m, 1H), 6.98-7.00 (m, 1H), 7.53-7.73 (m, 7H), 8.85 (s, 1H), 9.51 (br s, 1H).

APCI m/z (M+H)$^+$ 402.

Example 256

2-Isopropylamino-6-{2-methyl-5-[(2-morpholinopyridin-4-yl)carbonylamino]phenyl}quinazoline Compound 256

In a similar manner to Example 4,6-(5-amino-2-methylphenyl)-2-(isopropylamino)quinazoline was obtained using Compound A10 and 4-methyl-3-(4,4,5,5-tetramethyl-1,3,2-dioxaboran-2-yl)aniline. In a similar manner to Example 209, Compound 256 was obtained using the above-obtained 6-(5-amino-2-methylphenyl)-2-(isopropylamino)quinazoline and Compound A5.

$^1$H NMR (270 MHz, CDCl$_3$) δ (ppm) 1.29 (d, J=6.5 Hz, 6H), 2.29 (s, 3H), 3.57-3.61 (m, 4H), 3.81-3.85 (m, 4H), 4.29-4.37 (m, 1H), 5.15 (d, J=8.1 Hz, 1H), 6.91 (d, J=5.1 Hz, 1H), 7.13 (s, 1H), 7.30 (d, J=8.9 Hz, 1H), 7.55-7.72 (m, 4H), 7.57 (d, J=8.9 Hz, 1H), 7.81 (br s, 1H), 8.31 (d, J=5.1 Hz, 1H), 8.97 (s, 1H).

APCI m/z (M+H)$^+$ 483.

Example 257

2-Isopropylamino-6-{3-[(2-morpholinopyridin-4-yl)carbonylamino]phenyl}quinazoline Compound 257

In a similar manner to Example 4,6-(3-aminophenyl)-2-(isopropylamino)quinazoline was obtained using Compound A10 and 3-aminophenylboronic acid. In a similar manner to Example 209, Compound 257 was obtained using the above-obtained 6-(3-aminophenyl)-2-(isopropylamino)quinazoline and Compound A5.

$^1$H NMR (270 MHz, CDCl$_3$) δ (ppm) 1.32 (d, J=6.5 Hz, 6H), 3.59-3.63 (m, 4H), 3.83-3.86 (m, 4H), 4.29-4.37 (m, 1H), 5.15 (br s, 1H), 6.95 (d, J=4.9 Hz, 1H), 7.16 (s, 1H), 7.47-7.54 (m, 3H), 7.65 (d, J=8.1 Hz, 1H), 7.87 (s, 2H), 7.96 (d, J=8.1 Hz, 1H), 8.04 (br s, 1H), 8.34 (d, J=4.9 Hz, 1H), 9.01 (s, 1H).

APCI m/z (M+H)$^+$ 469.

Example 258

2-Isopropylamino-6-{3-[(1H-pyrrol-2-yl)carbonylamino]phenyl}quinazoline

Compound 258

In a similar manner to Example 209, Compound 258 was obtained using 6-(3-aminophenyl)-2-(isopropylamino)quinazoline obtained in Example 257.

$^1$H NMR (270 MHz, DMSO-d$_6$) δ (ppm) 1.22 (d, J=6.5 Hz, 6H), 4.18-4.25 (m, 1H), 6.18-6.19 (m, 1H), 6.98-6.99 (m, 1H), 7.09-7.10 (m, 1H), 7.33 (d, J=7.3 Hz, 1H), 7.43-7.45 (m, 2H), 7.56 (d, J=7.3 Hz, 1H), 7.78-7.80 (m, 1H), 7.97-8.01 (m, 1H), 8.05 (br s, 1H), 8.11 (br s, 1H), 9.85 (br s, 1H).

APCI m/z (M+H)$^+$ 372.

Example 259

2-Isopropylamino-6-{2-methyl-5-[(4-pyridyl)carbonylamino]phenyl}quinazoline

Compound 259

In a similar manner to Example 209, Compound 259 was obtained using 6-(5-amino-2-methylphenyl)-2-(isopropylamino)quinazoline obtained in Example 253 and isonicotinic acid.

$^1$H NMR (300 MHz, CDCl$_3$) δ (ppm) 1.31 (d, J=6.3 Hz, 6H), 2.29 (s, 3H), 4.28-4.39 (m, 1H), 5.16 (d, J=6.7 Hz, 1H), 7.31 (d, J=8.1 Hz, 1H), 7.59-7.68 (m, 5H), 7.71 (d, J=5.4 Hz, 2H), 7.96 (br s, 1H), 8.79 (d, J=5.4 Hz, 2H), 8.97 (s, 1H).

APCI m/z (M+H)$^+$ 398.

Example 260

2-Isopropylamino-6-{2-methyl-5-[(pyridin-1-oxide-4-yl)carbonylamino]phenyl}quinazoline Compound 260

In a similar manner to Example 209, Compound 260 was obtained using 6-(5-amino-2-methylphenyl)-2-(isopropylamino)quinazoline obtained in Example 253 and isonicotinic acid N-oxide.

$^1$H NMR (300 MHz, CDCl$_3$) δ (ppm) 1.32 (d, J=6.5 Hz, 6H), 2.29 (s, 3H), 4.29-4.36 (m, 1H), 5.16 (d, J=8.4 Hz, 1H), 7.31 (d, J=8.7 Hz, 1H), 7.54-7.67 (m, 4H), 7.61 (d, J=8.7 Hz, 1H), 7.77 (d, J=7.5 Hz, 2H), 8.07 (br s, 1H), 8.24 (d, J=7.5 Hz, 2H), 8.97 (s, 1H).

APCI m/z (M+H)$^+$ 414.

Example 261

2-Isopropylamino-6-[2-methyl-5-(pyrazinylcarbonylamino)phenyl]quinazoline

Compound 261

In a similar manner to Example 209, Compound 261 was obtained using 6-(5-amino-2-methylphenyl)-2-(isopropylamino)quinazoline obtained in Example 253 and 2-pyrazinecarboxylic acid.

$^1$H NMR (300 MHz, CDCl$_3$) δ (ppm) 1.32 (d, J=6.5 Hz, 6H), 2.30 (s, 3H), 4.28-4.38 (m, 1H), 5.15 (d, J=7.5 Hz, 1H), 7.33 (d, J=9.3 Hz, 1H), 7.60-7.73 (m, 5H), 8.58 (dd, J=7.4, 1.2 Hz, 1H), 8.81 (d, J=7.4 Hz, 1H), 8.98 (s, 1H), 9.51 (d, J=1.2 Hz, 1H), 9.69 (br s, 1H).

APCI m/z (M+H)$^+$ 399.

Example 262

2-Isopropylamino-6-{2-methyl-5-(2-pyridylcarbonylamino)phenyl}quinazoline

Compound 262

In a similar manner to Example 209, Compound 262 was obtained using 6-(5-amino-2-methylphenyl)-2-(isopropylamino)quinazoline obtained in Example 253 and picolinic acid.

$^1$H NMR (300 MHz, CDCl$_3$) δ (ppm) 1.32 (d, J=6.3 Hz, 6H), 2.29 (s, 3H), 4.31-4.38 (m, 1H), 5.14 (d, J=8.7 Hz, 1H), 7.31 (d, J=8.4 Hz, 1H), 7.33 (s, 1H), 7.48 (ddd, J=7.8, 4.5, 1.8 Hz, 1H), 7.62 (d, J=9.0 Hz, 1H), 7.63 (s, 1H), 7.69 (d, J=9.0 Hz, 1H), 7.70 (d, J=8.4 Hz, 1H), 7.74 (s, 1H), 7.91 (dt, J=7.8, 1.8 Hz, 1H), 8.30 (ddd, J=7.8, 1.8, 0.90 Hz, 1H), 8.61 (ddd, J=4.5, 1.8, 0.9 Hz, 1H), 8.98 (s, 1H).

APCI m/z (M+H)$^+$ 398.

Example 263

2-Isopropylamino-6-{2-methyl-5-[(pyridine-1-oxide-3-yl)carbonylamino]phenyl}quinazoline Compound 263

In a similar manner to Example 209, Compound 263 was obtained using 6-(5-amino-2-methylphenyl)-2-(isopropylamino)quinazoline obtained in Example 253 and nicotinic acid N-oxide.

$^1$H NMR (300 MHz, CDCl$_3$) δ (ppm) 1.31 (d, J=6.6 Hz, 6H), 2.29 (s, 3H), 4.31-4.38 (m, 1H), 5.29 (br s, 1H), 7.32 (d, J=8.1 Hz, 1H), 7.38 (d, J=6.3 Hz, 1H), 7.60-7.77 (m, 5H), 7.89 (d, J=8.1 Hz, 1H), 8.24 (d, J=6.3 Hz, 1H), 8.98 (s, 1H), 9.09 (s, 1H), 9.43 (br s, 1H).

APCI m/z (M+H)$^+$ 414.

Example 264

6-(5-Cyclopropylcarbonylamino-2-methylphenyl)-2-(isopropylamino)quinazoline

Compound 264

In a similar manner to Example 209, Compound 264 was obtained using 6-(5-amino-2-methylphenyl)-2-(isopropylamino)quinazoline obtained in Example 253 and cyclopropanecarboxylic acid.

¹H NMR (300 MHz, CDCl₃) δ (ppm) 0.83-0.87 (m, 2H), 1.08-1.12 (m, 2H), 1.33 (d, J=6.6 Hz, 6H), 1.50-1.70 (m, 1H), 2.27 (s, 3H), 4.31-4.38 (m, 1H), 5.20 (br s, 1H), 7.25 (d, J=8.1 Hz, 1H), 7.36-7.42 (m, 2H), 7.52 (br s, 1H), 7.59-7.62 (m, 2H), 7.66 (dd, J=8.1, 1.8 Hz, 1H), 8.98 (s, 1H).
APCI m/z (M+H)⁺ 361.

Example 265

6-(5-Cyclobutylcarbonylamino-2-methylphenyl)-2-(isopropylamino)quinazoline

Compound 265

In a similar manner to Example 209, Compound 265 was obtained using 6-(5-amino-2-methylphenyl)-2-(isopropylamino)quinazoline obtained in Example 253 and cyclobutanecarboxylic acid.
¹H NMR (300 MHz, CDCl₃) δ (ppm) 1.32 (d, J=6.6 Hz, 6H), 1.91-2.05 (m, 2H), 2.18-2.30 (m, 3H), 2.33-2.46 (m, 2H), 2.25 (s, 3H), 4.31-4.37 (m, 1H), 5.23 (br s, 1H), 7.00 (s, 1H), 7.23 (d, J=8.1 Hz, 1H), 7.43 (d, J=8.1 Hz, 1H), 7.49 (s, 1H), 7.58 (s, 1H), 7.59 (d, J=8.1 Hz, 1H), 7.66 (d, J=8.1 Hz, 1H), 8.97 (s, 1H).
APCI m/z (M+H)⁺ 375.

Example 266

6-{2-Hydroxy-5-[(2-morpholinopyridin-4-yl)carbonylamino]phenyl}-2-(isopropylamino)quinazoline Compound 266

In a similar manner to Reference Example 7, 2-isopropylamino-6-(4,4,5,5-tetramethyl-1,3,2-dioxaboran-2-yl)quinazoline was obtained using Compound A10. In a similar manner to Example 4, Example 50 and Example 186, 6-(5-amino-2-hydroxyphenyl)-2-(isopropylamino)quinazoline was obtained using the above-obtained 2-isopropylamino-6-(4,4,5,5-tetramethyl-1,3,2-dioxaboran-2-yl)quinazoline and 2-methoxy-5-nitrobromobenzene. In a similar manner to Example 209, Compound 266 was obtained using the above-obtained 6-(5-amino-2-hydroxyphenyl)-2-(isopropylamino)quinazoline and Compound A5.
¹H NMR (300 MHz, CDCl₃) δ (ppm) 1.31 (d, J=6.6 Hz, 6H), 3.55-3.61 (m, 4H), 3.82-3.85 (m, 4H), 4.31-4.36 (m, 1H), 5.20 (d, J=9.0 Hz, 1H), 6.92 (d, J=5.1 Hz, 1H), 7.01 (d, J=8.7 Hz, 1H), 7.13 (s, 1H), 7.47 (dd, J=8.4, 2.7 Hz, 1H), 7.64 (s, 1H), 7.65 (d, J=2.7 Hz, 1H), 7.78 (s, 1H), 7.81 (d, J=8.4 Hz, 1H), 7.82 (d, J=8.7 Hz, 1H), 8.32 (d, J=5.1 Hz, 1H), 8.95 (s, 1H).
APCI m/z (M+H)⁺ 485.

Example 267

6-{2-Hydroxy-5-[(1H-pyrrol-2-yl)carbonylamino]phenyl}-2-(isopropylamino)quinazoline Compound 267

In a similar manner to Example 209, Compound 267 was obtained using 6-(5-amino-2-hydroxyphenyl)-2-(isopropylamino)quinazoline obtained in Example 266.
¹H NMR (300 MHz, CDCl₃) δ (ppm) 1.21 (d, J=6.6 Hz, 6H), 4.16-4.23 (m, 1H), 6.14-6.16 (m, 1H), 6.92 (d, J=8.7 Hz, 1H), 6.93 (s, 1H), 7.00-7.02 (m, 1H), 7.25 (d, J=8.1 Hz, 1H), 7.49 (d, J=9.3 Hz, 1H), 7.54 (dd, J=8.7, 2.4 Hz, 1H), 7.69-7.71 (m, 1H), 7.91 (d, J=9.3 Hz, 1H), 7.93 (s, 1H), 9.63 (s, 1H), 11.6 (br s, 1H).
APCI m/z (M+H)⁺ 388.

Example 268

6-(5-Cyclopropylcarbamoyl-2-methylphenyl)-2-(isopropylamino)quinazoline

Compound 268

In a similar manner to Example 4, Compound 268 was obtained using Compound A10 and N-cyclopropyl-4-methyl-3-(4,4,5,5-tetramethyl-1,3,2-dioxaboran-2-yl)benzamide (WO03/093248).
¹H NMR (270 MHz, CDCl₃) δ (ppm) 0.56-0.64 (m, 2H), 0.80-0.90 (m, 2H), 1.32 (d, J=6.8 Hz, 6H), 2.31 (s, 3H), 2.85-2.96 (m, 1H), 4.24-4.42 (m, 1H), 5.13 (d, J=8.1 Hz, 1H), 6.23 (br s, 1H), 7.33 (d, J=7.6 Hz, 1H), 7.53-7.56 (m, 1H), 7.59-7.68 (m, 4H), 8.95 (s, 1H).
ESI m/z (M+H)⁺ 361.

Example 269

6-(3-Carboxyphenyl)-2-(isopropylamino)quinazoline

Compound 269

In a similar manner to Example 4, Compound 269 was obtained using Compound A10 and 3-carboxyphenylboronic acid.
¹H NMR (270 MHz, DMSO-d₆) δ (ppm) 1.24 (d, J=6.5 Hz, 6H), 4.15-4.30 (m, 1H), 6.97 (d, J=7.8 Hz, 1H), 7.51-7.64 (m, 2H), 7.89-8.05 (m, 3H), 8.11 (d, J=1.9 Hz, 1H), 8.27 (s, 1H), 9.16 (s, 1H).
APCI m/z (M+H)⁺ 308.

Example 270

6-[3-(Cyclopropylcarbamoyl)phenyl]-2-(isopropylamino)quinazoline

Compound 270

In a similar manner to Example 209, Compound 270 was obtained using Compound 269 and cyclopropylamine.
¹H NMR (270 MHz, CDCl₃) δ (ppm) 0.61-0.69 (m, 2H), 0.84-0.94 (m, 2H), 1.31 (d, J=6.2 Hz, 6H), 2.90-3.00 (m, 1H), 4.24-4.42 (m, 1H), 5.14 (d, J=7.8 Hz, 1H), 6.30 (s, 1H), 7.49 (t, J=7.8 Hz, 1H), 7.60-7.70 (m, 2H), 7.72-7.77 (m, 1H), 7.83-7.86 (m, 1H), 7.89-7.95 (m, 1H), 8.00-8.04 (m, 1H), 9.00 (s, 1H).
APCI m/z (M+H)⁺ 347.

Example 271

2-Isopropylamino-6-(pyridine-1-oxide-2-yl)quinazoline Compound 271

Compound A10 (133 mg, 0.500 mmol), pyridine N-oxide (190 mg, 2.00 mmol), potassium carbonate (138 mg, 1.00 mmol), palladium acetate(II) (6.0 mg, 0.025 mmol) and tributylphosphine tetrafluoroborate (22.0 mg, 0.0758 mmol) were suspended in toluene (3 mL) and the suspension was stirred at 110° C. for 16 hours under argon atmosphere. The reaction mixture was added with ethyl acetate and water, and the organic layer was separated. The organic layer was washed with water and saturated brine, and was dried over anhydrous magnesium sulfate, then evaporated under reduced pressure. The residue was purified by silica gel column chromatography (methanol/ethyl acetate=0/1 to 1/10) to obtain Compound 271 (70.0 mg, 50%).

$^1$H NMR (270 MHz, CDCl$_3$) δ (ppm) 1.31 (d, J=6.5 Hz, 6H), 4.24-4.42 (m, 1H), 5.23 (d, J=7.6 Hz, 1H), 7.20-7.28 (m, 1H), 7.29-7.36 (m, 1H), 7.48-7.54 (m, 1H), 7.63 (d, J=8.9 Hz, 1H), 8.10 (dd, J=8.9, 1.9 Hz, 1H), 8.25-8.30 (m, 1H), 8.33-8.38 (m, 1H), 9.00 (s, 1H).

APCI m/z (M+H)$^+$ 281.

Example 272

(S)-6-[5-acetylamino-2-(hydroxymethyl)phenyl]-2-(sec-butylamino)quinazoline

Compound 272

In a similar manner to Reference Example 4, (S)-6-bromo-2-(sec-butylamino)quinazoline was obtained using Compound A9 and (S)-(+)-sec-butylamine. In a similar manner to Example 4 and Example 52, Compound 272 was obtained using the above-obtained (S)-6-bromo-2-(sec-butylamino)quinazoline and anhydrous 5-amino-2-hydroxymethylphenylboronic acid.

$^1$H NMR (270 MHz, CDCl$_3$) δ (ppm) 1.00 (t, J=7.3 Hz, 3H), 1.27 (d, J=6.5 Hz, 3H), 1.59-1.66 (m, 2H), 2.19 (s, 3H), 4.12-4.22 (m, 1H), 4.58 (s, 2H), 5.16 (d, J=8.3 Hz, 1H), 7.32 (br s, 1H), 7.50-7.70 (m, 6H), 8.93 (s, 1H).

Example 273

(S)-2-(sec-Butylamino)-6-{2-hydroxymethyl-5-[(1H-pyrrol-2-yl)carbonylamino]phenyl}quinazoline Compound 273

In a similar manner to Example 209, Compound 273 was obtained using (S)-6-[5-amino-2-(hydroxymethyl)phenyl]-2-(sec-butylamino)quinazoline obtained in Example 272.

$^1$H NMR (270 MHz, CDCl$_3$) δ (ppm) 1.01 (t, J=7.5 Hz, 3H), 1.29 (d, J=6.6 Hz, 3H), 1.59-1.66 (m, 2H), 4.15-4.24 (m, 1H), 4.61 (s, 2H), 5.21 (br s, 1H), 6.29-6.33 (m, 1H), 6.73 (br s, 1H), 6.99-7.01 (m, 1H), 7.54-7.75 (m, 7H), 8.97 (s, 1H), 9.50 (br s, 1H).

Example 274

6-[3-(Acetylamino)phenyl]-2-[1-(methylsulfonyl)piperidin-4-ylamino]quinazoline

Compound 274

In a similar manner to Example 164, Compound 274 was obtained using Compound A9 and 3-(acetylamino)phenylboronic acid.

$^1$H NMR (300 MHz, DMSO-d$_6$) δ (ppm) 1.52-1.71 (m, 2H), 1.98-2.12 (m, 2H), 2.08 (s, 3H), 2.90 (s, 3H), 2.88-3.00 (m, 2H), 3.50-3.62 (m, 2H), 3.98-4.12 (m, 1H), 7.37-7.46 (m, 2H), 7.50-7.61 (m, 2H), 7.92-8.08 (m, 3H), 9.21 (s, 1H).

APCI m/z (M+H)$^+$ 440.

Example 275

6-(2-Methylphenyl)-2-[1-(methylsulfonyl)piperidin-4-ylamino]quinazoline

Compound 275

In a similar manner to Example 164, Compound 275 was obtained using Compound A9.

$^1$H NMR (300 MHz, DMSO-d$_6$) δ (ppm) 1.55-1.70 (m, 2H), 1.98-2.10 (m, 2H), 2.27 (s, 3H), 2.90 (s, 3H), 2.90-3.01 (m, 2H), 3.50-3.61 (m, 2H), 3.98-4.12 (m, 1H), 7.25-7.37 (m, 4H), 7.51 (d, J=8.4 Hz, 1H), 7.47-7.55 (m, 1H), 7.70 (dd, J=8.4, 2.1 Hz, 1H), 7.76 (d, J=2.1 Hz, 1H), 9.16 (s, 1H).

APCI m/z (M+H)$^+$ 397.

Example 276

6-(3-Hydroxyphenyl)-2-[1-(methylsulfonyl)piperidin-4-ylamino]quinazoline

Compound 276

In a similar manner to Example 164 and Example 110, Compound 276 was obtained using Compound A9 and 3-(benzyloxy)phenylboronic acid.

$^1$H NMR (300 MHz, DMSO-d$_6$) δ (ppm) 1.53-1.70 (m, 2H), 1.98-2.12 (m, 2H), 2.90 (s, 3H), 2.89-3.00 (m, 2H), 3.50-3.62 (m, 2H), 3.98-4.12 (m, 1H), 6.78 (dd, J=8.1, 1.5 Hz, 1H), 7.08-7.12 (m, 1H), 7.15 (d, J=8.1 Hz, 1H), 7.28 (t, J=8.1 Hz, 1H), 7.52 (d, J=8.7 Hz, 1H), 7.48-7.57 (m, 1H), 7.96 (dd, J=8.7, 2.1 Hz, 1H), 8.04 (d, J=2.1 Hz, 1H), 9.19 (s, 1H), 9.56 (s, 1H).

APCI m/z (M+H)$^+$ 399.

Example 277

6-[3-(Acetylamino)phenyl]-2-isopropylamino-7-methylquinazoline

Compound 277

In a similar manner to Example 4, Compound 277 was obtained using Compound A11 and 3-(acetylamino)phenylboronic acid.

$^1$H NMR (300 MHz, CDCl$_3$) δ (ppm) 1.30 (d, J=6.3 Hz, 6H), 2.20 (s, 3H), 2.38 (s, 3H), 4.26-4.37 (m, 1H), 7.09 (d, J=7.8 Hz, 1H), 7.38 (t, J=7.8 Hz, 1H), 7.47-7.53 (m, 4H), 8.89 (s, 1H).

APCI m/z (M+H)$^+$ 335.

Example 278

2-Isopropylamino-7-methyl-6-{3-[(1H-pyrrol-2-yl)carbonylamino]phenyl}quinazoline Compound 278

In a similar manner to Example 4 and Example 209, Compound 278 was obtained using Compound A11 and 3-aminophenylboronic acid.

$^1$H NMR (300 MHz, CDCl$_3$) δ (ppm) 1.31 (d, J=6.0 Hz, 6H), 2.40 (s, 3H), 4.26-4.35 (m, 1H), 5.13 (d, J=8.1 Hz, 1H), 6.29-6.33 (m, 1H), 6.71-6.74 (m, 1H), 6.99-7.01 (m, 1H), 7.11 (d, J=7.8 Hz, 1H), 7.42 (t, J=7.8 Hz, 1H), 7.48 (br s, 1H), 7.51 (s, 1H), 7.58-7.63 (m, 3H), 8.90 (s, 1H), 9.50 (br s, 1H).
APCI m/z (M+H)+ 386.

Example 279

2-Isopropylamino-7-methyl-6-{3-[(2-morpholinopyridin-4-yl)carbonylamino]phenyl}quinazoline Compound 279

In a similar manner to Example 209, Compound 279 was obtained using 6-(3-aminophenyl)-2-isopropylamino-7-methylquinazoline obtained in Example 278 and Compound A5.
$^1$H NMR (270 MHz, CDCl$_3$) δ (ppm) 1.31 (d, J=6.5 Hz, 6H), 2.40 (s, 3H), 3.58-3.62 (m, 4H), 3.82-3.85 (m, 4H), 4.28-4.36 (m, 1H), 5.10 (d, J=7.3 Hz, 1H), 6.92 (d, J=5.1 Hz, 1H), 7.13 (s, 1H), 7.17 (d, J=7.8 Hz, 1H), 7.45 (t, J=7.8 Hz, 1H), 7.48 (s, 1H), 7.50 (s, 1H), 7.60-7.68 (m, 2H), 7.86 (br s, 1H), 8.90 (s, 1H), 8.32 (d, J=5.1 Hz, 1H).
APCI m/z (M+H)+ 483.

Example 280

6-[(5-Acetylamino-2-hydroxymethyl)phenyl]-2-isopropylamino-7-methylquinazoline

Compound 280

In a similar manner to Example 4 and Example 52, Compound 280 was obtained using Compound A11 and anhydrous (5-amino-2-hydroxymethyl)phenylboronic acid.
$^1$H NMR (300 MHz, CDCl$_3$) δ (ppm) 1.31 (d, J=6.3 Hz, 6H), 2.17 (s, 3H), 2.18 (s, 3H), 4.28-4.37 (m, 3H), 5.22 (d, J=7.8 Hz, 1H), 7.35 (s, 1H), 7.39 (s, 1H), 7.46-7.55 (m, 5H), 8.85 (s, 1H).
APCI m/z (M+H)+ 365.

Example 281

6-{2-Hydroxymethyl-5-[(1H-pyrrol-2-yl)carbonylamino]phenyl}-2-isopropylamino-7-methylquinazoline Compound 281

In a similar manner to Example 209, Compound 281 was obtained using 6-[5-amino-2-(hydroxymethyl)phenyl]-2-isopropylamino-7-methylquinazoline obtained in Example 280.
$^1$H NMR (300 MHz, CDCl$_3$) δ (ppm) 1.33 (d, J=6.6 Hz, 6H), 2.22 (s, 3H), 4.33-4.42 (m, 3H), 5.30 (br s, 1H), 6.30-6.33 (m, 1H), 6.70-6.72 (m, 1H), 6.99-7.01 (m, 1H), 7.47-7.70 (m, 7H), 8.89 (s, 1H), 9.40 (br s, 1H).
APCI m/z (M+H)+ 416.

Example 282

7-Benzyloxy-2-isopropylamino-6-(3-nitrophenyl)quinazoline

Compound 282

In a similar manner to Example 4, Compound 282 was obtained using Compound A15 and 3-nitrophenylboronic acid.
$^1$H NMR (300 MHz, CDCl$_3$) δ (ppm) 1.32 (d, J=6.3 Hz, 6H), 4.26-4.39 (m, 1H), 5.18 (br s, 1H), 5.24 (s, 2H), 7.11 (s, 1H), 7.26-7.40 (m, 5H), 7.56 (t, J=8.1 Hz, 1H), 7.63 (s, 1H), 7.95-7.97 (m, 1H), 8.16-8.21 (m, 1H), 8.52 (t, J=1.8 Hz, 1H), 8.87 (s, 1H).
APCI m/z (M+H)+ 415.

Example 283

7-Hydroxy-2-isopropylamino-6-(3-nitrophenyl)quinazoline

Compound 283

In a similar manner to Example 186, Compound 283 was obtained using Compound 282.
$^1$H NMR (300 MHz, DMSO-d$_6$) δ (ppm) 1.18 (d, J=6.5 Hz, 6H), 4.05-4.25 (m, 1H), 6.88 (s, 1H), 7.15 (br s, 1H), 7.66-7.76 (m, 1H), 7.83 (s, 1H), 8.01-8.09 (m, 1H), 8.15-8.25 (m, 1H), 8.43 (s, 1H), 8.92 (s, 1H), 10.82 (s, 1H).
APCI m/z (M+H)+ 325.

Example 284

6-(3-Aminophenyl)-7-benzyloxy-2-(isopropylamino)quinazoline

Compound 284

In a similar manner to Example 4, Compound 284 was obtained using Compound A15 and 3-aminophenylboronic acid.
$^1$H NMR (300 MHz, DMSO-d$_6$) δ (ppm) 1.19 (d, J=6.6 Hz, 6H), 4.18 (dhept, J=6.7, 6.6 Hz, 1H), 5.07 (d, J=6.7 Hz, 1H), 5.28 (s, 2H), 6.52-6.55 (m, 1H), 6.70 (d, J=7.3 Hz, 1H), 6.77-6.79 (m, 1H), 6.98 (s, 1H), 7.05 (dd, J=7.7, 7.5 Hz, 1H), 7.12 (d, J=7.5 Hz, 1H), 7.28-7.45 (m, 6H), 7.62 (s, 1H), 8.94 (s, 1H).

Example 285

6-(3-Aminophenyl)-7-hydroxy-2-(isopropylamino)quinazoline

Compound 285

Compound 284 (526 mg, 1.27 mmol) was suspended in ethanol (80 mL) and the atmosphere of the reaction vessel was substituted with argon. The mixture was added with a solution of palladium carbon (50% aqueous, 212 mg) and ammonium formate (80.1 mg, 1.27 mmol) in water (2 mL) and stirred at 60° C. for 30 minutes. Then, the mixture was further added with a solution of ammonium formate (720 mg, 11.4 mmol) was dissolved in water (2 mL), followed by stirring at 60° C. for 1 hour. After substituting the atmosphere of the reaction vessel with argon, an insoluble matter was filtered off using Celite and the solvent was evaporated under reduced pressure. The residue was added with water and extracted with ethyl acetate. The organic layer was washed with saturated brine and dried over anhydrous magnesium sulfate, then the solvent was evaporated under reduced pressure. The residue was reslurried with methanol to obtain Compound 285 (250 mg, 67%).
$^1$H NMR (300 MHz, DMSO-d$_6$) δ (ppm) 1.19 (d, J=6.4 Hz, 6H), 4.10-4.21 (m, 1H), 6.54-6.58 (m, 1H), 6.70-6.72 (m, 1H), 6.79-6.80 (m, 1H), 6.86 (s, 1H), 7.06 (t, J=7.8 Hz, 1H), 7.60 (s, 1H), 8.91 (s, 1H).
ESI m/z (M+H)+ 295.

Example 286

7-Acetoxy-6-[3-(acetylamino)phenyl]-2-(isopropylamino)quinazoline

Compound 286

Compound 285 (200 mg, 0.679 mmol) was suspended in methylene chloride (5 mL) and the suspension was added with acetic anhydride (640 mL, 6.79 mmol) and triethylamine (95.0 mL, 0.679 mmol), followed by stirring for 4 hours. The reaction mixture was added with water and extracted with methylene chloride. The organic layer was washed with saturated brine and dried over anhydrous magnesium sulfate, then the solvent was evaporated under reduced pressure. The residue was reslurried with diethylether to obtain Compound 286 (114 mg, 44%).

$^1$H NMR (300 MHz, CDCl$_3$) δ (ppm) 1.30 (d, J=6.2 Hz, 6H), 2.13 (s, 3H), 2.20 (s, 3H), 4.30 (dhept, J=7.9, 6.2 Hz, 1H), 5.18 (d, J=7.9 Hz, 1H), 7.20-7.24 (m, 2H), 7.32 (s, 1H), 7.35-7.40 (m, 1H), 7.49-7.51 (m, 1H), 7.61 (br s, 1H), 7.66 (s, 1H), 8.94 (s, 1H).

Example 287

6-[3-(Acetylamino)phenyl]-7-hydroxy-2-(isopropylamino)quinazoline

Compound 287

In a similar manner to Example 286 and Example 186, Compound 287 was obtained using Compound 284.

$^1$H NMR (270 MHz, DMSO-d$_6$) δ (ppm) 1.19 (d, J=6.4 Hz, 6H), 2.05 (s, 3H), 3.27-3.43 (m, 1H), 6.84 (s, 1H), 7.01-7.04 (m, 1H), 7.20-7.22 (m, 1H), 7.29-7.35 (m, 1H), 7.57 (d, J=8.9 Hz, 1H), 7.61 (s, 1H), 7.75 (br s, 1H), 8.88 (s, 1H), 9.97 (s, 1H), 10.53 (br s, 1H).

ESI m/z (M+H)$^+$ 337.

Example 288

6-(5-Amino-2-methylphenyl)-7-benzyloxy-2-(isopropylamino)quinazoline

Compound 288

In a similar manner to Example 4, Compound 288 was obtained using Compound A15 and 4-methyl-3-(4,4,5,5-tetramethyl-1,3,2-dioxaboran-2-yl)aniline.

$^1$H NMR (300 MHz, DMSO-d$_6$) δ (ppm) 1.20 (d, J=6.4 Hz, 6H), 1.92 (s, 3H), 4.18 (dhept, J=6.8, 6.4 Hz, 1H), 4.85 (d, J=6.8 Hz, 1H), 5.24 (s, 2H), 6.44 (d, J=2.4 Hz, 1H), 6.48 (dd, J=8.1, 2.4 Hz, 1H), 6.89 (d, J=8.1 Hz, 1H), 6.97 (s, 1H), 7.11 (d, J=7.5 Hz, 1H), 7.25-7.36 (m, 6H), 7.47 (s, 1H), 8.91 (s, 1H).

Example 289

6-(5-Acetylamino-2-methylphenyl)-7-hydroxy-2-(isopropylamino)quinazoline

Compound 289

In a similar manner to Example 52 and Example 285, Compound 289 was obtained using Compound 288.

$^1$H NMR (270 MHz, DMSO-d$_6$) δ (ppm) 1.19 (d, J=6.6 Hz, 6H), 2.02 (s, 3H), 2.05 (s, 3H), 4.16 (dhept, J=8.3, 6.6 Hz, 1H), 6.83 (s, 1H), 7.00 (d, J=8.3 Hz, 1H), 7.15 (d, J=8.1 Hz, 1H), 7.39-7.47 (m, 3H), 8.85 (s, 1H), 9.87 (s, 1H), 10.41 (s, 1H).

ESI m/z (M+H)$^+$ 351.

Example 290

7-Hydroxy-2-isopropylamino-6-{3-[(2-morpholinopyridin-4-yl)carbonylamino]phenyl}quinazoline

Compound 290

In a similar manner to Example 209 and Example 285, Compound 290 was obtained using Compound 284 and Compound A5.

$^1$H NMR (300 MHz, DMSO-d$_6$) δ (ppm) 1.19 (d, J=6.6 Hz, 6H), 3.54 (t, J=4.6 Hz, 4H), 3.73 (t, J=4.9 Hz, 4H), 4.11-4.22 (m, 1H), 6.86 (s, 1H), 7.05 (d, J=7.9 Hz, 1H), 7.14 (d, J=5.0 Hz, 1H), 7.27 (s, 1H), 7.33 (d, J=7.9 Hz, 1H), 7.42 (dd, J=7.9, 7.8 Hz, 1H), 7.66 (s, 1H), 7.76 (d, J=7.8 Hz, 1H), 7.96 (s, 1H), 8.29 (d, J=5.0 Hz, 1H), 8.90 (s, 1H), 10.38 (s, 1H), 10.59 (s, 1H).

ESI m/z (M+H)$^+$ 485.

elemental analysis: as $C_{27}H_{28}N_6O_3$ 0.4i-PrOH
calculated value (%); C=66.60, H=6.18, N=16.52
found value (%); C=66.38, H=6.20, N=16.57
m.p. 258° C.

Example 291

6-{3-[(3-Dimethylaminophenyl)carbonylamino]phenyl}-7-hydroxy-2-(isopropylamino)quinazoline

Compound 291

In a similar manner to Example 209 and Example 285, Compound 291 was obtained using Compound 284 and 3-(dimethylamino)benzoic acid.

$^1$H NMR (270 MHz, DMSO-d$_6$) δ (ppm) 1.19 (d, J=6.4 Hz, 6H), 2.97 (s, 6H), 4.14-4.21 (m, 1H), 6.87 (s, 1H), 6.99 (dd, J=31.0, 7.3 Hz, 1H), 7.24-7.42 (m, 6H), 7.66 (s, 1H), 7.76 (d, J=7.3 Hz, 1H), 7.98 (s, 1H), 8.90 (s, 1H), 10.17 (s, 1H), 10.54 (s, 1H).

ESI m/z (M+H)$^+$ 442.

elemental analysis: as $C_{26}H_{27}N_5O_2$ 1.0H$_2$O 0.8 EtOH
calculated value (%); C=66.78, H=6.86, N=14.10
found value (%); C=67.00, H=6.70, N=13.97
m.p. 150° C.

Example 292

7-Hydroxy-2-isopropylamino-6-{3-[(1H-pyrrol-2-yl)carbonylamino]phenyl}quinazoline

Compound 292

In a similar manner to Example 209 and Example 285, Compound 292 was obtained using Compound 284.

$^1$H NMR (300 MHz, DMSO-d$_6$) δ (ppm) 1.19 (d, J=6.6 Hz, 6H), 4.11-4.22 (m, 1H), 6.16-6.18 (m, 1H), 6.86 (s, 1H), 6.97 (br s, 1H), 7.03-7.09 (m, 2H), 7.25 (d, J=7.9 Hz, 1H), 7.37 (dd, J=8.0, 7.9 Hz, 1H), 7.66 (s, 1H), 7.77 (d, J=8.0 Hz, 1H), 7.90-7.95 (m, 1H), 8.90 (s, 1H), 9.78 (s, 1H), 10.54 (s, 1H), 11.64 (s, 1H).

ESI m/z (M+H)$^+$ 388.

Example 293

6-(5-Cyclobutylcarbonylamino-2-methylphenyl)-7-hydroxy-2-(isopropylamino)quinazoline Compound 293

In a similar manner to Example 209 and Example 285, Compound 293 was obtained using Compound 288 and cyclobutanecarboxylic acid.
$^1$H NMR (300 MHz, DMSO-$d_6$) δ (ppm) 1.19 (d, J=6.6 Hz, 6H), 1.77-2.27 (m, 7H), 2.05 (s, 3H), 4.11-4.22 (m, 1H), 6.83 (s, 1H), 7.02 (d, J=8.1 Hz, 1H), 7.15 (d, J=8.4 Hz, 1H), 7.43-7.51 (m, 4H), 8.85 (s, 1H), 9.66 (s, 1H).
ESI m/z (M+H)$^+$ 391.

Example 294

6-[3-(Cyclobutylcarbonylamino)phenyl]-7-hydroxy-2-(isopropylamino)quinazoline

Compound 294

In a similar manner to Example 209 and Example 285, Compound 294 was obtained using Compound 284 and cyclobutanecarboxylic acid.
$^1$H NMR (300 MHz, DMSO-$d_6$) δ (ppm) 1.19 (d, J=6.6 Hz, 6H), 1.79-1.99 (m, 3H), 2.09-2.27 (m, 4H), 4.10-4.22 (m, 1H), 6.84 (s, 1H), 7.01 (d, J=7.5 Hz, 1H), 7.22 (d, J=7.7 Hz, 1H), 7.32 (dd, J=7.7, 7.5 Hz, 1H), 7.58-7.62 (m, 2H), 7.80 (s, 1H), 7.95 (s, 1H), 8.88 (s, 1H), 9.77 (s, 1H).
ESI m/z (M+H)$^+$ 377.

Example 295

6-(5-Cyclopropylcarbonylamino-2-methylphenyl)-7-hydroxy-2-(isopropylamino)quinazoline Compound 295

In a similar manner to Example 209 and Example 285, Compound 295 was obtained using Compound 288 and cyclopropanecarboxylic acid.
$^1$H NMR (300 MHz, DMSO-$d_6$) δ (ppm) 0.76-0.78 (m, 4H), 1.19 (d, J=6.4 Hz, 6H), 1.71-1.79 (m, 1H), 2.05 (s, 3H), 4.10-4.22 (m, 1H), 6.82 (s, 1H), 7.01 (d, J=8.1 Hz, 1H), 7.15 (d, J=8.2 Hz, 1H), 7.43-7.48 (m, 3H), 8.85 (s, 1H), 10.12 (s, 1H), 10.40 (s, 1H).
ESI m/z (M+H)$^+$ 377.

Example 296

6-[3-(Cyclopropylcarbonylamino)phenyl]-7-hydroxy-2-(isopropylamino)quinazoline

Compound 296

In a similar manner to Example 209 and Example 285, Compound 296 was obtained using Compound 284 and cyclopropanecarboxylic acid.
$^1$H NMR (270 MHz, DMSO-$d_6$) δ (ppm) 0.77-0.81 (m, 4H), 1.19 (d, J=6.4 Hz, 6H), 1.75-1.86 (m, 1H), 4.10-4.21 (m, 1H), 6.83 (s, 1H), 6.98-7.03 (m, 1H), 7.20-7.35 (m, 2H), 7.56-7.61 (m, 2H), 7.79 (s, 1H), 8.87 (s, 1H), 10.22 (s, 1H).
ESI m/z (M+H)$^+$ 363.
elemental analysis: as $C_{21}H_{22}N_4O_2$ 0.4MeOH
calculated value (%); C=68.49, H=6.34, N=14.93
found value (%); C=68.36, H=6.44, N=15.22

Example 297

7-Hydroxy-2-isopropylamino-6-[3-(propionylamino)phenyl]quinazoline

Compound 297

In a similar manner to Example 209 and Example 285, Compound 297 was obtained using Compound 284 and propionic acid.
$^1$H NMR (300 MHz, DMSO-$d_6$) δ (ppm) 1.09 (t, J=7.5 Hz, 3H), 1.19 (d, J=6.6 Hz, 6H), 2.33 (q, J=7.5 Hz, 2H), 4.10-4.22 (m, 1H), 6.84 (s, 1H), 7.04 (d, J=7.0 Hz, 1H), 7.21 (d, J=7.7 Hz, 1H), 7.32 (dd, J=7.7, 7.7 Hz, 1H), 7.57-7.62 (m, 2H), 7.79 (s, 1H), 8.89 (s, 1H), 9.90 (s, 1H), 10.52 (s, 1H).
ESI m/z (M+H)$^+$ 351.

Example 298

6-[3-(tert-Butylcarbonylamino)phenyl]-7-hydroxy-2-(isopropylamino)quinazoline

Compound 298

In a similar manner to Example 209 and Example 285, Compound 298 was obtained using Compound 284 and pivalic acid.
$^1$H NMR (300 MHz, DMSO-$d_6$) δ (ppm): 1.19 (d, J=6.6 Hz, 6H), 1.24 (s, 9H), 4.16 (dhept, J=7.9, 6.6 Hz, 1H), 6.85 (s, 1H), 7.03 (d, J=7.9 Hz, 1H), 7.24 (d, J=7.5 Hz, 1H), 7.32 (dd, J=7.8, 7.5 Hz, 1H), 7.62-7.65 (m, 2H), 7.84 (s, 1H), 8.90 (s, 1H), 9.24 (s, 1H), 10.53 (s, 1H).
ESI m/z (M+H)$^+$ 379.

Example 299

7-Hydroxy-2-isopropylamino-6-{3-[(1-methylcyclopropyl)carbonylamino]phenyl}quinazoline Compound 299

In a similar manner to Example 209 and Example 285, Compound 299 was obtained using Compound 284 and 1-methyl-cyclopropanecarboxylic acid.
$^1$H NMR (300 MHz, DMSO-$d_6$) δ (ppm): 0.62-0.65 (m, 2H), 1.08-1.11 (m, 2H), 1.19 (d, J=6.4 Hz, 6H), 1.42 (s, 3H), 4.16 (dhept, J=7.7, 6.6 Hz, 1H), 6.83 (s, 1H), 6.99 (d, J=7.7 Hz, 1H), 7.24-7.34 (m, 2H), 7.58-7.61 (m, 2H), 7.81 (s, 2H), 8.87 (s, 1H), 9.21 (s, 1H).
ESI m/z (M+H)$^+$ 377.

Example 300

7-Hydroxy-6-(2-methylphenyl)-2-(2,4,6-trimethylanilino)quinazoline

Compound 300

In a similar manner to Example 4, 2-amino-7-benzyloxy-6-(2-methylphenyl)quinazoline was obtained using Compound A14 and 2-methylphenylboronic acid. In a similar manner to Example 178 and Example 285, Compound 300 was obtained using the above-obtained 2-amino-7-benzyloxy-6-(2-methylphenyl)quinazoline and 2,4,6-trimethyliodobenzene.

$^1$H NMR (300 MHz, CDCl$_3$) δ (ppm) 2.19 (s, 3H), 2.24 (s, 6H), 2.32 (s, 3H), 6.97 (s, 2H), 7.12 (s, 1H), 7.20-7.40 (m, 4H), 7.47 (s, 1H), 8.86 (s, 1H).

ESI m/z (M+H)$^+$ 370.

m.p. 142° C.

Example 301

2-[(4-tert-Butyl-2,6-dimethyl)anilino]-7-hydroxy-6-(2-methylphenyl)quinazoline

Compound 301

In a similar manner to Example 178 and Example 285, Compound 301 was obtained using 2-amino-7-benzyloxy-6-(2-methylphenyl)quinazoline obtained in Example 300 and (4-tert-butyl-2,6-dimethyl)iodobenzene.

$^1$H NMR (300 MHz, CDCl$_3$) δ (ppm) 1.33 (s, 9H), 2.19 (s, 3H), 2.27 (s, 6H), 7.10 (s, 1H), 7.16 (s, 2H), 7.19-7.37 (m, 4H), 7.47 (s, 1H), 8.86 (s, 1H).

ESI m/z (M+H)$^+$ 412.

Example 302

2-[(2,6-Dimethyl-4-methoxy)anilino]-7-hydroxy-6-(2-methylphenyl)quinazoline

Compound 302

In a similar manner to Example 178 and Example 285, Compound 302 was obtained using 2-amino-7-benzyloxy-6-(2-methylphenyl)quinazoline obtained in Example 300 and (2,6-dimethyl-4-methoxy)iodobenzene.

$^1$H NMR (270 MHz, CDCl$_3$) δ (ppm) 2.19 (s, 3H), 2.22 (s, 6H), 3.80 (s, 3H), 6.68 (s, 2H), 6.60-6.81 (m, 1H), 7.04 (s, 1H), 7.16-7.40 (m, 4H), 7.44 (s, 1H), 8.82 (s, 1H).

ESI m/z (M+H)$^+$ 386.

m.p. 142° C.

Example 303

2-[(2,6-Dimethyl-4-hydroxy)anilino]-7-hydroxy-6-(2-(isopropylamino)quinazoline

Compound 303

In a similar manner to Example 186, Compound 303 was obtained using Compound 302.

$^1$H NMR (300 MHz, CDCl$_3$) δ (ppm) 2.19 (s, 3H), 2.21 (s, 6H), 6.50 (s, 2H), 6.42-6.58 (m, 1H), 7.17 (s, 1H), 7.20-7.41 (m, 4H), 7.49 (s, 1H), 8.91 (s, 1H).

ESI m/z (M+H)$^+$ 372.

m.p. 247-250° C.

Example 304

2-[(4-Amino-2,6-dichloro)anilino]-7-benzyloxy-6-(2-methylphenyl)quinazoline

Compound 304

In a similar manner to Example 178, 7-benzyloxy-2-[(2,6-dichloro-4-nitro)anilino]-6-(2-methylphenyl)quinazoline was obtained using 2-amino-7-benzyloxy-6-(2-methylphenyl)quinazoline obtained in Example 300 and (2,6-dichloro-4-nitro)iodobenzene. The obtained 7-benzyloxy-2-[(2,6-dichloro-4-nitro)anilino]-6-(2-methylphenyl)quinazoline (790 mg, 1.49 mmol) was suspended in methanol (7.5 mL) and the suspension was added with tin chloride dihydrate (1.34 g, 5.95 mmol), followed by heating under reflux for 10 minutes. The solvent was evaporated under reduced pressure and the residue was added with ethyl acetate and saturated aqueous sodium hydrogencarbonate solution. An insoluble matter was filtered off using Celite. The organic layer was separated and washed with water and saturated brine, followed by drying over anhydrous magnesium sulfate. The solvent was evaporated under reduced pressure to obtain Compound 304 (730 mg, 98%).

$^1$H NMR (300 MHz, CDCl$_3$) δ (ppm) 2.15 (s, 3H), 3.84 (s, 2H), 5.17 (s, 2H), 6.67 (s, 1H), 6.75 (s, 2H), 7.09 (s, 1H), 7.15-7.33 (m, 9H), 7.50 (s, 1H), 8.92 (s, 1H).

ESI m/z (M+H)$^+$ 501.

Example 305

2-[(4-Amino-2,6-dichloro)anilino]-7-hydroxy-6-(2-methylphenyl)quinazoline

Compound 305

In a similar manner to Example 186, Compound 305 was obtained using Compound 304.

$^1$H NMR (270 MHz, CDCl$_3$) δ (ppm) 2.18 (s, 3H), 3.83 (s, 2H), 6.74 (s, 2H), 7.12 (s, 1H), 7.20-7.40 (m, 4H), 7.49 (s, 1H), 8.92 (s, 1H).

ESI m/z (M+H)$^+$ 411.

m.p. 250-254° C.

Example 306

7-Benzyloxy-2-{[2,6-dichloro-4-(methylsulfonyl)amino]anilino}-6-(2-methylphenyl)quinazoline Compound 306

Compound 304 (143 mg, 0.29 mmol) was dissolved in methylene chloride (1.2 mL) and cooled to 0° C., then the solution was added with pyridine (92 μL, 1.14 mmol) and methanesulfonyl chloride (29 μL, 0.37 mmol), followed by stirring at room temperature for 3 hours. The reaction mixture was added with saturated aqueous ammonium chloride solution and extracted with ethyl acetate. The organic layer was washed with water and saturated brine and dried over anhydrous magnesium sulfate, then the solvent was evaporated under reduced pressure. The residue was purified by preparative thin-layer chromatography (ethyl acetate/hexane=1/1) to obtain Compound 306 (144 mg, 87%).

$^1$H NMR (270 MHz, CDCl$_3$) δ (ppm) 2.16 (s, 3H), 3.11 (s, 3H), 5.14 (s, 2H), 7.08 (s, 1H), 7.13-7.37 (m, 11H), 7.55 (s, 1H), 8.95 (s, 1H).

Example 307

2-{[2,6-Dichloro-4-(methylsulfonyl)amino]anilino}-7-hydroxy-6-(2-methylphenyl)quinazoline Compound 307

In a similar manner to Example 186, Compound 307 was obtained using Compound 306.

¹H NMR (300 MHz, CDCl₃) δ (ppm) 2.19 (s, 3H), 3.13 (s, 3H), 7.12 (s, 1H), 7.29 (s, 2H), 7.23-7.41 (m, 4H), 7.54 (s, 1H), 8.95 (s, 1H).
ESI m/z (M+H)⁺ 489.
m.p. 168-170° C.

Example 308

2-Amino-7-benzyloxy-6-(3-nitrophenyl)quinazoline

Compound 308

In a similar manner to Example 4, Compound 308 was obtained using Compound A14 and 3-nitrophenylboronic acid.
¹H NMR (270 MHz, CDCl₃) δ (ppm) 5.20 (br s, 2H), 5.24 (s, 2H), 7.10 (s, 1H), 7.32-7.37 (m, 5H), 7.58 (dd, J=7.9, 7.9 Hz, 1H), 7.69 (s, 1H), 7.91 (m, 1H), 8.21 (m, 1H), 8.52 (m, 1H), 8.94 (s, 1H).

Example 309

7-Benzyloxy-2-(2,6-dimethylanilino)-6-(3-nitrophenyl)quinazoline

Compound 309

In a similar manner to Example 178, Compound 309 was obtained using Compound 308 and 2,6-dimethyliodobenzene.
¹H NMR (270 MHz, CDCl₃) δ (ppm) 2.31 (s, 6H), 5.16 (s, 2H), 5.25 (br s, 1H), 7.09 (m, 1H), 7.19 (m, 3H), 7.30-7.37 (m, 5H), 7.56 (dd, J=8.1, 7.9 Hz, 1H), 7.68 (s, 1H), 7.90 (m, 1H), 8.20 (m, 1H), 8.51 (m, 1H), 8.96 (s, 1H).

Example 310

6-(3-Aminophenyl)-7-benzyloxy-2-(2,6-dimethylanilino)quinazoline

Compound 310

In a similar manner to Example 304, Compound 310 was obtained using Compound 309.
¹H NMR (300 MHz, CDCl₃) δ (ppm) 2.30 (s, 6H), 3.67 (br s, 2H), 5.14 (s, 2H), 6.69 (m, 1H), 6.91 (m, 1H), 6.97-6.99 (m, 2H), 7.17-7.23 (m, 4H), 7.27-7.36 (m, 5H), 7.62 (s, 1H), 8.90 (s, 1H).

Example 311

7-Benzyloxy-2-(2,6-dimethylanilino)-6-{3-[(2-morpholinopyridin-4-yl)carbonylamino]phenyl}quinazoline Compound 311

In a similar manner to Example 209, Compound 311 was obtained using Compound 310 and Compound A5.
¹H NMR (300 MHz, CDCl₃) δ (ppm) 2.30 (s, 6H), 3.60 (t, J=5.0 Hz, 4H), 3.84 (t, J=5.0 Hz, 4H), 5.19 (s, 2H), 6.86-6.90 (m, 1H), 7.09 (s, 1H), 7.12 (s, 1H), 7.17 (s, 3H), 7.23-7.47 (m, 7H), 7.68 (s, 1H), 7.62-7.70 (m, 1H), 7.78 (br s, 1H), 7.85 (br s, 1H), 8.93 (s, 1H).
ESI m/z (M+H)⁺ 637.

Example 312

2-(2,6-Dimethylanilino)-7-hydroxy-6-{3-[(2-morpholinopyridin-4-yl)carbonylamino]phenyl}quinazoline Compound 312

In a similar manner to Example 285, Compound 312 was obtained using Compound 311.
¹H NMR (270 MHz, DMSO-d₆) δ (ppm) 2.18 (s, 6H), 3.51-3.58 (m, 4H), 3.69-3.77 (m, 4H), 6.82 (s, 1H), 7.05-7.15 (m, 4H), 7.24 (s, 1H), 7.30-7.43 (m, 2H), 7.68 (s, 1H), 7.70-7.77 (m, 1H), 7.92-7.98 (m, 1H), 8.27 (d, J=5.1 Hz, 1H), 8.40 (s, 1H), 8.93 (s, 1H), 10.15 (s, 1H).
ESI m/z (M+H)⁺ 547.
m.p. 185° C.

Example 313

7-Benzyloxy-6-{3-[(3-dimethylaminophenyl)carbonylamino]phenyl}-2-(2,6-dimethylanilino)quinazoline Compound 313

In a similar manner to Example 209, Compound 313 was obtained using Compound 310 and 3-(dimethylamino)benzoic acid.
¹H NMR (300 MHz, CDCl₃) δ (ppm) 2.31 (s, 6H), 3.02 (s, 6H), 5.15 (s, 2H), 6.88 (dd, J=8.4, 2.4 Hz, 1H), 7.03 (s, 1H), 7.01-7.07 (m, 1H), 7.17 (s, 3H), 7.26-7.45 (m, 8H), 7.65-7.71 (m, 1H), 7.69 (s, 1H), 7.81 (br s, 1H), 7.84-7.88 (m, 1H), 8.92 (s, 1H).
ESI m/z (M+H)⁺ 594.

Example 314

6-{3-[(3-Dimethylaminophenyl)carbonylamino]phenyl}-2-(2,6-dimethylanilino)-7-hydroxyquinazoline Compound 314

In a similar manner to Example 285, Compound 314 was obtained using Compound 313.
¹H NMR (270 MHz, DMSO-d₆) δ (ppm) 2.18 (s, 6H), 2.97 (s, 6H), 6.81 (s, 1H), 6.86-6.95 (m, 1H), 7.09 (s, 3H), 7.21-7.42 (m, 6H), 7.68 (s, 1H), 7.71-7.77 (m, 1H), 7.96 (s, 1H), 8.37 (s, 1H), 8.92 (s, 1H), 9.95 (s, 1H).
ESI m/z (M+H)⁺ 504.

Example 315

2-Amino-7-benzyloxy-6-(5-cyclopropylcarbamoyl-2-methylphenyl)quinazoline

Compound 315

In a similar manner to Example 4, Compound 315 was obtained using Compound A14 and N-cyclopropyl-4-methyl-3-(4,4,5,5-tetramethyl-1,3,2-dioxaboran-2-yl)benzamide (WO03/093248).
¹H NMR (300 MHz, CDCl₃) δ (ppm) 0.54-0.64 (m, 2H), 0.80-0.90 (m, 2H), 2.18 (s, 3H), 2.83-2.94 (m, 1H), 5.15 (s, 2H), 5.27 (s, 2H), 6.38 (br s, 1H), 7.03 (s, 1H), 7.16-7.35 (m, 6H), 7.47 (s, 1H), 7.60 (d, J=2.4 Hz, 1H), 7.70 (dd, J=8.1, 2.4 Hz, 1H), 8.85 (s, 1H).

Example 316

7-Benzyloxy-6-(5-cyclopropylcarbamoyl-2-methylphenyl)-2-(2,6-dimethylanilino)quinazoline Compound 316

In a similar manner to Example 178, Compound 316 was obtained using Compound 315 and 2,6-dimethyliodobenzene.

$^1$H NMR (300 MHz, CDCl$_3$) δ (ppm) 0.53-0.64 (m, 2H), 0.79-0.93 (m, 2H), 2.18 (s, 3H), 2.31 (s, 6H), 2.82-2.93 (m, 1H), 5.02 (s, 2H), 6.23 (s, 1H), 6.97 (s, 1H), 7.12-7.37 (m, 9H), 7.46 (s, 1H), 7.54 (d, J=2.7 Hz, 1H), 7.68 (dd, J=7.8, 2.7 Hz, 1H), 8.87 (s, 1H).

Example 317

6-(5-Cyclopropylcarbamoyl-2-methylphenyl)-2-(2,6-dimethylanilino)-7-hydroxyquinazoline Compound 317

In a similar manner to Example 285, Compound 317 was obtained using Compound 316.

$^1$H NMR (270 MHz, DMSO-d$_6$) δ (ppm) 0.50-0.60 (m, 2H), 0.62-0.72 (m, 2H), 2.16 (s, 3H), 2.17 (s, 6H), 2.80-2.90 (m, 1H), 6.77 (br s, 1H), 7.07-7.14 (m, 3H), 7.33 (d, J=7.6 Hz, 1H), 7.53 (s, 1H), 7.65 (d, J=1.6 Hz, 1H), 7.74 (dd, J=7.6, 1.6 Hz, 1H), 8.32-8.40 (m, 1H), 8.92 (s, 1H).

ESI m/z (M+H)$^+$ 439.

m.p. 210-213° C.

Example 318

7-Benzyloxy-6-(5-cyclopropylcarbamoyl-2-methylphenyl)-2-(2,6-dichloroanilino)quinazoline Compound 318

In a similar manner to Example 178, Compound 318 was obtained using Compound 315 and 2,6-dichloroiodobenzene.

$^1$H NMR (300 MHz, CDCl$_3$) δ (ppm) 0.54-0.62 (m, 2H), 0.80-0.90 (m, 2H), 2.18 (s, 3H), 2.83-2.94 (m, 1H), 5.13 (s, 2H), 6.22 (s, 1H), 7.10 (s, 1H), 7.13-7.35 (m, 7H), 7.45 (d, J=8.1 Hz, 2H), 7.53 (s, 1H), 7.57 (d, J=2.1 Hz, 1H), 7.69 (dd, J=7.8, 2.1 Hz, 1H), 8.94 (s, 1H).

Example 319

6-(5-Cyclopropylcarbamoyl-2-methylphenyl)-2-(2,6-dichloroanilino)-7-hydroxyquinazoline Compound 319

In a similar manner to Example 186, Compound 319 was obtained using Compound 318.

$^1$H NMR (300 MHz, DMSO-d$_6$) δ (ppm) 0.50-0.60 (m, 2H), 0.61-0.71 (m, 2H), 2.16 (s, 3H), 2.79-2.88 (m, 1H), 6.84 (s, 1H), 7.30-7.40 (m, 2H), 7.53-7.62 (m, 3H), 7.64-7.67 (m, 1H), 7.72-7.77 (m, 1H), 8.37 (d, J=4.5 Hz, 1H), 8.97 (s, 1H), 9.22 (s, 1H).

ESI m/z (M+H)$^+$ 479.

m.p. 190-193° C.

Example 320

2-[(4-Amino-2,6-dichloro)anilino]-6-(5-cyclopropylcarbamoyl-2-methylphenyl)-7-hydroxyquinazoline Compound 320

In a similar manner to Example 178, 7-benzyloxy-6-(5-cyclopropylcarbamoyl-2-methylphenyl)-2-[(4-nitro-2,6-dichloro)anilino]quinazoline was obtained using Compound 315 and 4-nitro-2,6-dichloroiodobenzene. The obtained 7-benzyloxy-6-(5-cyclopropylcarbamoyl-2-methylphenyl)-2-[(4-nitro-2,6-dichloro)anilino]quinazoline (153 mg, 0.25 mmol) was dissolved in ethanol (2 mL) and DMF (0.5 mL) and the solution was added with zinc bromide (56 mg, 0.25 mmol) and 10% palladium on carbon (50% aqueous, 200 mg), followed by stirring at room temperature overnight under hydrogen atmosphere. After filtering off using Celite, the solvent was evaporated under reduced pressure. The residue was added with water and extracted with ethyl acetate. The organic layer was washed with water and saturated brine, and dried over anhydrous magnesium sulfate. The solvent was evaporated under reduced pressure to obtain Compound 320 (100 mg, 81%).

$^1$H NMR (300 MHz, DMSO-d$_6$) δ (ppm) 0.49-0.57 (m, 2H), 0.58-0.70 (m, 2H), 2.15 (s, 3H), 2.77-2.90 (m, 1H), 5.57-5.68 (m, 1H), 6.68 (s, 2H), 6.76 (br s, 1H), 7.32 (d, J=8.1 Hz, 1H), 7.54 (s, 1H), 7.65 (d, J=1.2 Hz, 1H), 7.74 (dd, J=8.1, 1.2 Hz, 1H), 8.35 (d, J=4.2 Hz, 1H), 8.68 (s, 1H), 8.93 (br s, 1H), 10.55 (s, 1H).

ESI m/z (M+H)$^+$ 494.

m.p. 207-210° C.

Example 321

7-Benzyloxy-6-(5-cyclopropylcarbamoyl-2-methylphenyl)-2-(isopropylamino)quinazoline Compound 321

In a similar manner to Example 4, Compound 321 was obtained using Compound A15 and N-cyclopropyl-4-methyl-3-(4,4,5,5-tetramethyl-1,3,2-dioxaboran-2-yl)benzamide (WO03/093248).

$^1$H NMR (270 MHz, CDCl$_3$) δ (ppm) 0.53-0.65 (m, 2H), 0.80-0.90 (m, 2H), 1.31 (d, J=6.5 Hz, 6H), 2.18 (s, 3H), 2.82-2.97 (m, 1H), 4.23-4.38 (m, 1H), 5.05-5.21 (m, 1H), 5.16 (s, 2H), 6.25 (s, 1H), 7.05 (s, 1H), 7.15-7.35 (m, 6H), 7.42 (s, 1H), 7.57 (d, J=1.9 Hz, 1H), 7.69 (dd, J=8.7, 1.9 Hz, 1H), 8.80 (s, 1H).

Example 322

6-(5-Cyclopropylcarbamoyl-2-methylphenyl)-7-hydroxy-2-(isopropylamino)quinazoline Compound 322

In a similar manner to Example 285, Compound 322 was obtained using Compound 321.

$^1$H NMR (300 MHz, DMSO-d$_6$) δ (ppm) 0.51-0.59 (m, 2H), 0.62-0.71 (m, 2H), 1.19 (d, J=6.3 Hz, 6H), 2.15 (s, 3H), 2.78-2.92 (m, 1H), 4.10-4.23 (m, 1H), 6.84 (s, 1H), 6.99-7.07

(m, 1H), 7.33 (d, J=7.5 Hz, 1H), 7.48 (s, 1H), 7.66 (d, J=1.8 Hz, 1H), 7.74 (dd, J=7.5, 1.8 Hz, 1H), 8.34-8.40 (m, 1H), 8.86 (s, 1H), 10.47 (s, 1H).
ESI m/z (M+H)+ 377.
m.p. 156-160° C.

Example 323

7-Benzyloxy-6-{5-[(3-dimethylaminophenyl)carbamoyl]-2-methylphenyl}-2-(isopropylamino)quinazoline Compound 323

In a similar manner to Example 4, Compound 323 was obtained using Compound A15 and Compound A41.
$^1$H NMR (270 MHz, CDCl$_3$) δ (ppm) 1.28 (d, J=6.5 Hz, 6H), 2.20 (s, 3H), 2.94 (s, 6H), 4.22-4.37 (m, 1H), 5.08-5.14 (m, 1H), 5.14 (s, 2H), 6.47-6.54 (m, 1H), 6.81-6.88 (m, 1H), 7.05 (s, 1H), 7.13-7.41 (m, 9H), 7.73 (d, J=1.9 Hz, 1H), 7.81 (dd, J=7.8, 1.9 Hz, 1H), 7.98 (br s, 1H), 8.77 (s, 1H).

Example 324

6-{5-[(3-Dimethylaminophenyl)carbamoyl]-2-methylphenyl}-7-hydroxy-2-(isopropylamino)quinazoline Compound 324

In a similar manner to Example 285, Compound 324 was obtained using Compound 323.
$^1$H NMR (270 MHz, DMSO-d$_6$) δ (ppm) 1.20 (d, J=6.5 Hz, 6H), 2.20 (s, 3H), 2.88 (s, 6H), 4.10-4.23 (m, 1H), 6.44-6.50 (m, 1H), 6.86 (s, 1H), 7.00-7.06 (m, 1H), 7.11 (t, J=8.1 Hz, 1H), 7.15-7.21 (m, 2H), 7.41 (d, J=7.8 Hz, 1H), 7.54 (s, 1H), 7.83 (d, J=2.2 Hz, 1H), 7.89 (dd, J=7.8, 2.2 Hz, 1H), 8.87 (s, 1H), 9.96 (s, 1H).
ESI m/z (M+H)+ 456.
m.p. 217-218° C.

Example 325

6-{3-[(3-Dimethylaminophenyl)carbamoyl]phenyl}-7-hydroxy-2-(isopropylamino)quinazoline Compound 325

In a similar manner to Example 4 and Example 285, Compound 325 was obtained using Compound A15 and Compound A42.
$^1$H NMR (300 MHz, DMSO-d$_6$) δ (ppm) 1.19 (d, J=6.6 Hz, 6H), 2.90 (s, 6H), 4.10-4.22 (m, 1H), 6.45-6.53 (m, 1H), 6.88 (s, 1H), 7.05-7.11 (m, 1H), 7.11-7.25 (m, 3H), 7.53-7.61 (m, 1H), 7.77 (s, 1H), 7.76-7.82 (m, 1H), 7.86-7.93 (m, 1H), 8.14 (s, 1H), 8.91 (s, 1H).
ESI m/z (M+H)+ 442.
m.p. 236° C.

Example 326

7-Hydroxy-2-isopropylamino-6-(naphthalen-1-yl)quinazoline

Compound 326

In a similar manner to Example 4 and Example 186, Compound 326 was obtained using Compound A15 and 1-naphthaleneboronic acid.

$^1$H NMR (300 MHz, CDCl$_3$) δ (ppm) 1.31 (d, J=6.3 Hz, 6H), 4.27-4.41 (m, 1H), 5.03-5.16 (m, 1H), 7.13 (s, 1H), 7.43-7.68 (m, 6H), 7.92-8.02 (m, 2H), 8.82 (s, 1H).
ESI m/z (M+H)+ 330.

Example 327

7-Benzyloxy-2-isopropylamino-6-{3-[(3-morpholinophenyl)carbamoyl]phenyl}quinazoline Compound 327

In a similar manner to Example 4, Compound 327 was obtained using Compound A15 and Compound A18.
$^1$H NMR (270 MHz, CDCl$_3$) δ (ppm) 1.31 (d, J=6.4 Hz, 6H), 3.17-3.20 (m, 4H), 3.84-3.87 (m, 4H), 4.25-4.37 (m, 1H), 5.11-5.14 (m, 1H), 5.23 (s, 2H), 6.70 (dd, J=8.2, 2.1 Hz, 1H), 6.79-6.82 (m, 1H), 7.10 (s, 1H), 7.19-7.37 (m, 6H), 7.47 (dd, J=2.0, 2.0 Hz, 1H), 7.53 (dd, J=7.7, 7.7 Hz, 1H), 7.60-7.61 (m, 1H), 7.75-7.79 (m, 2H), 7.86 (ddd, J=7.9, 1.3, 1.2 Hz, 1H), 8.06-8.07 (m, 1H), 8.84 (s, 1H).

Example 328

7-Hydroxy-2-isopropylamino-6-{3-[(3-morpholinophenyl)carbamoyl]phenyl}quinazoline Compound 328

In a similar manner to Example 285, Compound 328 was obtained using Compound 327.
$^1$H NMR (270 MHz, DMSO-d$_6$) δ (ppm) 1.18 (d, J=6.4 Hz, 6H), 3.07-3.10 (m, 4H), 3.72-3.76 (m, 4H), 4.12-4.20 (m, 1H), 6.70 (dd, J=8.3, 1.5 Hz, 1H), 6.87 (s, 1H), 7.06 (d, J=7.9 Hz, 1H), 7.18 (dd, J=8.3, 7.9 Hz, 1H), 7.30 (br s, 1H), 7.42 (s, 1H), 7.56 (dd, J=7.8, 7.8 Hz, 1H), 7.76-7.80 (m, 2H), 7.89 (d, J=7.8 Hz, 1H), 8.13 (s, 1H), 8.90 (s, 1H), 10.13 (s, 1H), 10.63 (br s, 1H).
ESI m/z (M+H)+ 484.
m.p. 248-249° C.

Example 329

7-Benzyloxy-2-isopropylamino-6-{3-[3-(pyrrolidin-1-yl)phenylcarbamoyl]phenyl}quinazoline Compound 329

In a similar manner to Example 4, Compound 329 was obtained using Compound A15 and Compound A19.
$^1$H NMR (270 MHz, CDCl$_3$) δ (ppm) 1.31 (d, J=6.4 Hz, 6H), 1.98-2.03 (m, 4H), 3.28-3.33 (m, 4H), 4.25-4.38 (m, 1H), 5.09-5.12 (m, 1H), 5.24 (s, 2H), 6.36 (dd, J=7.7, 2.0 Hz, 1H), 6.64 (dd, J=7.7, 2.0 Hz, 1H), 7.06 (dd, J=2.0, 2.0 Hz, 1H), 7.17 (dd, J=8.1, 8.1 Hz, 1H), 7.29-7.38 (m, 6H), 7.53 (dd, J=7.7, 7.7 Hz, 1H), 7.63 (s, 1H), 7.70 (br s, 1H), 7.76 (ddd, J=7.7, 1.4, 1.3 Hz, 1H), 7.86 (ddd, J=7.7, 1.4, 1.3 Hz, 1H), 8.08 (dd, J=1.4, 1.3 Hz, 1H), 8.85 (s, 1H).

Example 330

7-Hydroxy-2-isopropylamino-6-{3-[3-(pyrrolidin-1-yl)phenylcarbamoyl]phenyl}quinazoline Compound 330

In a similar manner to Example 285, Compound 330 was obtained using Compound 329.

¹H NMR (300 MHz, DMSO-d₆) δ (ppm) 1.20 (d, J=6.4 Hz, 6H), 1.94-1.98 (m, 4H), 3.20-3.24 (m, 4H), 4.11-4.23 (m, 1H), 6.28-6.32 (m, 1H), 6.88 (s, 1H), 7.06-7.12 (m, 4H), 7.56 (dd, J=7.9, 7.5 Hz, 1H), 7.77-7.80 (m, 2H), 7.89-7.91 (m, 1H), 8.14 (s, 1H), 8.92 (s, 1H), 10.07 (s, 1H), 10.63 (br s, 1H).
ESI m/z (M+H)⁺ 468.
elemental analysis: as $C_{28}H_{29}N_5O_2 \cdot 0.5H_2O$
calculated value (%); C=70.56, H=6.34, N=14.7
found value (%); C=70.53, H=6.02, N=14.53
m.p. 251-253° C.

Example 331

7-Benzyloxy-6-[3-(3-fluoro-5-morpholinobenzoylamino)phenyl]-2-(isopropylamino)quinazoline Compound 331

In a similar manner to Example 4, Compound 331 was obtained using Compound A15 and Compound A20.
¹H NMR (300 MHz, CDCl₃) δ (ppm) 1.31 (d, J=6.4 Hz, 6H), 3.21-3.24 (m, 4H), 3.84-3.87 (m, 4H), 5.08-5.10 (m, 1H), 5.23 (s, 2H), 6.70-6.75 (m, 1H), 6.88-6.92 (m, 1H), 7.06 (s, 1H), 7.21-7.22 (m, 1H), 7.25-7.42 (m, 7H), 7.62 (s, 1H), 7.67-7.71 (m, 1H), 7.73 (s, 1H), 7.80-7.81 (m, 1H), 8.83 (s, 1H).

Example 332

6-[3-(3-Fluoro-5-morpholinobenzoylamino)phenyl]-7-hydroxy-2-(isopropylamino)quinazoline Compound 332

In a similar manner to Example 285, Compound 332 was obtained using Compound 331.
¹H NMR (300 MHz, DMSO-d₆) δ (ppm) 1.19 (d, J=6.6 Hz, 6H), 3.23-3.26 (m, 4H), 3.74-3.77 (m, 4H), 4.13-4.20 (m, 1H), 6.86 (s, 1H), 6.98-7.04 (m, 2H), 7.16 (d, J=8.8 Hz, 1H), 7.31-7.33 (m, 2H), 7.40 (dd, J=8.1, 7.7 Hz, 1H), 7.66 (s, 1H), 7.76 (dd, J=7.7, 1.1 Hz, 1H), 7.95-7.96 (m, 1H), 8.90 (s, 1H), 10.24 (s, 1H), 10.55 (br s, 1H).
ESI m/z (M+H)⁺ 502.
m.p. 217-219° C.

Example 333

7-Benzyloxy-6-[3-(cyclopropylcarbamoyl)phenyl]-2-(isopropylamino)quinazoline

Compound 333

In a similar manner to Example 4, Compound 333 was obtained using Compound A15 and Compound A21.
¹H NMR (270 MHz, CDCl₃) δ (ppm) 0.49-0.55 (m, 2H), 0.59-0.65 (m, 2H), 1.31 (d, J=6.4 Hz, 6H), 2.83-2.94 (m, 1H), 4.25-4.38 (m, 1H), 5.09-5.11 (m, 1H), 5.22 (s, 2H), 7.08 (s, 1H), 7.34-7.49 (m, 6H), 7.61 (s, 1H), 7.69-7.76 (m, 1H), 7.91-7.99 (m, 2H), 8.85 (s, 1H).

Example 334

6-[3-(Cyclopropylcarbamoyl)phenyl]-7-hydroxy-2-(isopropylamino)quinazoline

Compound 334

In a similar manner to Example 285, Compound 334 was obtained using Compound 333.
¹H NMR (270 MHz, DMSO-d₆) δ (ppm) 0.55-0.61 (m, 2H), 0.65-0.74 (m, 2H), 1.19 (d, J=6.6 Hz, 6H), 2.82-2.92 (m, 1H), 4.10-4.23 (m, 1H), 6.86 (s, 1H), 7.02-7.05 (m, 1H), 7.48 (dd, J=7.6, 7.6 Hz, 1H), 7.70-7.78 (m, 3H), 8.00 (s, 1H), 8.46 (d, J=4.0 Hz, 1H), 8.89 (s, 1H), 10.67 (br s, 1H).
ESI m/z (M+H)⁺ 363.
m.p. 250° C. (decomp.).

Example 335

7-Benzyloxy-2-isopropylamino-6-{3-[2-(pyrrolidin-1-yl)pyridin-4-ylcarbonylamino]phenyl}quinazoline Compound 335

In a similar manner to Example 4, Compound 335 was obtained using Compound A16 and Compound A25.
¹H NMR (300 MHz, CDCl₃) δ (ppm) 1.31 (d, J=6.6 Hz, 6H), 2.01-2.06 (m, 4H), 3.49-3.53 (m, 4H), 4.26-4.37 (m, 1H), 5.08-5.14 (m, 1H), 5.24 (s, 2H), 6.75 (dd, J=5.1, 1.1 Hz, 1H), 6.83 (s, 1H), 7.06 (s, 1H), 7.24-7.42 (m, 7H), 7.62 (s, 1H), 7.67-7.70 (m, 1H), 7.81-7.83 (m, 1H), 7.85 (s, 1H), 8.27 (d, J=5.1 Hz, 1H), 8.84 (s, 1H).

Example 336

7-Hydroxy-2-isopropylamino-6-{3-[2-(pyrrolidin-1-yl)pyridin-4-ylcarbonylamino]phenyl}quinazoline Compound 336

In a similar manner to Example 285, Compound 336 was obtained using Compound 335.
¹H NMR (300 MHz, DMSO-d₆) δ (ppm) 1.19 (d, J=6.4 Hz, 6H), 1.95-1.99 (m, 4H), 3.43-3.48 (m, 4H), 4.11-4.22 (m, 1H), 6.87 (s, 1H), 6.90 (s, 1H), 7.00 (dd, J=5.1, 1.1 Hz, 1H), 7.05 (d, J=8.0 Hz, 1H), 7.32-7.34 (m, 1H), 7.41 (dd, J=8.0, 7.8 Hz, 1H), 7.66 (s, 1H), 7.75-7.78 (m, 1H), 7.97 (s, 1H), 8.21 (d, J=5.1 Hz, 1H), 8.90 (s, 1H), 10.33 (s, 1H), 10.57 (br s, 1H).
ESI m/z (M+H)⁺ 470.
elemental analysis: as $C_{27}H_{28}N_6O_2$
calculated value (%); C=69.21, H=6.02, N=17.94
found value (%); C=69.07, H=6.06, N=17.89
m.p. 248-249° C.

Example 337

7-Benzyloxy-2-isopropylamino-6-{5-[(2-methoxy-5-trifluoromethylphenyl)carbamoyl]-2-methylphenyl}quinazoline Compound 337

In a similar manner to Example 4, Compound 337 was obtained using Compound A15 and Compound A36.
¹H NMR (270 MHz, CDCl₃) δ (ppm) 1.32 (d, J=6.4 Hz, 6H), 2.17 (s, 3H), 2.24 (s, 3H), 4.26-4.38 (m, 1H), 5.11-5.14, (m, 1H), 5.20 (s, 2H), 6.96 (d, J=8.6 Hz, 1H), 7.09 (s, 1H), 7.20-7.29 (m, 5H), 7.35 (dd, J=8.6, 2.3 Hz, 1H), 7.40 (d, J=8.0

Hz, 1H), 7.48 (s, 1H), 7.77 (d, J=1.9 Hz, 1H), 7.83 (dd, J=8.0, 1.9 Hz, 1H), 8.57 (s, 1H), 8.83 (s, 1H), 8.90 (d, J=2.3 Hz, 1H).

Example 338

7-Hydroxy-2-isopropylamino-6-{5-[(2-methoxy-5-trifluoromethylphenyl)carbamoyl]-2-methylphenyl}quinazoline Compound 338

In a similar manner to Example 285, Compound 338 was obtained using Compound 337.
$^1$H NMR (300 MHz, DMSO-$d_6$) δ (ppm) 1.20 (d, J=6.4 Hz, 6H), 2.21 (s, 3H), 3.91 (s, 3H), 4.11-4.24 (m, 1H), 6.86 (s, 1H), 7.03 (d, J=7.9 Hz, 1H), 7.28 (d, J=8.8 Hz, 1H), 7.43 (d, J=8.1 Hz, 1H), 7.53-7.57 (m, 2H), 7.80 (d, J=1.8 Hz, 1H), 7.88 (dd, J=7.9, 2.2 Hz, 1H), 8.14 (d, J=2.2 Hz, 1H), 8.87 (s, 1H), 9.63 (s, 1H), 10.49 (s, 1H).
ESI m/z (M+H)$^+$ 511.
m.p. 280-281° C.

Example 339

7-Benzyloxy-2-isopropylamino-6-[3-(3-morpholinobenzoylamino)phenyl]quinazoline

Compound 339

In a similar manner to Example 4, Compound 339 was obtained using Compound A15 and Compound A22.
$^1$H NMR (300 MHz, CDCl$_3$) δ (ppm) 1.31 (d, J=6.4 Hz, 6H), 3.22-3.25 (m, 4H), 3.86-3.89 (m, 4H), 4.26-4.37 (m, 1H), 5.07-5.10 (m, 1H), 5.24 (s, 2H), 7.06 (s, 1H), 7.06-7.10 (m, 1H), 7.20-7.42 (m, 9H), 7.47-7.48 (m, 1H), 7.63 (s, 1H), 7.67-7.71 (m, 1H), 7.81 (s, 1H), 7.83-7.84 (m, 1H), 8.84 (s, 1H).

Example 340

7-Hydroxy-2-isopropylamino-6-[3-(3-morpholinobenzoylamino)phenyl]quinazoline

Compound 340

In a similar manner to Example 285, Compound 340 was obtained using Compound 339.
$^1$H NMR (270 MHz, DMSO-$d_6$) δ (ppm) 1.18 (d, J=6.7 Hz, 6H), 3.18 (m, 4H), 3.74-3.78 (m, 4H), 4.12-4.19 (m, 1H), 6.85 (s, 1H), 7.00 (d, J=8.1 Hz, 1H), 7.13-7.17 (m, 1H), 7.29 (d, J=7.6 Hz, 1H), 7.33-7.41 (m, 3H), 7.46-7.47 (m, 1H), 7.65 (s, 1H), 7.73-7.77 (m, 1H), 7.95-7.96 (m, 1H), 8.89 (s, 1H), 10.18 (s, 1H), 10.55 (br s, 1H).
ESI m/z (M+H)$^+$ 484.
elemental analysis: as $C_{28}H_{29}N_5O_3$ 0.2H$_2$O 0.3AcOEt
calculated value (%); C=68.29, H=6.24, N=13.64
found value (%); C=68.13, H=6.08, N=13.79
m.p. 230° C.

Example 341

7-Benzyloxy-2-isopropylamino-6-{3-[(2-morpholinopyridin-4-yl)carbamoyl]phenyl}quinazoline Compound 341

In a similar manner to Example 4, Compound 341 was obtained using Compound A16 and Compound A39.

$^1$H NMR (300 MHz, CDCl$_3$) δ (ppm) 1.31 (d, J=6.4 Hz, 6H), 3.51-3.54 (m, 4H), 3.80-3.84 (m, 4H), 4.25-4.36 (m, 1H), 5.10-5.12 (m, 1H), 5.24 (s, 2H), 6.46 (dd, J=5.7, 1.7 Hz, 1H), 7.10 (s, 1H), 7.25-7.38 (m, 6H), 7.56 (dd, J=7.9, 7.7 Hz, 1H), 7.61 (s, 1H), 7.78 (s, 1H), 7.78-7.87 (m, 2H), 8.05-8.06 (m, 1H), 8.09 (d, J=5.7 Hz, 1H), 8.84 (s, 1H).

Example 342

7-Hydroxy-2-isopropylamino-6-{3-[(2-morpholinopyridin-4-yl)carbamoyl]phenyl}quinazoline Compound 342

In a similar manner to Example 285, Compound 342 was obtained using Compound 341.
$^1$H NMR (270 MHz, DMSO-$d_6$) δ (ppm) 1.20 (d, J=6.6 Hz, 6H), 3.38-3.42 (m, 4H), 3.70-3.73 (m, 4H), 4.13-4.21 (m, 1H), 6.88 (s, 1H), 7.06 (d, J=8.1 Hz, 1H), 7.18 (dd, J=5.5, 1.2 Hz, 1H), 7.32 (d, J=1.2 Hz, 1H), 7.60 (dd, J=7.9, 7.6 Hz, 1H), 7.77 (s, 1H), 7.83 (d, J=7.9 Hz, 1H), 7.91 (d, J=7.6 Hz, 1H), 8.06 (d, J=5.5 Hz, 1H), 8.15 (s, 1H), 8.91 (s, 1H), 10.40 (s, 1H), 10.65 (br s, 1H).
ESI m/z (M+H)$^+$ 485.
m.p. 255-257° C.

Example 343

7-Benzyloxy-6-(5-cyclopropylcarbamoyl-3-fluoro-2-methylphenyl)-2-(isopropylamino)quinazoline Compound 343

In a similar manner to Example 4, Compound 343 was obtained using Compound A15 and N-cyclopropyl-5-fluoro-4-methyl-3-(4,4,5,5-tetramethyl-1,3,2-dioxaboran-2-yl)benzamide (WO03/093248).
$^1$H NMR (270 MHz, CDCl$_3$) δ (ppm) 0.55-0.61 (m, 2H), 0.80-0.85 (m, 2H), 1.30 (d, J=6.4, 6H), 2.08 (d, J=2.3 Hz, 3H), 2.82-2.92 (m, 1H), 4.25-4.37 (m, 1H), 5.15 (s, 2H), 5.15-5.19 (m, 1H), 6.39-6.43 (m, 1H), 7.05 (s, 1H), 7.17-7.21 (m, 2H), 7.27-7.30 (m, 3H), 7.37-7.40 (m, 2H), 7.48 (dd, J=10.0, 1.5 Hz, 1H), 8.79 (s, 1H).

Example 344

6-(5-Cyclopropylcarbamoyl-3-fluoro-2-methylphenyl)-7-hydroxy-2-(isopropylamino)quinazoline Compound 344

In a similar manner to Example 285, Compound 344 was obtained using Compound 343.
$^1$H NMR (300 MHz, DMSO-$d_6$) δ (ppm) 0.52-0.57 (m, 2H), 0.64-0.70 (m, 2H), 1.18 (d, J=6.6 Hz, 6H), 2.04 (d, J=2.2 Hz, 3H), 2.81-2.87 (m, 1H), 4.10-4.21 (m, 1H), 6.84 (s, 1H), 7.06 (d, J=8.1 Hz, 1H), 7.52 (s, 1H), 7.55 (s, 1H), 7.59 (dd, J=10.6, 1.5 Hz, 1H), 8.46 (d, J=4.0 Hz, 1H), 8.86 (s, 1H), 10.53 (s, 1H).
ESI m/z (M+H)$^+$ 395.
m.p. 175-177° C.

Example 345

7-Benzyloxy-2-isopropylamino-6-{2-methyl-5-[(2-morpholinopyridin-4-yl)carbonylamino]phenyl}quinazoline

Compound 345

In a similar manner to Example 4, Compound 345 was obtained using Compound A15 and Compound A23.

$^1$H NMR (270 MHz, CDCl$_3$) δ (ppm) 1.30 (d, J=6.4 Hz, 6H), 2.14 (s, 3H), 3.54-3.58 (m, 4H), 3.79-3.82 (m, 4H), 4.24-4.37 (m, 1H), 5.09-5.12 (m, 1H), 5.17 (s, 2H), 6.89 (d, J=5.1 Hz, 1H), 7.04 (s, 1H), 7.10 (s, 1H), 7.20-7.32 (m, 6H), 7.43 (s, 1H), 7.47 (d, J=2.0 Hz, 1H), 7.62 (dd, J=8.2, 2.0 Hz, 1H), 7.86-7.90 (m, 1H), 8.29 (d, J=5.1 Hz, 1H), 8.79 (s, 1H).

Example 346

7-Hydroxy-2-isopropylamino-6-{2-methyl-5-[(2-morpholinopyridin-4-yl)carbonylamino]phenyl}quinazoline

Compound 346

In a similar manner to Example 285, Compound 346 was obtained using Compound 345.

$^1$H NMR (270 MHz, DMSO-d$_6$) δ (ppm) 1.18 (d, J=6.3 Hz, 6H), 2.09 (s, 3H), 3.49-3.53 (m, 4H), 3.69-3.72 (m, 4H), 4.12-4.19 (m, 1H), 6.83 (s, 1H), 6.99 (d, J=8.2 Hz, 1H), 7.09-7.11 (m, 1H), 7.22-7.25 (m, 2H), 7.45 (s, 1H), 7.56 (s, 1H), 7.68 (d, J=8.2 Hz, 1H), 8.26 (d, J=5.0 Hz, 1H), 8.85 (s, 1H), 10.24 (s, 1H), 10.40 (br s, 1H).

ESI m/z (M+H)$^+$ 499.

elemental analysis: as C$_{28}$H$_{30}$N$_6$O$_3$ 0.6AcOEt
calculated value (%); C=66.21, H=6.36, N=15.24
found value (%); C=65.86, H=6.09, N=15.25
m.p. 169-172° C.

Example 347

7-Benzyloxy-6-{5-[(5-tert-butyl-2-methoxy-3-methylsulfonylaminophenyl)carbamoyl]-2-methylphenyl}-2-(isopropylamino)quinazoline

Compound 347

In a similar manner to Example 4, Compound 347 was obtained using Compound A15 and Compound A37.

$^1$H NMR (270 MHz, CDCl$_3$) δ (ppm) 1.32 (d, J=6.7 Hz, 6H), 1.34 (s, 9H), 2.24 (s, 3H), 3.06 (s, 3H), 3.77 (s, 3H), 4.26-4.38 (m, 1H), 5.11-5.14 (m, 1H), 5.20 (s, 2H), 6.76 (br s, 1H), 7.08 (s, 1H), 7.19-7.29 (m, 5H), 7.32-7.33 (m, 1H), 7.40 (d, J=8.2 Hz, 1H), 7.47 (s, 1H), 7.79 (s, 1H), 7.81-8.23 (m, 2H), 8.27 (d, J=2.0 Hz, 1H), 8.82 (s, 1H).

Example 348

6-{5-[(5-tert-Butyl-2-methoxy-3-methylsulfonylaminophenyl)carbamoyl]-2-methylphenyl}-7-hydroxy-2-(isopropylamino)quinazoline

Compound 348

In a similar manner to Example 285, Compound 348 was obtained using Compound 347.

$^1$H NMR (270 MHz, DMSO-d$_6$) δ (ppm) 1.19 (d, J=6.6 Hz, 6H), 1.26 (s, 9H), 2.21 (s, 3H), 3.04 (s, 3H), 3.70 (s, 3H), 4.13-4.21 (m, 1H), 6.86 (s, 1H), 7.02 (d, J=7.9 Hz, 1H), 7.23-7.24 (m, 1H), 7.40-7.44 (m, 2H), 7.53 (s, 1H), 7.82-7.83 (m, 1H), 7.89-7.92 (m, 1H), (s, 1H), 9.12 (br s, 1H), 9.79 (s, 1H), 10.48 (br s, 1H).

ESI m/z (M+H)$^+$ 592.
m.p. 251-253° C.

Example 349

7-Hydroxy-2-isopropylamino-6-{3-[(2-piperidinopyridin-4-yl)carbonylamino]phenyl}quinazoline

Compound 349

In a similar manner to Example 4 and Example 285, Compound 349 was obtained using Compound A16 and Compound A24.

$^1$H NMR (270 MHz, DMSO-d$_6$) δ (ppm) 1.18 (d, J=6.6 Hz, 6H), 1.56-1.59 (m, 6H), 3.57-3.61 (m, 4H), 4.12-4.22 (m, 1H), 6.85 (s, 1H), 7.02 (dd, J=5.1, 0.5 Hz, 1H), 7.04 (br s, 1H), 7.22-7.23 (m, 1H), 7.32 (d, J=7.9 Hz, 1H), 7.40 (dd, J=7.7, 7.7 Hz, 1H), (s, 1H), 7.74 (d, J=8.2 Hz, 1H), 7.95 (s, 1H), 8.23 (d, J=5.1 Hz, 1H), 8.89 (s, 1H), 10.32 (s, 1H), 10.55 (s, 1H).

ESI m/z (M+H)$^+$ 483.

elemental analysis: as C$_{28}$H$_{30}$N$_6$O$_2$
calculated value (%); C=69.69, H=6.27, N=17.41
found value (%); C=69.58, H=6.29, N=17.41
m.p. 226-227° C.

Example 350

7-Benzyloxy-6-{3-[3-fluoro-5-(pyrrolidin-1-yl)benzoylamino]phenyl}-2-(isopropylamino)quinazoline

Compound 350

In a similar manner to Example 4, Compound 350 was obtained using Compound A15 and Compound A26.

$^1$H NMR (270 MHz, CDCl$_3$) δ (ppm) 1.31 (d, J=6.6 Hz, 6H), 2.02-2.06 (m, 4H), 3.30-3.35 (m, 4H), 4.27-4.37 (m, 1H), 5.06-5.09 (m, 1H), 5.24 (s, 2H), 6.35-6.41 (m, 1H), 6.65-6.70 (m, 1H), 6.84 (s, 1H), 7.07 (s, 1H), 7.27-7.42 (m, 7H), 7.64 (s, 1H), 7.67-7.76 (m, 2H), 7.82 (s, 1H), 8.84 (s, 1H).

Example 351

6-{3-[3-Fluoro-5-(pyrrolidin-1-yl)benzoylamino]phenyl}-7-hydroxy-2-(isopropylamino)quinazoline

Compound 351

In a similar manner to Example 285, Compound 351 was obtained using Compound 350.

$^1$H NMR (270 MHz, DMSO-d$_6$) δ (ppm) 1.18 (d, J=6.7 Hz, 6H), 1.95-1.99 (m, 4H), 3.27-3.29 (m, 4H), 4.13-4.19 (m, 1H), 6.48-6.52 (m, 1H), 6.85 (s, 1H), 6.91-7.04 (m, 2H), 7.28-7.32 (m, 1H), 7.39 (dd, J=7.9, 7.9 Hz, 1H), 7.65 (s, 1H), 7.73-7.77 (m, 1H), 7.96-7.97 (m, 1H), 8.89 (s, 1H), 10.18 (s, 1H), 10.53 (s, 1H).

ESI m/z (M+H)$^+$ 486.
m.p. 229° C.

Example 352

7-Benzyloxy-2-isopropylamino-6-(5-methoxycarbamoyl-2-methylphenyl)quinazoline

Compound 352

In a similar manner to Example 4, Compound 352 was obtained using Compound A16 and Compound A33.

$^1$H NMR (270 MHz, CDCl$_3$) δ (ppm) 1.27 (d, J=6.4 Hz, 6H), 2.16 (s, 3H), 3.88 (s, 3H), 4.21-4.34 (m, 1H), 5.11 (s, 2H), 5.28-5.31 (m, 1H), 7.03 (s, 1H), 7.14-7.17 (m, 2H), 7.22-7.33 (m, 5H), 7.58 (d, J=1.5 Hz, 1H), 7.78 (dd, J=7.9, 1.5 Hz, 1H), 8.68 (s, 1H), 10.10 (br s, 1H).

ESI m/z (M+H)$^+$ 367.

Example 353

7-Hydroxy-2-isopropylamino-6-(5-methoxycarbamoyl-2-methylphenyl)quinazoline

Compound 353

In a similar manner to Example 285, Compound 353 was obtained using Compound 352.

$^1$H NMR (300 MHz, DMSO-d$_6$) δ (ppm) 1.20 (d, J=6.2 Hz, 6H), 2.17 (s, 3H), 3.69 (s, 3H), 4.11-4.20 (m, 1H), 6.84 (s, 1H), 7.03 (d, J=7.9 Hz, 1H), 7.36 (d, J=7.9 Hz, 1H), 7.49 (s, 1H), 7.57 (s, 1H), 7.66-7.70 (m, 1H), 8.86 (s, 1H), 10.47 (br s, 1H), 11.68 (br s, 1H).

ESI m/z (M+H)$^+$ 367.

m.p. 158-161° C.

Example 354

7-Benzyloxy-6-{3-[2-(4-fluorophenyl)pyridin-4-ylcarbonylamino]phenyl}-2-(isopropylamino)quinazoline

Compound 354

In a similar manner to Example 4, Compound 354 was obtained using Compound A15 and Compound A17.

$^1$H NMR (270 MHz, CDCl$_3$) δ (ppm) 1.31 (d, J=6.6 Hz, 6H), 4.26-4.38 (m, 1H), 5.07-5.10 (m, 1H), 5.25 (s, 2H), 7.08 (s, 1H), 7.16-7.22 (m, 2H), 7.27-7.33 (m, 2H), 7.35-7.40 (m, 2H), 7.45-7.46 (m, 2H), 7.55-7.57 (m, 1H), 7.64 (s, 1H), 7.83-7.85 (m, 2H), 8.04-8.09 (m, 2H), 8.11 (s, 2H), 8.84 (s, 1H), 8.85 (s, 1H).

Example 355

6-{3-[2-(4-Fluorophenyl)pyridin-4-ylcarbonylamino]phenyl}-7-hydroxy-2-(isopropylamino)quinazoline

Compound 355

In a similar manner to Example 285, Compound 355 was obtained using Compound 354.

$^1$H NMR (270 MHz, DMSO-d$_6$) δ (ppm) 1.18 (d, J=6.4 Hz, 6H), 4.12-4.20 (m, 1H), 6.86 (s, 1H), 7.02-7.05 (m, 1H), 7.34-7.47 (m, 4H), 7.67 (s, 1H), 7.78-7.82 (m, 2H), 7.99-8.00 (m, 1H), 8.22-8.27 (m, 2H), 8.41 (s, 1H), 8.84-8.86 (m, 1H), 8.90 (s, 1H), 10.56 (s, 1H), 10.60 (s, 1H).

ESI m/z (M+H)$^+$ 494.

m.p. 243-245° C.

Example 356

7-Benzyloxy-2-isopropylamino-6-{2-methyl-5-[5-methyl-2-(4-methylphenyl)-2H-pyrazol-3-ylcarbamoyl]phenyl}quinazoline

Compound 356

In a similar manner to Example 4, Compound 356 was obtained using Compound A15 and Compound A35.

$^1$H NMR (270 MHz, CDCl$_3$) δ (ppm) 1.31 (d, J=6.6 Hz, 6H), 2.20 (s, 3H), 2.35 (s, 3H), 2.38 (s, 3H), 4.26-4.38 (m, 1H), 5.13-5.16 (m, 3H), 6.65 (s, 1H), 7.06 (s, 1H), 7.15-7.18 (m, 2H), 7.24-7.41 (m, 9H), 7.58 (dd, J=8.2, 1.8 Hz, 1H), 7.67 (d, J=1.8 Hz, 1H), 7.94 (s, 1H), 8.80 (s, 1H).

Example 357

7-Hydroxy-2-isopropylamino-6-{2-methyl-5-[5-methyl-2-(4-methylphenyl)-2H-pyrazol-3-ylcarbamoyl]phenyl}quinazoline

Compound 357

In a similar manner to Example 285, Compound 357 was obtained using Compound 356.

$^1$H NMR (270 MHz, DMSO-d$_6$) δ (ppm) 1.19 (d, J=6.4 Hz, 6H), 2.19 (s, 3H), 2.23 (s, 3H), 2.29 (s, 3H), 4.10-4.23 (m, 1H), 6.22 (s, 1H), 6.84 (s, 1H), 7.03 (d, J=8.0 Hz, 1H), 7.21-7.24 (m, 2H), 7.36-7.40 (m, 3H), 7.50 (s, 1H), 7.70-7.71 (m, 1H), 7.78 (dd, J=8.0, 1.7 Hz, 1H), 8.86 (s, 1H), 10.20 (s, 1H), 10.49 (br s, 1H).

ESI m/z (M+H)$^+$ 507.

m.p. 173-175° C.

Example 358

7-Benzyloxy-6-{3-[5-tert-butyl-2-(4-methylphenyl)-2H-pyrazol-3-ylcarbonylamino]phenyl}-2-(isopropylamino)quinazoline

Compound 358

In a similar manner to Example 4, Compound 358 was obtained using Compound A15 and Compound A27.

$^1$H NMR (270 MHz, CDCl$_3$) δ (ppm) 1.30 (d, J=6.6 Hz, 6H), 1.37 (s, 9H), 2.35 (s, 3H), 4.24-4.37 (m, 1H), 5.15-5.18 (m, 1H), 5.20 (s, 2H), 6.70-6.71 (m, 1H), 7.04 (s, 1H), 7.19-7.22 (m, 2H), 7.29-7.46 (m, 10H), 7.55 (s, 1H), 7.55-7.65 (m, 2H), 8.81 (s, 1H).

Example 359

6-{3-[5-tert-Butyl-2-(4-methylphenyl)-2H-pyrazol-3-ylcarbonylamino]phenyl}-7-hydroxy-2-(isopropylamino)quinazoline

Compound 359

In a similar manner to Example 285, Compound 359 was obtained using Compound 358.

$^1$H NMR (300 MHz, DMSO-d$_6$) δ (ppm) 1.17 (d, J=6.2 Hz, 6H), 1.33 (s, 9H), 2.32 (s, 3H), 4.09-4.20 (m, 1H), 6.54 (s, 1H), 6.83 (s, 1H), 6.95 (s, 1H), 7.02 (d, J=8.1 Hz, 1H), 7.23-7.38 (m, 5H), 7.60 (s, 1H), 7.60-7.63 (m, 1H), 7.86 (s, 1H), 8.59 (s, 1H), 8.87 (s, 1H), 10.51 (s, 1H).
ESI m/z (M+H)+ 395.

Example 360

(S)-7-Benzyloxy-2-(sec-butylamino)-6-(5-cyclopropylcarbamoyl-2-methylphenyl)quinazoline Compound 360

In a similar manner to Reference Example 3 and Reference Example 4, (S)-7-benzyloxy-6-bromo-2-(sec-butylamino)quinazoline was obtained using Compound A14 and (S)-(+)-sec-butylamine. In a similar manner to Example 4, Compound 360 was obtained using the above-obtained (S)-7-benzyloxy-6-bromo-2-(sec-butylamino)quinazoline and N-cyclopropyl-4-methyl-3-(4,4,5,5-tetramethyl-1,3,2-dioxaboran-2-yl)benzamide (WO03/093248).

$^1$H NMR (270 MHz, CDCl$_3$) δ (ppm) 0.55-0.61 (m, 2H), 0.81-0.88 (m, 2H), 1.00 (t, J=7.2, 3H), 1.27 (d, J=6.4 Hz, 3H), 1.58-1.68 (m, 2H), 2.18 (s, 3H), 2.84-2.93 (m, 1H), 4.08-4.22 (m, 1H), 5.06-5.09 (m, 1H), 5.16 (s, 2H), 6.23 (s, 1H), 7.05 (s, 1H), 7.17-7.20 (m, 2H), 7.27-7.32 (m, 4H), 7.42 (s, 1H), 7.57 (d, J=1.6 Hz, 1H), 7.69 (dd, J=8.1, 1.6 Hz, 1H), 8.80 (s, 1H).

Example 361

(S)-2-(sec-Butylamino)-6-(5-cyclopropylcarbamoyl-2-methylphenyl)-7-hydroxyquinazoline Compound 361

In a similar manner to Example 285, Compound 361 was obtained using Compound 360.

$^1$H NMR (300 MHz, DMSO-d$_6$) δ (ppm) 0.53-0.58 (m, 2H), 0.64-0.70 (m, 2H), 0.90 (t, J=7.5 Hz, 3H), 1.16 (d, J=6.6 Hz, 3H), 1.46-1.64 (m, 2H), 2.15 (s, 3H), 2.80-2.88 (m, 1H), 3.97-4.06 (m, 1H), 6.85 (s, 1H), 7.33 (d, J=8.0 Hz, 1H), 7.49 (s, 1H), 7.65 (d, J=1.7 Hz, 1H), 7.74 (dd, J=8.0, 1.7 Hz, 1H), 8.13 (s, 1H), 8.37 (d, J=4.2 Hz, 1H), 8.87 (s, 1H), 10.45 (br s, 1H).
ESI m/z (M+H)+ 391.
m.p. 153° C.

Example 362

(S)-7-Benzyloxy-2-(sec-butylamino)-6-{3-[(2-morpholinopyridin-4-yl)carbonylamino]phenyl}quinazoline Compound 362

In a similar manner to Example 4, Compound 362 was obtained using (S)-7-benzyloxy-6-bromo-2-(sec-butylamino)quinazoline obtained in Example 360 and Compound A28.

$^1$H NMR (270 MHz, CDCl$_3$) δ (ppm) 1.00 (t, J=7.6 Hz, 3H), 1.27 (d, J=6.6 Hz, 3H), 1.59-1.68 (m, 2H), 3.57-3.61 (m, 4H), 3.81-3.85 (m, 4H), 4.11-4.22 (m, 1H), 5.04-5.08 (m, 1H), 5.24 (s, 2H), 6.88 (dd, J=5.1, 0.7 Hz, 1H), 7.06 (s, 1H), 7.12 (s, 1H), 7.28-7.43 (m, 7H), 7.62 (s, 1H), 7.65-7.71 (m, 1H), 7.78 (s, 1H), 7.82 (s, 1H), 8.32 (d, J=5.2 Hz, 1H), 8.83 (s, 1H).

Example 363

(S)-2-(sec-butylamino)-7-hydroxy-6-{3-[(2-morpholinopyridin-4-yl)carbonylamino]phenyl}quinazoline Compound 363

In a similar manner to Example 285, Compound 363 was obtained using Compound 362.

$^1$H NMR (270 MHz, DMSO-d$_6$) δ (ppm) 0.90 (t, J=7.6 Hz, 3H), 1.15 (d, J=6.3 Hz, 3H), 1.45-1.64 (m, 2H), 3.52-3.56 (m, 4H), 3.71-3.76 (m, 4H), 3.96-4.06 (m, 1H), 6.85 (s, 1H), 6.98-7.01 (m, 1H), 7.13-7.15 (m, 1H), 7.27 (s, 1H), 7.33 (dd, J=7.6, 1.2 Hz, 1H), 7.41 (dd, J=7.7, 7.6 Hz, 1H), 7.65 (s, 1H), 7.76 (d, J=7.7 Hz, 1H), 7.95 (s, 1H), 8.29 (d, J=5.3 Hz, 1H), 8.89 (s, 1H), 10.32 (s, 1H), 10.53 (br s, 1H).
ESI m/z (M+H)+ 499.
elemental analysis: as C$_{28}$H$_{30}$N$_6$O$_3$ 0.3H$_2$O
calculated value (%); C=66.73, H=6.12, N=16.68
found value (%); C=67.01, H=5.79, N=15.64
m.p. 183-184° C.

Example 364

7-Benzyloxy-6-(5-cyclopropylcarbamoyl-2-methylphenyl)-2-(3-pentylamino)quinazoline Compound 364

In a similar manner to Reference Example 3 and Reference Example 4, 7-benzyloxy-6-bromo-2-(3-pentylpropylamino)quinazoline was obtained using Compound A14 and 3-pentylamine. In a similar manner to Example 4, Compound 364 was obtained using the above-obtained 7-benzyloxy-6-bromo-2-(3-pentylamino)quinazoline and N-cyclopropyl-4-methyl-3-(4,4,5,5-tetramethyl-1,3,2-dioxaboran-2-yl)benzamide (WO03/093248).

$^1$H NMR (270 MHz, CDCl$_3$) δ (ppm) 0.55-0.61 (m, 2H), 0.82-0.88 (m, 2H), 0.98 (t, J=7.4 Hz, 6H), 1.51-1.70 (m, 4H), 2.18 (s, 3H), 2.85-2.92 (m, 1H), 4.02-4.15 (m, 1H), 5.00-5.04 (m, 1H), 5.16 (s, 2H), 6.18 (s, 1H), 7.03 (s, 1H), 7.16-7.20 (m, 2H), 7.26-7.32 (m, 4H), 7.42 (s, 1H), 7.56 (d, J=1.6 Hz, 1H), 7.68 (dd, J=7.7, 1.6 Hz, 1H), 8.80 (s, 1H).

Example 365

6-(5-Cyclopropylcarbamoyl-2-methylphenyl)-2-(3-pentylamino)-7-hydroxyquinazoline Compound 365

In a similar manner to Example 285, Compound 365 was obtained using Compound 364.

$^1$H NMR (270 MHz, DMSO-d$_6$) δ (ppm) 0.52-0.58 (m, 2H), 0.64-0.69 (m, 2H), 0.88 (t, J=7.4 Hz, 6H), 1.47-1.60 (m, 4H), 2.16 (s, 3H), 2.81-2.88 (m, 1H), 3.88-3.96 (m, 1H), 6.81 (s, 1H), 6.92-6.95 (m, 1H), 7.32 (d, J=8.0 Hz, 1H), 7.46 (s, 1H), 7.65 (d, J=1.2 Hz, 1H), 7.74 (dd, J=8.0, 1.2 Hz, 1H), 8.36 (d, J=3.9 Hz, 1H), 8.84 (s, 1H), 10.40 (s, 1H).
ESI m/z (M+H)+ 405.
elemental analysis: as C$_{24}$H$_{28}$N$_4$O$_2$
calculated value (%); C=71.26, H=6.98, N=13.85 found value (%); C=71.18, H=7.24, N=13.60
m.p. 210° C.

Example 366

6-{3-[(3-Dimethylaminophenyl)carbonylamino]phenyl}-2-(3-pentylamino)-7-hydroxyquinazoline Compound 366

In a similar manner to Example 4 and Example 285, Compound 366 was obtained using 7-benzyloxy-6-bromo-2-(3-pentylamino)quinazoline obtained in Example 364 and Compound A31.
$^1$H NMR (270 MHz, DMSO-$d_6$) δ (ppm) 0.88 (t, J=7.3 Hz, 6H), 1.47-1.61 (m, 4H), 2.97 (s, 6H), 3.91 (br s, 1H), 6.83 (s, 1H), 6.91-6.94 (m, 2H), 7.24-7.41 (m, 5H), 7.64 (s, 1H), 7.76 (d, J=8.4 Hz, 1H), 7.97 (s, 1H), 8.89 (s, 1H), 10.16 (s, 1H), 10.50 (s, 1H).
ESI m/z (M+H)$^+$ 470.
m.p. 152° C.

Example 367

7-Benzyloxy-2-(3-pentylamino)-6-{3-[(2-morpholinopyridin-4-yl)carbonylamino]phenyl}quinazoline Compound 367

In a similar manner to Example 4, Compound 367 was obtained using 7-benzyloxy-6-bromo-2-(3-pentylamino)quinazoline obtained in Example 364 and Compound A28.
$^1$H NMR (270 MHz, CDCl$_3$) δ (ppm) 0.97 (t, J=7.4 Hz, 6H), 1.48-1.78 (m, 4H), 3.57-3.61 (m, 4H), 3.81-3.84 (m, 4H), 4.02-4.15 (m, 1H), 5.02-5.06 (m, 1H), 5.23 (s, 2H), 6.88 (d, J=5.4 Hz, 1H), 7.04 (s, 1H), 7.12 (s, 1H), 7.30-7.43 (m, 7H), 7.61 (s, 1H), 7.65-7.71 (m, 1H), 7.81 (s, 1H), 7.81 (s, 1H), 8.32 (d, J=5.1 Hz, 1H), 8.83 (s, 1H).

Example 368

2-(3-Pentylamino)-7-hydroxy-6-{3-[(2-morpholinopyridin-4-yl)carbonylamino]phenyl}quinazoline Compound 368

In a similar manner to Example 285, Compound 368 was obtained using Compound 367.
$^1$H NMR (270 MHz, DMSO-$d_6$) δ (ppm) 0.88 (t, J=7.4 Hz, 6H), 1.47-1.60 (m, 4H), 3.52-3.55 (m, 4H), 3.58-3.65 (m, 1H), 3.71-3.75 (m, 4H), 6.83 (s, 1H), 6.94-6.97 (m, 1H), 7.14 (d, J=5.0 Hz, 1H), 7.27 (s, 1H), 7.33 (d, J=7.6 Hz, 1H), 7.41 (dd, J=7.7, 7.6 Hz, 1H), 7.64 (s, 1H), 7.76 (d, J=7.7 Hz, 1H), 7.95 (s, 1H), (d, J=5.0 Hz, 1H), 8.88 (s, 1H), 10.36 (br s, 1H), 10.52 (s, 1H).
ESI m/z (M+H)$^+$ 513.
m.p. 154-155° C.

Example 369

7-Benzyloxy-6-{3-[3-fluoro-5-(piperidino)benzoylamino]phenyl}-2-(isopropylamino)quinazoline Compound 369

In a similar manner to Example 4, Compound 369 was obtained using Compound A15 and Compound A29.
$^1$H NMR (270 MHz, CDCl$_3$) δ (ppm) 1.31 (d, J=6.2 Hz, 6H), 1.63-1.70 (m, 6H), 3.23-3.27 (m, 4H), 4.25-4.38 (m, 1H), 5.15-5.18 (m, 1H), (s, 2H), 6.70-6.75 (m, 1H), 6.80-6.83 (m, 1H), 7.06 (s, 1H), 7.20-7.41 (m, 8H), 7.63 (s, 1H), 7.67-7.72 (m, 2H), 7.81 (s, 1H), (s, 1H).

Example 370

6-{3-[3-Fluoro-5-(piperidino)benzoylamino]phenyl}-7-hydroxy-2-(isopropylamino)quinazoline Compound 370

In a similar manner to Example 285, Compound 370 was obtained using Compound 369.
$^1$H NMR (270 MHz, DMSO-$d_6$) δ (ppm) 1.19 (d, J=6.2 Hz, 6H), 1.54-1.67 (m, 6H), 3.26-3.32 (m, 4H), 4.10-4.23 (m, 1H), 6.86 (s, 1H), 6.92-6.96 (m, 1H), 7.01-7.09 (m, 2H), 7.30-7.33 (m, 2H), 7.39 (dd, J=8.3, 7.8 Hz, 1H), 7.66 (s, 1H), 7.74-7.77 (m, 1H), 7.95 (s, 1H), 8.90 (s, 1H), 10.21 (s, 1H), 10.53 (br s, 1H).
ESI m/z (M+H)$^+$ 500.
m.p. 215-217° C.

Example 371

7-Benzyloxy-2-isopropylamino-6-{3-[2-(pyrrolidin-1-yl)pyridin-4-ylcarbamoyl]phenyl}quinazoline Compound 371

In a similar manner to Example 4, Compound 371 was obtained using Compound A16 and Compound A40.
$^1$H NMR (300 MHz, DMSO-$d_6$) δ (ppm) 1.21 (d, J=6.6 Hz, 6H), 1.92-1.97 (m, 4H), 3.31-3.37 (m, 4H), 4.16-4.26 (m, 1H), 5.31 (s, 2H), 7.01-7.09 (m, 3H), 7.22-7.35 (m, 4H), 7.43-7.46 (m, 2H), 7.56-7.61 (m, 1H), 7.81-7.84 (m, 2H), 7.90-7.99 (m, 2H), 8.22 (s, 1H), 8.99 (s, 1H), 10.33 (s, 1H).

Example 372

7-Hydroxy-2-isopropylamino-6-{3-[2-(pyrrolidin-1-yl)pyridin-4-ylcarbamoyl]phenyl}quinazoline Compound 372

In a similar manner to Example 285, Compound 372 was obtained using Compound 371.
$^1$H NMR (270 MHz, DMSO-$d_6$) δ (ppm) 1.19 (d, J=6.5 Hz, 6H), 1.92-1.97 (m, 4H), 3.34-3.37 (m, 4H), 4.11-4.22 (m, 1H), 6.87 (s, 1H), 6.99-7.01 (m, 2H), 7.04-7.07 (m, 1H), 7.55-7.60 (m, 1H), 7.76 (s, 1H), 7.81 (d, J=7.5 Hz, 1H), 7.90 (d, J=7.8 Hz, 1H), 7.95 (d, J=5.1 Hz, 1H), 8.13 (s, 1H), 8.90 (s, 1H), 10.31 (s, 1H), 10.63 (s, 1H).
ESI m/z (M+H)$^+$ 469.
m.p. 275-279° C.

Example 373

7-Benzyloxy-2-isopropylamino-6-{3-[2-(4-methylpiperazin-1-yl)pyridin-4-ylcarbonylamino]phenyl}quinazoline Compound 373

In a similar manner to Example 4, Compound 373 was obtained using Compound A15 and Compound A30.

¹H NMR (270 MHz, CDCl₃) δ (ppm) 1.30 (d, J=6.5 Hz, 6H), 2.35 (s, 3H), 2.51-2.54 (m, 4H), 3.63-3.67 (m, 4H), 4.25-4.36 (m, 1H), 5.07-5.10 (m, 1H), 5.24 (s, 2H), 6.83-6.85 (m, 1H), 7.07-7.13 (m, 2H), 7.25-7.44 (m, 5H), 7.59-7.73 (m, 4H), 7.79-7.83 (m, 2H), 8.30 (d, J=5.1 Hz, 1H), 8.84 (s, 1H).

Example 374

7-Hydroxy-2-isopropylamino-6-{3-[2-(4-methylpiperazin-1-yl)pyridin-4-ylcarbonylamino]phenyl}quinazoline Compound 374

In a similar manner to Example 285, Compound 374 was obtained using Compound 373.
¹H NMR (270 MHz, DMSO-d₆) δ (ppm) 1.18 (d, J=6.7 Hz, 6H), 2.23 (s, 3H), 2.40-2.44 (m, 4H), 3.54-3.58 (m, 4H), 4.10-4.20 (m, 1H), 6.86 (s, 1H), 7.00-7.09 (m, 1H), 7.26 (s, 1H), 7.31-7.34 (m, 1H), 7.40 (dd, J=7.5, 7.5 Hz, 1H), 7.65 (s, 1H), 7.74-7.77 (m, 1H), 7.95 (s, 1H), 8.15 (s, 1H), 8.25 (d, J=5.1 Hz, 1H), 8.89 (s, 1H), 10.34 (br s, 1H).
ESI m/z (M+H)⁺ 498.
m.p. 178° C.

Example 375

7-Benzyloxy-2-isopropylamino-6-{3-[3-(pyrrolidin-1-yl)benzoylamino]phenyl}quinazoline Compound 375

In a similar manner to Example 4, Compound 375 was obtained using Compound A15 and Compound A32.
¹H NMR (270 MHz, CDCl₃) δ (ppm) 1.30 (d, J=6.5 Hz, 6H), 2.00-2.04 (m, 4H), 3.31-3.36 (m, 4H), 4.20-4.37 (m, 1H), 5.07-5.10 (m, 1H), 5.23 (s, 2H), 6.69-6.73 (m, 1H), 6.98-7.01 (m, 1H), 7.06-7.09 (m, 3H), 7.26-7.40 (m, 7H), 7.63 (s, 1H), 7.67-7.71 (m, 1H), 7.81-7.85 (m, 2H), 8.84 (s, 1H).

Example 376

7-Hydroxy-2-isopropylamino-6-{3-[3-(pyrrolidin-1-yl)benzoylamino]phenyl}quinazoline Compound 376

In a similar manner to Example 285, Compound 376 was obtained using Compound 375.
¹H NMR (270 MHz, DMSO-d₆) δ (ppm) 1.18 (d, J=6.5 Hz, 6H), 1.95-2.00 (m, 4H), 3.27-3.32 (m, 4H), 4.10-4.22 (m, 1H), 6.72 (dd, J=7.7, 1.9 Hz, 1H), 6.85 (s, 1H), 7.02 (d, J=7.7 Hz, 1H), 7.05 (s, 1H), 7.16-7.19 (m, 1H), 7.26-7.31 (m, 2H), 7.37 (dd, J=7.7, 7.7 Hz, 1H), 7.65 (s, 1H), 7.75 (d, J=7.7 Hz, 1H), 7.97 (s, 1H), 8.89 (s, 1H), 10.13 (s, 1H), 10.53 (s, 1H).
ESI m/z (M+H)⁺ 468.
m.p. 235-236° C.

Example 377

7-Benzyloxy-6-(5-carbamoyl-2-methylphenyl)-2-(isopropylamino)quinazoline

Compound 377

In a similar manner to Example 4, Compound 377 was obtained using Compound A15 and Compound A38.
¹H NMR (270 MHz, CDCl₃) δ (ppm) 1.31 (d, J=6.5 Hz, 6H), 2.21 (s, 3H), 4.28-4.38 (m, 1H), 5.08-5.11 (m, 1H), 5.18 (s, 2H), 7.06 (s, 1H), 7.17-7.21 (m, 1H), 7.26-7.36 (m, 5H), 7.44 (s, 1H), 7.68-7.69 (m, 1H), 7.72-7.77 (m, 1H), 8.81 (s, 1H).

Example 378

6-(5-Carbamoyl-2-methylphenyl)-7-hydroxy-2-(isopropylamino)quinazoline

Compound 378

In a similar manner to Example 285, Compound 378 was obtained using Compound 377.
¹H NMR (270 MHz, DMSO-d₆) δ (ppm) 1.18 (d, J=6.7 Hz, 6H), 2.15 (s, 3H), 4.10-4.22 (m, 1H), 6.83 (s, 1H), 6.99 (d, J=7.5 Hz, 1H), 7.24 (br s, 1H), 7.32 (d, J=7.8 Hz, 1H), 7.48 (s, 1H), 7.70 (s, 1H), 7.76-7.79 (m, 1H), 7.91 (br s, 1H), 8.85 (s, 1H), 10.44 (s, 1H).
ESI m/z (M+H)⁺ 337.
m.p. 235-236° C.

Example 379

7-Benzyloxy-6-(5-ethoxycarbamoyl-2-methylphenyl)-2-(isopropylamino)quinazoline

Compound 379

In a similar manner to Example 4, Compound 379 was obtained using Compound A16 and Compound A34.
¹H NMR (270 MHz, CDCl₃) δ (ppm) 1.30 (d, J=6.5 Hz, 6H), 1.33 (t, J=7.2 Hz, 3H), 2.17 (s, 3H), 4.09 (q, J=7.2 Hz, 2H), 4.24-4.36 (m, 1H), 5.15-5.19 (m, 3H), 7.05 (s, 1H), 7.17-7.20 (m, 2H), 7.26-7.37 (m, 5H), 7.58 (s, 1H), 7.71 (dd, J=7.8, 1.6 Hz, 1H), 8.76 (s, 1H), 9.08 (br s, 1H).

Example 380

6-(5-Ethoxycarbamoyl-2-methylphenyl)-7-hydroxy-2-(isopropylamino)quinazoline

Compound 380

In a similar manner to Example 285, Compound 380 was obtained using Compound 379.
¹H NMR (270 MHz, DMSO-d₆) δ (ppm) 1.17-1.20 (m, 9H), 2.16 (s, 3H), 3.90 (q, J=7.1 Hz, 2H), 4.13-4.20 (m, 1H), 6.84 (s, 1H), 7.35 (d, J=8.1 Hz, 1H), 7.48 (s, 1H), 7.57 (s, 1H), 7.66 (d, J=8.1 Hz, 1H), 8.85 (s, 1H), 10.46 (br s, 1H), 11.56 (br s, 1H).
ESI m/z (M+H)⁺ 381.
elemental analysis: as C₂₁H₂₄N₄O₃ 0.9H₂O 0.1 Hexane
calculated value (%); C=64.01, H=6.76, N=13.82
found value (%); C=63.88, H=6.78, N=13.70
m.p. 157° C.

Example 381

7-Benzyloxy-2-(3-pentylamino)-6-{3-[2-(pyrrolidin-1-yl)pyridin-4-ylcarbonylamino]phenyl}quinazoline Compound 381

In a similar manner to Example 4, Compound 381 was obtained using 7-benzyloxy-6-bromo-2-(3-pentylamino)quinazoline obtained in Example 364 and Compound A43.

¹H NMR (300 MHz, CDCl₃) δ (ppm) 0.98 (t, J=7.5 Hz, 6H), 1.53-1.66 (m, 4H), 2.03-2.04 (m, 4H), 3.49-3.53 (m, 4H), 4.09-4.11 (m, 1H), 5.01-5.05 (m, 1H), 5.24 (s, 2H), 6.74-6.76 (m, 1H), 6.83 (s, 1H), 7.04 (s, 1H), 7.28-7.42 (m, 7H), 7.62 (s, 1H), 7.67-7.70 (m, 1H), 7.78-7.79 (m, 1H), 7.83 (s, 1H), 8.27 (d, J=5.1 Hz, 1H), 8.83 (s, 1H).

Example 382

2-(3-Pentylamino)-7-hydroxy-6-{3-[2-(pyrrolidin-1-yl)pyridin-4-ylcarbonylamino]phenyl}quinazoline Compound 382

In a similar manner to Example 285, Compound 382 was obtained using Compound 381.
¹H NMR (270 MHz, DMSO-d₆) δ (ppm) 0.87 (t, J=7.3 Hz, 6H), 1.46-1.57 (m, 4H), 1.95-1.98 (m, 4H), 3.42-3.44 (m, 4H), 3.87-3.94 (m, 1H), 6.81 (s, 1H), 6.88-7.00 (m, 3H), 7.30-7.33 (m, 1H), 7.63 (s, 1H), 7.37-7.42 (m, 1H), 7.73-7.76 (m, 1H), 7.95 (s, 1H), 8.20 (d, J=5.1 Hz, 1H), 8.86 (br s, 1H), 10.31 (s, 1H).
ESI m/z (M+H)⁺ 497.
m.p. 194° C.

Example 383

(S)-7-Benzyloxy-2-(sec-butylamino)-6-{3-[2-(pyrrolidin-1-yl)pyridin-4-ylcarbonylamino]phenyl}quinazoline Compound 383

In a similar manner to Example 4, Compound 383 was obtained using (S)-7-benzyloxy-6-bromo-2-(sec-butylamino)quinazoline obtained in Example 360 and Compound A43.
¹H NMR (300 MHz, CDCl₃) δ (ppm) 1.00 (t, J=7.5 Hz, 3H), 1.27 (d, J=5.9 Hz, 3H), 1.59-1.65 (m, 2H), 2.01-2.05 (m, 4H), 3.48-3.50 (m, 4H), 4.12-4.21 (m, 1H), 5.11-5.14 (m, 1H), 5.23 (s, 2H), 6.75 (dd, J=5.3, 1.5 Hz, 1H), 6.82 (s, 1H), 7.05 (s, 1H), 7.28-7.42 (m, 7H), 7.61 (s, 1H), 7.66-7.70 (m, 1H), 7.84-7.86 (m, 2H), 8.26 (d, J=5.3 Hz, 1H), 8.83 (s, 1H).

Example 384

(S)-2-(sec-Butylamino)-7-hydroxy-6-{3-[2-(pyrrolidin-1-yl)pyridin-4-ylcarbonylamino]phenyl}quinazoline Compound 384

In a similar manner to Example 285, Compound 384 was obtained using Compound 383.
¹H NMR (270 MHz, DMSO-d₆) δ (ppm) 0.89 (t, J=7.5 Hz, 3H), 1.13-1.16 (m, 3H), 1.49-1.58 (m, 2H), 1.94-1.98 (m, 4H), 3.42-3.46 (m, 4H), 3.98-4.03 (m, 1H), 6.83 (s, 1H), 6.88 (s, 1H), 6.98-7.00 (m, 2H), 7.31-7.40 (m, 2H), 7.64 (s, 1H), 7.73-7.76 (m, 1H), 7.95 (s, 1H), 8.20 (d, J=5.1 Hz, 1H), 8.88 (s, 1H), 10.31 (s, 1H).
ESI m/z (M+H)⁺ 483.
m.p. 165-168° C.

Example 385

7-Benzyloxy-2-isopropylamino-6-{3-[3-(piperidino)benzoylamino]phenyl}quinazoline Compound 385

In a similar manner to Example 4, Compound 385 was obtained using Compound A15 and Compound A44.
¹H NMR (270 MHz, CDCl₃) δ (ppm) 1.30 (d, J=6.5 Hz, 6H), 1.59-1.71 (m, 6H), 3.21-3.25 (m, 4H), 4.24-4.37 (m, 1H), 5.09-5.11 (m, 1H), 5.22 (s, 2H), 7.05-7.10 (m, 2H), 7.15-7.46 (m, 10H), 7.62 (s, 1H), 7.66-7.70 (m, 1H), 7.84-7.86 (m, 2H), 8.83 (s, 1H).

Example 386

7-Hydroxy-2-isopropylamino-6-{3-[3-(piperidino)benzoylamino]phenyl}quinazoline

Compound 386

In a similar manner to Example 285, Compound 386 was obtained using Compound 385.
¹H NMR (270 MHz, DMSO-d₆) δ (ppm) 1.18 (d, J=6.7 Hz, 6H), 1.56-1.64 (m, 6H), 3.19-3.23 (m, 4H), 4.11-4.22 (m, 1H), 6.85 (s, 1H), 7.02 (d, J=8.6 Hz, 1H), 7.10-7.16 (m, 1H), 7.27-7.45 (m, 5H), 7.65 (s, 1H), 7.76 (d, J=7.3 Hz, 1H), 7.96 (s, 1H), 8.89 (s, 1H), 10.17 (s, 1H), 10.53 (br s, 1H).
ESI m/z (M+H)⁺ 482.
m.p. 230° C.

Example 387

7-Benzyloxy-6-{3-[2-(4-fluoro-2-methylphenyl)pyridin-4-ylcarbonylamino]phenyl}-2-(isopropylamino)quinazoline Compound 387

In a similar manner to Example 4, Compound 387 was obtained using Compound A15 and Compound A45.
¹H NMR (270 MHz, CDCl₃) δ (ppm) 1.30 (d, J=6.7 Hz, 6H), 2.38 (s, 3H), 4.25-4.37 (m, 1H), 5.08-5.11 (m, 1H), 5.23 (s, 2H), 6.96-7.07 (m, 4H), 7.22-7.45 (m, 7H), 7.61-7.90 (m, 6H), 8.83-8.86 (m, 2H).

Example 388

6-{3-[2-(4-Fluoro-2-methylphenyl)pyridin-4-ylcarbonylamino]phenyl}-7-hydroxy-2-(isopropylamino)quinazoline Compound 388

In a similar manner to Example 285, Compound 388 was obtained using Compound 387.
¹H NMR (300 MHz, DMSO-d₆) δ (ppm) 1.19 (d, J=6.6 Hz, 6H), 2.38 (s, 3H), 4.11-4.20 (m, 1H), 6.86 (s, 1H), 7.04-7.06 (m, 1H), 7.15-7.25 (m, 2H), 7.35 (d, J=7.8 Hz, 1H), 7.43 (dd, J=7.8, 7.8 Hz, 1H), 7.55 (dd, J=8.4, 6.3 Hz, 1H), 7.66 (s, 1H), 7.78-7.81 (m, 1H), 7.86 (dd, J=5.1, 1.5 Hz, 1H), 7.99 (s, 1H), 8.02 (s, 1H), 8.86 (d, J=5.1 Hz, 1H), 8.90 (s, 1H), 10.56-10.57 (m, 2H).
ESI m/z (M+H)⁺ 508.

Example 389

7-(3-Hydroxyphenyl)-2-isopropylamino-6-{3-[(2-piperidinopyridin-4-yl)carbonylamino]phenyl}quinazoline Compound 389

In a similar manner to Example 41, Compound 389 was obtained using Compound 349 and 3-hydroxyphenylboronic acid.

ESI m/z (M+H)$^+$ 559.

Example 390

6-(5-Cyclopropylcarbamoyl-2-methylphenyl)-7-(4-hydroxyphenyl)-2-isopropylaminoquinazoline Compound 390

In a similar manner to Example 41, Compound 390 was obtained using Compound 322 and 4-hydroxyphenylboronic acid.

ESI m/z (M+H)$^+$ 453.

Example 391

2-(Isoquinolin-5-ylamino)-6,7-bis(4-trifluoromethylphenyl)quinazoline

Compound 391

In a similar manner to Example 4, 2-amino-7-benzyloxy-6-(4-trifluoromethylphenyl)quinazoline was obtained using Compound A14 and 4-trifluoromethylphenylboronic acid. In a similar manner to Reference Example 3 and Example 16, 7-benzyloxy-2-(isoquinolin-5-ylamino)-6-(4-trifluoromethylphenyl)quinazoline was obtained using the above-obtained 2-amino-7-benzyloxy-6-(4-trifluoromethylphenyl)quinazoline and isoquinolin-5-ylamine. In a similar manner to Example 285 and Example 41, Compound 391 was obtained using the above-obtained 7-benzyloxy-2-(isoquinolin-5-ylamino)-6-(4-trifluoromethylphenyl)quinazoline and 4-trifluoromethylphenylboronic acid.

ESI m/z (M+H)$^+$ 561.

Example 392

2-Isopropylamino-6-{3-[(2-piperidinopyridin-4-yl)carbonylamino]phenyl}-7-(3-pyridyl)quinazoline Compound 392

In a similar manner to Example 41, Compound 392 was obtained using Compound 349 and 3-pyridylboronic acid.

ESI m/z (M+H)$^+$ 544.

INDUSTRIAL APPLICABILITY

The present invention provides 2-aminoquinazoline derivatives having p38MAP kinase inhibitory activity 1, and the like.

The invention claimed is:

1. A 2-aminoquinazoline compound represented by formula (I):

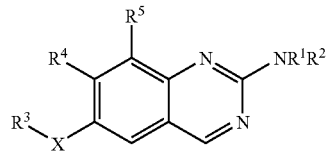

wherein $R^1$ and $R^2$ may be the same or different and each represents a hydrogen atom, substituted or unsubstituted lower alkyl, substituted or unsubstituted lower alkenyl, substituted or unsubstituted lower alkynyl, substituted or unsubstituted cycloalkyl, substituted or unsubstituted cycloalkenyl, substituted or unsubstituted lower alkanoyl, substituted or unsubstituted cycloalkylcarbonyl, substituted or unsubstituted aryl, a substituted or unsubstituted heterocyclic group, or CONR$^{6a}$R$^{6b}$ wherein R$^{6a}$ and R$^{6b}$ may be the same or different and each represents a hydrogen atom or substituted or unsubstituted lower alkyl;

X represents a bond or CR$^{7a}$R$^{7b}$ wherein R$^{7a}$ and R$^{7b}$ may be the same or different and each represents a hydrogen atom, halogen, hydroxy, substituted or unsubstituted lower alkyl, or substituted or unsubstituted lower alkoxy, or R$^{7a}$ and R$^{7b}$ are combined to form an oxygen atom;

when X is a bond, R$^3$ represents substituted or unsubstituted aryl or a substituted or unsubstituted aromatic heterocyclic group;

when X is CR$^{7a}$R$^{7b}$ wherein R$^{7a}$ and R$^{7b}$ have the same meanings as defined above, respectively, R$^3$ represents substituted or unsubstituted lower alkoxy, substituted or unsubstituted aryl, a substituted or unsubstituted aromatic heterocyclic group, or NR$^{8a}$R$^{8b}$ wherein R$^{8a}$ and R$^{8b}$ may be the same or different and each represents a hydrogen atom, substituted or unsubstituted lower alkyl, substituted or unsubstituted lower alkenyl, substituted or unsubstituted lower alkynyl, substituted or unsubstituted cycloalkyl, substituted or unsubstituted lower alkoxy, substituted or unsubstituted aryl, or a substituted or unsubstituted heterocyclic group; or R$^{8a}$ and R$^{8b}$ are combined together with the adjacent nitrogen atom thereto to form a substituted or unsubstituted heterocyclic group;

R$^4$ represents hydroxy or substituted or unsubstituted lower alkoxy; and

R$^5$ represents a hydrogen atom, halogen, hydroxy, substituted or unsubstituted lower alkyl, substituted or unsubstituted lower alkenyl, substituted or unsubstituted lower alkoxy, substituted or unsubstituted aryl, a substituted or unsubstituted heterocyclic group, CONR$^{11a}$R$^{11b}$ wherein R$^{11a}$ and R$^{11b}$ may be the same or different and each represents a hydrogen atom, substituted or unsubstituted lower alkyl, substituted or unsubstituted lower alkenyl, substituted or unsubstituted lower alkynyl, substituted or unsubstituted cycloalkyl, substituted or unsubstituted lower alkoxy, substituted or unsubstituted aryl, or a substituted or unsubstituted heterocyclic group; or R$^{11a}$ and R$^{11b}$ are combined together with the adjacent nitrogen atom thereto to form a substituted or unsubstituted heterocyclic group, respectively, or $COR^{12}$ wherein $R^{12}$ represents a hydrogen atom, hydroxy, substituted or unsubstituted lower alkyl, substituted or unsubstituted lower alkenyl, substituted or unsubstituted lower alkynyl, substituted or unsubstituted cycloalkyl, substituted or unsubstituted lower alkoxy, substituted or unsubstituted aryl, or a substituted or unsubstituted heterocyclic group, or a pharmaceutically acceptable salt thereof.

2. A 2-aminoquinazoline compound represented by formula (I):

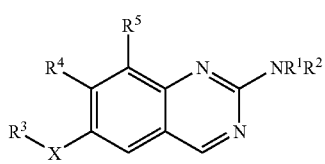

(I)

wherein $R^1$ and $R^2$ may be the same or different and each represents a hydrogen atom, substituted or unsubstituted lower alkyl, substituted or unsubstituted lower alkenyl, substituted or unsubstituted lower alkynyl, substituted or unsubstituted cycloalkyl, substituted or unsubstituted cycloalkenyl, substituted or unsubstituted lower alkanoyl, substituted or unsubstituted cycloalkylcarbonyl, substituted or unsubstituted aryl, a substituted or unsubstituted heterocyclic group, or $CONR^{6a}R^{6b}$ wherein $R^{6a}$ and $R^{6b}$ may be the same or different and each represents a hydrogen atom or substituted or unsubstituted lower alkyl;

X represents a bond or $CR^{7a}R^{7b}$ wherein $R^{7a}$ and $R^{7b}$ may be the same or different and each represents a hydrogen atom, halogen, hydroxy, substituted or unsubstituted lower alkyl, or substituted or unsubstituted lower alkoxy, or $R^{7a}$ and $R^{7b}$ are combined to form an oxygen atom;

when X is a bond, $R^3$ represents substituted or unsubstituted aryl or a substituted or unsubstituted aromatic heterocyclic group;

when X is $CR^{7a}R^{7b}$ wherein $R^{7a}$ and $R^{7b}$ have the same meanings as defined above, respectively, $R^3$ represents substituted or unsubstituted lower alkoxy, substituted or unsubstituted aryl, a substituted or unsubstituted aromatic heterocyclic group, or $NR^{8a}R^{8b}$ wherein $R^{8a}$ and $R^{8b}$ may be the same or different and each represents a hydrogen atom, substituted or unsubstituted lower alkyl, substituted or unsubstituted lower alkenyl, substituted or unsubstituted lower alkynyl, substituted or unsubstituted cycloalkyl, substituted or unsubstituted lower alkoxy, substituted or unsubstituted aryl, or a substituted or unsubstituted heterocyclic group; or $R^{8a}$ and $R^{8b}$ are combined together with the adjacent nitrogen atom thereto to form a substituted or unsubstituted heterocyclic group;

$R^4$ represents substituted or unsubstituted aryl; and $R^5$ represents a hydrogen atom, halogen, hydroxy, substituted or unsubstituted lower alkyl, substituted or unsubstituted lower alkenyl, substituted or unsubstituted lower alkoxy, substituted or unsubstituted aryl, a substituted or unsubstituted heterocyclic group, $CONR^{11a}R^{11b}$ wherein $R^{11a}$ and $R^{11b}$ have the same meanings as defined above, respectively, or $COR^{12}$ wherein $R^{12}$ represents a hydrogen atom, hydroxy, substituted or unsubstituted lower alkyl, substituted or unsubstituted lower alkenyl, substituted or unsubstituted lower alkynyl, substituted or unsubstituted cycloalkyl, substituted or unsubstituted lower alkoxy, substituted or unsubstituted aryl, or a substituted or unsubstituted heterocyclic group, or a pharmaceutically acceptable salt thereof.

3. A 2-aminoquinazoline compound represented by formula (I):

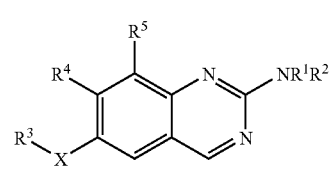

(I)

wherein $R^1$ and $R^2$ may be the same or different and each represents a hydrogen atom, substituted or unsubstituted lower alkyl, substituted or unsubstituted lower alkenyl, substituted or unsubstituted lower alkynyl, substituted or unsubstituted cycloalkyl, substituted or unsubstituted cycloalkenyl, substituted or unsubstituted lower alkanoyl, substituted or unsubstituted cycloalkylcarbonyl, substituted or unsubstituted aryl, a substituted or unsubstituted heterocyclic group, or $CONR^{6a}R^{6b}$ wherein $R^{6a}$ and $R^{6b}$ may be the same or different and each represents a hydrogen atom or substituted or unsubstituted lower alkyl;

X represents a bond or $CR^{7a}R^{7b}$ wherein $R^{7a}$ and $R^{7b}$ may be the same or different and each represents a hydrogen atom, halogen, hydroxy, substituted or unsubstituted lower alkyl, or substituted or unsubstituted lower alkoxy, or $R^{7a}$ and $R^{7b}$ are combined to form an oxygen atom; when X is a bond, $R^3$ represents substituted or unsubstituted aryl or a substituted or unsubstituted aromatic heterocyclic group;

when X is $CR^{7a}R^{7b}$ wherein $R^{7a}$ and $R^{7b}$ have the same meanings as defined above, respectively, $R^3$ represents substituted or unsubstituted lower alkoxy, substituted or unsubstituted aryl, a substituted or unsubstituted aromatic heterocyclic group, or $NR^{8a}R^{8b}$ wherein $R^{8a}$ and $R^{8b}$ may be the same or different and each represents a hydrogen atom, substituted or unsubstituted lower alkyl, substituted or unsubstituted lower alkenyl, substituted or unsubstituted lower alkynyl, substituted or unsubstituted cycloalkyl, substituted or unsubstituted lower alkoxy, substituted or unsubstituted aryl, or a substituted or unsubstituted heterocyclic group; or $R^{8a}$ and $R^{8b}$ are combined together with the adjacent nitrogen atom thereto to form a substituted or unsubstituted heterocyclic group;

$R^4$ represents a substituted or unsubstituted aromatic heterocyclic group; and $R^5$ represents a hydrogen atom, halogen, hydroxy, substituted or unsubstituted lower alkyl, substituted or unsubstituted lower alkenyl, substituted or unsubstituted lower alkoxy, substituted or unsubstituted aryl, a substituted or unsubstituted heterocyclic group, $CONR^{11a}R^{11b}$ wherein $R^{11a}$ and $R^{11b}$ have the same meanings as defined above, respectively, or $COR^{12}$ wherein $R^{12}$ represents a hydrogen atom, hydroxy, substituted or unsubstituted lower alkyl, substituted or unsubstituted lower alkenyl, substituted or unsubstituted lower alkynyl, substituted or unsubstituted cycloalkyl, substituted or unsubstituted lower alkoxy, substituted or unsubstituted aryl, or a substituted or unsubstituted heterocyclic group, or a pharmaceutically acceptable salt thereof.

4. A 2-aminoquinazoline compound represented by formula (I):

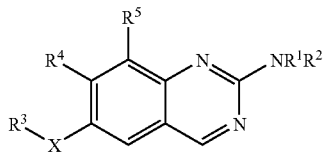

(I)

wherein $R^1$ and $R^2$ may be the same or different and each represents a hydrogen atom, substituted or unsubstituted lower alkyl, substituted or unsubstituted lower alkenyl, substituted or unsubstituted lower alkynyl, substituted or unsubstituted cycloalkyl, substituted or unsubstituted cycloalkenyl, substituted or unsubstituted lower alkanoyl, substituted or unsubstituted cycloalkylcarbonyl, substituted or unsubstituted aryl, a substituted or unsubstituted heterocyclic group, or $CONR^{6a}R^{6b}$ wherein $R^{6a}$ and $R^{6b}$ may be the same or different and each represents a hydrogen atom or substituted or unsubstituted lower alkyl;

X represents a bond or $CR^{7a}R^{7b}$ wherein $R^{7a}$ and $R^{7b}$ may be the same or different and each represents a hydrogen atom, halogen, hydroxy, substituted or unsubstituted lower alkyl, or substituted or unsubstituted lower alkoxy, or $R^{7a}$ and $R^{7b}$ are combined to form an oxygen atom; when X is a bond, $R^3$ represents substituted or unsubstituted aryl or a substituted or unsubstituted aromatic heterocyclic group;

when X is $CR^{7a}R^{7b}$ wherein $R^{7a}$ and $R^{7b}$ have the same meanings as defined above, respectively, $R^3$ represents substituted or unsubstituted lower alkoxy, substituted or unsubstituted aryl, a substituted or unsubstituted aromatic heterocyclic group, or $NR^{8a}R^{8b}$ wherein $R^{8a}$ and $R^{8b}$ may be the same or different and each represents a hydrogen atom, substituted or unsubstituted lower alkyl, substituted or unsubstituted lower alkenyl, substituted or unsubstituted lower alkynyl, substituted or unsubstituted cycloalkyl, substituted or unsubstituted lower alkoxy, substituted or unsubstituted aryl, or a substituted or unsubstituted heterocyclic group; or $R^{8a}$ and $R^{8b}$ are combined together with the adjacent nitrogen atom thereto to form a substituted or unsubstituted heterocyclic group;

$R^4$ represents substituted or unsubstituted aroyloxy; and $R^5$ represents a hydrogen atom, halogen, hydroxy, substituted or unsubstituted lower alkyl, substituted or unsubstituted lower alkenyl, substituted or unsubstituted lower alkoxy, substituted or unsubstituted aryl, a substituted or unsubstituted heterocyclic group, $CONR^{11a}R^{11b}$ wherein $R^{11a}$ and $R^{11b}$ have the same meanings as defined above, respectively, or $COR^{12}$ wherein $R^{12}$ represents a hydrogen atom, hydroxy, substituted or unsubstituted lower alkyl, substituted or unsubstituted lower alkenyl, substituted or unsubstituted lower alkynyl, substituted or unsubstituted cycloalkyl, substituted or unsubstituted lower alkoxy, substituted or unsubstituted aryl, or a substituted or unsubstituted heterocyclic group, or a pharmaceutically acceptable salt thereof.

5. A 2-aminoquinazoline compound represented by formula (I):

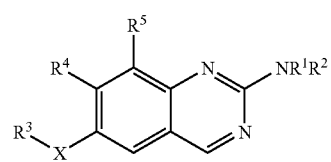

(I)

wherein $R^1$ and $R^2$ may be the same or different and each represents a hydrogen atom, substituted or unsubstituted lower alkyl, substituted or unsubstituted lower alkenyl, substituted or unsubstituted lower alkynyl, substituted or unsubstituted cycloalkyl, substituted or unsubstituted cycloalkenyl, substituted or unsubstituted lower alkanoyl, substituted or unsubstituted cycloalkylcarbonyl, substituted or unsubstituted aryl, a substituted or unsubstituted heterocyclic group, or $CONR^{6a}R^{6b}$ wherein $R^{6a}$ and $R^{6b}$ may be the same or different and each represents a hydrogen atom or substituted or unsubstituted lower alkyl;

X represents a bond or $CR^{7a}R^{7b}$ wherein $R^{7a}$ and $R^{7b}$ may be the same or different and each represents a hydrogen atom, halogen, hydroxy, substituted or unsubstituted lower alkyl, or substituted or unsubstituted lower alkoxy, or $R^{7a}$ and $R^{7b}$ are combined to form an oxygen atom;

when X is a bond, $R^3$ represents substituted or unsubstituted aryl or a substituted or unsubstituted aromatic heterocyclic group;

when X is $CR^{7a}R^{7b}$ wherein $R^{7a}$ and $R^{7b}$ have the same meanings as defined above, respectively, $R^3$ represents substituted or unsubstituted lower alkoxy, substituted or unsubstituted aryl, a substituted or unsubstituted aromatic heterocyclic group, or $NR^{8a}R^{8b}$ wherein $R^{8a}$ and $R^{8b}$ may be the same or different and each represents a hydrogen atom, substituted or unsubstituted lower alkyl, substituted or unsubstituted lower alkenyl, substituted or unsubstituted lower alkynyl, substituted or unsubstituted cycloalkyl, substituted or unsubstituted lower alkoxy, substituted or unsubstituted aryl, or a substituted or unsubstituted heterocyclic group; or $R^{8a}$ and $R^{8b}$ are combined together with the adjacent nitrogen atom thereto to form a substituted or unsubstituted heterocyclic group;

$R^4$ represents halogen, hydroxy, substituted or unsubstituted lower alkyl, substituted or unsubstituted lower alkenyl, substituted or unsubstituted lower alkynyl, substituted or unsubstituted lower alkoxy, substituted or unsubstituted lower alkanoyloxy, substituted or unsubstituted aryl, substituted or unsubstituted aroyloxy, or a substituted or unsubstituted heterocyclic group; and $R^5$ represents substituted or unsubstituted aryl, or a pharmaceutically acceptable salt thereof.

6. A 2-aminoquinazoline compound represented by formula (I):

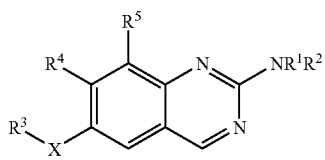

wherein $R^1$ and $R^2$ may be the same or different and each represents a hydrogen atom, substituted or unsubstituted lower alkyl, substituted or unsubstituted lower alkenyl, substituted or unsubstituted lower alkynyl, substituted or unsubstituted cycloalkyl, substituted or unsubstituted cycloalkenyl, substituted or unsubstituted lower alkanoyl, substituted or unsubstituted cycloalkylcarbonyl, substituted or unsubstituted aryl, a substituted or unsubstituted heterocyclic group, or $CONR^{6a}R^{6b}$ wherein $R^{6a}$ and $R^{6b}$ may be the same or different and each represents a hydrogen atom or substituted or unsubstituted lower alkyl;

X represents a bond or $CR^{7a}R^{7b}$ wherein $R^{7a}$ and $R^{7b}$ may be the same or different and each represents a hydrogen atom, halogen, hydroxy, substituted or unsubstituted lower alkyl, or substituted or unsubstituted lower alkoxy, or $R^{7a}$ and $R^{7b}$ are combined to form an oxygen atom;

when X is a bond, $R^3$ represents substituted or unsubstituted aryl or a substituted or unsubstituted aromatic heterocyclic group;

when X is $CR^{7a}R^{7b}$ wherein $R^{7a}$ and $R^{7b}$ have the same meanings as defined above, respectively, $R^3$ represents substituted or unsubstituted lower alkoxy, substituted or unsubstituted aryl, a substituted or unsubstituted aromatic heterocyclic group, or $NR^{8a}R^{8b}$ wherein $R^{8a}$ and $R^{8b}$ may be the same or different and each represents a hydrogen atom, substituted or unsubstituted lower alkyl, substituted or unsubstituted lower alkenyl, substituted or unsubstituted lower alkynyl, substituted or unsubstituted cycloalkyl, substituted or unsubstituted lower alkoxy, substituted or unsubstituted aryl, or a substituted or unsubstituted heterocyclic group; or $R^{8a}$ and $R^{8b}$ are combined together with the adjacent nitrogen atom thereto to form a substituted or unsubstituted heterocyclic group;

$R^4$ represents halogen, hydroxy, substituted or unsubstituted lower alkyl, substituted or unsubstituted lower alkenyl, substituted or unsubstituted lower alkynyl, substituted or unsubstituted lower alkoxy, substituted or unsubstituted lower alkanoyloxy, substituted or unsubstituted aryl, substituted or unsubstituted aroyloxy, or a substituted or unsubstituted heterocyclic group; and $R^5$ represents a substituted or unsubstituted aromatic heterocyclic group, or a pharmaceutically acceptable salt thereof.

7. A pharmaceutical composition which comprises, as an active ingredient, the 2-aminoquinazoline compound or the pharmaceutically acceptable salt thereof described in any one of claims 1-4, 5 or 6, and a pharmaceutically acceptable carrier.

* * * * *